(12) United States Patent
Gouze et al.

(10) Patent No.: US 11,697,678 B2
(45) Date of Patent: Jul. 11, 2023

(54) SOLUBLE FIBROBLAST GROWTH FACTOR RECEPTOR 3 (SFGFR3) POLYPEPTIDES AND USES THEREOF

(71) Applicants: Pfizer Inc., New York, NY (US); INSERM (Institut National de la Santé et de la Recherche Médicale), Paris (FR); Université Côte d'Azur, Nice (FR)

(72) Inventors: Elvire Gouze, Vallauris (FR); Stéphanie Garcia, Nice (FR)

(73) Assignees: Pfizer Inc., New York, NY (US); INSERM (Institut National de la Santé et de la Recherche Médicale), Paris (FR); Université Côte d'Azur, Nice (FR)

( * ) Notice: Subject to any disclaimer, the term of this patent is extended or adjusted under 35 U.S.C. 154(b) by 108 days.

(21) Appl. No.: 17/234,841

(22) Filed: Apr. 20, 2021

(65) Prior Publication Data
US 2021/0309718 A1    Oct. 7, 2021

Related U.S. Application Data

(60) Division of application No. 16/417,174, filed on May 20, 2019, now Pat. No. 11,021,528, which is a continuation of application No. 15/943,436, filed on Apr. 2, 2018, now Pat. No. 10,294,289, which is a continuation of application No. PCT/EP2017/067119, filed on Jul. 7, 2017.

(60) Provisional application No. 62/467,478, filed on Mar. 6, 2017, provisional application No. 62/359,607, filed on Jul. 7, 2016.

(51) Int. Cl.
| | |
|---|---|
| *A61K 38/17* | (2006.01) |
| *C07K 14/71* | (2006.01) |
| *A61P 19/00* | (2006.01) |
| *A61K 38/00* | (2006.01) |

(52) U.S. Cl.
CPC ............ *C07K 14/71* (2013.01); *A61K 38/179* (2013.01); *A61K 38/1709* (2013.01); *A61P 19/00* (2018.01); *A61K 38/00* (2013.01)

(58) Field of Classification Search
CPC .. A61K 38/179; A61K 38/1709; C07K 14/71; C12N 15/09; C12N 15/11
See application file for complete search history.

(56) References Cited

U.S. PATENT DOCUMENTS

| | | | |
|---|---|---|---|
| 5,015,573 A | 5/1991 | Yarranton et al. | |
| 6,743,425 B2 | 6/2004 | Nakao | |
| 7,276,481 B2 | 10/2007 | Golembo et al. | |
| 7,498,416 B2 | 3/2009 | Yayon et al. | |
| 7,598,027 B2 | 10/2009 | Fernandez-Salas et al. | |
| 7,678,890 B2 | 3/2010 | Bosch et al. | |
| 7,982,014 B2 | 7/2011 | Williams et al. | |
| 8,043,618 B2 | 10/2011 | Sun et al. | |
| 8,101,721 B2 | 1/2012 | Yayon et al. | |
| 8,187,601 B2 | 5/2012 | Wenq et al. | |
| 8,338,569 B2 | 12/2012 | Marshall et al. | |
| 8,404,240 B2 | 3/2013 | Sun | |
| 8,410,250 B2 | 4/2013 | Ashkenazi et al. | |
| 8,426,396 B2 | 4/2013 | Horton et al. | |
| 8,445,445 B2 | 5/2013 | Brennan et al. | |
| 8,481,038 B2 | 7/2013 | Keer | |
| 8,614,183 B2 | 12/2013 | Hardinq et al. | |
| 8,685,931 B2 | 4/2014 | Brennan et al. | |
| 8,710,189 B2 | 4/2014 | Ashkenazi et al. | |
| 8,828,385 B2 | 9/2014 | Yavon et al. | |
| 8,962,556 B2 | 2/2015 | Yayon et al. | |
| 9,273,137 B2 | 3/2016 | Fang et al. | |
| 10,294,289 B2 | 5/2019 | Gouze et al. | |
| 10,724,014 B2 | 7/2020 | Gouze et al. | |
| 11,021,528 B2 | 6/2021 | Gouze et al. | |
| 2002/0193309 A1 | 12/2002 | Yayon | |
| 2003/0068313 A1 | 4/2003 | Nakao | |
| 2003/0235589 A1 | 12/2003 | Demopulos et al. | |
| 2004/0109850 A1 | 6/2004 | Jaiswal et al. | |
| 2005/0147612 A1 | 7/2005 | Yavon et al. | |
| 2008/0044419 A1 | 2/2008 | Yayon | |
| 2008/0171689 A1 | 7/2008 | Williams et al. | |
| 2009/0192133 A1 | 7/2009 | Horton et al. | |
| 2009/0202547 A1 | 8/2009 | Yayon et al. | |
| 2010/0003258 A1 | 1/2010 | Weng et al. | |
| 2010/0047251 A1 | 2/2010 | Yayon et al. | |
| 2010/0087627 A1 | 4/2010 | Marshall et al. | |
| 2010/0158911 A1 | 6/2010 | Williams et al. | |
| 2010/0291114 A1 | 11/2010 | Wiesmann | |

(Continued)

FOREIGN PATENT DOCUMENTS

| | | |
|---|---|---|
| CN | 102219860 A | 10/2011 |
| CN | 105121464 A | 12/2015 |

(Continued)

OTHER PUBLICATIONS

International Search Report dated Aug. 7, 2013, for International Application No. PCT/IB2013/001480.

(Continued)

*Primary Examiner* — Xiaozhen Xie

(74) *Attorney, Agent, or Firm* — Wolf, Greenfield & Sacks, P.C.

(57) ABSTRACT

The invention features soluble fibroblast growth factor receptor 3 (sFGFR3) polypeptides. The invention also features methods of using sFGFR3 polypeptides to treat skeletal growth regardation disorders, such as achondroplasia.

19 Claims, 46 Drawing Sheets

Specification includes a Sequence Listing.

(56) References Cited

U.S. PATENT DOCUMENTS

| | | |
|---|---|---|
| 2011/0053841 A1 | 3/2011 | Yayon et al. |
| 2012/0009200 A1 | 1/2012 | Sun et al. |
| 2012/0183541 A1 | 7/2012 | Brennan et al. |
| 2012/0219563 A1 | 8/2012 | Sun |
| 2012/0321606 A1 | 12/2012 | Wiesmann |
| 2012/0328599 A1 | 12/2012 | Bae et al. |
| 2013/0004492 A1 | 1/2013 | Marshall et al. |
| 2013/0046078 A1 | 2/2013 | Ashkenazi et al. |
| 2013/0058928 A1 | 3/2013 | Brennan et al. |
| 2013/0287776 A1 | 10/2013 | Ashkenazi et al. |
| 2014/0030259 A1 | 1/2014 | French |
| 2014/0187754 A1 | 7/2014 | Ashkenazi et al. |
| 2014/0274898 A1 | 9/2014 | Brennan et al. |
| 2014/0348817 A1 | 11/2014 | Jiang et al. |
| 2015/0344855 A1 | 12/2015 | Gouze |
| 2015/0353624 A1 | 12/2015 | Gouze |
| 2018/0148494 A1 | 5/2018 | Gouze et al. |
| 2018/0230197 A1 | 8/2018 | Gouze et al. |
| 2020/0190162 A1 | 6/2020 | Gouze et al. |
| 2020/0297799 A1 | 9/2020 | Gouze et al. |
| 2021/0009657 A1 | 1/2021 | Gouze et al. |
| 2021/0032607 A1 | 2/2021 | Gouze |
| 2021/0032608 A1 | 2/2021 | Gouze |

FOREIGN PATENT DOCUMENTS

| | | | |
|---|---|---|---|
| EP | 2083081 A1 | 7/2009 | |
| EP | 1423428 B1 | 8/2009 | |
| EP | 1910542 B1 | 12/2009 | |
| EP | 1423428 B2 | 11/2012 | |
| EP | 2679600 A1 | 1/2014 | |
| JP | H11-507828 A | 7/1999 | |
| JP | H11508358 A | 7/1999 | |
| JP | 2003-104908 A | 4/2003 | |
| JP | 2005-500034 A | 1/2005 | |
| JP | 2007-526770 A | 9/2007 | |
| JP | 2008-222711 A | 9/2008 | |
| JP | 2011-529705 A | 12/2011 | |
| JP | 2014-519308 A | 8/2014 | |
| JP | 2016-506912 A | 3/2016 | |
| RU | 2568066 C2 | 11/2015 | |
| RU | 2751483 C2 | 7/2021 | |
| WO | WO 96/41523 A1 | 12/1996 | |
| WO | WO 02/102972 A2 | 12/2002 | |
| WO | WO 02/102973 A2 | 12/2002 | |
| WO | WO 2004/110487 A1 | 12/2004 | |
| WO | WO 2005/082096 A2 | 9/2005 | |
| WO | WO 2007/014123 A2 | 2/2007 | |
| WO | WO 2007/144893 A2 | 12/2007 | |
| WO | WO 2008/133873 A2 | 11/2008 | |
| WO | WO 2010/002862 A2 | 1/2010 | |
| WO | WO 2010/017198 A2 | 2/2010 | |
| WO | WO 2010/048026 A2 | 4/2010 | |
| WO | WO 2010/111367 A1 | 9/2010 | |
| WO | WO 2011/034940 A1 | 3/2011 | |
| WO | WO 2011/084711 A2 | 7/2011 | |
| WO | WO 2011/088196 A2 | 7/2011 | |
| WO | WO-2011084711 A2 * | 7/2011 | ........... A61K 31/473 |
| WO | WO 2012/088608 A1 | 7/2012 | |
| WO | WO 2013/087744 A1 | 6/2013 | |
| WO | WO 2014/018673 A2 | 1/2014 | |
| WO | WO 2014/018841 A1 | 1/2014 | |
| WO | WO 2014/071419 A2 | 5/2014 | |
| WO | WO 2014/111467 A1 | 7/2014 | |
| WO | WO 2014/111744 A1 | 7/2014 | |
| WO | WO-2014111467 A1 * | 7/2014 | ........... A61K 38/179 |
| WO | WO 2015/112886 A2 | 7/2015 | |
| WO | WO 2016/110786 A1 | 7/2016 | |
| WO | WO 2018/007597 A1 | 1/2018 | |
| WO | WO 2019/057820 A1 | 3/2019 | |

OTHER PUBLICATIONS

International Preliminary Report and Written Opinion dated Jul. 21, 2015, for International Application No. PCT/IB2013/001480.

Extended European Search Report dated Oct. 8, 2020, for Application No. EP 20167861.2.

International Search Report dated Mar. 7, 2014, for International Application No. PCT/EP2014/050800.

International Preliminary Report and Written Opinion dated Jul. 21, 2015, for International Application No. PCT/EP2014/050800.

International Search Report and Written Opinion dated Sep. 6, 2016, for International Application No. PCT/IB2016/000403.

International Preliminary Report on Patentability dated Jul. 20, 2017, for International Application No. PCT/IB2016/000403.

International Search Report and Written Opinion dated Sep. 25, 2017, for International Application No. PCT/EP2017/067119.

International Preliminary Report on Patentability dated Jan. 17, 2019, for International Application No. PCT/EP2017/067119.

International Search Report and Written Opinion dated Dec. 14, 2018, for International Application No. PCT/EP2018/075471.

International Preliminary Report on Patentability dated Apr. 2, 2020, for International Application No. PCT/EP2018/075471.

[No Author Listed], GenBank Accession No. P22607, downloaded from: https://www.ncbi.nlm.nih.gov/protein/P22607 on Apr. 5, 2018. 25 pages.

[No Author Listed], GenBank Accession No. NP_000133.1, downloaded from www.ncbi.nlm.nih.gov/protein/4503711. Sep. 21, 2020. 4.

[No Author Listed], GenBank Accession No. NP_075254.1, downloaded from: www.ncbi.nlm.nih.gov/protein/NP_075254.1. Jun. 19, 2020. 3 pages.

[No Author Listed], Japan Forum of Fetal Skeletal Dysplasia Wiki, 5. Fetal skeletal dysplasia. Accessible at: plaza.umin.ac.jp/-fskel/cgi-bin/wiki/wiki.cgi?page=%C2%DB%BB%F9%B9%FC%B7%CF%C5%FD%BC%CO%B4%B5%B3%C6%CF%C0. Aug. 8, 2011. 8 pages.

Altaf et al., Ascorbate-enhanced chondrogenesis of ATDC5 cells. Eur Cell Mater. Nov. 9, 2006;12:64-9; discussion 69-70.

Auclair et al., Signal peptidase I: cleaving the way to mature proteins. Protein Sci. Jan. 2012;21(1):13-25. doi: 10.1002/pro.757. Epub Nov. 22, 2011.

Aviezer et al., Fibroblast growth factor receptor-3 as a therapeutic target for Achondroplasia—Genetic short limbed dwarfism. Curr Drug Targets. 2003;4(5):353-65.

Bellus et al., Achondroplasia is defined by recurrent G380R mutations of FGFR3. Am J Hum Genet. 1995;56(2):368-73.

Bertola et al., Hepatocyte growth factor induces glucose uptake in 3T3-L1 adipocytes through A Gab1/phosphatidylinositol 3-kinase/Glut4 pathway. J Biol Chem. Apr. 6, 2007;282(14):10325-32. Epub Feb. 6, 2007.

Cassagnaud et al., Biotherapy for achondroplasia. European Society of Gene and Cell Therapy French Society of Cell and Gene Therapy Collaborative Congress. Oct. 29, 2012;A76-A77, Abstract P043.

Chellaiah et al., Mapping ligand binding domains in chimeric fibroblast growth factor receptor molecules. Multiple regions determine ligand binding specificity. J Biol Chem. Dec. 3, 1999;274(49):34785-94. doi: 10.1074/jbc.274.49.34785.

Chen et al., Interaction of cartilage oligomeric matrix protein/thrombospondin 5 with aggrecan. J Biol Chem. Aug. 24, 2007;282(34):24591-8. Epub Jun. 22, 2007.

Chusho et al., Dwarfism and early death in mice lacking C-type natriuretic peptide. Proc Natl Acad Sci USA. 2001;98(7):4016-21.

Davidson et al., Fibroblast growth factor (FGF) 18 signals through FGF receptor 3 to promote chondrogenesis. J Biol Chem. 2005;280(21):20509-15.

Deng et al., Fibroblast growth factor receptor 3 is a negative regulator of bone growth. Cell. 1996;84(6):911-21.

Garcia et al., Postnatal soluble FGFR3 therapy rescues achondroplasia symptoms and restores bone growth in mice. Sci Transl Med. 2013;5(203):203ra124(1-11).

Garofalo et al., Skeletal dysplasia and defective chondrocyte differentiation by targeted overexpression of fibroblast growth factor 9 in transgenic mice. J Bone Miner Res. 1999;14(11):1909-15.

(56) References Cited

OTHER PUBLICATIONS

Ghivizzani, Gene therapy for achondroplasia. Accessible at: www.asgct.org/members/asgct_news/summer10/index.php?pagecontent=page2.html. Retrieved on Dec. 20, 2013 (1 page).
Guo et al., Protein tolerance to random amino acid change. Proc Natl Acad Sci U S A. Jun. 22, 2004;101(25):9205-10. doi: 10.1073/pnas.0403255101. Epub Jun. 14, 2004.
Harada et al., Sustained phosphorylation of mutated FGFR3 is a crucial feature of genetic dwarfism and induces apoptosis in the ATDC5 chondrogenic cell line via PLCgamma-activated STAT1. Bone. Aug. 2007;41(2):273-81. Epub Feb. 9, 2007.
He et al., FGFR3 heterodimerization in achondroplasia, the most common form of human dwarfism. J Biol Chem. 2011;286(15):13272-81.
He et al., Physical basis behind achondroplasia, the most common form of human dwarfism. J Biol Chem. 2010;285(39):30103-14.
Horton et al., Achondroplasia. Lancet. 2007;370(9582):162-72.
Horton et al., Fibroblast growth factor receptor 3 mutations in achondroplasia and related forms of dwarfism. Rev Endocr Metab Disord. Dec. 2002;3(4):381-5.
Hunt et al., Bioactivity and metabolism of C-type natriuretic peptide in normal man. J Clin Endocrinol Metab. Jun. 1994;78(6):1428-35.
Hwang et al., High-level expression and purification of a designed angiopoietin-1 chimeric protein, COMP-Ang1, produced in Chinese hamster ovary cells. Protein J. Aug. 2008;27(5):319-26. doi: 10.1007/s10930-008-9140-5.
Jang, Identification and characterization of soluble isoform of fibroblast growth factor receptor 3 in human SaOS-2 osteosarcoma cells. Biochem Biophys Res Commun. 2002;292(2):378-82.
Jin et al., A novel FGFR3-binding peptide inhibits FGFR3 signaling and reverses the lethal phenotype of mice mimicking human thanatophoric dysplasia. Hum Mol Genet. 2012;21(26):5443-55.
Johnston et al., Fibroblast Growth Factor Receptors (FGFRs) Localize in Different Cellular Compartments. J Biol Chem. 1995;270(51):30643-50.
Krejci et al., NF449 is a novel inhibitor of fibroblast growth factor receptor 3 (FGFR3) signaling active in chondrocytes and multiple myeloma cells. J Biol Chem. 2010;285(27):20644-53.
Laederich et al., FGFR3 targeting strategies for achondroplasia. Expert Rev Mol Med. 2012;14:e11(1-17). Published Jan. 19, 2012. doi:10.1017/erm.2012.4.
Laws et al., Progression of kyphosis in mdx mice. J Appl Physiol (1985). Nov. 2004;97(5):1970-7. Epub Jul. 2, 2004.
Li et al., A novel decoy receptor fusion protein for FGF-2 potently inhibits tumour growth. Br J Cancer. Jul. 8, 2014;111(1):68-77. doi: 10.1038/bjc.2014.282. Epub May 29, 2014.
Lodish et al., Section 17.4: Translocation of Secretory Proteins across the ER Membrane. Molecular Cell Biology, Fourth Edition. W.H. Freeman and Company (2000) (5 pages).
Lorget et al., Evaluation of the therapeutic potential of a CNP analog in a Fgfr3 mouse model recapitulating achondroplasia. Am J Hum Genet. 2012;91(6):1108-14.
Louboutin et al., Strategies for CNS-directed gene delivery: in vivo gene transfer to the brain using SV40-derived vectors. Gene Ther. Jun. 2007;14(12):939-49. Epub Apr. 19, 2007.
Martinez-Frias et al., Review of the recently defined molecular mechanisms underlying thanatophoric dysplasia and their potential therapeutic implications for achondroplasia. Am J Med Genet A. 2010;152A(1):245-55. doi:10.1002/ajmg.a.33188.
Matsui et al., Genotype phenotype correlation in achondroplasia and hypochondroplasia. J Bone Joint Surg Br. Nov. 1998;80(6):1052-6. doi: 10.1302/0301-620x.80b6.9277.
Ming et al., The research progress in FGFR3 mutations and achondroplasia. Chinese Journal of Birth Health & Heredity. 2010;18(5):1-2; 13.
Monsonego-Ornan et al., FGF receptors ubiquitylation: dependence on tyrosine kinase activity and role in downregulation. FEBS Lett. 2002;528(1-3):83-9.
Monsonego-Ornan et al., The transmembrane mutation G380R in fibroblast growth factor receptor 3 uncouples ligand-mediated receptor activation from down-regulation. Mol Cell Biol. 2000;20(2):516-22.
Naski et al., Repression of hedgehog signaling and BMP4 expression in growth plate cartilage by fibroblast growth factor receptor 3. Development. 1998;125(24):4977-88.
Ornitz, FGF signaling in the developing endochondral skeleton. Cytokine Growth Factor Rev. 2005;16(2):205-213. doi:10.1016/j.cytogfr.2005.02.003. Author Manuscript. 15 pages.
Papakostas et al., Development of an efficiently cleaved, bioactive, highly pure FLAG-tagged recombinant human Mullerian Inhibiting Substance. Protein Expr Purif. Mar. 2010;70(1):32-8. doi: 10.1016/j.pep.2009.09.004. Epub Sep. 13, 2009.
Place et al., Aggrecan-mimetic, glycosaminoglycan-containing nanoparticles for growth factor stabilization and delivery. Biomacromolecules. 2014;15(2):680-9.
Placone et al., Direct assessment of the effect of the Gly380Arg achondroplasia mutation on FGFR3 dimerization using quantitative imaging FRET. PLoS One. 2012;7(10):e46678(1-7).
Ramaswami et al., Treatment of achondroplasia with growth hormone: six years of experience. Pediatr Res. Oct. 1999;46(4):435-9. doi: 10.1203/00006450-199910000-00012.
Reardon et al., Craniosynostosis associated with FGFR3 pro250arg mutation results in a range of clinical presentations including unisutural sporadic craniosynostosis. J Med Genet. 1997;34(8):632-6.
Richette et al., Achondroplasia: from genotype to phenotype. Joint Bone Spine. 2008;75(2):125-30.
Rodino-Klapac et al., Persistent expression of FLAG-tagged micro dystrophin in nonhuman primates following intramuscular and vascular delivery. Mol Ther. Jan. 2010;18(1):109-17. doi: 10.1038/mt.2009.254. Epub Nov. 10, 2009.
Rousseau et al., Mutations in the gene encoding fibroblast growth factor receptor-3 in achondroplasia. Nature. 1994;371(6494):252-4.
Rousseau et al., Mutations of the fibroblast growth factor receptor-3 gene in achondroplasia. HormRes. 1996;45(1-2):108-10.
Roussel et al., A point mutation in the extracellular domain of the human CSF-1 receptor (c-fms proto-oncogene product) activates its transforming potential. Cell. Dec. 23, 1988;55(6):979-88. (Abstract only).
Salles et al., Translation studies in children. Arch Pediatr. 2009;16(6):664-6. (8 pages).
Shiang et al., Mutations in the transmembrane domain of FGFR3 cause the most common genetic form of dwarfism, achondroplasia. Cell. 1994;78(2):335-42.
Shirley et al., Achondroplasia: manifestations and treatment. J Am Acad Orthop Surg. Apr. 2009;17(4):231-41.
Sturla et al., FGFR3IIIS: a novel soluble FGFR3 spliced variant that modulates growth is frequently expressed in tumour cells. Br J Cancer. 2003;89(7):1276-84.
Su et al., Reduction of arthritis and pneumonitis in motheaten mice by soluble tumor necrosis factor receptor. Arthritis Rheum. 1998;41(1):139-49.
Terada et al., Fibroblast growth factor receptor 3 lacking the Ig IIIb and transmembrane domains secreted from human squamous cell carcinoma DJM-1 binds to FGFs. Mol Cell Biol Res Commun. 2001;4(6):365-73.
Terpe, Overview of tag protein fusions: from molecular and biochemical fundamentals to commercial systems. Appl Microbiol Biotechnol. Jan. 2003;60(5):523-33. Epub Nov. 7, 2002.
Tomlinson et al., Alternative splicing of fibroblast growth factor receptor 3 produces a secreted isoform that inhibits fibroblast growth factor-induced proliferation and is repressed in urothelial carcinoma cell lines. Cancer Res. 2005;65(22):10441-9.
Vajo et al., The molecular and genetic basis of fibroblast growth factor receptor 3 disorders: the achondroplasia family of skeletal dysplasias, Muenke craniosynostosis, and Crouzon syndrome with acanthosis niqricans. Endocr Rev. 2000;21(1):23-39.
Wang et al., Antitumor activity of a recombinant soluble ectodomain of mutant human fibroblast growth factor receptor-2 IIIc. Mol Cancer Ther. 2011;10(9):1656-66.

(56) References Cited

OTHER PUBLICATIONS

Webster et al., Constitutive activation of fibroblast growth factor receptor 3 by the transmembrane domain point mutation found in achondroplasia. EMBO J. 1996;15(3):520-7.

Wright et al., Clinical management of achondroplasia. Arch Dis Child. 2012;97(2):129-34.

Xie et al., Intermittent PTH (1-34) injection rescues the retarded skeletal development and postnatal lethality of mice mimicking human achondroplasia and thanatophoric dysplasia. Hum Mol Genet. 2012;21(18):3941-55.

Yasoda et al., Systemic administration of C-type natriuretic peptide as a novel therapeutic strategy for skeletal dysplasias. Endocrinology. 2009;150(7):3138-44.

Yu et al., Soluble vascular endothelial growth factor decoy receptor FP3 exerts potent antiangiogenic effects. Mol Ther. 2012;20(5):938-47.

[No Author Listed], GenBank Accession No. JV574764.1. TSA: Macaca mulatta Mamu_241725 mRNA sequence. https://www.ncbi.nlm.nih.gov/nuccore/JV574764.1. Nov. 4, 2014. 2 pages.

Babat et al., Spinal surgery in patients with Parkinson's disease: construct failure and progressive deformity. Spine (Phila Pa 1976). Sep. 15, 2004;29(18):2006-12. doi: 10.1097/01.brs.0000138306.02425.21.

Bhattacharya et al., Impact of genetic variation on three dimensional structure and function of proteins. PLoS One. Mar. 15, 2017;12(3):e0171355. doi: 10.1371/journal.pone.0171355. eCollection 2017.

Bose et al., Stress and obesity: the role of the hypothalamic-pituitary-adrenal axis in metabolic disease. Curr Opin Endocrinol Diabetes Obes. Oct. 2009;16(5):340-6. doi: 10.1097/MED.0b013e32832fa137.

Chen et al., The extracellular domain of fibroblast growth factor receptor 3 inhibits ligand-independent dimerization. Sci Signal. Nov. 30, 2010;3(150):ra86. doi: 10.1126/scisignal.2001195.

Fenton et al., Rheostat positions: A new classification of protein positions relevant to pharmacogenomics. Med Chem Res. Jul. 2020;29(7):1133-1146. doi: 10.1007/s00044-020-02582-9. Epub Jun. 7, 2020.

Huang et al., A molecular mechanism for the generation of ligand-dependent differential outputs by the epidermal growth factor receptor. Elife. Nov. 30, 2021;10:e73218. doi: 10.7554/eLife.73218.

Hunter et al., Standard weight for height curves in achondroplasia. Am J Med Genet. Mar. 29, 1996;62(3):255-61. doi: 10.1002/(SICI)1096-8628(19960329)62:3<255::AID-AJMG10>3.0.CO;2-J.

Johnsson et al., Hand deformities are important signs of disease severity in patients with early rheumatoid arthritis. Rheumatology (Oxford). Nov. 2009;48(II):1398-401. doi: 10.1093/rheumatology/kep253. Epub Aug. 31, 2009.

Owen et al., Resting metabolic rate and body composition of achondroplastic dwarfs.Medicine (Baltimore). Jan. 1990;69(1):56-67. doi: 10.1097/00005792-199001000-00005.

Saint-Laurent et al., Early postnatal soluble FGFR3 therapy prevents the atypical development of obesity in achondroplasia. PLoS One. Apr. 13, 2018;13(4):e0195876. doi: 10.1371/journal.pone.0195876. eCollection 2018.

Van Buick et al., Novel Approaches for the Treatment of Alzheimer's and Parkinson's Disease. Int. J Mol Sci. 2019; 20(3): 719. https://doi.org/10.3390/ijms20030719.

Zhang et al., Research progress on the FGFR3 gene mutation and achondroplasia. Chinese Journal of Birth Health & Heredity. Dec. 2010; 18(5): 1-3.

Zimin et al., A new rhesus macaque assembly and annotation for next-generation sequencing analyses. Biol Direct. Oct. 14, 2014;9(1):20. doi: 10.1186/1745-6150-9-20.

* cited by examiner

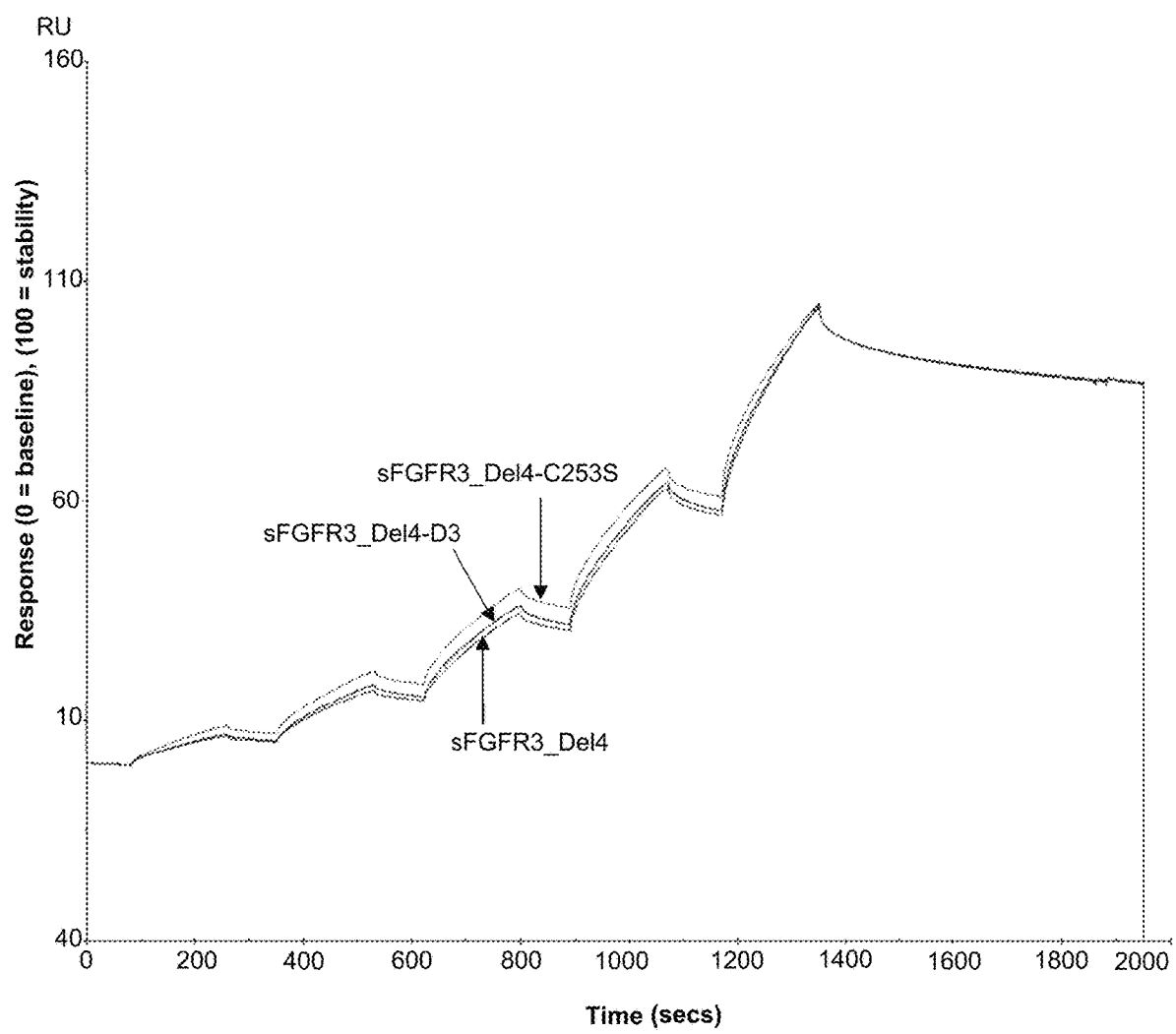

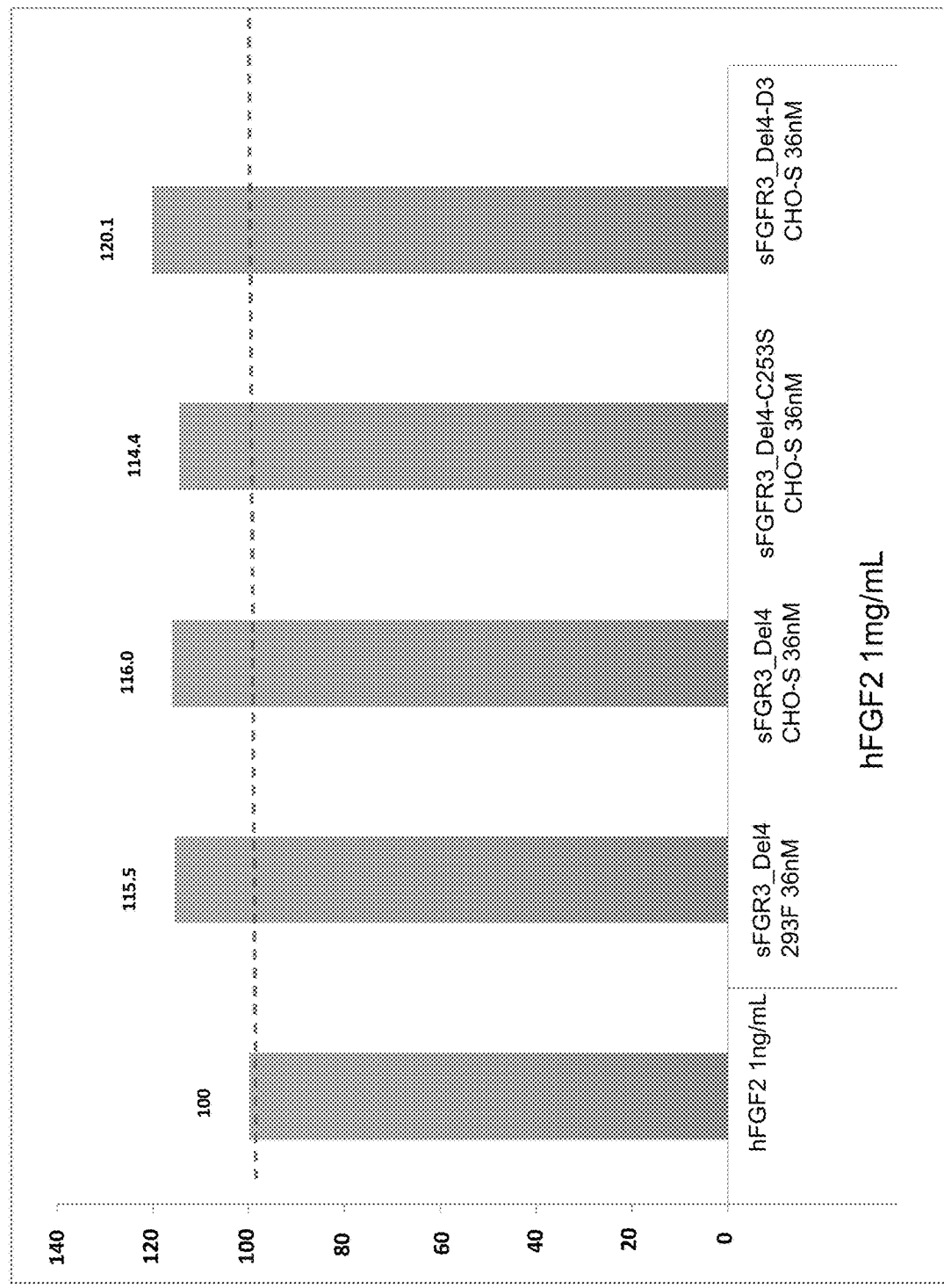

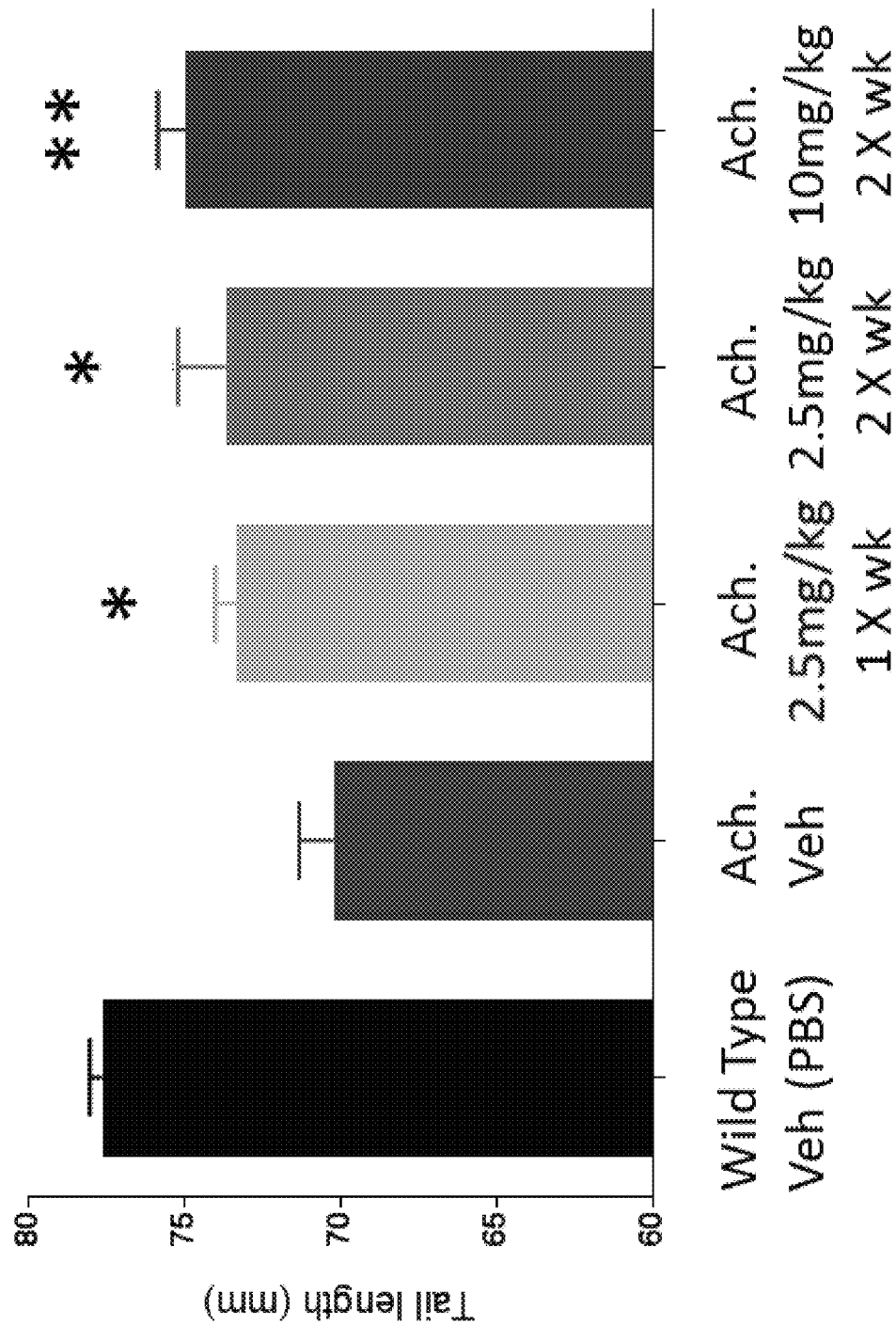

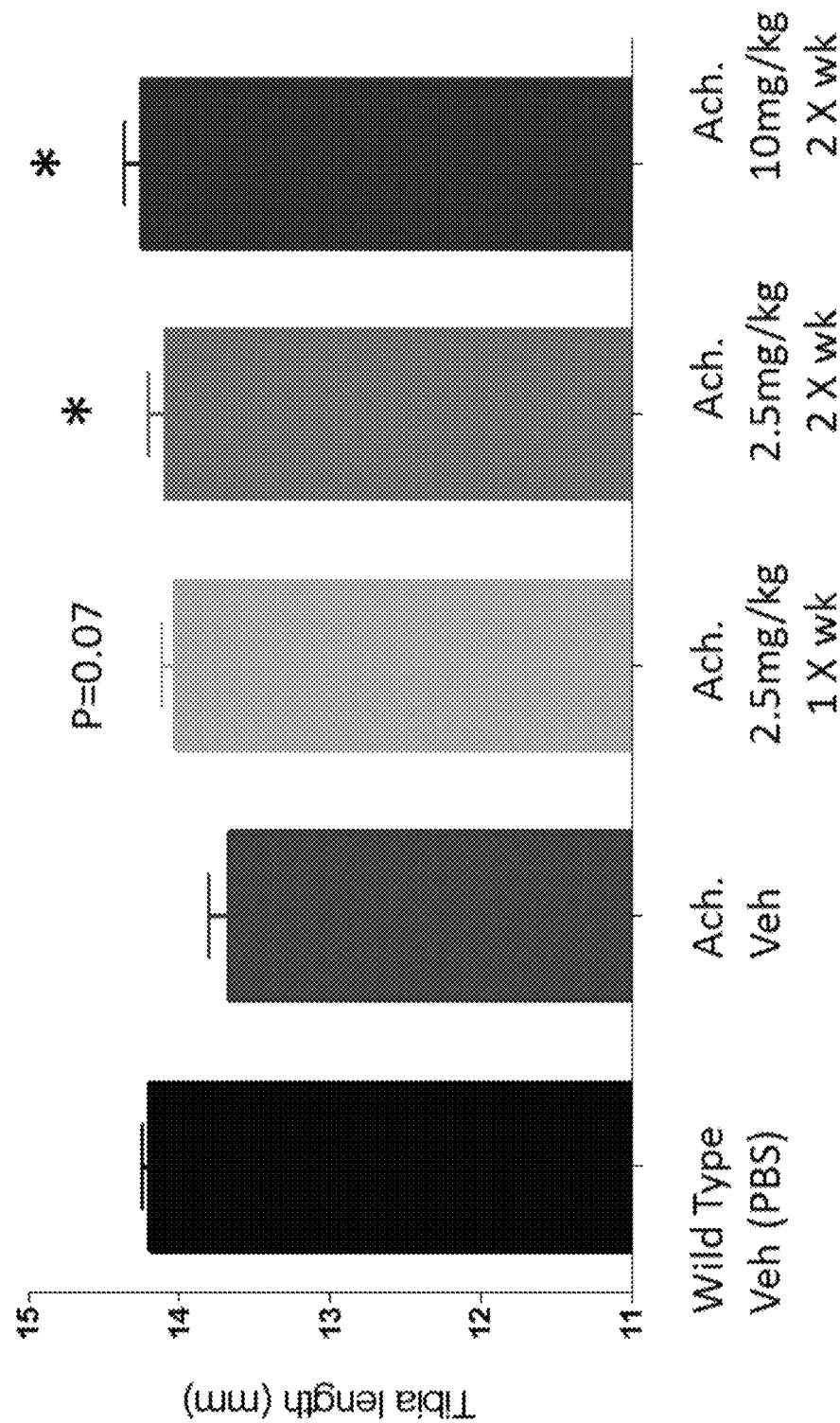

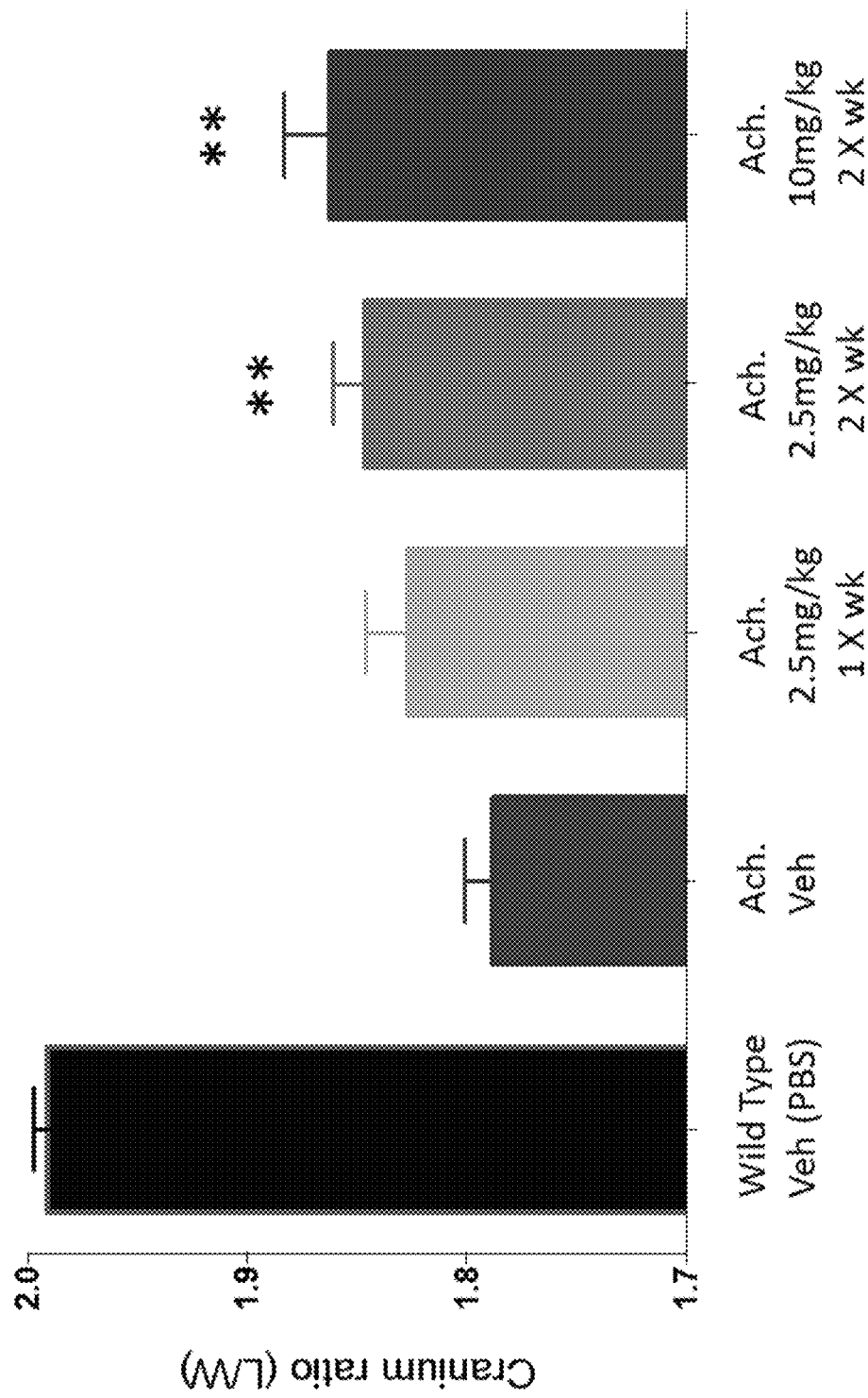

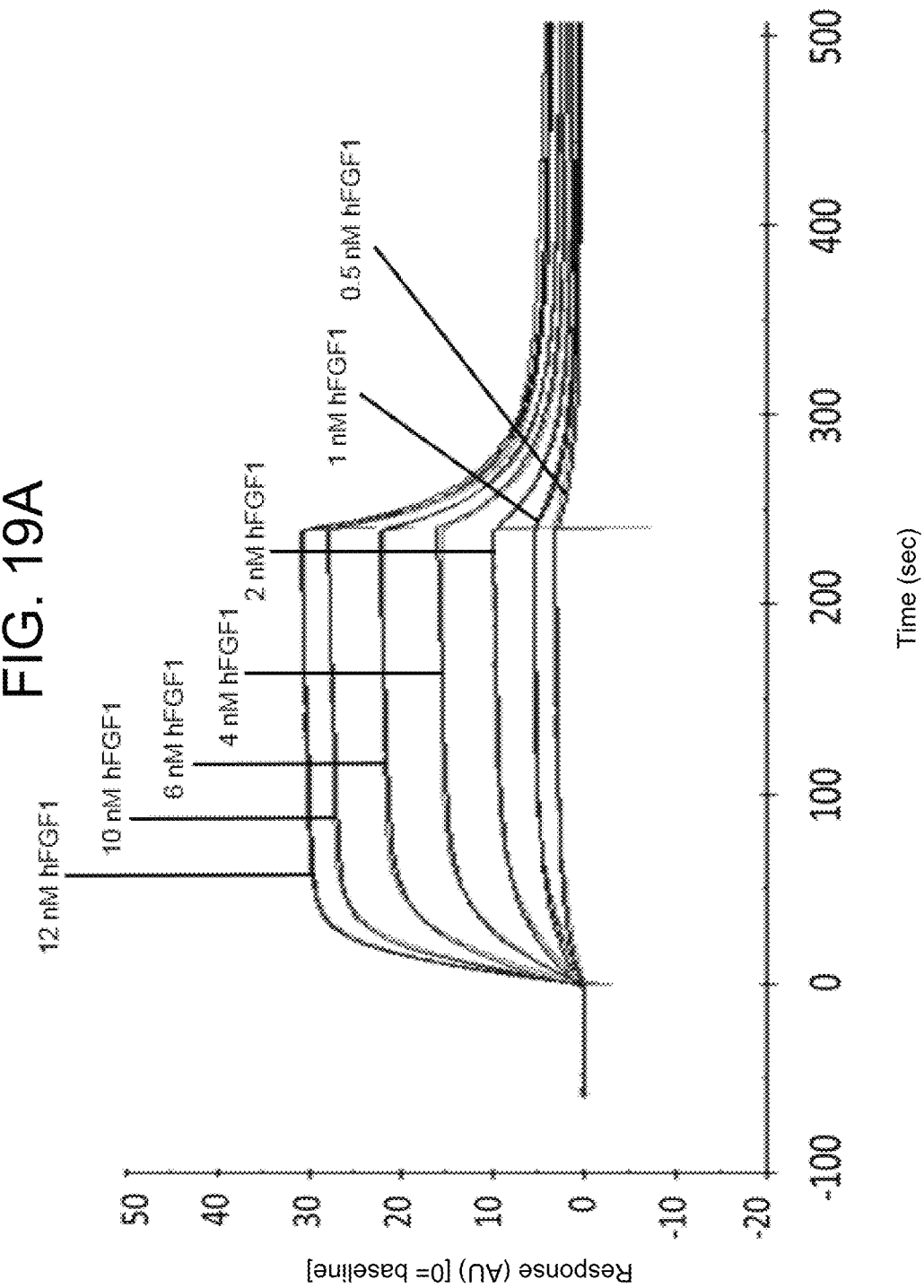

SOLUBLE FIBROBLAST GROWTH FACTOR RECEPTOR 3 (SFGFR3) POLYPEPTIDES AND USES THEREOF

RELATED APPLICATIONS

This application is a divisional of U.S. application Ser. No. 16/417,174 filed on May 20, 2019, which is a continuation of U.S. application Ser. No. 15/943,436 filed on Apr. 2, 2018, now U.S. Pat. No. 10,294,289, which is a continuation of PCT International Application No. PCT/EP2017/067119, with an international filing date of Jul. 7, 2017, which claims the benefit under 35 U.S.C. § 119(e) to U.S. Provisional Application No. 62/467,478 filed on Mar. 6, 2017, and claims the benefit under 35 U.S.C. § 119(e) to U.S. Provisional Application No. 62/359,607 filed on Jul. 7, 2016.

REFERENCE TO THE SEQUENCE LISTING

The application contains a Sequence Listing submitted electronically on May 20, 2019, which is incorporated herein by reference. The Sequence Listing was provided as a Text File entitled 51088-006004 Sequence Listing.txt, created on May 20, 2019, and which is 105,291 bytes in size.

FIELD OF THE INVENTION

The invention features soluble fibroblast growth factor receptor 3 (sFGFR3) polypeptides and compositions thereof. The invention also features methods to treat skeletal growth retardation disorders, such as achondroplasia.

BACKGROUND OF THE INVENTION

Fibroblast growth factor receptor 3 (FGFR3) is a member of the fibroblast growth factor (FGFR) family, in which there is high amino acid sequence conservation between family members. Members of the FGFR family are differentiated by both ligand binding affinities and tissue distribution. A full-length FGFR polypeptide contains an extracellular domain (ECD), a hydrophobic transmembrane domain, and a cytoplasmic tyrosine kinase domain. The ECD of FGFR polypeptides interacts with fibroblast growth factors (FGFs) to mediate downstream signaling, which ultimately influences cellular differentiation. In particular, activation of the FGFR3 protein plays a role in bone development by inhibiting chondrocyte proliferation at the growth plate and limiting bone elongation.

Gain-of-function point mutations in FGFR3 are known to cause several types of human skeletal growth retardation disorders, such as achondroplasia, thanatophoric dysplasia type I (TDI), thanatophoric dysplasia type II (TDII), severe achondroplasia with developmental delay and acanthosis nigricans (SADDAN), hypochondroplasia, and craniosynostosis syndromes (e.g., Muenke syndrome, Crouzon syndrome, and Crouzonodermoskeletal syndrome). Loss-of-function point mutations in FGFR3 are also known to cause skeletal growth retardation disorders, such as camptodactyly, tall stature, and hearing loss syndrome (CATSHL). Achondroplasia is the most common form of short-limb dwarfism and is characterized by disproportionate shortness of limbs and relative macrocephaly. Approximately 97% of achondroplasia is caused by a single point mutation in the gene encoding FGFR3, in which a glycine residue is substituted with an arginine residue at position 380 of the FGFR3 amino acid sequence. Upon ligand binding, the mutation decreases the elimination of the receptor/ligand complex resulting in prolonged intracellular signaling. This prolonged FGFR3 signaling inhibits the proliferation and differentiation of the cartilage growth plate, consequently impairing endochondral bone growth.

There exists a need for improved therapeutics that target dysfunctional FGFR3 for treating skeletal growth retardation disorders, such achondroplasia.

SUMMARY OF THE INVENTION

The invention features soluble fibroblast growth factor receptor 3 (sFGFR3) polypeptides and uses thereof, including the use of the sFGFR3 polypeptides for the treatment of skeletal growth retardation disorders (e.g., achondroplasia) in a patient (e.g., a human, particularly an infant, a child, or an adolescent). In particular, the sFGFR3 polypeptides of the invention feature a deletion of, e.g., amino acids 289 to 400 of the amino acid sequence of the wildtype FGFR3 polypeptide (e.g., a polypeptide having the amino acid sequence of SEQ ID NO: 5 or 32), to provide the following sFGFR3 polypeptides: sFGFR3_Del4 including an amino acid substitution of a cysteine residue with a serine residue at position 253 (sFGFR3_Del4-C253S; SEQ ID NO: 2) and sFGFR3_Del4 including an extended Ig-like C2-type domain 3 (sFGFR3_Del4-D3; SEQ ID NO: 33) and variants thereof, such as a sFGFR3 polypeptide having the amino acid sequence of SEQ ID NO: 4. Additionally, the sFGFR3 polypeptides of the invention may include a signal peptide, such as a sFGFR3 polypeptide having the amino acid sequence of SEQ ID NO: 18 or 34.

A first aspect of the invention features a soluble fibroblast growth factor receptor 3 (sFGFR3) polypeptide including a polypeptide sequence having at least 90% amino acid sequence identity (e.g., at least 91%, 92%, 93%, 94%, 95%, 96%, 97%, 98%, 99%, or more (e.g., 100%) sequence identity) to amino acid residues 23 to 357 of SEQ ID NO: 32. In particular, the polypeptide lacks a signal peptide (e.g., amino acids 1-22 of SEQ ID NO: 32) and a transmembrane domain of FGFR3 (e.g., amino acids of 367-399 of SEQ ID NO: 32) and (i) is less than 500 amino acids in length (e.g., less than 475, 450, 425, 400, 375, or 350 amino acids in length); (ii) includes 200 consecutive amino acids or fewer (e.g., 175, 150, 125, 100, 75, 50, 40, 30, 20, 15, or fewer consecutive amino acids) of an intracellular domain of FGFR3; and/or (iii) lacks a tyrosine kinase domain of FGFR3. The sFGFR3 polypeptide can also include an intracellular domain of FGFR3, such as amino acid residues 423 to 435 of SEQ ID NO: 32 or an amino acid sequence having at least 90%, 92%, 95%, 97%, or 99% sequence identity to amino acid residues 423 to 435 of SEQ ID NO: 32. In particular, the polypeptide includes an amino acid sequence having at least 92%, 95%, 97%, 99%, or 100% sequence identity to SEQ ID NO: 33 (e.g., the polypeptide includes or consists of SEQ ID NO: 33). The sFGFR3 polypeptides can also include a signal peptide (e.g., the signal peptide can have the amino acid sequence of SEQ ID NO: 6 or 35 or an amino acid sequence having at least 92%, 95%, 97%, or 99% sequence identity to SEQ ID NO: 6 or 35). For example, the sFGFR3 polypeptide may have an amino acid sequence with at least 92%, 95%, 97%, 99%, or 100% sequence identity to SEQ ID NO: 34 (e.g., the sFGFR3 polypeptide includes or consists of SEQ ID NO: 34). The sFGFR3 polypeptide may also have a heterologous signal peptide (e.g., the polypeptide includes a heterologous signal peptide having the amino acid sequenceo of SEQ ID NO: 35).

A second aspect of the invention features an sFGFR3 polypeptide including an amino acid sequence having at least 85% sequence identity (e.g., at least 86%, 87%, 88%, 89%, 90%, 91%, 92%, 93%, 94%, 95%, 96%, 97%, 98%, 99%, or more sequence identity) to the amino acid sequence of SEQ ID NO: 1, in which the sFGFR3 polypeptide further includes an amino acid substitution that removes a cysteine residue at position 253 of SEQ ID NO: 1. For example, the cysteine residue at position 253 is substituted with a serine residue or, e.g., another conservative amino acid substitution, such as alanine, glycine, proline, or threonine. In particular, the sFGFR3 polypeptide includes or consists of the amino acid sequence of SEQ ID NO: 2. For instance, the sFGFR3 polypeptide can be an isolated sFGFR3 polypeptide. The sFGFR3 polypeptides can also include a signal peptide (e.g., the signal peptide can have the amino acid sequence of SEQ ID NO: 6 or 35 or an amino acid sequence having at least 92%, 95%, 97%, or 99% sequence identity to SEQ ID NO: 6 or 35). For example, the sFGFR3 may have an amino acid sequence with at least 92%, 95%, 97%, 99%, or 100% sequence identity to SEQ ID NO: 18 (e.g., the sFGFR3 polypeptide includes or consists of SEQ ID NO: 18). The sFGFR3 polypeptide may also have a heterologous signal peptide (e.g., the polypeptide includes a heterologous signal peptide having the amino acid sequenceo of SEQ ID NO: 35).

A third aspect of the invention features a sFGFR3 polypeptide including an amino acid sequence having at least 85% sequence identity (e.g., at least 86%, 87%, 88%, 89%, 90%, 91%, 92%, 93%, 94%, 95%, 96%, 97%, 98%, 99%, or more sequence identity) to the amino acid sequence of SEQ ID NO: 1, in which the sFGFR3 polypeptide further includes a domain including an amino acid sequence having at least 85% sequence identity (e.g., at least 85%, 86%, 87%, 88%, 89%, 90%, 91%, 92%, 93%, 94%, 95%, 96%, 97%, 98%, 99%, or more sequence identity) to all or a fragment of the amino acid sequence of SEQ ID NO: 3 (e.g., at least 10, 20, 30, 40, 45, or more consecutive amino acids of SEQ ID NO: 3), in which the domain is inserted between amino acid residues 288 and 289 of SEQ ID NO: 1. For example, the domain can include an amino acid sequence having at least 85%, 90%, 92%, 95%, 97%, or 99% sequence identity to the amino acid sequence of SEQ ID NO: 3 (e.g., the domain can include or consists of the amino acid sequence of SEQ ID NO: 3). Optionally, the sFGFR3 polypeptide includes an amino acid substitution of a cysteine residue with a serine residue or, e.g., another conservative amino acid substitution, such as alanine, glycine, proline, or threonine, at position 253 of SEQ ID NO: 1 and/or position 28 of SEQ ID NO: 3. In particular, the sFGFR3 polypeptide includes or consists of the amino acid sequence of SEQ ID NO: 4. For example, the sFGFR3 polypeptide can be an isolated sFGFR3 polypeptide.

Also featured is a polynucleotide (e.g., an isolated polynucleotide) that encodes the sFGFR3 polypeptide of the first, second, or third aspect of the invention including a nucleic acid sequence having at least 85%, 90%, 92%, 95%, 97%, or 99% sequence identity to the nucleic acid sequence of SEQ ID NO: 20, 21, 36, or 37 (e.g., the polynucleotide includes or consists of the nucleic acid of SEQ ID NO: 20, 21, 36, or 37). The invention also features a vector (e.g., an isolated vector) including the polynucleotide, such as a plasmid, an artificial chromosome, a viral vector, or a phage vector. Additionally, the invention features a host cell (e.g., an isolated host cell) including the polynucleotide, such as a HEK 293 cell or CHO cell.

The invention features a composition including the sFGFR3 polypeptide of the first, second, or third aspects of the invention or the polynucleotide that encodes the sFGFR3 polypeptide of the first, second, or third aspects of the invention. In addition, the vector or host cell that includes the polynucleotide encoding the sFGFR3 polypeptide can be formulated in a composition. The composition can further include a pharmaceutically acceptable excipient, carrier, or diluent. The composition including the sFGFR3 polypeptide, polynucleotide, or vector can be formulated for administration at a dose of about 0.002 mg/kg to about 30 mg/kg, such as about 0.001 mg/kg to about 10 mg/kg. The composition including the host cell can be formulated for administration at a dose of about $1 \times 10^3$ cells/mL to about $1 \times 10^{12}$ cells/mL. The composition can be formulated for daily, weekly, or monthly administration, such as seven times a week, six times a week, five times a week, four times a week, three times a week, twice a week, weekly, every two weeks, or once a month. For example, the composition including the sFGFR3 polypeptide, polynucleotide, or vector is formulated for administration at a dose of about 0.25 mg/kg to about 10 mg/kg once or twice a week. The composition can be formulated for parenteral administration (e.g., subcutaneous administration, intravenous administration, intramuscular administration, intra-arterial administration, intrathecal administration, or intraperitoneal administration), enteral administration, or topical administration. Preferably, the composition is formulated for subcutaneous administration. The invention also features a medicament that includes one or more of the compositions described above.

The invention also features a method of delivering an sFGFR3 polypeptide to tissue (e.g., skeletal tissue) in a patient (e.g. a human) having a skeletal growth retardation disorder (e.g., achondroplasia) including administering to the patient an effective amount of the sFGFR3 polypeptide of the first, second, or third aspect of the invention, a polynucleotide encoding the sFGFR3 polypeptide, a vector containing the polynucleotide, a host cell containing the polynucleotide or vector, or a composition containing the polypeptide, polynucleotide, vector, or host cell.

A fourth aspect of the invention features a method of treating a skeletal growth retardation disorder (e.g., a FGFR3-related skeletal disease) in a patient (e.g., a human) that includes administering the polypeptide of the first, second, or third aspect of the invention or a polynucleotide encoding the polypeptide, a vector containing the polynucleotide, a host cell containing the polynucleotide or vector, or a composition containing the polypeptide, polynucleotide, vector, or host cell. The FGFR3-related skeletal disease is selected from the group consisting of achondroplasia, thanatophoric dysplasia type I (TDI), thanatophoric dysplasia type II (TDII), severe achondroplasia with developmental delay and acanthosis nigricans (SADDAN), hypochondroplasia, a craniosynostosis syndrome (e.g., Muenke syndrome, Crouzon syndrome, and Crouzonodermoskeletal syndrome), and camptodactyly, tall stature, and hearing loss syndrome (CATSHL). In particular, the skeletal growth retardation disorder is achondroplasia.

The FGFR3-related skeletal disease can be caused by expression in the patient of a constitutively active FGFR3, such as an amino acid substitution of a glycine residue with an arginine residue at position 380 of SEQ ID NO: 5 or 32. In particular, the patient may be diagnosed with the skeletal growth retardation disorder (e.g., prior to treatment). For instance, the patient exhibits one or more symptoms of the skeletal growth retardation disorder selected from the group consisting of short limbs, short trunk, bowlegs, a waddling gait, skull malformations, cloverleaf skull, craniosynostosis, wormian bones, anomalies of the hands, anomalies of the feet, hitchhiker thumb, and chest anomalies, such that the patient exhibits an improvement in the one or more symptoms of the skeletal growth retardation disorder after administration of the sFGFR3 polypeptide (or a polynucleotide encoding the polypeptide, a vector containing the polynucleotide, a host cell containing the polynucleotide or vector, or a composition containing the polypeptide, polynucleotide, vector, or host cell). Additionally, the patient may have not been previously administered the sFGFR3 polypeptide. For example, the patient may be an infant, a child, an adolescent, or an adult.

For example, the polypeptide is administered to the patient at a dose of about 0.002 mg/kg to about 30 mg/kg (e.g., a dose of about 0.001 mg/kg to about 10 mg/kg). The polypeptide may be administered to the patient one or more times daily, weekly (e.g., twice a week, three times a week, four times a week, five times a week, six times a week, or seven times a week), every two weeks, monthly, or yearly. For example, the polypeptide is administered to the patient at a dose of about 0.25 mg/kg to about 30 mg/kg at least about once or twice a week or more (e.g., the polypeptide is administered to the patient at a dose of about 2.5 mg/kg or about 10 mg/kg once or twice weekly). The polypeptide can be administered to the patient in a composition including a pharmaceutically acceptable excipient, carrier, or diluent. The polypeptide can be administered to the patient parenterally (e.g., subcutaneously, intravenously, intramuscularly, intra-arterially, intrathecally, or intraperitoneally), enterally, or topically. Preferably, the composition is administered to the patient by subcutaneous injection. Additionally, the polypeptide can bind to fibroblast growth factor 1 (FGF1), fibroblast growth factor 2 (FGF2), fibroblast growth factor 9 (FGF9), fibroblast growth factor 18 (FGF18), fibroblast growth factor 19 (FGF19), or fibroblast growth factor 21 (FGF21). In particular, the binding can be characterized by an equilibrium dissociation constant ($K_d$) of about 0.2 nM to about 20 nM, such as the binding is characterized by a $K_d$ of about 1 nM to about 10 nM (e.g., about 1 nm, about 2 nm, about 3 nm, about 4 nm, about 5 nm, about 6 nm, about 7 nm, about 8 nm, about 9 nm, or about 10 nm). The polypeptide can exhibit greater binding affinity to FGF1, FGF2, FGF9, and FGF18 relative to the binding affinity of the polypeptide to FGF19 and FGF21.

The polypeptide can have an in vivo half-life of between about 2 hours to about 25 hours (e.g., 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, or 25 hours). Preferably, administration of the polypeptide provides one or more, or all, of the following: an increase in survival of the patient, an improvement in locomotion of the patient, an improvement in abdominal breathing in the patient, an increase in body and/or bone length of the patient, an improvement in the cranial ratio of the patient, and/or restoration of the foramen magnum shape in the patient, e.g., relative to an untreated patient (e.g., an untreated achondroplasia patient).

The invention also features a method of producing the sFGFR3 polypeptide of the first, second, or third aspect of the invention, which includes culturing the host cell described above (e.g., a CHO cell or HEK 293 cell) in a culture medium under conditions suitable to effect expression of the sFGFR3 polypeptide and recovering the sFGFR3 polypeptide from the culture medium. In particular, the recovering includes chromatography, such as affinity chromatography (e.g., ion exchange chromatography or anti-FLAG chromatography, such as immunoprecipitation) or size exclusion chromatography.

A fifth aspect of the invention features the polypeptide of the first, second, or third aspect of the invention (or a polynucleotide encoding the polypeptide, a vector containing the polynucleotide, a host cell containing the polynucleotide or vector, or a composition containing the polypeptide, polynucleotide, vector, or host cell) for treating a skeletal growth retardation disorder in a patient. In particular, the sFGFR3 polypeptide can bind to fibroblast growth factor 1 (FGF1), fibroblast growth factor 2 (FGF2), fibroblast growth factor 9 (FGF9), fibroblast growth factor 18 (FGF18), fibroblast growth factor 19 (FGF19), or fibroblast growth factor 21 (FGF21).

A sixth aspect of the invention features a sFGFR3 polypeptide (or a polynucleotide encoding the polypeptide, a vector containing the polynucleotide, a host cell containing the polynucleotide or vector, or a composition containing the polypeptide, polynucleotide, vector, or host cell) including an amino acid sequence having at least 85% sequence identity (e.g., at least 86%, 87%, 88%, 89%, 90%, 91%, 92%, 93%, 94%, 95%, 96%, 97%, 98%, 99%, or more sequence identity) to the amino acid sequence of SEQ ID NO: 1 for treating a skeletal growth retardation disorder in a patient (e.g., a human), in which the sFGFR3 polypeptide further includes an amino acid substitution that removes a cysteine residue at position 253 of SEQ ID NO: 1. For example, the cysteine residue at position 253 is substituted with a serine residue or, e.g., another conservative amino acid substitution, such as alanine, glycine, proline, or threonine. In particular, the sFGFR3 polypeptide includes or consists of the amino acid sequence of SEQ ID NO: 2. For example, the sFGFR3 polypeptide can be an isolated sFGFR3 polypeptide. Furthermore, the sFGFR3 polypeptide can bind to fibroblast growth factor 1 (FGF1), fibroblast growth factor 2 (FGF2), fibroblast growth factor 9 (FGF9), fibroblast growth factor 18 (FGF18), fibroblast growth factor 19 (FGF19), or fibroblast growth factor 21 (FGF21).

A seventh aspect of the invention features a sFGFR3 polypeptide (or a polynucleotide encoding the polypeptide, a vector containing the polynucleotide, a host cell containing the polynucleotide or vector, or a composition containing the polypeptide, polynucleotide, vector, or host cell) including an amino acid sequence having at least 85% sequence identity (e.g., at least 86%, 87%, 88%, 89%, 90%, 91%, 92%, 93%, 94%, 95%, 96%, 97%, 98%, 99%, or more sequence identity) to the amino acid sequence of SEQ ID NO: 1 for treating a skeletal growth retardation disorder in a patient (e.g., a human), in which the sFGFR3 polypeptide further includes a domain including an amino acid sequence having at least 85% sequence identity (e.g., at least 85%, 86%, 87%, 88%, 89%, 90%, 91%, 92%, 93%, 94%, 95%, 96%, 97%, 98%, 99%, or more sequence identity) to all or a fragment of the amino acid sequence of SEQ ID NO: 3 (e.g., at least 10, 20, 30, 40, 45, or more consecutive amino acids of SEQ ID NO: 3), in which the domain is inserted between amino acid residues 288 and 289 of SEQ ID NO: 1. For example, the domain can include an amino acid sequence having at least 85%, 90%, 92%, 95%, 97%, or 99% sequence identity to the amino acid sequence of SEQ ID NO: 3 (e.g., the domain can include or consists of the amino acid sequence of SEQ ID NO: 3). Optionally, the sFGFR3 polypeptide includes an amino acid substitution of a cysteine residue with a serine residue or, e.g., another conservative amino acid substitution, such as alanine, glycine, proline, or threonine, at position 253 of SEQ ID NO:

1 and/or position 28 of SEQ ID NO: 3. In particular, the sFGFR3 polypeptide includes or consists of the amino acid sequence of SEQ ID NO: 4. For example, the sFGFR3 polypeptide can be an isolated sFGFR3 polypeptide. Furthermore, the sFGFR3 polypeptide can bind to fibroblast growth factor 1 (FGF1), fibroblast growth factor 2 (FGF2), fibroblast growth factor 9 (FGF9), fibroblast growth factor 18 (FGF18), fibroblast growth factor 19 (FGF19), or fibroblast growth factor 21 (FGF21).

The use of the fifth, sixth, or seventh aspect also features the administration of a polynucleotide, vector, host cell, or composition of the first, second, or third aspect of the invention. The sFGFR3 polypeptide of the sixth aspect of the invention can be encoded by a polynucleotide including a nucleic acid sequence having at least 85%, 90%, 92%, 95%, 97%, or 99% sequence identity to the nucleic acid sequence of SEQ ID NO: 20 or 36 (e.g., the polynucleotide includes or consists of the nucleic acid of SEQ ID NO: 20 or 36). The sFGFR3 polypeptide of the fifth or seventh aspect of the invention can be encoded by a polynucleotide including a nucleic acid sequence having at least 85%, 90%, 92%, 95%, 97%, or 99% sequence identity to the nucleic acid sequence of SEQ ID NO: 21 or 37 (e.g., the polynucleotide includes or consists of the nucleic acid of SEQ ID NO: 21 or 37).

The skeletal growth retardation disorder of the fifth, sixth, or seventh aspect of the invention can be any FGFR3-related skeletal disease, such as achondroplasia, TDI, TDII, severe achondroplasia with developmental delay and acanthosis nigricans (SADDAN), hypochondroplasia, a craniosynostosis syndrome (e.g., Muenke syndrome, Crouzon syndrome, and Crouzonodermoskeletal syndrome), or CATSHL. In particular, the skeletal growth retardation disorder is achondroplasia. The FGFR3-related skeletal disease can be caused by expression in the patient of a constitutively active FGFR3, e.g., in which the constitutively active FGFR3 includes an amino acid substitution of a glycine residue with an arginine residue at position 380 of SEQ ID NO: 5.

The patient (e.g., a human) of the fifth, sixth, or seventh aspect of the invention can be one that has been diagnosed with the skeletal growth retardation disorder (e.g., prior to treatment). The patient can exhibit one or more symptoms of the skeletal growth retardation disorder (e.g., achondroplasia) selected from the group consisting of short limbs, short trunk, bowlegs, a waddling gait, skull malformations, cloverleaf skull, craniosynostosis, wormian bones, anomalies of the hands, anomalies of the feet, hitchhiker thumb, and chest anomalies. As a result of the methods, the patient can exhibit an improvement in the one or more symptoms of the skeletal growth retardation disorder after administration of the sFGFR3 polypeptide. Moreover, administration of the sFGFR3 polypeptide can increase survival of the patient and/or restore the shape of the foramen magnum of the patient. The patient can be an infant, a child, an adolescent, or an adult. Additionally, the patient can be one that has not been previously administered the sFGFR3 polypeptide (or a polynucleotide encoding the polypeptide, a vector containing the polynucleotide, a host cell containing the polynucleotide or vector, or a composition containing the polypeptide, polynucleotide, vector, or host cell).

The sFGFR3 polypeptide, polynucleotide, or vector of the fifth, sixth, or seventh aspect of the invention can be administered to the patient (e.g., a human) at a dose of about 0.002 mg/kg to about 30 mg/kg, such as about 0.001 mg/kg to about 10 mg/kg. The composition including the host cell of the fourth or fifth aspect of the invention can be administered to the patient (e.g., a human) at a dose of about $1\times10^3$ cells/mL to about $1\times10^{12}$ cells/mL. For example, the sFGFR3 polypeptide, polynucleotide, vector, or host cell is administered to the patient one or more times daily, weekly, monthly, or yearly (e.g., the sFGFR3 polypeptide is administered to the patient seven times a week, six times a week, five times a week, four times a week, three times a week, twice a week, weekly, every two weeks, or once a month). In particular, the sFGFR3 polypeptide is administered to the patient at a dose of about 0.25 mg/kg to about 10 mg/kg once or twice a week. The sFGFR3 polypeptide can be administered to the patient in a composition including a pharmaceutically acceptable excipient, carrier, or diluent. For example, the composition is administered to the patient parenterally (e.g., subcutaneously, intravenously, intramuscularly, intra-arterially, intrathecally, or intraperitoneally), enterally, or topically. In particular, the composition is administered to the patient by subcutaneous injection.

The invention features a method of manufacturing the sFGFR3 polypeptide of the first aspect of the invention by deleting the signal peptide, the transmembrane domain, and a portion of the intracellular domain from a FGFR3 polypeptide (e.g., to manufacture a polypeptide having the amino acid sequence of SEQ ID NO: 33). In particular, the intracellular domain consists of amino acid residues 436 to 806 of SEQ ID NO: 32. The invention also features a method of manufacturing the sFGFR3 polypeptide of the second aspect of the invention by introducing an amino acid substitution that removes a cysteine residue at position 253 of SEQ ID NO: 1 (e.g., to manufacture a polypeptide having the amino acid sequence of SEQ ID NO: 2). For example, the cysteine residue at position 253 is substituted with a serine residue or, e.g., another conservative amino acid substitution, such as alanine, glycine, proline, or threonine.

The invention also features a kit including the sFGFR3 polypeptide of the first, second, or third aspect of the invention (e.g., a polypeptide having the amino acid sequence of SEQ ID NO: 2, 4, or 33), the polynucleotide of the first, second, or third aspect of the invention (e.g., a polynucleotide having the nucleic acid sequence of SEQ ID NO: 20, 21, 36, or 37), the vector of the first, second, or third aspect of the invention (e.g., a plasmid, an artificial chromosome, a viral vector, or a phage vector), or the host cell of the first, second, or third aspect of the invention (e.g., a HEK 293 cell or a CHO cell), in which the kit optionally includes instructions for using the kit.

Definitions

As used herein, "a" and "an" means "at least one" or "one or more" unless otherwise indicated. In addition, the singular forms "a," "an," and "the" include plural referents unless the context clearly dictates otherwise.

As used herein, "about" refers to an amount that is ±10% of the recited value and is preferably ±5% of the recited value, or more preferably ±2% of the recited value. For instance, the term "about" can be used to modify all dosages or ranges recited herein by ±10% of the recited values or range endpoints.

The term "domain" refers to a conserved region of the amino acid sequence of a polypeptide (e.g. a FGFR3 polypeptide) having an identifiable structure and/or function within the polypeptide. A domain can vary in length from, e.g., about 20 amino acids to about 600 amino acids. Exemplary domains include the immunoglobulin domains of FGFR3 (e.g., Ig-like C2-type domain 1, Ig-like C2-type domain 2, and Ig-like C2-type domain 3).

The term "dosage" refers to a determined quantity of an active agent (e.g., an sFGFR3 polypeptide or variant thereof, such as a polypeptide having the amino acid sequence of SEQ ID NO: 2, 4, or 33) calculated to produce a desired therapeutic effect (e.g., treatment of a skeletal growth retardation disorder, such as achondroplasia) when the active agent is administered to a patient (e.g., a patient having a skeletal growth retardation disorder, such as achondroplasia). A dosage may be defined in terms of a defined amount of the active agent or a defined amount coupled with a particular frequency of administration. A dosage form can include an sFGFR3 polypeptide or fragment thereof in association with any suitable pharmaceutical excipient, carrier, or diluent.

The terms "effective amount," "amount effective to," and "therapeutically effective amount" refer to an amount of an sFGFR3 polypeptide, a vector encoding a sFGR3, and/or an sFGFR3 composition that is sufficient to produce a desired result, for example, the treatment of a skeletal growth retardation disorder (e.g., achondroplasia).

The terms "extracellular domain" and "ECD" refer to the portion of a FGFR3 polypeptide that extends beyond the transmembrane domain into the extracellular space. The ECD mediates binding of a FGFR3 to one or more fibroblast growth factors (FGFs). For instance, an ECD includes the Ig-like C2-type domains 1-3 of a FGFR3 polypeptide. In particular, the ECD includes the Ig-like C2-type domain 1 of a wildtype (wt) FGFR3 polypeptide (e.g., amino acids 36-88 of a wt FGFR3 polypeptide having the amino acid sequence of SEQ ID NO: 5 (a mature FGFR3 protein without a signal sequence) or amino acids 57-110 of a wt FGFR3 polypeptide having the amino acid sequence of SEQ ID NO: 32 (a precursor FGFR3 protein with the signal sequence)), the Ig-like C2-type domain 2 of a wildtype (wt) FGFR3 polypeptide (e.g., amino acids 139-234 of a wt FGFR3 polypeptide having the amino acid sequence of SEQ ID NO: 5 or amino acids 161-245 of a wt FGFR3 polypeptide having the amino acid sequence of SEQ ID NO: 32), and the Ig-like C2-type domain 3 of a wt FGFR3 polypeptide (e.g., amino acids 247-335 of a wt FGFR3 polypeptide having the amino acid sequence of SEQ ID NO: 5 or amino acids 268-310 of a wt FGFR3 polypeptide having the amino acid sequence of SEQ ID NO: 32). An ECD of a FGFR3 can also include a fragment of the wildtype FGFR3 Ig-like C2-type domain 3, for instance, aa 247-288 of SEQ ID NO: 1, which can further include, e.g., an amino acid substitution of a cysteine residue with a serine residue or another conservative amino acid substitution (e.g., alanine, glycine, proline, or threonine) at position 253 of SEQ ID NO: 1 (e.g., aa 247-288 of SEQ ID NO: 2). Additionally, an ECD can include an Ig-like C2-type domain 3 of, e.g., aa 247-335 of SEQ ID NO: 4. Thus, exemplary EGDs of FGFR3 polypeptides include, e.g., those polypeptides having the amino acid sequence of aa 1-288 of SEQ ID NOs: 1 and 2 or aa 1-335 of SEQ ID NOs: 4 and 33. In particular, the ECD of a FGFR3 polypeptide includes aa 1-335 of SEQ ID NO: 33.

The term "FGFR3-related skeletal disease," as used herein, refers to a skeletal disease that is caused by an abnormal increase in the activation of FGFR3, such as by expression of a gain-of-function mutant of the FGFR3. The phrase "gain-of-function mutant of the FGFR3" refers to a mutant of the FGFR3 exhibiting a biological activity, such as triggering downstream signaling, which is higher than the biological activity of the corresponding wild-type FGFR3 (e.g., a polypeptide having the amino acid sequence of SEQ ID NO: 5) in the presence of a FGF ligand. FGFR3-related skeletal diseases can include an inherited or a sporadic disease. Exemplary FGFR3-related skeletal diseases include, but are not limited to, achondroplasia, thanatophoric dysplasia type I (TDI), thanatophoric dysplasia type II (TDII), severe achondroplasia with developmental delay and acanthosis nigricans (SADDAN), hypochondroplasia, a craniosynostosis syndrome (e.g., Muenke syndrome, Crouzon syndrome, and Crouzonodermoskeletal syndrome), and camptodactyly, tall stature, and hearing loss syndrome (CATSHL).

The terms "fibroblast growth factor" and "FGF" refer to a member of the FGF family, which includes structurally related signaling molecules involved in various metabolic processes, including endocrine signaling pathways, development, wound healing, and angiogenesis. FGFs play key roles in the proliferation and differentiation of a wide range of cell and tissue types. The term preferably refers to FGF1, FGF2, FGF9, FGF18, FGF19, and FGF21, which have been shown to bind FGFR3. For instance, FGFs can include human FGF1 (e.g., a polypeptide having the amino acid sequence of SEQ ID NO: 13), human FGF2 (e.g., a polypeptide having the amino acid sequence of SEQ ID NO: 14), human FGF9 (e.g., a polypeptide having the amino acid sequence of SEQ ID NO: 15), human FGF18 (e.g., a polypeptide having the amino acid sequence of SEQ ID NO: 16), human FGF19 (e.g., a polypeptide having the amino acid sequence of SEQ ID NO: 38), and human FGF21 (e.g., a polypeptide having the amino acid sequence of SEQ ID NO: 39).

The terms "fibroblast growth factor receptor 3," "FGFR3," or "FGFR3 receptor," as used herein, refer to a polypeptide that specifically binds one or more FGFs (e.g., FGF1, FGF2, FGF9, FGF18, FGF19, and/or FGF21). The human FGFR3 gene, which is located on the distal short arm of chromosome 4, encodes an 806 amino acid protein precursor (fibroblast growth factor receptor 3 isoform 1 precursor), which contains 19 exons, and includes a signal peptide (e.g., a polypeptide having the amino acid sequence of SEQ ID NO: 6 or 35). Mutations in the FGFR3 amino acid sequence that lead to skeletal growth disorders, (e.g., achondroplasia), include, e.g., the substitution of a glycine residue at position 380 with an arginine residue (i.e., G380R). The naturally occurring human FGFR3 gene has a nucleotide sequence as shown in Genbank Accession number NM 000142.4 and the naturally occurring human FGFR3 protein has an amino acid sequence as shown in Genbank Accession number NP 000133, herein represented by SEQ ID NO: 5. The wildtype FGFR3 (e.g., a polypeptide having the amino acid sequence of SEQ ID NO: 5) consists of an extracellular immunoglobulin-like membrane domain including Ig-like C2-type domains 1-3 (amino acid residues 1 to 335), a transmembrane domain (amino acid residues 345 to 377), and an intracellular domain (amino acid residues 378 to 784). FGFR3s can include fragments and/or variants (e.g., splice variants, such as splice variants utilizing alternate exon 8 rather than exon 9) of the full-length, wild-type FGFR3 (e.g., a polypeptide having the amino acid sequence of SEQ ID NO: 5).

The terms "fragment" and "portion" refer to a part of a whole, such as a polypeptide or nucleic acid molecule that contains, preferably, at least 10%, 20%, 30%, 40%, 50%, 60%, 70%, 75%, 80%, 85%, 90%, 95%, 96%, 97%, 98%, 99%, or more of the entire length of the reference nucleic acid molecule or polypeptide. A fragment or portion may contain, e.g., 10, 15, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 500, 600, 700, or more amino acid residues, up to the entire length of the reference polypeptide (e.g., a polypeptide having the amino acid sequence of SEQ ID NO: 5 or 32). For example, a FGFR3 fragment can include any polypeptide having at least 200, 205, 210, 215, 220, 225, 235, 230, 240, 245, 250, 255, 260, 265, 275, 280, 285, 290, or 300 consecutive amino acids of SEQ ID NO: 1 or 2. Additionally, a FGFR3 fragment can include any polypeptide having at least 200, 205, 210, 215, 220, 225, 235, 230, 240, 245, 250, 255, 260, 265, 275, 280, 285, 290, 300, 305, 310, 315, 320, 325, 330, 335, 345, or 345 consecutive amino acids of SEQ ID NO: 4 or 33.

As used herein, the term "host cell" refers to a vehicle that includes the necessary cellular components, e.g., organelles, needed to express an sFGFR3 polypeptide from a corresponding polynucleotide. The nucleic acid sequence of the polynucleotide is typically included in a nucleic acid vector (e.g., a plasmid, an artificial chromosome, a viral vector, or a phage vector) that can be introduced into the host cell by conventional techniques known in the art (e.g., transformation, transfection, electroporation, calcium phosphate precipitation, and direct microinjection). A host cell may be a prokaryotic cell, e.g., a bacterial or an archaeal cell, or a eukaryotic cell, e.g., a mammalian cell (e.g., a Chinese Hamster Ovary (CHO) cell or a Human Embryonic Kidney 293 (HEK 293)). Preferably, the host cell is a mammalian cell, such as a CHO cell.

By "isolated" is meant separated, recovered, or purified from its natural environment. For example, an isolated sFGFR3 polypeptide (e.g., an sFGFR3 polypeptide or variant thereof, such as a polypeptide having the amino acid sequence of SEQ ID NO: 2 or 4) can be characterized by a certain degree of purity after isolating the sFGFR3 polypeptide from, e.g., cell culture media. An isolated sFGFR3 polypeptide can be at least 75% pure, such that the sFGFR3 polynucleotide constitutes at least 75% by weight of the total material (e.g., polypeptides, polynucleotides, cellular debris, and environmental contaminants) present in the preparation: (e.g., at least 80%, at least 85%, at least 90%, at least 95%, at least 96%, at least 97%, at least 99%, or at least 99.5% by weight of the total material present in the preparation). Likewise, an isolated polynucleotide encoding an sFGFR3 polypeptide (e.g., a polynucleotide having the nucleic acid sequence of SEQ ID NO: 20, 21, 36, or 37), or an isolated host cell (e.g., CHO cell, a HEK 293 cell, L cell, C127 cell, 3T3 cell, BHK cell, or COS-7 cell) can be at least 75% pure, such that the polynucleotide or host cell constitutes at least 75% by weight of the total material (e.g., polypeptides, polynucleotides, cellular debris, and environmental contaminants) present in the preparation (e.g., at least 80%, at least 85%, at least 90%, at least 95%, at least 96%, at least 97%, at least 99%, or at least 99.5% by weight of the total material present in the preparation).

"Polynucleotide" and "nucleic acid molecule," as used interchangeably herein, refer to polymers of nucleotides of any length, and include DNA and RNA. The nucleotides can be deoxyribonucleotides, ribonucleotides, modified nucleotides or bases, and/or analogs thereof, or any substrate that can be incorporated into a polymer by DNA or RNA polymerase or by a synthetic reaction. A polynucleotide can include modified nucleotides, such as methylated nucleotides and analogs thereof. If present, modification to the nucleotide structure can be imparted before or after assembly of the polymer. The sequence of nucleotides can be interrupted by non-nucleotide components. A polynucleotide can be further modified after synthesis, such as by conjugation with a label.

The terms "patient" and "subject" refer to a mammal, including, but not limited to, a human (e.g., a human having a skeletal growth retardation disorder, such as achondroplasia) or a non-human mammal (e.g., a non-human mammal having a skeletal growth retardation disorder, such as achondroplasia), such as a bovine, equine, canine, ovine, or feline. Preferably, the patient is a human having a skeletal growth retardation disorder (e.g., achondroplasia), particularly an infant, a child, or an adolescent having a skeletal growth retardation disorder (e.g., achondroplasia).

The terms "parenteral administration," "administered parenterally," and other grammatically equivalent phrases, as used herein, refer to a mode of administration of compositions including an sFGFR3 polypeptide (e.g., an sFGFR3 polypeptide or variant thereof, such as a polypeptide having the amino acid sequence of SEQ ID NO: 2, 4, or 33, or a sFGFR3 polypeptide including a signal peptide, such as a polypeptide having the amino acid sequence of SEQ ID NO: 18 or 34) other than enteral and topical administration, usually by injection, and include, without limitation, subcutaneous, intradermal, intravenous, intranasal, intraocular, pulmonary, intramuscular, intra-arterial, intrathecal, intracapsular, intraorbital, intracardiac, intradermal, intrapulmonary, intraperitoneal, transtracheal, subcuticular, intraarticular, subcapsular, subarachnoid, intraspinal, epidural, intracerebral, intracranial, intracarotid, and intrasternal injection and infusion.

By "pharmaceutically acceptable diluent, excipient, carrier, or adjuvant" is meant a diluent, excipient, carrier, or adjuvant, respectively that is physiologically acceptable to the subject (e.g., a human) while retaining the therapeutic properties of the pharmaceutical composition (e.g., an sFGFR3 polypeptide or variant thereof, such as a polypeptide having the amino acid sequence of SEQ ID NO: 2, 4, or 33, or a sFGFR3 polypeptide including a signal peptide, such as a polypeptide having the amino acid sequence of SEQ ID NO: 18 or 34) with which it is administered. One exemplary pharmaceutically acceptable carrier is physiological saline. Other physiologically acceptable diluents, excipients, carriers, or adjuvants and their formulations are known to one skilled in the art.

By "pharmaceutical composition" is meant a composition containing an active agent, such as an sFGFR3 (e.g., an sFGFR3 polypeptide or variant thereof, such as a polypeptide having the amino acid sequence of SEQ ID NO: 2, 4, or 33, or a sFGFR3 polypeptide including a signal peptide, such as a polypeptide having the amino acid sequence of SEQ ID NO: 18 or 34), formulated with at least one pharmaceutically acceptable excipient, carrier, or diluent. The pharmaceutical composition may be manufactured or sold with the approval of a governmental regulatory agency as part of a therapeutic regimen for the treatment of a disease or event (e.g., a skeletal growth retardation disorder, such achondroplasia) in a patient (e.g., a patient having a skeletal growth retardation disorder, such as a patient having achondroplasia). Pharmaceutical compositions can be formulated, e.g., for parenteral administration, such as for subcutaneous administration (e.g. by subcutaneous injection) or intravenous administration (e.g., as a sterile solution free of particulate emboli and in a solvent system suitable for intravenous use), or for oral administration (e.g., as a tablet, capsule, caplet, gelcap, or syrup).

As used herein, the term "sequence identity" refers to the percentage of amino acid (or nucleic acid) residues of a candidate sequence, e.g., an FGFR3 polypeptide, that are identical to the amino acid (or nucleic acid) residues of a reference sequence, e.g., a wild-type sFGFR3 polypeptide (e.g., a polypeptide having the amino acid sequence of SEQ ID NO: 5 or 32) or an sFGFR3 polypeptide (e.g., an sFGFR3 polypeptide or variant thereof, such as a polypeptide having the amino acid sequence of SEQ ID NO: 2, 4, or 33, or a sFGFR3 polypeptide including a signal peptide, such as a polypeptide having the amino acid sequence of SEQ ID NO: 18 or 34), after aligning the sequences and introducing gaps, if necessary, to achieve the maximum percent identity (e.g., gaps can be introduced in one or both of the candidate and reference sequences for optimal alignment and non-homologous sequences can be disregarded for comparison purposes). Alignment for purposes of determining percent identity can be achieved in various ways that are within the skill in the art, for instance, using publicly available computer software, such as BLAST, BLAST-2, BLAST-P, BLAST-N, BLAST-X, WU-BLAST-2, ALIGN, ALIGN-2, CLUSTAL, or Megalign (DNASTAR) software. Those skilled in the art can determine appropriate parameters for measuring alignment, including any algorithms needed to achieve maximal alignment over the full length of the sequences being compared. For instance, the percent amino acid (or nucleic acid) sequence identity of a given candidate sequence to, with, or against a given reference sequence (which can alternatively be phrased as a given candidate sequence that has or includes a certain percent amino acid (or nucleic acid) sequence identity to, with, or against a given reference sequence) is calculated as follows:

$$100 \times (\text{fraction of } A/B)$$

where A is the number of amino acid (or nucleic acid) residues scored as identical in the alignment of the candidate sequence and the reference sequence, and where B is the total number of amino acid (or nucleic acid) residues in the reference sequence. In particular, a reference sequence aligned for comparison with a candidate sequence can show that the candidate sequence exhibits from, e.g., 50% to 100% identity across the full length of the candidate sequence or a selected portion of contiguous amino acid (or nucleic acid) residues of the candidate sequence. The length of the candidate sequence aligned for comparison purpose is at least 30%, e.g., at least 40%, e.g., at least 50%, 60%, 70%, 80%, 90%, or 100% of the length of the reference sequence. When a position in the candidate sequence is occupied by the same amino acid (or nucleic acid) residue as the corresponding position in the reference sequence, then the molecules are identical at that position.

By "signal peptide" is meant a short peptide (e.g., 5-30 amino acids in length, such as 22 amino acids in length) at the N-terminus of a polypeptide that directs a polypeptide towards the secretory pathway (e.g., the extracellular space). The signal peptide is typically cleaved during secretion of the polypeptide. The signal sequence may direct the polypeptide to an intracellular compartment or organelle, e.g., the Golgi apparatus. A signal sequence may be identified by homology, or biological activity, to a peptide with the known function of targeting a polypeptide to a particular region of the cell. One of ordinary skill in the art can identify a signal peptide by using readily available software (e.g., Sequence Analysis Software Package of the Genetics Computer Group, University of Wisconsin Biotechnology Center, 1710 University Avenue, Madison, Wis. 53705, BLAST, or PILEUP/PRETTYBOX programs). A signal peptide can be one that is, for example, substantially identical to the amino acid sequence of SEQ ID NO: 6 or 35.

The term "skeletal growth retardation disorder," as used herein, refers to a skeletal disease characterized by deformities and/or malformations of the bones. These disorders include, but are not limiting to, skeletal growth retardation disorders caused by growth plate (physeal) fractures, idiopathic skeletal growth retardation disorders, or FGFR3-related skeletal diseases. In particular, a patient having a skeletal growth retardation disorder (e.g., achondroplasia) may have bones that are shorter than the bones of a healthy patient. For example, the skeletal growth retardation disorder may include a skeletal dysplasia, e.g., achondroplasia, homozygous achondroplasia, heterozygous achondroplasia, achondrogenesis, acrodysostosis, acromesomelic dysplasia, atelosteogenesis, camptomelic dysplasia, chondrodysplasia punctata, rhizomelic type of chondrodysplasia punctata, cleidocranial dysostosis, congenital short femur, craniosynostosis (e.g., Muenke syndrome, Crouzon syndrome, Apert syndrome, Jackson-Weiss syndrome, Pfeiffer syndrome, or Crouzonodermoskeletal syndrome), dactyly, brachydactyly, camptodactyly, polydactyly, syndactyly, diastrophic dysplasia, dwarfism, dyssegmental dysplasia, enchondromatosis, fibrochondrogenesis, fibrous dysplasia, hereditary multiple exostoses, hypochondroplasia, hypophosphatasia, hypophosphatemic rickets, Jaffe-Lichtenstein syndrome, Kniest dysplasia, Kniest syndrome, Langer-type mesomelic dysplasia, Marfan syndrome, McCune-Albright syndrome, micromelia, metaphyseal dysplasia, Jansen-type metaphyseal dysplasia, metatrophic dysplasia, Morquio syndrome, Nievergelt-type mesomelic dysplasia, neurofibromatosis, osteoarthritis, osteochondrodysplasia, osteogenesis imperfecta, perinatal lethal type of osteogenesis imperfecta, osteopetrosis, osteopoikilosis, peripheral dysostosis, Reinhardt syndrome, Roberts syndrome, Robinow syndrome, short-rib polydactyly syndromes, short stature, spondyloepiphyseal dysplasia congenita, and spondyloepimetaphyseal dysplasia.

The terms "soluble fibroblast growth factor receptor 3," "soluble FGFR3," and "sFGFR3" refer to a FGFR3 that is characterized by the absence or functional disruption of all or a substantial part of the transmembrane domain and any polypeptide portion that would anchor the FGFR3 polypeptide to a cell membrane (e.g., a tyrosine kinase domain). An sFGFR3 polypeptide is a non-membrane bound form of an FGFR3 polypeptide. In particular, the transmembrane domain of FGFR3 extends from amino acid residues 345 to 377 of the wild-type FGFR3 sequence (e.g, a polypeptide having the amino acid sequence of SEQ ID NO: 5) or amino acid residues 367 to 399 of the wild-type FGFR3 sequence including a signal peptide (e.g., a polypeptide having the amino acid sequence of SEQ ID NO: 32). Thus, the sFGFR3 polypeptide can include a deletion of a portion or all of amino acid residues 345 to 377 of the wild-type FGFR3 polypeptide sequence (e.g., a polypeptide having the amino acid sequence of SEQ ID NO: 5) or amino acid residues 367 to 399 of the wild-type FGFR3 sequence including a signal peptide (e.g., a polypeptide having the amino acid sequence of SEQ ID NO: 32). The sFGFR3 polypeptide can further include deletions of the cytoplasmic domain of the wild-type FGFR3 polypeptide sequence (amino acid residues 378 to 784 of SEQ ID NO: 5) or the wild-type FGFR3 polypeptide sequence including a signal peptide sequence (amino acid residues 378 to 806 of SEQ ID NO: 32).

Exemplary sFGFR3 polypeptides can include, but are not limited to, at least amino acids 1 to 100, 1 to 125, 1 to 150, 1 to 175, 1 to 200, 1 to 205, 1 to 210, 1 to 215, 1 to 220, 1 to 225, 1 to 230, 1 to 235, 1 to 240, 1 to 245, 1 to 250, 1 to 252, 1 to 255, 1 to 260, 1 to 265, 1 to 270, 1 to 275, 1 to 280, 1 to 285, 1 to 290, 1 to 295, or 1 to 300, or 1 to 301 of SEQ ID NOs: 1 or 2. sFGFR3 polypeptides can include any polypeptide having at least 50% (e.g., 55%, 60%, 65%, 70%, 75%, 80%, 85%, 86%, 87%, 88%, 89%, 90%, 91%, 92%, 93%, 94%, 95%, 96%, 97%, 98%, 99%, or more) sequence identity to any of these sFGFR3 polypeptides of SEQ ID NO: 1 or 2. Additionally, exemplary sFGFR3 polypeptides can include, but are not limited to, at least amino acids 1 to 100, 1 to 125, 1 to 150, 1 to 175, 1 to 200, 1 to 205, 1 to 210, 1 to 215, 1 to 220, 1 to 225, 1 to 230, 1 to 235, 1 to 240, 1 to 245, 1 to 250, 1 to 255, 1 to 260, 1 to 265, 1 to 270, 1 to 275, 1 to 280, 1 to 285, 1 to 290, 1 to 295, 1 to 300, 1 to 305, 1 to 310, 1 to 315, 1 to 320, 1 to 325, 1 to 330, 1 to 335, 1 to 340, 1 to 345, or 1 to 348 of SEQ ID NO: 4 or 33. sFGFR3 polypeptides can include any polypeptide having at least 50% (e.g., 55%, 60%, 65%, 70%, 75%, 80%, 85%, 86%, 87%, 88%, 89%, 90%, 91%, 92%, 93%, 94%, 95%, 96%, 97%, 98%, 99%, or more) sequence identity to any of these sFGFR3 polypeptides having the amino acid sequence of SEQ ID NO: 4 or 33. Any of the above sFGFR3 polypeptides or variants thereof can optionally include a signal peptide at the N-terminal position, such as amino acids 1 to 22 of SEQ ID NO: 6 (MGAPACALALCVAVAIVAGASS) or amino acids 1 to 19 of SEQ ID NO: 35 (e.g., MMSFVSLLLVGILFHATQA).

By "treating" and "treatment" is meant a reduction (e.g., by at least about 10%, about 15%, about 20%, about 25%, about 30%, about 35%, about 40%, about 45%, about 50%, about 60%, about 70%, about 80%, about 90%, about 95%, about 99%, or even 100%) in the progression or severity of a skeletal growth retardation disorder (e.g., achondroplasia), or in the progression, severity, or frequency of one or more symptoms of a skeletal growth retardation disorder (e.g., achondroplasia) in a patient (e.g., a human, such as an infant, a child, or an adolescent). Treatment can occur for a treatment period, in which an sFGFR3 polypeptide is administered for a period of time (e.g., days, months, years, or longer) to treat a patient (e.g., a human, such as an infant, a child, or an adolescent) having a skeletal growth retardation disorder, such as achondroplasia. Exemplary symptoms of achondroplasia that can be treated with an sFGFR3 (e.g., an sFGFR3 polypeptide or variant thereof, such as a polypeptide having the amino acid sequence of SEQ ID NO: 2, 4, or 33, or a sFGFR3 polypeptide including a signal peptide, such as a polypeptide having the amino acid sequence of SEQ ID NO: 18 or 34) include, but are not limited to, short stature, a long trunk, shortened limbs, an adult height of between about 42 to about 56 inches, a relatively large head, a forehead that is prominent, underdeveloped portions of the face, genu valgum (e.g., "knock-knee"), a waddling gait, short and stubby fingers, short and stubby toes, limited ability to straighten the arm at the elbow, an excessive curve of the lower back, dental problems (e.g. from overcrowding of teeth), weight control problems, neurological problems, respiratory problems, and/or pain and numbness in the lower back and/or spine.

The term "variant," with respect to a polypeptide, refers to a polypeptide (e.g., an sFGFR3 polypeptide or variant thereof, such as a polypeptide having the amino acid sequence of SEQ ID NO: 2, 4, or 33, or a sFGFR3 polypeptide including a signal peptide, such as a polypeptide having the amino acid sequence of SEQ ID NO: 18 or 34) that differs by one or more changes in the amino acid sequence from the polypeptide from which the variant is derived (e.g., the parent polypeptide, such a polypeptide having the amino acid sequence of SEQ ID NO: 1 or 7). The term "variant," with respect to a polynucleotide, refers to a polynucleotide (e.g., a polynucleotide encoding a sFGFR3 polypeptide, such as a polynucleotide having the nucleic acid sequence of SEQ ID NO: 20, 21, 36, or 37) that differs by one or more changes in the nucleic acid sequence from the polynucleotide from which the variant is derived (e.g., the parent polynucleotide). The changes in the amino acid or nucleic acid sequence of the variant can be, e.g., amino acid or nucleic acid substitutions, insertions, deletions, N-terminal truncations, or C-terminal truncations, or any combination thereof. In particular, the amino acid substitutions may be conservative and/or non-conservative substitutions. A variant can be characterized by amino acid sequence identity or nucleic acid sequence identity to the parent polypeptide (e.g., an sFGFR3 polypeptide or variant thereof, such as a polypeptide having the amino acid sequence of SEQ ID NO: 2, 4, or 33, or a sFGFR3 polypeptide including a signal peptide, such as a polypeptide having the amino acid sequence of SEQ ID NO: 18 or 34) or parent polynucleotide (e.g., a polynucleotide encoding a sFGFR3 polypeptide, such as a polynucleotide having the nucleic acid sequence of SEQ ID NO: 20, 21, 36, or 37), respectively. For example, a variant can include any polypeptide having at least 50% (e.g., 55%, 60%, 65%, 70%, 75%, 80%, 85%, 86%, 87%, 88%, 89%, 90%, 91%, 92%, 93%, 94%, 95%, 96%, 97%, 98%, 99%, or more) sequence identity to a polypeptide having the amino acid sequence of SEQ ID NO: 1, 2, 4, or 33. A variant can also include any polynucleotide having at least 50% (e.g., 55%, 60%, 65%, 70%, 75%, 80%, 85%, 86%, 87%, 88%, 89%, 90%, 91%, 92%, 93%, 94%, 95%, 96%, 97%, 98%, 99%, or more) sequence identity to a polynucleotide having the nucleic acid sequence of SEQ ID NO: 20, 21, 36, or 37.

By "vector" is meant a DNA construct that includes one or more polynucleotides, or fragments thereof, encoding an sFGFR3 polypeptide (e.g., an sFGFR3 polypeptide or variant thereof, such as a polypeptide having the amino acid sequence of SEQ ID NO: 2, 4, or 33, or a sFGFR3 polypeptide including a signal peptide, such as a polypeptide having the amino acid sequence of SEQ ID NO: 18 or 34). The vector can be used to infect a cell (e.g., a host cell or a cell of a patient having a human skeletal growth retardation disorder, such as achondroplasia), which results in the translation of the polynucleotides of the vector into a sFGFR3 polypeptide. One type of vector is a "plasmid," which refers to a circular double stranded DNA loop into which additional DNA segments may be ligated. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. In general, expression vectors of utility in recombinant DNA techniques are often in the form of plasmids.

The term "unit dosage form(s)" refers to physically discrete unit(s) suitable as unitary dosages for human subjects and other mammals, each unit containing a predetermined quantity of active material calculated to produce the desired therapeutic effect, in association with any suitable pharmaceutical excipient, carrier, or diluent.

The recitation herein of numerical ranges by endpoints is intended to include all numbers subsumed within that range (e.g., a recitation of 1 to 5 includes 1, 1.5, 2, 2.75, 3, 3.80, 4, and 5).

Other features and advantages of the invention will be apparent from the following Detailed Description and from the claims.

BRIEF DESCRIPTION OF THE SEVERAL VIEWS OF THE DRAWINGS

FIGS. 1A-1D are graphs showing sensorgrams of the sFGFR3 polypeptides. Sensorgrams are shown for sFGFR3_Del1 (SEQ ID NO: 7), sFGFR3_Del4 (SEQ ID NO: 1), and sFGFR3_Del4-LK1-LK2 (SEQ ID NO: 10; FIG. 1A); sFGFR3_Del1 (SEQ ID NO: 7) and sFGFR3 Del1-D3 (SEQ ID NO: 9; FIG. 1B); sFGFR3_Del4-LK1-LK2 (SEQ ID NO: 10), sFGFR3_Del4-LK1-LK2-C253S (SEQ ID NO: 11), and sFGFR3_Del4-LK1-LK2-D3 (SEQ ID NO: 12; FIG. 1C); and sFGFR3_Del4 (SEQ ID NO: 1), sFGFR3_Del4-0253S (SEQ ID NO: 2), and sFGFR3_Del4-D3 (SEQ ID NO: 33; FIG. 1D).

FIGS. 3A-3B are graphs showing a sensorgram (FIG. 3A) and proliferation assays of sFGFR3_Del4, sFGFR3_Del4-C253S, and sFGFR3_Del4-D3 (FIG. 3B) using Fgfr3$^{ach/+}$ chondrocyte cells in the presence of FGF2.

FIG. 9A: FPLC elution profiles are shown for sFGFR3_Del4-D3 at 0 minutes, 2 hours, and 24 hours in cpm/fraction; FIGS. 9B-9D: sFGFR3_Del4-D3 administered by intravenous bolus at 1 minute, 15 minutes, 30 minute, 2 hours, and 24 hours in cpm/fraction and as normalized to the highest peak; FIGS. 9E-9G: sFGFR3_Del4-D3 administered by subcutaneous injection at 30 minutes, 2 hours, 4 hours, and 24 hours in cpm/fraction and as normalized to the highest peak (shown in FIG. 9C cont.).

FIGS. 18A-18B are a graph showing the cranium ratio and an x-ray radiograph showing the skulls of Fgfr3$^{ach/+}$ mice administered sFGFR3_Del4-D3, respectively. Shown in the graph (FIG. 18A) is the cranium ratio (L/VV) of wild type mice administered PBS as vehicle and Fgfr3$^{ach/+}$ mice administered PBS as vehicle, 2.5 mg/kg sFGFR3_Del4-D3 once weekly, 2.5 mg/kg sFGFR3_Del4-D3 twice weekly, and 10 mg/kg sFGFR3_Del4-D3 twice weekly. Shown in the x-ray radiograph (FIG. 18B) is the skulls of wild type mice administered PBS as vehicle, Fgfr3$^{ach/+}$ mice administered PBS as vehicle, wild type mice administered 10 mg/kg sFGFR3_Del4-D3 twice weekly, and Fgfr3$^{ach/+}$ mice administered 10 mg/kg sFGFR3_Del4-D3 twice weekly.

FIGS. 19A-19F are graphs showing the kinetic profile for the binding of different concentrations of hFGF1, FGF2, hFGF9, hFGF18, hFGF19, and hFGF21 to immobilized SFGFR3_DEL4-D3 in real time. Shown are the kinetic profiles for binding of hFGF1 at concentrations of 0.5 nM to 12 nM to immobilized SFGFR3_DEL4-D3 (FIG. 19A); hFGF2 at concentrations of 2 nM to 10 nM to immobilized SFGFR3_DEL4-D3 (FIG. 19B); hFGF9 at concentrations of 1 nM to 5 nM to immobilized SFGFR3_DEL4-D3 (FIG. 19C); hFGF18 at concentrations of 1 nM to 10 nM to immobilized SFGFR3_DEL4-D3 (FIG. 19D); hFGF19 at concentrations of 2 nM to 20 nM to immobilized SFGFR3_DEL4-D3 (FIG. 19E); and hFGF21 at concentrations of 100 nM to 10000 nM to immobilized SFGFR3_DEL4-D3 (FIG. 19F). The darker, overlapping lines represent the 2:1 binding model used to generate the $K_d$ values.

DETAILED DESCRIPTION OF THE INVENTION

Figure 1A:
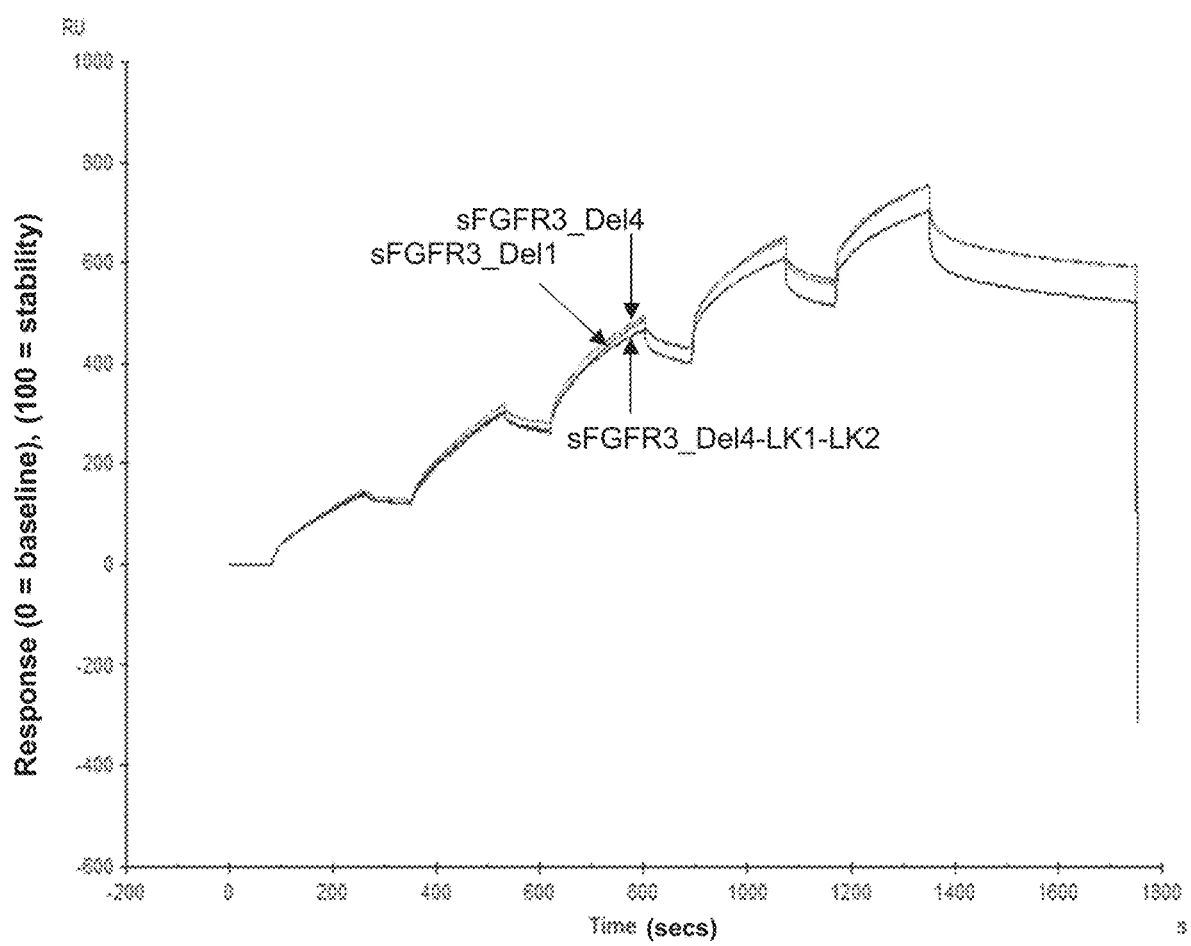
Figure 1B:
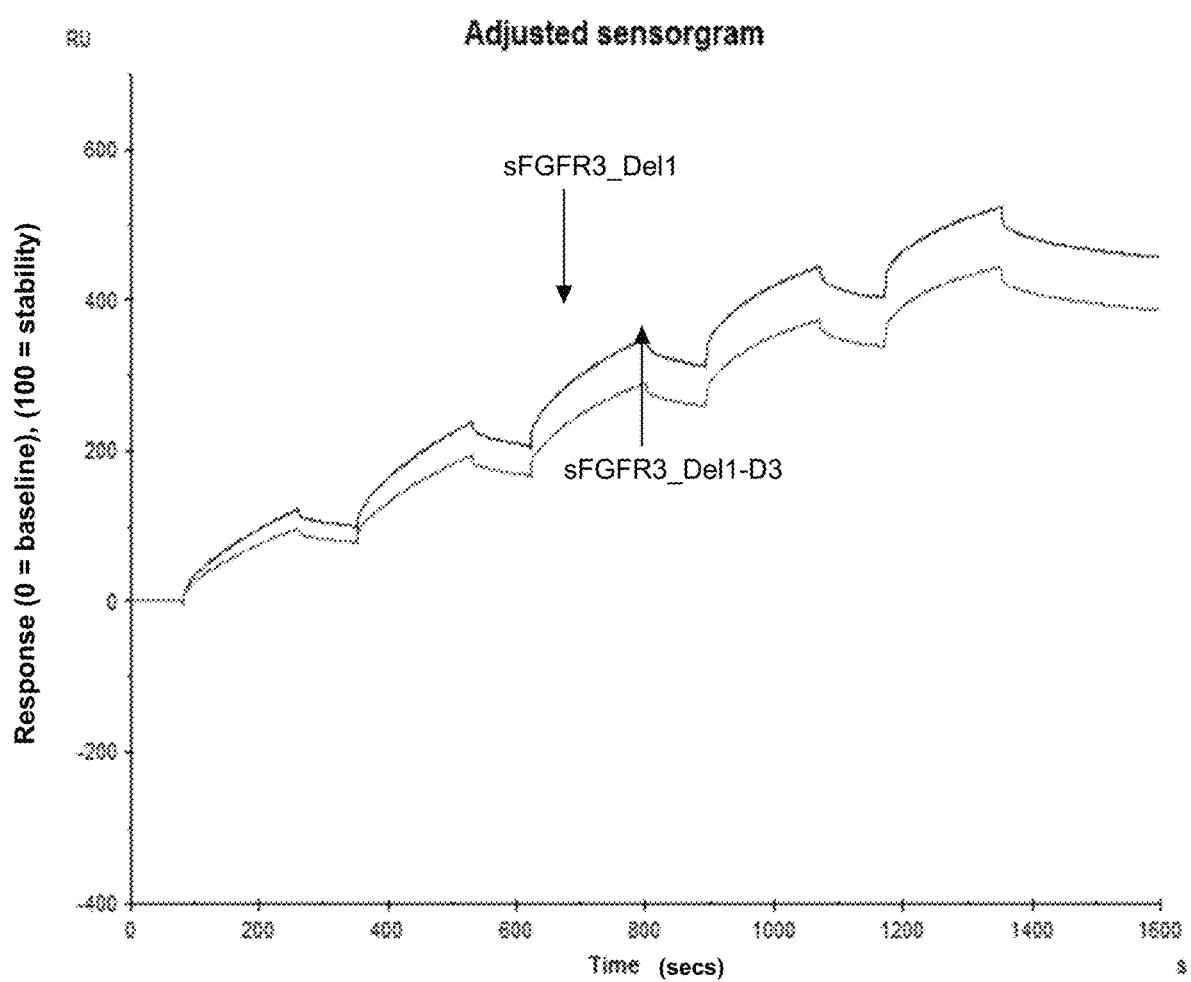
Figure 1C:
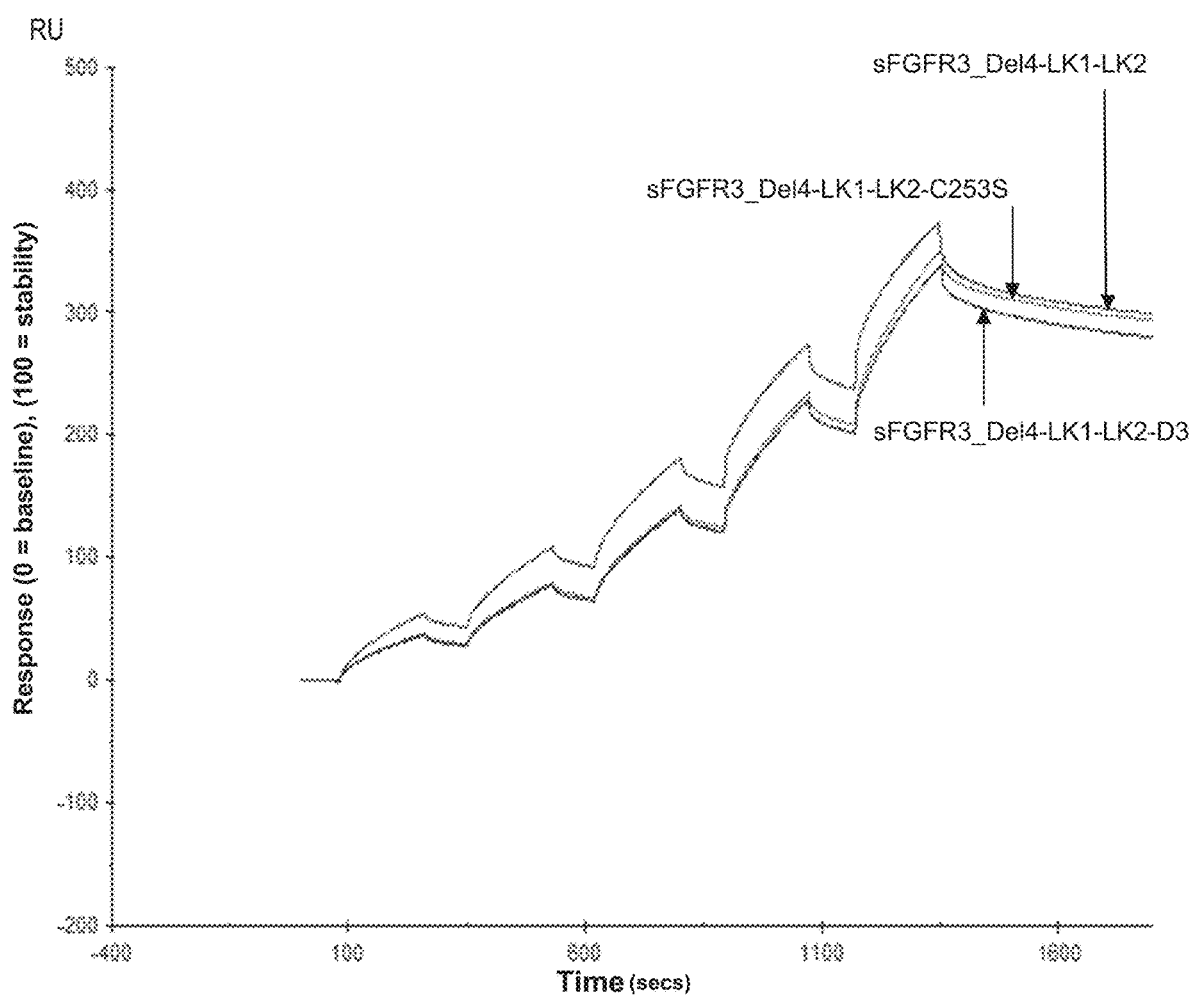

We have discovered that soluble fibroblast growth factor receptor 3 (sFGFR3) polypeptides and variants thereof can be used to treat skeletal growth retardation disorders, such as achondroplasia, in a patient (e.g., a human, particularly an infant, a child, or an adolescent). In particular, sFGFR3 polypeptides of the invention feature a deletion of, e.g., amino acids 289 to 400 of SEQ ID NO: 5 or amino acids 311 to 422 of SEQ ID NO: 32, to provide the following exemplary sFGFR3 polypeptides: sFGFR3_Del4 including an amino acid substitution of a cysteine residue with a serine residue at position 253 (sFGFR3_Del4-C253S; SEQ ID NO: 2) and sFGFR3_Del4 including an extended Ig-like C2-type domain 3 (sFGFR3_Del4-D3; SEQ ID NO: 33) and variants thereof, such as a sFGFR3 polypeptide having the amino acid sequence of SEQ ID NO: 4. Additionally, the sFGFR3 polypeptides may include a signal peptide, such as a sFGFR3 polypeptide having the amino acid sequence of SEQ ID NO: 18 or 34. See U.S. Provisional Application No. 62/276,222 and International Application No. PCT/US16/12553 for a description of sFGFR3_Del4 (SEQ ID NO: 1), each of which is hereby incorporated herein by reference in their entirety.

For example, sFGFR3 polypeptides and variants thereof having at least 85% sequence identity (e.g., at least 85%, 86%, 87%, 88%, 89%, 90%, 91%, 92%, 93%, 94%, 95%, 96%, 97%, 98%, 99%, or more sequence identity) to the amino acid sequence of SEQ ID NO: 1 can include an amino acid substitution that removes a cysteine residue at position 253 of SEQ ID NO: 1 (e.g. sFGFR3_Del4-C253S; a polypeptide having the amino acid sequence of SEQ ID NO: 2). In particular, an sFGFR3 polypeptide of the invention can include a substitution of a cysteine residue at position 253 of SEQ ID NO: 1 with, e.g., a serine residue. For example, the cysteine residue at position 253 is substituted with a serine residue or, e.g., another conservative amino acid substitution, such as alanine, glycine, proline, or threonine.

The sFGFR3 polypeptides can also include a polypeptide sequence having at least 90% (e.g., at least 91%, 92%, 93%, 94%, 95%, 96%, 97%, 98%, 99%, or more sequence identity) amino acid sequence identity to amino acid residues 23 to 357 of SEQ ID NO: 32, in which the polypeptide lacks a signal peptide and a transmembrane domain of FGFR3 and (i) is less than 500 amino acids in length; (ii) comprises 200 consecutive amino acids or fewer of an intracellular domain of FGFR3; and/or (iii) lacks a tyrosine kinase domain of FGFR3 (e.g., sFGFR3_Del4-D3; a polypeptide having the amino acid sequence of SEQ ID NO: 33). Methods for administering the sFGFR3 polypeptides of the invention to treat skeletal growth retardation disorders (e.g., achondroplasia) in a patient (e.g., a human, particularly an infant, a child, or an adolescent) are also described.

The sFGFR3 polypeptides, methods of production, methods of treatment, compositions, and kits of the invention are described herein.

Soluble Fibroblast Growth Factor Receptor 3 (sFGFR3) Polypeptides

The invention features sFGFR3 polypeptides and variants thereof formulated for the treatment of skeletal growth retardation disorders (e.g., achondroplasia). In particular, the sFGFR3 polypeptides can have at least 85% sequence identity (e.g., 86%, 87%, 88%, 89%, 90%, 91%, 92%, 93%, 94%, 95%, 96%, 97%, 98%, 99%, or more sequence identity) to the amino acid sequence of SEQ ID NO: 1, in which the sFGFR3 polypeptide includes an amino acid substitution that removes a cysteine residue at position 253 of SEQ ID NO: 1 (e.g. sFGFR3_Del4-C253S; a polypeptide having the amino acid sequence of SEQ ID NO: 2). For example, the cysteine residue at position 253 of SEQ ID NO: 1 is substituted with a serine residue or a conservative amino acid substitution, such as alanine, glycine, proline, or threonine.

The sFGFR3 polypeptides and variants thereof can also include fragments of the amino acid sequence of SEQ ID NO: 2 (e.g., at least amino acids 1 to 200, 1 to 205, 1 to 210, 1 to 215, 1 to 220, 1 to 225, 1 to 235, 1 to 230, 1 to 240, 1 to 245, 1 to 250, 1 to 253, 1 to 255, 1 to 260, 1 to 265, 1 to 275, 1 to 280, 1 to 285, 1 to 290, or 1 to 300, of SEQ ID NO: 2) having at least 50% sequence identity (e.g., 55%, 60%, 65%, 70%, 75%, 80%, 85%, 86%, 87%, 88%, 89%, 90%, 91%, 92%, 93%, 94%, 95%, 96%, 97%, 98%, 99%, or more sequence identity) to SEQ ID NO: 2. Additionally, sFGFR3 polypeptides can include amino acids 1 to 301 of SEQ ID NO: 1, in which the sFGFR3 polypeptide includes an amino acid substitution of a cysteine residue with a serine residue at position 253 of SEQ ID NO: 1 (e.g., a polypeptide having the amino acid sequence of SEQ ID NO: 2).

The sFGFR3 polypeptides and variants thereof can also include fragments of the amino acid sequence of SEQ ID NO: 33 (e.g., at least amino acids 1 to 200, 1 to 210, 1 to 220, 1 to 230, 1 to 240, 1 to 250, 1 to 260, 1 to 270, 1 to 280, 1 to 290, 1 to 300, 1 to 310, 1 to 320, 1 to 330, 1 to 340, 1 to 340, or 1 to 345 of SEQ ID NO: 33) having at least 50% sequence identity (e.g., 55%, 60%, 65%, 70%, 75%, 80%, 85%, 86%, 87%, 88%, 89%, 90%, 91%, 92%, 93%, 94%, 95%, 96%, 97%, 98%, 99%, or more sequence identity) to SEQ ID NO: 33. In addition, the cysteine residue at position 253 of SEQ ID NO: 4 or 33 and/or position 316 of SEQ ID NO: 4, if present, can be substituted with a serine residue or a conservative amino acid substitution, such as alanine, glycine, proline, or threonine.

Given the results described herein, the invention is not limited to a particular sFGFR3 polypeptide or variants thereof. In addition to the exemplary sFGFR3 polypeptides and variants thereof discussed above, any polypeptide that binds one or more FGFs (e.g., FGF1 (e.g., a polypeptide having the amino acid sequence of SEQ ID NO: 13), FGF2 (e.g., a polypeptide having the amino acid sequence of SEQ ID NO: 14), FGF9 (e.g., a polypeptide having the amino acid sequence of SEQ ID NO: 15), FGF18 (e.g., a polypeptide having the amino acid sequence of SEQ ID NO: 16), FGF19 (e.g., a polypeptide having the amino acid sequence of SEQ ID NO: 38), and/or FGF21 (e.g., a polypeptide having the amino acid sequence of SEQ ID NO: 39)) with similar binding affinity as the sFGFR3 polypeptides of the invention (e.g. sFGFR3_Del4-C253S (SEQ ID NO: 2), sFGFR3_Del4-D3 (SEQ ID NO: 33), and variants thereof (SEQ ID NO: 4) or a sFGFR3 polypeptide including a signal peptide (SEQ ID NO: 18 or 34)) can be used in the methods, such as for treating a skeletal growth retardation disorder, e.g., achondroplasia. The sFGFR3 polypeptides can be, for example, fragments of FGFR3 isoform 2 lacking exons 8 and 9 encoding the C-terminal half of the Ig-like C2-type domain 3 and exon 10 including the transmembrane domain (e.g., fragments of the amino acid sequence of SEQ ID NO: 5 or 32), corresponding to fragments of FGFR3 transcript variant 2 (Accession No. NM_022965).

An sFGFR3 polypeptide of the invention (e.g. sFGFR3_Del4-C253S (SEQ ID NO: 2), sFGFR3_Del4-D3 (SEQ ID NO: 33), and variants thereof (SEQ ID NO: 4)) can include a signal peptide at the N-terminal position. An exemplary signal peptide can include, but is not limited to, amino acids 1 to 22 of SEQ ID NO: 6 (e.g., MGAPACALALCVAVAIVAGASS) or amino acids 1 to 19 of SEQ ID NO: 35 (e.g., MMSFVSLLLVGILFHATQA). Accordingly, the sFGFR3 polypeptides include both secreted forms, which lack the N-terminal signal peptide, and non-secreted forms, which include the N-terminal signal peptide. For instance, a secreted sFGFR3 polypeptide can include the amino acid sequence of SEQ ID NOs: 2, 4, or 33. Alternatively, the sFGFR3 polypeptide does include a signal peptide, such the amino acid sequence of SEQ ID NOs: 18, 19, or 34. One skilled in the art will appreciate that the position of the N-terminal signal peptide will vary in different sFGFR3 polypeptides and can include, for example, the first 5, 8, 10, 11, 12, 13, 14, 15, 16, 17, 18, 19, 20, 21, 22, 23, 24, 25, 27, 30, or more amino acid residues on the N-terminus of the polypeptide. One of skill in the art can predict the position of a signal sequence cleavage site, e.g., by an appropriate computer algorithm such as that described in Bendtsen et al. (*J. Mol. Biol.* 340(4):783-795, 2004) and available on the Web at cbs.dtu.dk/services/SignalP/.

Additionally, sFGFR3 polypeptides (e.g. sFGFR3_Del4-C253S (SEQ ID NO: 2), sFGFR3_Del4-D3 (SEQ ID NO: 33), and variants thereof (SEQ ID NO: 4) or a sFGFR3 polypeptide including a signal peptide (SEQ ID NO: 18 or 34)) of the invention can be glycosylated. In particular, a sFGFR3 polypeptide can be altered to increase or decrease the extent to which the sFGFR3 polypeptide is glycosylated. Addition or deletion of glycosylation sites to an sFGFR3 polypeptide can be accomplished by altering the amino acid sequence such that one or more glycosylation sites is created or removed. For example, N-linked glycosylation, in which an oligosaccharide is attached to the amide nitrogen of an asparagine residue, can occur at position Asn76, Asn148, Asn169, Asn 203, Asn240, Asn272, and/or Asn 294 of the amino acid sequence of sFGFR3_Del4-C253S (SEQ ID NO: 2), sFGFR3_Del4-D3 (SEQ ID NO: 4 or 33), and variants thereof. One or more of these Asn residues can also be substituted to remove the glycosylation site. For instance, O-linked glycosylation, in which an oligosaccharide is attached to an oxygen atom of an amino acid residue, can occur at position Ser109, Thr126, Ser199, Ser274, Thr281, Ser298, Ser299, and/or Thr301 of the amino acid sequence of sFGFR3_Del4-C253S (SEQ ID NO: 2), sFGFR3_Del4-D3 (SEQ ID NO: 33), variants thereof (SEQ ID NO: 4), and sFGFR3 polypeptides including a signal peptide (SEQ ID NO: 18 or 34). Additionally, O-linked glycosylation can occur at position Ser310 and/or Ser321 of sFGFR3_Del4-D3 (SEQ ID NO: 33) and variants thereof (SEQ ID NO: 4). One or more of these Ser or Thr residues can also be substituted to remove the glycosylation site.

sFGFR3 Fusion Polypeptides sFGFR3 polypeptides of the invention (e.g. sFGFR3_Del4-C253S (SEQ ID NO: 2), sFGFR3_Del4-D3 (SEQ ID NO: 33), and variants thereof (SEQ ID NO: 4) or a sFGFR3 polypeptide including a signal peptide (SEQ ID NO: 18 or 34)) can be fused to a functional domain from a heterologous polypeptide (e.g., a fragment crystallizable region of an immunoglobulin (Fc region; such as a polypeptide having the amino acid sequence of SEQ ID NOs: 25 and 26) or human serum albumin (HSA; such as a polypeptide having the amino acid sequence of SEQ ID NO: 27)) to provide a sFGFR3 fusion polypeptide. Optionally, a flexible linker, can be included between the sFGFR3 polypeptide and the heterologous polypeptide (e.g., an Fc region or HSA), such as a serine or glycine-rich sequence (e.g., a poly-glycine or a poly-glycine/serine linker, such as SEQ ID NOs: 28 and 29).

For example, the sFGFR3 polypeptides (e.g. sFGFR3_Del4-C253S (SEQ ID NO: 2), sFGFR3_Del4-D3 (SEQ ID NO: 33), and variants thereof (SEQ ID NO: 4) or a sFGFR3 polypeptide including a signal peptide (SEQ ID NO: 18 or 34)) can be a fusion polypeptide including, e.g., an Fc region of an immunoglobulin at the N-terminal or C-terminal domain. In particular, useful Fc regions can include the Fc fragment of any immunoglobulin molecule, including IgG, IgM, IgA, IgD, or IgE and their various subclasses (e.g., IgG-1, IgG-2, IgG-3, IgG-4, IgA-1, IgA-2) from any mammal (e.g., a human). For instance, the Fc fragment human IgG-1 (SEQ ID NO: 25) or a variant of human IgG-1, such as a variant including a substitution of asparagine at position 297 of SEQ ID NO: 25 with alanine (e.g., a polypeptide having the amino acid sequence of SEQ ID NO: 26). The Fc fragments of the invention can include, for example, the CH2 and CH3 domains of the heavy chain and any portion of the hinge region. The sFGFR3 fusion polypeptides of the invention can also include, e.g., a monomeric Fc, such as a CH2 or CH3 domain. The Fc region may optionally be glycosylated at any appropriate one or more amino acid residues known to those skilled in the art. An Fc fragment as described herein may have 1, 2, 3, 4, 5, 6, 7, 8, 9, 10, 11, 12, 13, 14, 15, 16, 17, 18, 19, 20, 25, 30, 35, 40, 50, or more additions, deletions, or substitutions relative to any of the Fc fragments described herein.

Additionally, the sFGFR3 polypeptides (e.g. sFGFR3_Del4-C253S (SEQ ID NO: 2), sFGFR3_Del4-D3 (SEQ ID NO: 33), and variants thereof (SEQ ID NO: 4) or a sFGFR3 polypeptide including a signal peptide (SEQ ID NO: 18 or 34)) can be conjugated to other molecules at the N-terminal or C-terminal domain for the purpose of improving the solubility and stability of the protein in aqueous solution. Examples of such molecules include human serum albumin (HSA), PEG, PSA, and bovine serum albumin (BSA). For instance, the sFGFR3 polypeptides can be conjugated to human HSA (e.g., a polypeptide having the amino acid sequence of SEQ ID NO: 27) or a fragment thereof.

The sFGFR3 fusion polypeptides can include a peptide linker region between the sFGFR3 polypeptide (e.g. sFGFR3_Del4-C253S (SEQ ID NO: 2), sFGFR3_Del4-D3 (SEQ ID NO: 4), and variants thereof (SEQ ID NO: 4) or a sFGFR3 polypeptide including a signal peptide (SEQ ID NO: 18 or 34)) and the heterologous polypeptide (e.g., an Fc region or HSA). The linker region may be of any sequence and length that allows the sFGFR3 to remain biologically active, e.g., not sterically hindered. Exemplary linker lengths are between 1 and 200 amino acid residues, e.g., 1-5, 6-10, 11-15, 16-20, 21-25, 26-30, 31-35, 36-40, 41-45, 46-50, 51-55, 56-60, 61-65, 66-70, 71-75, 76-80, 81-85, 86-90, 91-95, 96-100, 101-110, 111-120, 121-130, 131-140, 141-150, 151-160, 161-170, 171-180, 181-190, or 191-200 amino acid residues. For instance, linkers include or consist of flexible portions, e.g., regions without significant fixed secondary or tertiary structure. Preferred ranges are 5 to 25 and 10 to 20 amino acids in length. Such flexibility is generally increased if the amino acids are small and do not have bulky side chains that impede rotation or bending of the amino acid chain. Thus, preferably the peptide linker of the present invention has an increased content of small amino acids, in particular of glycines, alanines, serines, threonines, leucines and isoleucines.

Exemplary flexible linkers are glycine-rich linkers, e.g., containing at least 50%, 60%, 65%, 70%, 75%, 80%, 85%, 90%, 95%, or even 100% glycine residues. Linkers may also contain, e.g., serine-rich linkers, e.g., containing at least 50%, 60%, 65%, 70%, 75%, 80%, 85%, 90%, 95%, or even 100% serine residues. In some cases, the amino acid sequence of a linker consists only of glycine and serine residues. For example, the linker can be the amino acid sequence of GGGGAGGGG (SEQ ID NO: 28) or GGGGSGGGGSGGGGS (SEQ ID NO: 29). A linker can optionally be glycosylated at any appropriate one or more amino acid residues. The linker can also be absent, in which the FGFR3 polypeptide and the heterologous polypeptide (e.g., an Fc region or HSA) are fused together directly, with no intervening residues.

Polynucleotides Encoding the sFGFR3 Polypeptides

The invention further includes polynucleotides encoding the sFGFR3 polypeptides (e.g. sFGFR3_Del4-C253S (SEQ ID NO: 2), sFGFR3_Del4-D3 (SEQ ID NO: 33), and variants thereof (SEQ ID NO: 4) or a sFGFR3 polypeptide including a signal peptide (SEQ ID NO: 18 or 34)) that can be used to treat skeletal growth retardation disorders (e.g., achondroplasia) in a patient (e.g., a human, such as an infant, a child, or an adolescent), such as SEQ ID NOs: 20, 21, 36, or 37. For example, the polynucleotide can be the nucleic acid sequence of SEQ ID NO: 20 or 36, which encode sFGFR3_Del4-C253S (SEQ ID NO: 2), or a variant having at least 85% sequence identity (e.g., 86%, 87%, 88%, 89%, 90%, 91%, 92%, 93%, 94%, 95%, 96%, 97%, 98%, 99%, or more sequence identity) to the nucleic acid sequence of SEQ ID NO: 20 or 36. Additionally, the polynucleotide can be the nucleic acid sequence of SEQ ID NO: 21 or 37, which encodes sFGFR3_Del4-D3 (SEQ ID NO: 33), having at least 85% sequence identity (e.g., 86%, 87%, 88%, 89%, 90%, 91%, 92%, 93%, 94%, 95%, 96%, 97%, 98%, 99%, or more sequence identity) to the nucleic acid sequence of SEQ ID NO: 21 or 37. The invention also includes polynucleotides encoding sFGFR3 fusion polypeptides (e.g., a sFGFR3 polypeptide fused to a heterologous polypeptide, such as a Fc region or HSA) and polynucleotides encoding sFGFR3 polypeptides without a signal peptide (e.g., polypeptides having the amino acid sequence of SEQ ID NOs: 2, 4, and 33) or with a signal peptide (e.g., polypeptides having the amino acid sequence of SEQ ID NOs: 18, 19, and 34). Additionally, the invention includes polynucleotides include one or more mutations to alter any of the glycosylation sites described herein.

Optionally, the sFGFR3 polynucleotides of the invention (e.g. sFGFR3_Del4-C253S (SEQ ID NO: 2), sFGFR3_Del4-D3 (SEQ ID NO: 33), and variants thereof (SEQ ID NO: 4) or a sFGFR3 polypeptide including a signal peptide (SEQ ID NO: 18 or 34)) can be codon optimized to alter the codons in the nucleic acid, in particular to reflect the typical codon usage of the host organism (e.g., a human) without altering the sFGFR3 polypeptide encoded by the nucleic acid sequence of the polynucleotide. Codon-optimized polynucleotides (e.g., a polynucleotide having the nucleic acid sequence of SEQ ID NO: 20, 21, 36, or 37) can, e.g., facilitate genetic manipulations by decreasing the GC content and/or for expression in a host cell (e.g., a HEK 293 cell or a CHO cell). Codon-optimization can be performed by the skilled person, e.g. by using online tools such as the JAVA Codon Adaption Tool (www.jcat.de) or Integrated DNA Technologies Tool (www.eu.idtdna.com/CodonOpt) by simply entering the nucleic acid sequence of the polynucleotide and the host organism for which the codons are to be optimized. The codon usage of different organisms is available in online databases, for example, www.kazusa.or.jp/codon.

Host Cells for Expression of the sFGFR3 Polypeptides

Mammalian cells can be used as host cells for expression of the sFGFR3 polypeptides of the invention (e.g. sFGFR3_Del4-C253S (SEQ ID NO: 2), sFGFR3_Del4-D3 (SEQ ID NO: 33), and variants thereof (SEQ ID NO: 4) or a sFGFR3 polypeptide including a signal peptide (SEQ ID NO: 18 or 34)). Exemplary mammalian cell types useful in the methods include, but are not limited to, human embryonic kidney (HEK; e.g., HEK 293) cells, Chinese Hamster Ovary (CHO) cells, L cells, C127 cells, 3T3 cells, BHK cells, COS-7 cells, HeLa cells, PC3 cells, Vero cells, MC3T3 cells, NSO cells, Sp2/0 cells, VERY cells, BHK, MDCK cells, W138 cells, BT483 cells, Hs578T cells, HTB2 cells, BT20 cells, T47D cells, NSO cells, CRL7O3O cells, and HsS78Bst cells, or any other suitable mammalian host cell known in the art. Alternatively, E. coli cells can be used as host cells for expression of the sFGFR3 polypeptides. Examples of E. coli strains include, but are not limited to, E. coli 294 (ATCC®31,446), E. coli A 1776 (ATCC®31,537, E. coli BL21 (DE3) (ATCC® BAA-1025), E. coli RV308 (ATCC®31,608), or any other suitable E. coli strain known in the art.

Vectors Including Polynucleotides Encoding the sFGFR3 Polypeptides

The invention also features recombinant vectors including any one or more of the polynucleotides described above. The vectors of the invention can be used to deliver a polynucleotide encoding a sFGFR3 polypeptide of the invention (e.g. sFGFR3_Del4-C253S (SEQ ID NO: 2), sFGFR3_Del4-D3 (SEQ ID NO: 33), and variants thereof (SEQ ID NO: 4) or a sFGFR3 polypeptide including a signal peptide (SEQ ID NO: 18 or 34)), which can include mammalian, viral, and bacterial expression vectors. For example, the vectors can be plasmids, artificial chromosomes (e.g. BAG, PAC, and YAC), and virus or phage vectors, and may optionally include a promoter, enhancer, or regulator for the expression of the polynucleotide. The vectors can also contain one or more selectable marker genes, such as an ampicillin, neomycin, and/or kanamycin resistance gene in the case of a bacterial plasmid or a resistance gene for a fungal vector. Vectors can be used in vitro for the production of DNA or RNA or used to transfect or transform a host cell, such as a mammalian host cell for the production of a sFGFR3 polypeptide encoded by the vector. The vectors can also be adapted to be used in vivo in a method of gene therapy.

Exemplary viral vectors that can be used to deliver a polynucleotide encoding a sFGFR3 polypeptide of the invention (e.g. sFGFR3_Del4-C253S (SEQ ID NO: 2), sFGFR3_Del4-D3 (SEQ ID NO: 33), and variants thereof (SEQ ID NO: 4) or a sFGFR3 polypeptide including a signal peptide (SEQ ID NO: 18 or 34)) include a retrovirus, adenovirus (e.g., Ad2, Ad5, Ad11, Ad12, Ad24, Ad26, Ad34, Ad35, Ad40, Ad48, Ad49, Ad50, and Pan9 (also known as AdC68)), parvovirus (e.g., adeno-associated viruses), coronavirus, negative strand RNA viruses such as orthomyxovirus (e.g., influenza virus), rhabdovirus (e.g., rabies and vesicular stomatitis virus), paramyxovirus (e.g. measles and Sendai), positive strand RNA viruses, such as picornavirus and alphavirus, and double stranded DNA viruses including adenovirus, herpesvirus (e.g., Herpes Simplex virus types 1 and 2, Epstein-Barr virus, cytomegalovirus), and poxvirus (e.g., vaccinia, modified vaccinia Ankara (MVA), fowlpox and canarypox). Other viruses useful for delivering polynucleotides encoding sFGFR3 polypeptides include Norwalk virus, togavirus, flavivirus, reoviruses, papovavirus, hepadnavirus, and hepatitis virus. Examples of retroviruses include avian leukosis-sarcoma, mammalian C-type, B-type viruses, D-type viruses, HTLV-BLV group, lentivirus, and spumavirus (Coffin, J. M., Retroviridae: The viruses and their replication, *In Fundamental Virology*, Third Edition, B. N. Fields, et al., Eds., Lippincott-Raven Publishers, Philadelphia, 1996).

Methods of Production

Polynucleotides encoding sFGFR3 polypeptides of the invention (e.g. sFGFR3_Del4-C253S (SEQ ID NO: 2), sFGFR3_Del4-D3 (SEQ ID NO: 33), and variants thereof (SEQ ID NO: 4) or a sFGFR3 polypeptide including a signal peptide (SEQ ID NO: 18 or 34)) can be produced by any method known in the art. For instance, a polynucleotide is generated using molecular cloning methods and is placed within a vector, such as a plasmid, an artificial chromosome, a viral vector, or a phage vector. The vector is used to transform the polynucleotide into a host cell appropriate for the expression of the sFGFR3 polypeptide.

Nucleic Acid Vector Construction and Host Cells

The sFGFR3 polypeptide of the invention (e.g. sFGFR3_Del4-C253S (SEQ ID NO: 2), sFGFR3_Del4-D3 (SEQ ID NO: 33), and variants thereof (SEQ ID NO: 4) or a sFGFR3 polypeptide including a signal peptide (SEQ ID NO: 18 or 34)) can be produced from a host cell. The polynucleotides (e.g., polynucleotides having the nucleic acid sequence of SEQ ID NO: 20, 21, 36, or 37 and variants thereof) encoding sFGFR3 polypeptides can be included in vectors that can be introduced into the host cell by conventional techniques known in the art (e.g., transformation, transfection, electroporation, calcium phosphate precipitation, direct microinjection, or infection). The choice of vector depends in part on the host cells to be used. Generally, host cells are of either prokaryotic (e.g., bacterial) or eukaryotic (e.g., mammalian) origin.

A polynucleotide encoding an sFGFR3 polypeptide of the invention (e.g. sFGFR3_Del4-C253S (SEQ ID NO: 2), sFGFR3_Del4-D3 (SEQ ID NO: 33), and variants thereof (SEQ ID NO: 4) or a sFGFR3 polypeptide including a signal peptide (SEQ ID NO: 18 or 34)) can be prepared by a variety of methods known in the art. These methods include, but are not limited to, oligonucleotide-mediated (or site-directed) mutagenesis and PCR mutagenesis. A polynucleotide encoding an sFGFR3 polypeptide can be obtained using standard techniques, e.g., gene synthesis. Alternatively, a polynucleotide encoding a wild-type sFGFR3 polypeptide (e.g., a polypeptide having the amino acid sequence of SEQ ID NO: 5 or 32) can be mutated to contain specific amino acid substitutions (e.g., an amino acid substitution of a cysteine residue with a serine residue or a conservative amino acid substitution, such as alanine, glycine, proline, or threonine, at position 253 of SEQ ID NO: 33 and/or position 316 of SEQ ID NO: 4) using standard techniques in the art, e.g., QuikChange™ mutagenesis. Polynucleotides encoding an sFGFR3 polypeptide can be synthesized using, e.g., a nucleotide synthesizer or PCR techniques.

Polynucleotides encoding sFGFR3 polypeptide of the invention (e.g. sFGFR3_Del4-C253S (SEQ ID NO: 2), sFGFR3_Del4-D3 (SEQ ID NO: 33), and variants thereof (SEQ ID NO: 4) or a sFGFR3 polypeptide including a signal peptide (SEQ ID NO: 18 or 34)) can be inserted into a vector capable of replicating and expressing the polynucleotide in prokaryotic or eukaryotic host cells. Exemplary vectors useful in the methods can include, but are not limited to, a plasmid, an artificial chromosome, a viral vector, and a phage vector. For example, a viral vector can include the viral vectors described above, such as a retroviral vector, adenoviral vector, or poxviral vector (e.g., vaccinia viral vector, such as Modified Vaccinia Ankara (MVA)), adeno-associated viral vector, and alphaviral vector)) containing the nucleic acid sequence of a polynucleotide encoding the sFGFR3 polypeptide. Each vector can contain various components that may be adjusted and optimized for compatibility with the particular host cell. For example, the vector components may include, but are not limited to, an origin of replication, a selection marker gene, a promoter, a ribosome binding site, a signal sequence, the nucleic acid sequence of the polynucleotide encoding the sFGFR3 polypeptide, and/or a transcription termination sequence.

The above-described vectors may be introduced into appropriate host cells (e.g., HEK 293 cells or CHO cells) using conventional techniques in the art, e.g., transformation, transfection, electroporation, calcium phosphate precipitation, and direct microinjection. Once the vectors are introduced into host cells for the production of an sFGFR3 polypeptide of the invention (e.g. sFGFR3_Del4-C253S (SEQ ID NO: 2), sFGFR3_Del4-D3 (SEQ ID NO: 33), and variants thereof (SEQ ID NO: 4) or a sFGFR3 polypeptide including a signal peptide (SEQ ID NO: 18 or 34)), host cells are cultured in conventional nutrient media modified as appropriate for inducing promoters, selecting transformants, or amplifying the polynucleotides (e.g. SEQ ID NOs: 20 and 21 and variants thereof) encoding the sFGFR3 polypeptide. Methods for expression of therapeutic proteins, such as sFGFR3 polypeptides, are known in the art, see, for example, Paulina Balbas, Argelia Lorence (eds.) Recombinant Gene Expression: Reviews and Protocols (*Methods in Molecular Biology*), Humana Press; 2nd ed. 2004 (Jul. 20, 2004) and Vladimir Voynov and Justin A. Caravella (eds.) *Therapeutic Proteins: Methods and Protocols* (*Methods in Molecular Biology*) Humana Press; 2nd ed. 2012 (Jun. 28, 2012), each of which is hereby incorporated by reference in its entirety.

sFGFR3 Polypeptide Production, Recovery, and Purification

Host cells (e.g., HEK 293 cells or CHO cells) used to produce the sFGFR3 polypeptide of the invention (e.g. sFGFR3_Del4-C253S (SEQ ID NO: 2), sFGFR3_Del4-D3 (SEQ ID NO: 33), and variants thereof (SEQ ID NO: 4) or a sFGFR3 polypeptide including a signal peptide (SEQ ID NO: 18 or 34)) can be grown in media known in the art and suitable for culturing of the selected host cells. Examples of suitable media for mammalian host cells include Minimal Essential Medium (MEM), Dulbecco's Modified Eagle's Medium (DMEM), Expi293™ Expression Medium, DMEM with supplemented fetal bovine serum (FBS), and RPMI-1640. Examples of suitable media for bacterial host cells include Luria broth (LB) plus necessary supplements, such as a selection agent, e.g., ampicillin. Host cells are cultured at suitable temperatures, such as from about 20° C. to about 39° C., e.g., from 25° C. to about 37° C., preferably 37° C., and $CO_2$ levels, such as 5 to 10% (preferably 8%). The pH of the medium is generally from about 6.8 to 7.4, e.g., 7.0, depending mainly on the host organism. If an inducible promoter is used in the expression vector, sFGFR3 polypeptide expression is induced under conditions suitable for the activation of the promoter.

An sFGFR3 polypeptide of the invention (e.g. sFGFR3_Del4-C253S (SEQ ID NO: 2), sFGFR3_Del4-D3 (SEQ ID NO: 33), and variants thereof (SEQ ID NO: 4) or a sFGFR3 polypeptide including a signal peptide (SEQ ID NO: 18 or 34)) can be recovered from the supernatant of the host cell. Alternatively, the sFGFR3 polypeptide can be recovered by disrupting the host cell (e.g., using osmotic shock, sonication, or lysis), followed by centrifugation and filtration to remove the sFGFR3 polypeptide. Upon recovery of the sFGFR3 polypeptide, the sFGFR3 polypeptide can then be further purified. An sFGFR3 polypeptide can be purified by any method known in the art of protein purification, such as protein A affinity, other chromatography (e.g., ion exchange, affinity, and size-exclusion column chromatography), centrifugation, differential solubility, or by any other standard technique for the purification of proteins (see *Process Scale Purification of Antibodies*, Uwe Gottschalk (ed.) John Wiley & Sons, Inc., 2009, hereby incorporated by reference in its entirety).

Optionally, the sFGFR3 polypeptide of the invention (e.g. sFGFR3_Del4-C253S (SEQ ID NO: 2), sFGFR3_Del4-D3 (SEQ ID NO: 33), and variants thereof (SEQ ID NO: 4) or a sFGFR3 polypeptide including a signal peptide (SEQ ID NO: 18 or 34)) can be conjugated to a detectable label for purification. Examples of suitable labels for use in purification of the sFGFR3 polypeptides include, but are not limited to, a protein tag, a fluorophore, a chromophore, a radiolabel, a metal colloid, an enzyme, or a chemiluminescent, or bioluminescent molecule. In particular, protein tags that are useful for purification of the sFGFR3 polypeptides can include, but are not limited to, chromatography tags (e.g., peptide tags consisting of polyanionic amino acids, such as a FLAG-tag, or a hemagglutinin "HA" tag), affinity tags (e.g., a poly(His) tag, chitin binding protein (CBP), maltose binding protein (MBP), or glutathione-S-transferase (GST)), solubilization tags (e.g., thioredoxin (TRX) and poly(NANP)), epitope tags (e.g., V5-tag, Myc-tag, and HA-tag), or fluorescence tags (e.g., GFP, GFP variants, RFP, and RFP variants).

Methods of Treatment

Provided herein are methods for treating a skeletal growth retardation disorder in a patient, such as a patient having achondroplasia (e.g., a human having achondroplasia). In particular, the patient is one that exhibits or is likely to develop one or more symptoms of a skeletal growth retardation disorder (e.g., achondroplasia). The method involves administering an sFGFR3 polypeptide of the invention (e.g. sFGFR3_Del4-C253S (SEQ ID NO: 2), sFGFR3_Del4-D3 (SEQ ID NO: 33), and variants thereof (SEQ ID NO: 4) or a sFGFR3 polypeptide including a signal peptide (SEQ ID NO: 18 or 34)) to the patient having a skeletal growth retardation disorder, such as a patient having achondroplasia (e.g., a human having achondroplasia). In particular, the method involves administering sFGFR3_Del4-C253S (SEQ ID NO: 2) or sFGFR3_Del4-D3 (SEQ ID NO: 33) to the patient having a skeletal growth retardation disorder, such as a patient having achondroplasia (e.g., a human having achondroplasia). For example, the patient is an infant or child having a skeletal growth retardation disorder, such as an infant, a child, or an adolescent having achondroplasia (e.g., a human having achondroplasia).

The patient (e.g., a human) can be treated before symptoms of a skeletal growth retardation disorder (e.g., achondroplasia) appear or after symptoms of a skeletal growth retardation disorder (e.g., achondroplasia) develop. In particular, patients that can be treated with a sFGFR3 polypeptide of the invention (e.g. sFGFR3_Del4-C253S (SEQ ID NO: 2), sFGFR3_Del4-D3 (SEQ ID NO: 33), and variants thereof (SEQ ID NO: 4) or a sFGFR3 polypeptide including a signal peptide (SEQ ID NO: 18 or 34)) are those exhibiting symptoms including, but not limited to, short limbs, short trunk, bowlegs, a waddling gait, skull malformations, cloverleaf skull, craniosynostosis, wormian bones, anomalies of the hands, anomalies of the feet, hitchhiker thumb, and/or chest anomalies. Furthermore, treatment with an sFGFR3 polypeptide can result in an improvement in one or more of the aforementioned symptoms of a skeletal growth retardation disorder (e.g., relative to an untreated patient), such as achondroplasia.

The patient (e.g., a human) can be diagnosed with a skeletal growth retardation disorder, such as achondroplasia, before administration of an sFGFR3 polypeptide of the invention (e.g. sFGFR3_Del4-C253S (SEQ ID NO: 2), sFGFR3_Del4-D3 (SEQ ID NO: 33), and variants thereof (SEQ ID NO: 4) or a sFGFR3 polypeptide including a signal peptide (SEQ ID NO: 18 or 34)). Additionally, the patient having a skeletal growth retardation disorder, such as achondroplasia, can be one that has not previously been treated with an sFGFR3 polypeptide.

Skeletal Growth Retardation Disorders

Skeletal growth retardation disorders can be treated by administering an sFGFR3 polypeptide as described herein to a patient (e.g., a human) in need thereof. The method involves administering to the patient (e.g., a human) having the skeletal growth retardation disorder an sFGFR3 polypeptide of the invention (e.g. sFGFR3_Del4-C253S (SEQ ID NO: 2), sFGFR3_Del4-D3 (SEQ ID NO: 33), and variants thereof (SEQ ID NO: 4) or a sFGFR3 polypeptide including a signal peptide (SEQ ID NO: 18 or 34)). Skeletal growth retardation disorders that can be treated with the sFGFR3 polypeptides are characterized by deformities and/or malformations of the bones and can include, but are not limited to, FGFR3-related skeletal diseases. In particular, the patient is treated with sFGFR3_Del4-C253S (SEQ ID NO: 2) or sFGFR3_Del4-D3 (SEQ ID NO: 33).

Administration of an sFGFR3 polypeptide of the invention (e.g. sFGFR3_Del4-C253S (SEQ ID NO: 2), sFGFR3_Del4-D3 (SEQ ID NO: 33), and variants thereof (SEQ ID NO: 4) or a sFGFR3 polypeptide including a signal peptide (SEQ ID NO: 18 or 34)) can treat a skeletal growth retardation disorder including, but not limited to, achondroplasia, achondrogenesis, acrodysostosis, acromesomelic dysplasia, atelosteogenesis, camptomelic dysplasia, chondrodysplasia *punctata*, rhizomelic type of chondrodysplasia *punctata*, cleidocranial dysostosis, congenital short femur, Crouzon syndrome, Apert syndrome, Jackson-Weiss syndrome, Pfeiffer syndrome, Crouzonodermoskeletal syndrome, dactyly, brachydactyly, camptodactyly, polydactyly, syndactyly, diastrophic dysplasia, dwarfism, dyssegmental dysplasia, enchondromatosis, fibrochondrogenesis, fibrous dysplasia, hereditary multiple exostoses, hypophosphatasia, hypophosphatemic rickets, Jaffe-Lichtenstein syndrome, Kniest dysplasia, Kniest syndrome, Langer-type mesomelic dysplasia, Marfan syndrome, McCune-Albright syndrome, micromelia, metaphyseal dysplasia, Jansen-type metaphyseal dysplasia, metatrophic dysplasia, Morquio syndrome, Nievergelt-type mesomelic dysplasia, neurofibromatosis (such as type 1 (e.g., with bone manifestations or without bone manifestations), type 2, or schwannomatosis), osteoarthritis, osteochondrodysplasia, osteogenesis imperfecta, perinatal lethal type of osteogenesis imperfecta, osteopetrosis, osteopoikilosis, peripheral dysostosis, Reinhardt syndrome, Roberts syndrome, Robinow syndrome, short-rib polydactyly syndromes, short stature, spondyloepiphyseal dysplasia congenita, and spondyloepimetaphyseal dysplasia.

For instance, the sFGFR3 polypeptides of the invention (e.g. sFGFR3_Del4-C253S (SEQ ID NO: 2), sFGFR3_Del4-D3 (SEQ ID NO: 33), and variants thereof (SEQ ID NO: 4) or a sFGFR3 polypeptide including a signal peptide (SEQ ID NO: 18 or 34)) can be used to treat symptoms associated with a skeletal growth retardation disorder, including the disorders described above, such as achondroplasia. Non-limiting examples of symptoms of skeletal growth retardation disorders that can be treated with the sFGFR3 polypeptides, include short limbs and trunk, bowlegs, a waddling gait, skull malformations (e.g., a large head), cloverleaf skull, craniosynostosis (e.g., premature fusion of the bones in the skull), wormian bones (e.g., abnormal thread-like connections between the bones in the skull), anomalies of the hands and feet (e.g., polydactyly or extra fingers), "hitchhiker" thumbs and abnormal fingernails and toenails, and chest anomalies (e.g., pear-shaped chest or narrow thorax). Additional symptoms that can treated by administering sFGFR3 polypeptides can also include non-skeletal abnormalities in patients having skeletal growth retardation disorders, such as anomalies of the eyes, mouth, and ears, such as congenital cataracts, myopia, cleft palate, or deafness; brain malformations, such as hydrocephaly, porencephaly, hydranencephaly, or agenesis of the corpus callosum; heart defects, such as atrial septal defect, patent ductus arteriosus, or transposition of the great vessels; developmental delays; or mental disabilities.

Treatment with the sFGFR3 polypeptides of the invention (e.g. sFGFR3_Del4-C253S (SEQ ID NO: 2), sFGFR3_Del4-D3 (SEQ ID NO: 33), and variants thereof (SEQ ID NO: 4) or a sFGFR3 polypeptide including a signal peptide (SEQ ID NO: 18 or 34)) can also increase survival of patients (e.g., humans) with skeletal growth retardation disorders (e.g., achondroplasia). For example, the survival rate of patients treated with the sFGFR3 polypeptides can increase by at least 10%, 20%, 30%, 40%, 50%, 60%, 70%, 80%, 90%, 95%, or more relative to, e.g., an untreated patient with a skeletal growth retardation disorder (e.g., achondroplasia), over a treatment period of days, months, years, or longer. In particular, administration of sFGFR3_Del4-D3 can increase survival of patients (e.g., humans) with skeletal growth retardation disorders (e.g., relative to an untreated patient), such as achondroplasia.

Any skeletal growth retardation disorder that is a FGFR3-related skeletal disease (e.g., caused by or associated with overactivation of FGFR3 as result of a gain-of-function FGFR3 mutation) can be treated by administering an sFGFR3 polypeptide of the invention ((e.g. sFGFR3_Del4-C253S (SEQ ID NO: 2), sFGFR3_Del4-D3 (SEQ ID NO: 33), and variants thereof (SEQ ID NO: 4) or a sFGFR3 polypeptide including a signal peptide (SEQ ID NO: 18 or 34)) to a patient (e.g., a human). For example, FGFR3-related skeletal diseases can include, but are not limited to, achondroplasia, thanatophoric dysplasia type I (TDI), thanatophoric dysplasia type II (TDII), severe achondroplasia with developmental delay and acanthosis nigricans (SADDAN), hypochondroplasia, and craniosynostosis (e.g., Muenke syndrome, Crouzon syndrome, and Crouzonodermoskeletal syndrome).

Patients (e.g., humans) with mutations in the FGFR3 gene associated with different FGFR3-related skeletal disorders, such as achondroplasia, hypochondroplasia, SADDAN, TDI, and TDII, can be treated with sFGFR3 polypeptides of the invention (e.g. sFGFR3_Del4-C253S (SEQ ID NO: 2), sFGFR3_Del4-D3 (SEQ ID NO: 33), and variants thereof (SEQ ID NO: 4) or a sFGFR3 polypeptide including a signal peptide (SEQ ID NO: 18 or 34)). For example, the sFGFR3 polypeptides can be administered to treat achondroplasia resulting from the G380R, G375C, G346E or S279C mutations of the FGFR3 gene. Administration of the sFGFR3 polypeptides can be used to treat the following exemplary FGFR3-related skeletal disorders: hypochondroplasia resulting from the G375C, G346E or S279C mutations of the FGFR3 gene; TDI resulting from the R248C, S248C, G370C, S371C, Y373C, X807R, X807C, X807G, X807S, X807W and K650M mutations of the FGFR3 gene; TDII resulting from the K650E mutation of the FGFR3 gene; and SADDAN resulting from the K650M mutation of the FGFR3 gene.

Any of the aforementioned mutations in the FGFR3 gene (e.g., the G380R mutation of the FGFR3 gene) can be detected in a sample from the patient (e.g., a human with achondroplasia, hypochondroplasia, SADDAN, TDI, and TDII) prior to or after treatment with an sFGFR3 polypeptide of the invention (e.g. sFGFR3_Del4-C253S (SEQ ID NO: 2), sFGFR3_Del4-D3 (SEQ ID NO: 33), and variants thereof (SEQ ID NO: 4) or a sFGFR3 polypeptide including a signal peptide (SEQ ID NO: 18 or 34)). Additionally, the parents of the patient and/or fetal samples (e.g., fetal nucleic acid obtained from maternal blood, placental, or fetal samples) can be tested by methods known in the art for the mutation in the FGFR3 gene to determine their need for treatment.

Achondroplasia

Achondroplasia is the most common cause of dwarfism in humans and can be treated by administering sFGFR3 polypeptides as described herein. In particular, achondroplasia can be treated by administering an sFGFR3 polypeptide of the invention (e.g. sFGFR3_Del4-C253S (SEQ ID NO: 2), sFGFR3_Del4-D3 (SEQ ID NO: 33), and variants thereof (SEQ ID NO: 4) or a sFGFR3 polypeptide including a signal peptide (SEQ ID NO: 18 or 34)). Accordingly, administration of the sFGFR3 polypeptides can result in an improvement in symptoms including, but not limited to, growth retardation, skull deformities, orthodontic defects, cervical cord compression (with risk of death, e.g., from central apnea or seizures), spinal stenosis (e.g., leg and lower back pain), hydrocephalus (e.g., requiring cerebral shunt surgery), hearing loss due to chronic otitis, cardiovascular disease, neurological disease, respiratory problems, fatigue, pain, numbness in the lower back and/or spine, and/or obesity.

Patients treated using the sFGFR3 polypeptides of the invention (e.g. sFGFR3_Del4-C253S (SEQ ID NO: 2), sFGFR3_Del4-D3 (SEQ ID NO: 33), and variants thereof (SEQ ID NO: 4) or a sFGFR3 polypeptide including a signal peptide (SEQ ID NO: 18 or 34)) can include infants, children, and adults with achondroplasia. In particular, infants are often diagnosed with achondroplasia at birth, and thus, treatment with the sFGFR3 polypeptides can begin as early as possible in the patient's life, e.g., shortly after birth, or prior to birth (in utero).

Symptoms of achondroplasia in patients (e.g., humans) can also be monitored prior to or after a patient is treated with an sFGFR3 polypeptide of the invention (e.g. sFGFR3_Del4-C253S (SEQ ID NO: 2), sFGFR3_Del4-D3 (SEQ ID NO: 33), and variants thereof (SEQ ID NO: 4) or a sFGFR3 polypeptide including a signal peptide (SEQ ID NO: 18 or 34)). For instance, symptoms of achondroplasia can be monitored prior to treatment to assess the severity of achondroplasia and condition of the patient prior to performing the methods.

The methods can include diagnosis of achondroplasia in a patient and monitoring the patient for changes in the symptoms of achondroplasia, such as changes in body weight and skull size (e.g., skull length and/or skull width) of the patient. Changes in body weight and skull size can be monitored over a period of time, e.g., 1, 2, 3, 4 or more times per month or per year or approximately every 1, 2, 3, 4, 5, 6, 7, 8, 12 or 16 weeks over the course of treatment with the sFGFR3 polypeptide of the invention (e.g. sFGFR3_Del4-C253S (SEQ ID NO: 2), sFGFR3_Del4-D3 (SEQ ID NO: 33), and variants thereof (SEQ ID NO: 4) or a sFGFR3 polypeptide including a signal peptide (SEQ ID NO: 18 or 34)). Body weight and/or skull size of the patient having achondroplasia can also be determined at treatment specific events, such as before and/or after administration of the sFGFR3 polypeptide.

For example, body weight and/or skull size can be measured in response to administration of the sFGFR3 polypeptide of the invention (e.g. sFGFR3_Del4-C253S (SEQ ID NO: 2), sFGFR3_Del4-D3 (SEQ ID NO: 33), and variants thereof (SEQ ID NO: 4) or a sFGFR3 polypeptide including a signal peptide (SEQ ID NO: 18 or 34)). Body weight can be measured by weighing the patient having achondroplasia on a scale, preferably in a standardized manner, such as with the same or no clothes or at a certain time of the day, preferably in a fasting state (e.g., in the morning before breakfast or after at least 1, 2, 3, 4, 5 or more hours of fasting). Skull size can be represented by length, height, width, and/or circumference of the skull. Measurements can be performed using any known or self-devised standardized method. For a human subject, the measurement of skull circumference is preferred, which can be measured using a flexible and non-stretchable material, such as a tape, wrapped around the widest possible circumference of the head (e.g. from the most prominent part of the forehead around to the widest part of the back of the head). The height of the skull of the subject (e.g., human) can also be determined from the underside of the chin to the uppermost point of the head. Preferably, any measurement is performed more than once, e.g. at least 2, 3, 4, 5, 6, 7, 8, 9, 10, or more times.

Administration of sFGFR3 Polypeptides

An sFGFR3 polypeptide of the invention (e.g. sFGFR3_Del4-C253S (SEQ ID NO: 2), sFGFR3_Del4-D3 (SEQ ID NO: 33), and variants thereof (SEQ ID NO: 4) or a sFGFR3 polypeptide including a signal peptide (SEQ ID NO: 18 or 34)) can be administered by any route known in the art, such as by parenteral administration, enteral administration, or topical administration. In particular, the sFGFR3 polypeptide can be administered to the patient having a skeletal growth retardation disorder (e.g., achondroplasia) subcutaneously (e.g., by subcutaneous injection), intravenously, intramuscularly, intra-arterially, intrathecally, or intraperitoneally.

An sFGFR3 polypeptide of the invention (e.g. sFGFR3_Del4-C253S (SEQ ID NO: 2), sFGFR3_Del4-D3 (SEQ ID NO: 33), and variants thereof (SEQ ID NO: 4) or a sFGFR3 polypeptide including a signal peptide (SEQ ID NO: 18 or 34)) can be administered to a patient (e.g., a human) at a predetermined dosage, such as in an effective amount to treat a skeletal growth retardation disorder (e.g., achondroplasia), without inducing significant toxicity. For example, sFGFR3 polypeptides can be administered to a patient having skeletal growth retardation disorders (e.g., achondroplasia) in individual doses ranging from about 0.002 mg/kg to about 50 mg/kg (e.g., from 2.5 mg/kg to 30 mg/kg, from 0.002 mg/kg to 20 mg/kg, from 0.01 mg/kg to 2 mg/kg, from 0.2 mg/kg to 20 mg/kg, from 0.01 mg/kg to 10 mg/kg, from 10 mg/kg to 100 mg/kg, from 0.1 mg/kg to 50 mg/kg, 0.5 mg/kg to 20 mg/kg, 1.0 mg/kg to 10 mg/kg, 1.5 mg/kg to 5 mg/kg, or 0.2 mg/kg to 3 mg/kg). In particular, the sFGFR3 polypeptide can be administered in individual doses of, e.g., 0.001 mg/kg to 50 mg/kg, such as 2.5 mg/kg to about 10 mg/kg.

Exemplary doses of an sFGFR3 polypeptide of the invention (e.g. sFGFR3_Del4-C253S (SEQ ID NO: 2), sFGFR3_Del4-D3 (SEQ ID NO: 33), and variants thereof (SEQ ID NO: 4) or a sFGFR3 polypeptide including a signal peptide (SEQ ID NO: 18 or 34)) for administration to a patient (e.g., a human) having a skeletal growth retardation disorder (e.g., achondroplasia) include, e.g., 0.005, 0.01, 0.02, 0.05, 0.1, 0.2, 0.3, 0.4, 0.5, 0.6, 0.7, 0.8, 0.9, 1, 2, 2.5, 3, 3.5, 4, 4.5, 5, 5.5, 6, 6.5, 7, 7.5, 8, 8.5, 9, 9.5, 10, 11, 12, 13, 14, 15, 20, 25, 30, 35, 40, 45, or 50 mg/kg. These doses can be administered one or more times (e.g., 2, 3, 4, 5, 6, 7, 8, 9, 10, 11, or 12 or more times) per day, week, month, or year. For example, an sFGFR3 polypeptide can be administered to patients in a weekly dosage ranging, e.g., from about 0.0014 mg/kg/week to about 140 mg/kg/week, e.g., about 0.14 mg/kg/week to about 105 mg/kg/week, or, e.g., about 1.4 mg/kg/week to about 70 mg/kg/week (e.g., 2.5 mg/kg/week, 5 mg/kg/week, 10 mg/kg/week, 20 mg/kg/week, 30 mg/kg/week, 40 mg/kg/week, or 50 mg/kg/week).

Gene Therapy

An sFGFR3 polypeptide of the invention (e.g. sFGFR3_Del4-C253S (SEQ ID NO: 2), sFGFR3_Del4-D3 (SEQ ID NO: 33), and variants thereof (SEQ ID NO: 4) or a sFGFR3 polypeptide including a signal peptide (SEQ ID NO: 18 or 34)) can also be delivered through gene therapy, where a polynucleotide encoding the sFGFR3 polypeptide is delivered to tissues of interest and expressed in vivo. Gene therapy methods are discussed, e.g., in Verme et al. (*Nature* 389: 239-242, 1997), Yamamoto et al. (*Molecular Therapy* 17: S67-S68, 2009), and Yamamoto et al., (*J. Bone Miner. Res.* 26: 135-142, 2011), each of which is hereby incorporated by reference.

An sFGFR3 polypeptide of the invention (e.g. sFGFR3_Del4-C253S (SEQ ID NO: 2), sFGFR3_Del4-D3 (SEQ ID NO: 33), and variants thereof (SEQ ID NO: 4) or a sFGFR3 polypeptide including a signal peptide (SEQ ID NO: 18 or 34)) can be produced by the cells of a patient (e.g., a human) having a skeletal growth retardation disorder (e.g., achondroplasia) by administrating a vector (e.g., a plasmid, an artificial chromosome (e.g. BAG, PAC, and YAC), or a viral vector) containing the nucleic acid sequence of a polynucleotide encoding the sFGFR3 polypeptide. For example, a viral vector can be a retroviral vector, adenoviral vector, or poxviral vector (e.g., vaccinia viral vector, such as Modified Vaccinia Ankara (MVA)), adeno-associated viral vector, or alphaviral vector. The vector, once inside a cell of the patient (e.g., a human) having a skeletal growth retardation disorder (e.g., achondroplasia), by, e.g., transformation, transfection, electroporation, calcium phosphate precipitation, or direct microinjection, will promote expression of the sFGFR3 polypeptide, which is then secreted from the cell. The invention further includes cell-based therapies, in which the patient (e.g., a human) is administered a cell expressing the sFGFR3 polypeptide.

Pharmaceutical Compositions

Pharmaceutical compositions of the invention can include an sFGFR3 polypeptide (e.g. sFGFR3_Del4-C253S (SEQ ID NO: 2), sFGFR3_Del4-D3 (SEQ ID NO: 33), and variants thereof (SEQ ID NO: 4) or a sFGFR3 polypeptide including a signal peptide (SEQ ID NO: 18 or 34)), polynucleotide, vector, and/or host cell of the invention. Compositions including an sFGFR3 polypeptide, polynucleotide, vector, and/or host cell can be formulated at a range of dosages, in a variety of formulations, and in combination with pharmaceutically acceptable excipients, carriers, or diluents.

A pharmaceutical composition including an sFGFR3 polypeptide (e.g. sFGFR3_Del4-C253S (SEQ ID NO: 2), sFGFR3_Del4-D3 (SEQ ID NO: 33), and variants thereof (SEQ ID NO: 4) or a sFGFR3 polypeptide including a signal peptide (SEQ ID NO: 18 or 34)), polynucleotide, vector, and/or host cell of the invention can be formulated at a specific dosage, such as a dosage that is effective for treating a patient (e.g., a human) skeletal growth retardation disorder (e.g., achondroplasia), without inducing significant toxicity. For example, the compositions can be formulated to include between about 1 mg/mL and about 500 mg/mL of the sFGFR3 polypeptide (e.g., between 10 mg/mL and 300 mg/mL, 20 mg/mL and 120 mg/mL, 40 mg/mL and 200 mg/mL, 30 mg/mL and 150 mg/mL, 40 mg/mL and 100 mg/mL, 50 mg/mL and 80 mg/mL, or 60 mg/mL and 70 mg/mL of the sFGFR3 polypeptide).

The pharmaceutical compositions including an sFGFR3 polypeptide (e.g. sFGFR3_Del4-C253S (SEQ ID NO: 2), sFGFR3_Del4-D3 (SEQ ID NO: 33), and variants thereof (SEQ ID NO: 4) or a sFGFR3 polypeptide including a signal peptide (SEQ ID NO: 18 or 34)), polynucleotide, vector, and/or host cell of the invention can be prepared in a variety of forms, such as a liquid solution, dispersion or suspension, powder, or other ordered structure suitable for stable storage. For example, compositions including an sFGFR3 polypeptide intended for systemic or local delivery can be in the form of injectable or infusible solutions, such as for parenteral administration (e.g., subcutaneous, intravenous, intramuscular, intra-arterial, intrathecal, or intraperitoneal administration). sFGFR3 compositions for injection (e.g., subcutaneous or intravenous injection) can be formulated using a sterile solution or any pharmaceutically acceptable liquid as a vehicle. Pharmaceutically acceptable vehicles include, but are not limited to, sterile water, physiological saline, and cell culture media (e.g., Dulbecco's Modified Eagle Medium (DMEM), α-Modified Eagles Medium (α-MEM), F-12 medium). Formulation methods are known in the art, see e.g., Banga (ed.) *Therapeutic Peptides and Proteins: Formulation, Processing and Delivery Systems* (2nd ed.) Taylor & Francis Group, CRC Press (2006), which is hereby incorporated by reference in its entirety.

Compositions including an sFGFR3 polypeptide (e.g. sFGFR3_Del4-C253S (SEQ ID NO: 2), sFGFR3_Del4-D3 (SEQ ID NO: 33), and variants thereof (SEQ ID NO: 4) or a sFGFR3 polypeptide including a signal peptide (SEQ ID NO: 18 or 34)), polynucleotide, vector, and/or host cell of the invention can be provided to patients (e.g., humans) having skeletal growth retardation disorders (e.g. achondroplasia) in combination with pharmaceutically acceptable excipients, carriers, or diluents. Acceptable excipients, carriers, or diluents can include buffers, antioxidants, preservatives, polymers, amino acids, and carbohydrates. Aqueous excipients, carriers, or diluents can include water, water-alcohol solutions, emulsions or suspensions including saline, buffered medical parenteral vehicles including sodium chloride solution, Ringer's dextrose solution, dextrose plus sodium chloride solution, Ringer's solution containing lactose, and fixed oils. Examples of non-aqueous excipients, carriers, or diluents are propylene glycol, polyethylene glycol, vegetable oil, fish oil, and injectable organic esters.

Pharmaceutically acceptable salts can also be included in the compositions including an sFGFR3 polypeptide (e.g. sFGFR3_Del4-C253S (SEQ ID NO: 2), sFGFR3_Del4-D3 (SEQ ID NO: 33), and variants thereof (SEQ ID NO: 4) or a sFGFR3 polypeptide including a signal peptide (SEQ ID NO: 18 or 34)), polynucleotide, vector, and/or host cell of the invention. Exemplary pharmaceutically acceptable salts can include mineral acid salts (e.g., hydrochlorides, hydrobromides, phosphates, and sulfates) and salts of organic acids (e.g., acetates, propionates, malonates, and benzoates). Additionally, auxiliary substances, such as wetting or emulsifying agents and pH buffering substances, can be present. A thorough discussion of pharmaceutically acceptable excipients, carriers, and diluents is available in *Remington: The Science and Practice of Pharmacy,* $22^{nd}$ Ed., Allen (2012), which is hereby incorporated by reference in its entirety.

Pharmaceutical compositions including an sFGFR3 polypeptide (e.g. sFGFR3_Del4-C253S (SEQ ID NO: 2), sFGFR3_Del4-D3 (SEQ ID NO: 33), and variants thereof (SEQ ID NO: 4) or a sFGFR3 polypeptide including a signal peptide (SEQ ID NO: 18 or 34)), polynucleotide, vector, and/or host cell of the invention can also be formulated with a carrier that will protect the sFGFR3 polypeptide against rapid release, such as a controlled release formulation, including implants and microencapsulated delivery systems. For example, the sFGFR3 composition can be entrapped in microcapsules prepared by coacervation techniques or by interfacial polymerization, such as hydroxymethylcellulose, gelatin, or poly-(methylmethacylate) microcapsules; colloidal drug delivery systems (e.g., liposomes, albumin microspheres, microemulsions, nano-particles, or nanocapsules); or macroemulsions. Additionally, an sFGFR3 composition can be formulated as a sustained-release composition. For example, sustained-release compositions can include semipermeable matrices of solid hydrophobic polymers containing the sFGFR3 polypeptides, polynucleotides, vectors, or host cells of the invention, in which the matrices are in the form of shaped articles, such as films or microcapsules.

Kits

Kits of the invention can include one or more sFGFR3 polypeptides (e.g. sFGFR3_Del4-C253S (SEQ ID NO: 2), sFGFR3_Del4-D3 (SEQ ID NO: 33), and variants thereof (SEQ ID NO: 4) or a sFGFR3 polypeptide including a signal peptide (SEQ ID NO: 18 or 34)), polynucleotides, vectors, and/or cells of the invention as described herein. For example, the sFGFR3 polypeptide, polynucleotide, vector, and/or cell can be present in a container (e.g., a glass vial) in liquid form (e.g., in water or a buffered salt solution, such as, 2 mM to 20 mM of sodium phosphate, pH 6.5 or 7.0, and 25 mM to 250 mM sodium chloride). Alternatively, the sFGFR3 polypeptide, polynucleotide, and/or vector is present in a container (e.g., a glass vial) in lyophilized form, which can optionally include a diluent (e.g., water or a buffered salt solution) for reconstitution of the lyophilized sFGFR3 polypeptide, polynucleotide, vector, and/or cell into liquid form prior to administration. The sFGFR3 polypeptide, polynucleotide, vector, and/or cell can also be present in a kit in another formulation as described herein. The kit components can be provided in dosage form to facilitate administration, and optionally, can include materials required for administration and/or instructions for patient treatment consistent with the methods. For example, the kit can include instructions for use, which guides the user (e.g., the physician) with respect to the administration of the sFGFR3 polypeptide, polynucleotide, vector, and/or cell.

EXAMPLES

The following examples are intended to illustrate, rather than limit, the disclosure. These studies feature the administration of the sFGFR3 polypeptides of sFGFR3_Del4-C253S (SEQ ID NO: 2) and sFGFR3_Del4-D3 (SEQ ID NO: 33) to patients (e.g., humans) having achondroplasia, to treat achondroplasia and symptoms associated therewith.

Example 1: Production of sFGFR3 Polypeptides sFGFR3_Del4-C253S (SEQ ID NO: 2) and sFGFR3_Del4-D3 (SEQ ID NO: 33) were produced by transient transfection in three different suspension cell types: HEK 293 freestyle, CHO—S freestyle cells and Expi CHO—S cells. For production in HEK 293 freestyle and CHO—S freestyle cells, transfection was performed using polyethylenimine (PEIpro®—Polyplus-transfection), according to the manufacturer's directions. Proteins were harvested after three days. For sFGFR3 polypeptide production in Expi CHO—S cells, transfection was performed using Expifectamine as described by the manufacturer using the High Titer production protocol. A time course was performed and sFGFR3 polypeptides were optimally harvested after 12 days. Western blots were then performed using 50 ng of sFGFR3 polypeptide. Classical western blot protocols were used with B9 as a primary antibody (anti FGFR3, sc-13121, Santa Cruz) diluted 1:2000 in blocking buffer and anti-mouse IgG secondary antibody (Anti-mouse IgG, #7076, Cell signaling) diluted 1:5000 in blocking buffer.

Example 2: Purification of sFGFR3 Polypeptides sFGFR3_Del4-C253S and sFGFR3_Del4-D3 were each purified using a two-step purification process including ion exchange chromatography and size exclusion chromatography.

For ion exchange chromatography, 300 mL of culture supernatant was purified by cross flow filtration (ÄKTA™ flux, GE Healthcare) using 5 µm and 0.2 µm capsules (KGF-A0504 TT and KMP-HEC 9204 TT, GE Healthcare, respectively). The purified sample including sFGFR3_Del4-C253S or sFGFR3_Del4-D3 was then loaded on an equilibrated column at 20 mL/min, after adjusting the sample's conductivity to 14 mS/cm (ÄKTA™ pure 25 (GE Healthcare)). Columns used were HiPrep Q FF 26/10 (GE Healthcare) with a bed volume of 53 mL. The binding buffer was 1×PBS and the elution buffer was PBS 1×+1 M NaCl. The column was washed with four column volumes of 1×PBS. Elution of sFGFR3_Del4-C253S and sFGFR3_Del4-D3 was performed by two steps of 5% NaCl and 10% NaCl using four column volumes of each. Both 5% NaCl and 10% NaCl were pooled and concentrated by cross flow filtration (ÄKTA™ flux, GE Healthcare). The remaining volume was then concentrated on a 30 kDa filter by centrifugation at 4° C., 3,900 g for 10 min (MILLLIPORE® UFC903024 AMICON® Ultra-15 Centrifugal Filter Concentrator). For size exclusion chromatography, the remaining volume was loaded on a HiLoad 26/600 SUPERDEX™ 200 prep grade (28-9893-36, GE Healthcare) with a bed volume of 320 mL. Loading volume did not exceed 12.8 mL. Elution was performed in 1×PBS.

Example 3: Kinetic Assays and Dissociation Constant ($K_d$) Measurements of sFGFR3 Polypeptides Calibration Free Concentration Analysis and kinetic assays of sFGFR3_Del4-C253S and sFGFR3_Del4-D3 were performed with a Sensor Chip CM5 (GE Healthcare). Human FGF2 (hFGF2) was covalently immobilized to the Sensor Chip CM5 at a level of about 5000 RU by amine coupling. To achieve 5000 RU, hFGF2 was immobilized for 420 seconds at a flow rate 10 µl/min and a concentration 25 µg/ml. Running buffer was HBS-EP+ Buffer (GE Healthcare). Regeneration buffer was 100 mM sodium acetate with 2M sodium chloride pH 4.5. FGF binding, dissociation constant ($K_d$) measurements, and kinetic parameters were determined by Surface Plasmon Resonance using a BIACORE™ T200 (GE Healthcare). The model used for kinetic assays and $K_d$ determination was a 1:1 binding algorithm.

Example 4: Proliferation Assays of sFGFR3 Polypeptides

Both ATDC5 and ATDC5 FGFR3$^{G380R}$ cell lines were seeded at a density of 25,000 cells/cm$^2$ in NUNC™ MICROWELL™ 96-Well Optical-Bottom Plates with Polymer Base (ThermoFisher Scientific, Catalog No. 165305). After a 24 hour incubation period, cells were depleted for 48 hour in 0.5% BSA and then stimulated for 72 hour with sFGFR3_Del4-C253S or sFGFR3_Del4-D3 with and without hFGF2 (Peprotech). Cell proliferation was then measured using the CyQUANT® Direct Cell Proliferation Assay (Molecular Probes, Catalog No. C35012). After stimulation, 10 µL of CyQUANT® Direct Cell Proliferation (Invitrogen; 1 mL 1×PBS, 250 µL background suppressor, and 50 µL nuclear stain) was added per well. ATDC5 and ATDC5 FGFR3$^{G380R}$ cells were then incubated at room temperature in the dark for 2 hours.

Fluorescence was read using the VARIOSKAN™ LUX multimode microplate reader (ThermoFisher Scientific).

Example 5: Luciferase Assays of sFGFR3 Polypeptides

Serum Response Element-Luciferase (SRE-Luc) HEK cells expressing FGFR3$^{G380R}$ were seeded at a density of 100,000 cells/cm$^2$ in a standard culture 96 well plate. Cells were then depleted for 24 hours with 0.5% heat inactivated Fetal Bovine Serum (hiFBS), before being treated with sFGFR3_Del4-D3 at concentrations of 0 nm, 70 nm, and 280 nm with or without 1 ng/ml of hFGF2 for 24 h. The culture plate was equilibrated to room temperature for 15 minutes prior to adding 100 µL per well of Firefly Luc One-Step Glow Assay Working Solution (ThermoFisher Scientific, Catalog No. 16197), then shaken at 600 rpm for 3 minutes. The plate was incubated at room temperature for 10 minutes and each cell lysate was transferred to a white opaque 96 well plate to increase luminescence signal and decrease cross contamination. The luminescence signal was read using the VARIOSKAN™ LUX multimode microplate reader (Thermo Fisher Scientific).

Example 6: In Vivo Efficacy Study of sFGFR3 Polypeptides

Experiments were performed on transgenic Fgfr3$^{ach/+}$ animals in which expression of the mutant FGFR3 is driven by the Col2a1 promoter/enhancer. Mice were exposed to a 12 hour light/dark cycle and had free access to standard laboratory food and water. Genotypes were verified by PCR of genomic DNA using the primers 5'-AGGTGGCCTTTGACACCTACCAGG-3' (SEQ ID NO: 30) and 5'-TCTGTTGTGTTTCCTCCCTGTTGG-3' (SEQ ID NO: 31), which amplify 360 bp of the FGFR3 transgene.

sFGFR3_Del4-D3 produced using CHO cells was evaluated at a subcutaneous dose of 0.25 mg/kg twice weekly. At day 3, all newborn mice from a single litter received the same dose. Control litters received 10 μl of PBS (vehicle). Thereafter, subcutaneous injections of sFGFR3_Del4-D3 (0.25 mg/kg) were administered twice a week for three weeks, alternatively on the left and right sides of the back. Mice were observed daily with particular attention to locomotion and urination alterations. Breeding was performed to generate litters with half wild type and half heterozygous Fgfr3$^{ach/+}$ mice. To avoid bias due to phenotype penetrance variations, experiments were performed on at least two litters (one treated and one control) from the same breeders. Previous data indicated there was no statistical difference between males and females, and thus, males and females were considered one group for all analyses.

At day 22, all animals were sacrificed by lethal injection of pentobarbital, and gender was determined. All subsequent measurements and analyses were performed without knowledge of mice genotype to avoid investigator bias. Genotyping was performed at the end of the study to reveal the correspondence of data with a specific genotype. Since achondroplasia is a disease with phenotypic variability, all animals were included in the study. Animals dead before day 22 were used to investigate the impact of treatment on premature death. Surviving animals at day 22 were used for all analyses. All experiments and data measurements were performed by blinded experimenters at all time points.

Following sacrifice at day 22, body weights were measured. Cadavers were carefully skinned, eviscerated, and skeletal measurements were performed based on X-rays. Organs were harvested, weighed, and stored in 10% formalin for further histological analysis using standard paraffin-embedded techniques. Organs were then observed for macroscopic abnormalities, such as modification of color or texture and presence of nodules. The Principles of Laboratory Animal Care (NIH publication no. 85-23, revised 1985; grants1.nih.gov/grants/olaw/references/phspol.htm) and the European commission guidelines for the protection of animals used for scientific purposes (ec.europa.eu/environment/chemicals/lab_animals/legislation_en.htm) were followed during all animal experiments. All procedures were approved by the Institutional Ethic Committee for the use of Laboratory Animals (CIEPAL Azur) (approval #NCE-2012-52).

Example 7: The Cell Line Used to Produce sFGFR3 Polypeptides Did not Impact Activity The FGF2 binding activity, Kd, and effect on cellular signaling of sFGFR3_Del1 (SEQ ID NO: 7), sFGFR3_Del4 (SEQ ID NO: 1), and sFGFR3_Del4-LK1-LK2 (SEQ ID NO: 10) produced in suspension HEK 293 cells or CHO cells were compared. HEK 293 cells or CHO cells differ in post-translation modification of proteins. Expression of the sFGFR3 polypeptides in different cell lines did not impact Kd, binding activity, or the effect of the sFGFR3 polypeptides on intracellular signaling inhibition (FIGS. 1A-1D).

Example 8: Improved Production of sFGFR3_Del4-C2538 and sFGFR3_Del4-D3

Figure 2A:
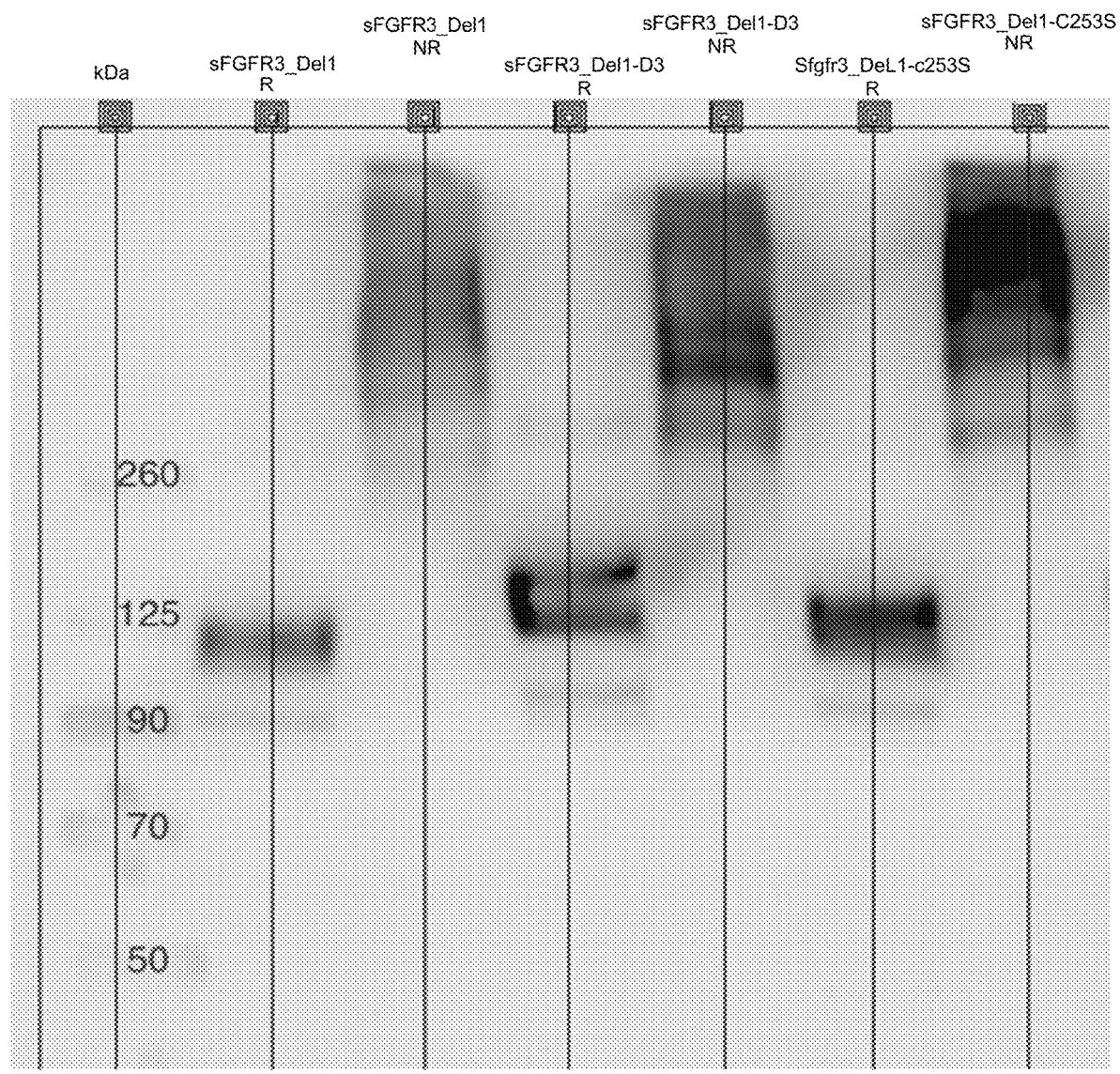
FIGS. 2A-2C are images of Western blots of the sFGFR3 polypeptides. Western blots under reducing (R) and non-reducing (NR) conditions are shown for sFGFR3 Del1, sFGFR3 Del1-C253S (SEQ ID NO: 8), and sFGFR3 Del1-D3 (FIG. 2A); sFGFR3_Del4-LK1-LK2, sFGFR3_Del4-LK1-LK2-C253S, and sFGFR3_Del4-LK1-LK2-D3 (FIG. 2B); and sFGFR3_Del4, sFGFR3_Del4-C253S, and sFGFR3_Del4-D3 (FIG. 2C).
Figure 2B:
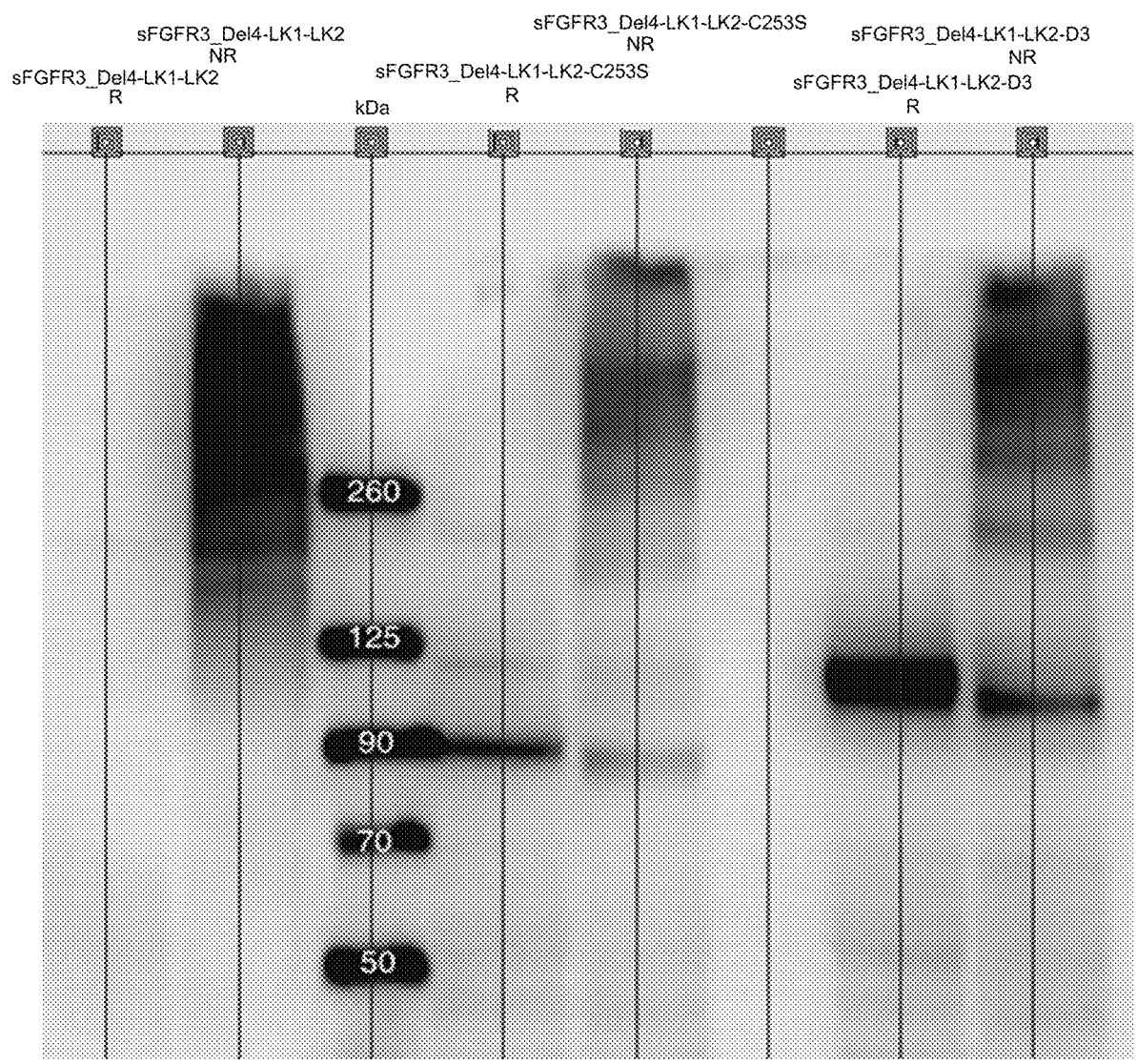
Figure 2C:
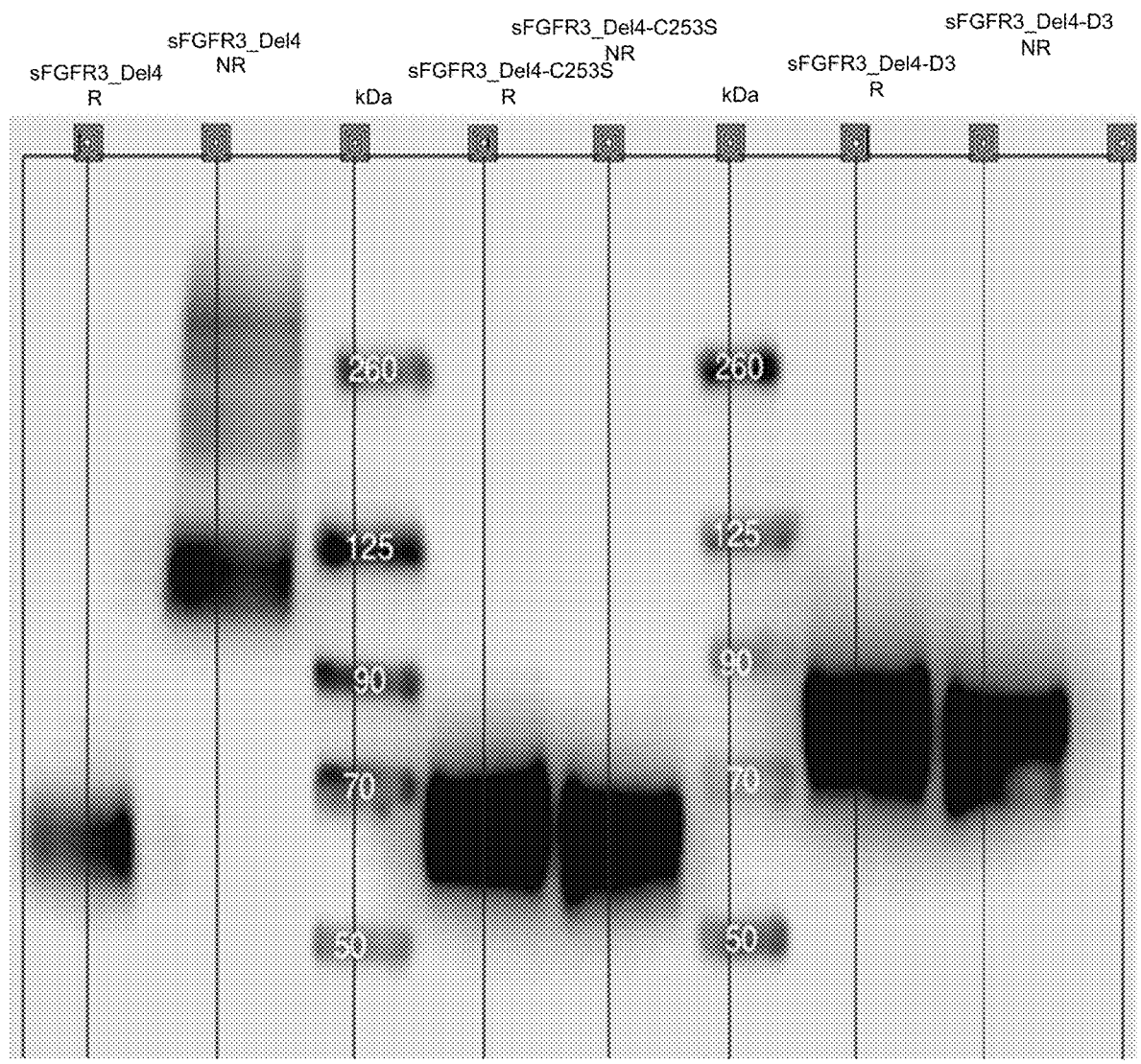

The sFGFR3 polypeptides of sFGFR3_Del1 (SEQ ID NO: 7), sFGFR3_Del4 (SEQ ID NO: 1), and sFGFR3_Del4-LK1-LK2 (SEQ ID NO: 10) were each modified to include either an amino acid substitution of a cysteine residue with a serine residue at position 253 or an extended Ig-like C2-type domain 3 (SEQ ID NO: 33). These modifications of sFGFR3_Del1 and sFGFR3_Del4-LK1-LK2 had no or minimal effect on production of the sFGFR3 polypeptides, since aggregation was still visible (FIGS. 2A and 2B, respectively). Surprisingly, modification of sFGFR3_Del4 to include either an amino acid substitution of a cysteine residue with a serine residue at position 253 (sFGFR3_Del4-C253S) or an extended Ig-like C2-type domain 3 (SEQ ID NO: 33)) improved production of the sFGFR3 polypeptides. In particular, there was minimal aggregation of sFGFR3_Del4-C253S and sFGFR3_Del4-D3 under both reducing and non-reducing conditions (FIG. 2C). The inclusion of C253S or D3 also resulted in a relative increase in production compared to sFGFR3_Del4, a two-fold increase in sFGFR3_Del4-C253S production and a 3-fold increase in sFGFR3_Del4-D3 production.

Figure 3A:
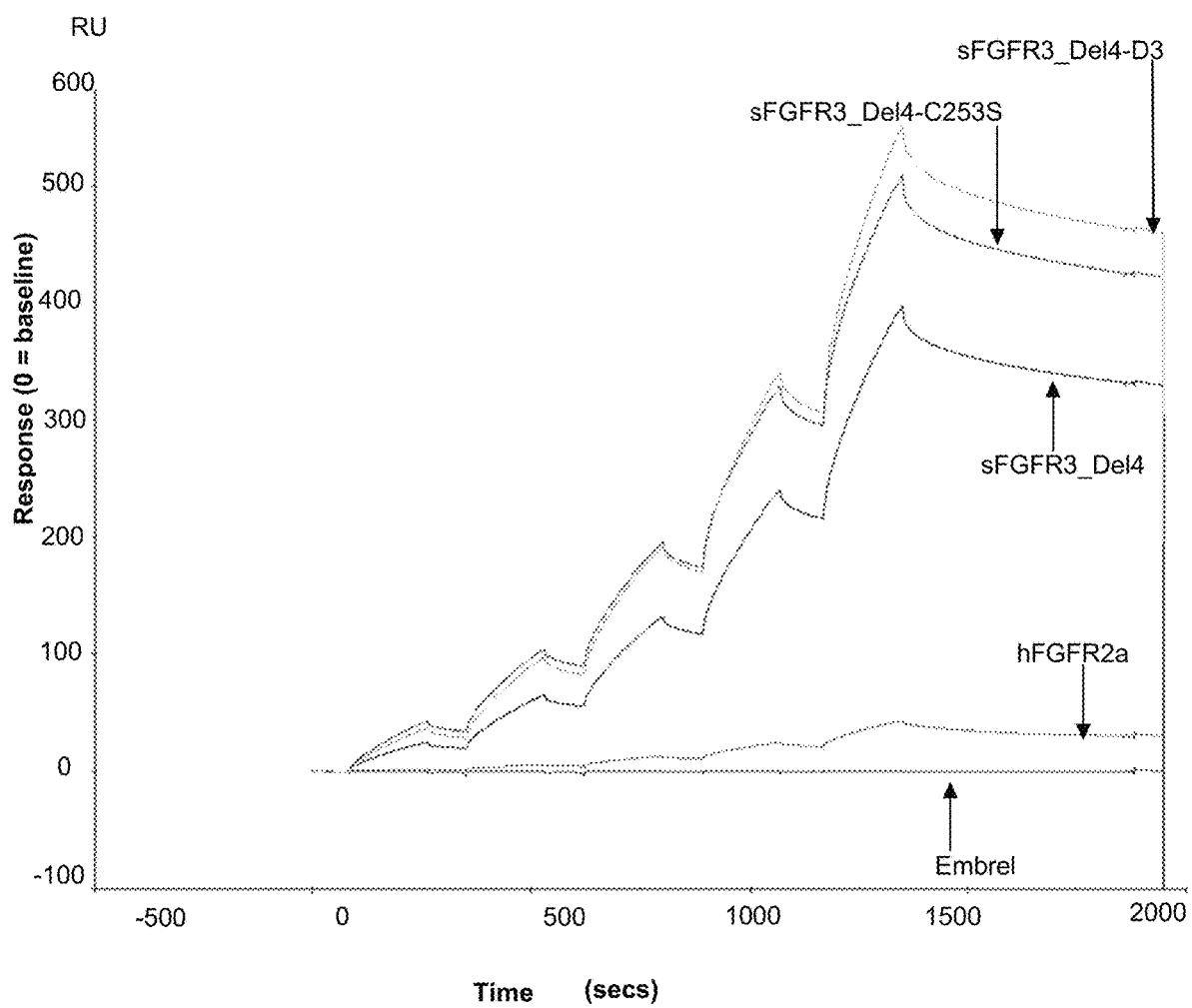

Additionally, sFGFR3_Del4, sFGFR3_Del4-C253S, and sFGFR3_Del4-D3 exhibited similar Kd and were not affected by cell type specific changes in post translational modifications. In Expi CHO cells, the Kd of sFGFR3_Del4 was 0.8 nM, the Kd of sFGFR3_Del4-C253S was 0.6 nM, and the Kd of sFGFR3_Del4-D3 was 0.7 nM (FIG. 3A and Table 1).

TABLE 1

| Dissociation constant (Kd) of sFGFR3 polypeptides. | |
|---|---|
| SFGFR3 Polypeptide | Kd (nM) |
| sFGFR3_Del4 | 0.8 |
| sFGFR3_Del4-C253S | 0.6 |
| sFGFR3_Del4-D3 | 0.7 |

Figure 4:
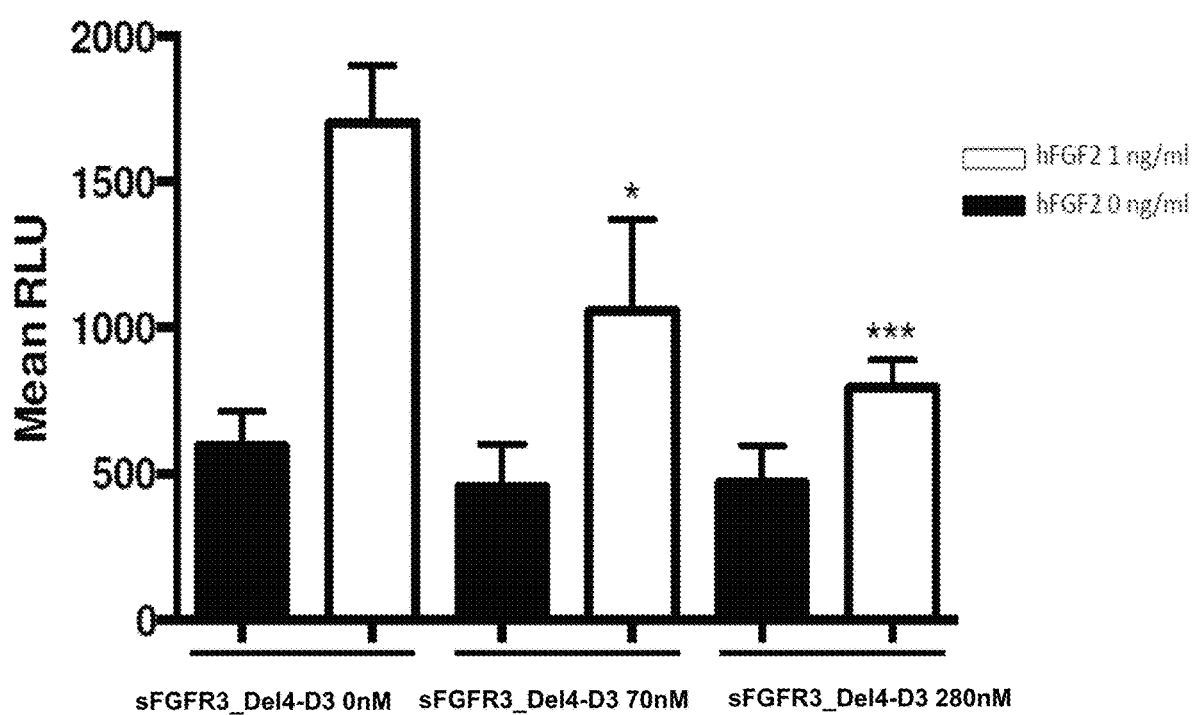
FIG. 4 is a graph showing luciferase signaling in Serum Response Element-Luciferase (SRE-Luc) HEK cells expressing FGFR3$^{G380R}$ incubated with sFGFR3_Del4-D3 at 0 nM, 70 nM, and 280 nM with or without 1 ng/mL of hFGF2 (* indicates p value<0.05; *** indicates a p value<0.001 compared to sFGFR3_Del4-D3 at 0 nM).

Example 9: sFGFR3_Del4-C253S and sFGFR3_Del4-D3 are Equally Active In Vitro sFGFR3_Del4, sFGFR3_Del4-C253S, and sFGFR3_Del4-D3 restored proliferation of ATDC5 cells genetically modified to overexpress the FGFR3$^{ach}$ mutation (ATDC5 FGFR3$^{G380R}$ cell lines). At a dose of 36 nM, sFGFR3_Del4 produced using HEK 293 cells increased proliferation to 115.5%, sFGFR3_Del4 produced using CHO—S cells increased proliferation to 116%, sFGFR3_Del4-C253S produced using CHO—S cells increased proliferation to 114.4%, and sFGFR3_Del4-D3 using CHO—S cells increased proliferation to 120.1% (FIG. 3B).

sFGFR3_Del4-D3 was also tested in the FGFR3$^{G380R}$ expressing SRE(-Luc) HEK cell line at doses of 0 nM, 70 nM, and 280 nM with or without 1 ng/ml of hFGF2 (FIG. 4;

n=8). Data shown in FIG. 4 are the mean+/−standard error of the mean (SEM). These data followed a normal law and have equal variance based on the D'Agostino-Pearson omnibus normality test. Statistical comparisons with and without sFGFR3_Del4-D3 were performed using a student t-test. As shown in FIG. 4, sFGFR3_Del4-D3 decreases luciferase signaling in the SRE cell line.

Figure 5:
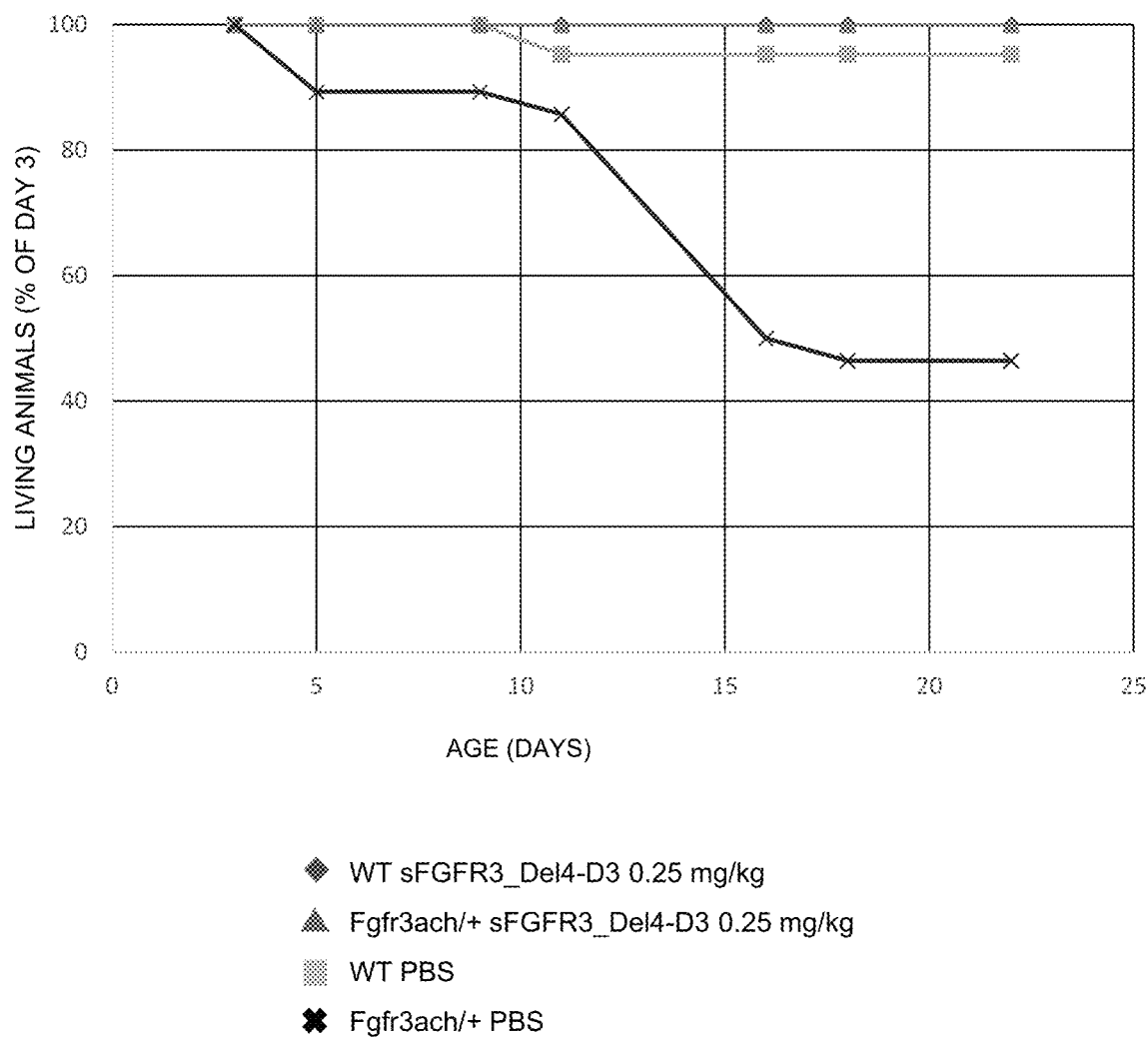
FIG. 5 is a graph showing the percentage of living animals (wild type (wt) and Fgfr3$^{ach/+}$ mice) after 3 days of treatment with a low dose (0.25 mg/kg) of sFGFR3_Del4-D3 relative to age (days). The percentage of living wt mice receiving vehicle (PBS) is also shown.

Example 10: sFGFR3_Del4-D3 Restores Bone Growth, Prevents Mortality, and Restores Foramen Magnum Shape in Mice with Achondroplasia An in vivo efficacy study was performed as in Example 6 using a low dose (0.25 mg/kg) of sFGFR3_Del4-D3. A total of 60 mice were included in the vehicle group, with 32 wild type (wt) mice and 28 Fgfr3$^{ach/+}$ mice. The treated group included 40 mice, with 19 wt mice and 21 Fgfr3$^{ach/+}$ mice. Surprisingly, the low dose of sFGFR3_Del4-D3 almost completely prevented the premature death of mice with achondroplasia (FIG. 5). In the control group, 53.6% of the Fgfr3$^{ach/+}$ mice died before weaning, whereas only 4.8% of mice in the treated group died before day 22 and 20% of mice died following treatment with sFGFR3_Del1 at 0.25 mg/kg (Table 2; see also Garcia et al. Sci. Transl. Med. 5:203ra124, 2013, hereby incorporated by reference in its entirety).

sFGFR3_Del4-D3 also partially restored bone growth with correction of the initial discrepancy between wt and Fgfr3$^{ach/+}$ mice on the axial and appendicular skeleton (Table 2). In contrast to prior results of treatment with a low dose of sFGFR3 Del1, treatment with low dose of sFGFR3_Del4-D3 restored normal foramen magnum shape.

TABLE 2

In vivo results of administering a high dose of sFGFR3_Del1, a low dose of sFGFR3_Del1, and a low dose of sFGFR3_Del4-D3 to mice with achondroplasia

|  | 2.5 mg/kg sFGFR3_Del1 (Garcia et al.) | 0.25 mg/kg sFGFR3_Del1 (Garcia et al.) | 0.25 mg/kg sFGFR3_Del4-D3 |
|---|---|---|---|
| Mortality | 12% | 20% | 4.8% |
| Axial correction | 77% | 24% | 10% |
| Appendicular correction | 150-215% | 18-42% | 11-42% |
| Foramen shape correction (ratio W/H) | Not determined | Not determined | 111% |

Example 11: Treatment of Achondroplasia by Administration of sFGFR3_Del4-C253S

Figure 6:
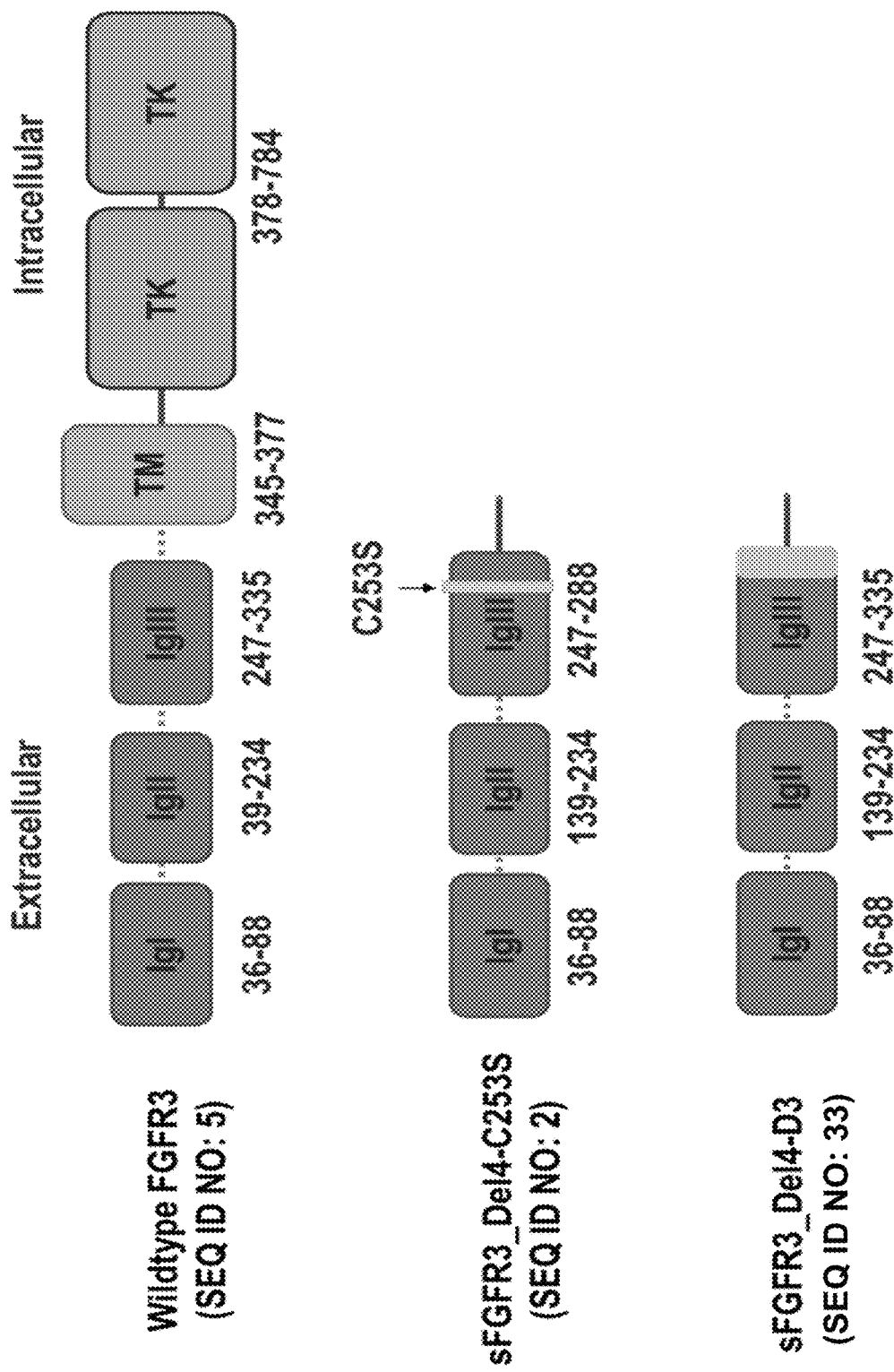
FIG. 6 is an image showing the amino acid residues corresponding to the Ig-like C2-type domains 1 (Ig1), 2 (Ig11), and 3 (Ig111) of wildtype FGFR3 polypeptide (SEQ ID NO: 5 or 32), sFGFR3_Del4-C253S (SEQ ID NO: 2), and a variant of sFGFR3_Del4-D3 (SEQ ID NO:33). sFGFR3_Del4-C253S includes an amino acid substitution of a cysteine residue with a serine residue at position 253 of SEQ ID NO: 1.

A human patient (e.g., an infant, child, adolescent, or adult) suffering from achondroplasia can be treated by administering sFGFR3_Del4-C253S (FIG. 6; SEQ ID NO: 2) by an appropriate route (e.g., by subcutaneous injection) at a particular dosage (e.g., between 0.0002 mg/kg/day to about 20 mg/kg/day, such as 0.001 mg/kg/day to 7 mg/kg/day) over a course of days, weeks, months, or years. The progression of achondroplasia that is treated with sFGFR3_Del4-C253S can be monitored by one or more of several established methods. A physician can monitor the patient by direct observation in order to evaluate how the symptoms of achondroplasia exhibited by the patient have changed in response to treatment. For instance, a physician may monitor changes in body weight, skull length, and/or skull width of the patient over a period of time, e.g., 1, 2, 3, 4 or more times per month or per year or approximately every 1, 2, 3, 4, 5, 6, 7, 8, 12, or 16 weeks over the course of treatment with sFGFR3_Del4-C253S. Body weight and/or skull size of the patient or changes thereof can also be determined at treatment specific events, e.g. before and/or after administration of sFGFR3_Del4-C253S. For example, body weight and/or skull size are measured in response to administration of sFGFR3_Del4-C253S.

Example 12: Treatment of Achondroplasia by Administration of sFGFR3_Del4-D3

Additionally, a human patient (e.g., an infant, child, adolescent, or adult) suffering from achondroplasia can be treated by administering the sFGFR3 polypeptide of sFGFR3_Del4-D3 (SEQ ID NO: 33) by an appropriate route (e.g., by subcutaneous injection) at a particular dosage (e.g., between 0.0002 mg/kg/day to about 20 mg/kg/day, such as 0.001 mg/kg/day to 7 mg/kg/day) over a course of days, weeks, months, or years. The progression of achondroplasia that is treated with sFGFR3_Del4-D3 can be monitored by one or more of several established methods. A physician can monitor the patient by direct observation in order to evaluate how the symptoms of achondroplasia exhibited by the patient have changed in response to treatment. For instance, a physician may monitor changes in body weight, skull length, and/or skull width of the patient over a period of time, e.g., 1, 2, 3, 4 or more times per month or per year or approximately every 1, 2, 3, 4, 5, 6, 7, 8, 12, or 16 weeks over the course of treatment with sFGFR3_Del4-D3. Body weight and/or skull size of the patient or changes thereof can also be determined at treatment specific events, e.g. before and/or after administration of sFGFR3_Del4-D3. For example, body weight and/or skull size are measured in response to administration of sFGFR3_Del4-D3.

Example 13: Production of sFGFR3_Del4-D3 and sFGFR3_Del4-C253S

Figure 7A:
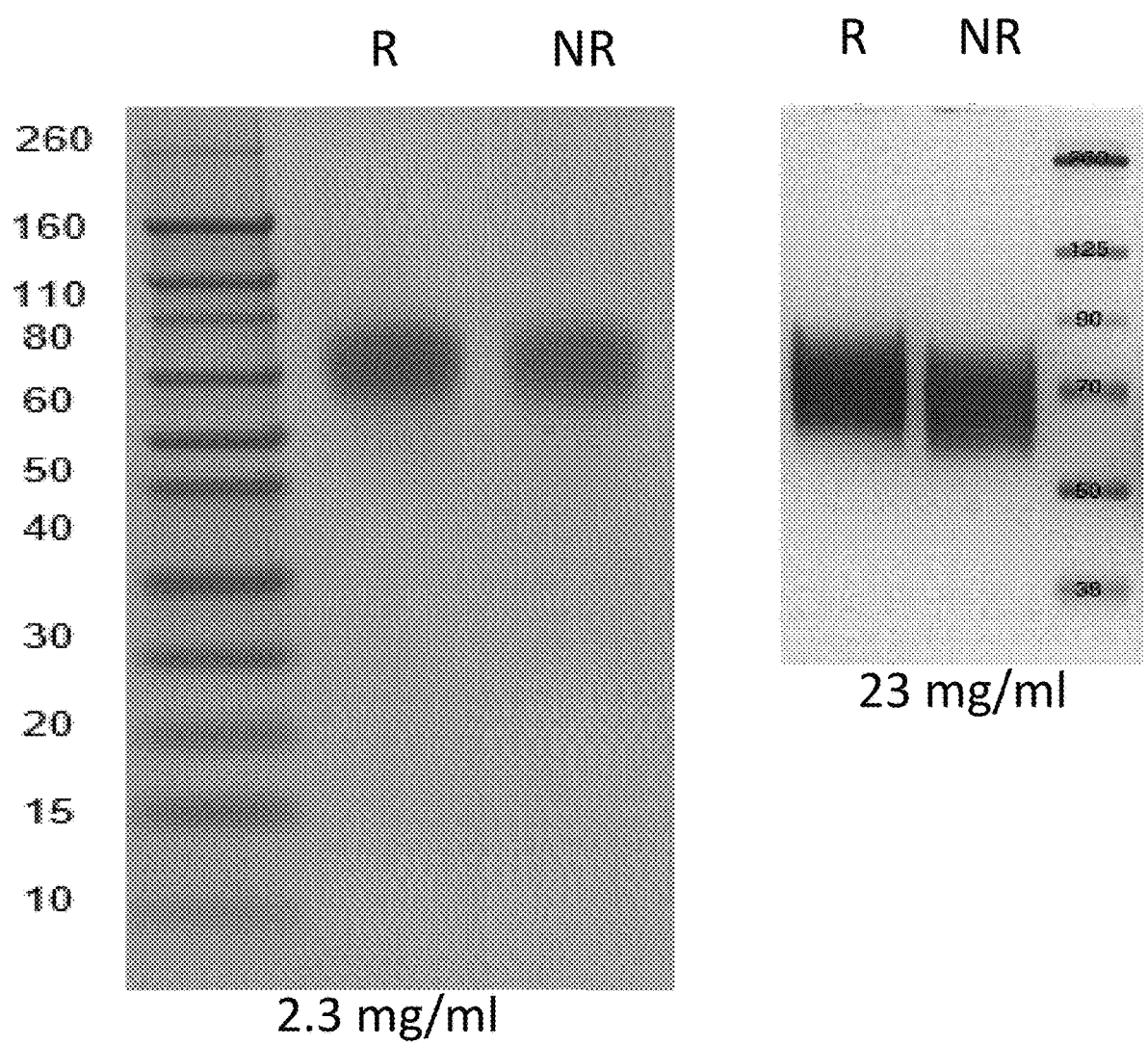
FIGS. 7A-7B are images of Western blots of the sFGFR3 polypeptides. Western blots under reducing (R) and non-reducing (NR) conditions are shown for 2.3 mg/ml and 23 mg/ml sFGFR3 Del1-D3 (FIG. 7A) and 1.5 mg/ml and 15 mg/ml sFGFR3 Del1-C253S (FIG. 7B).
Figure 7B:
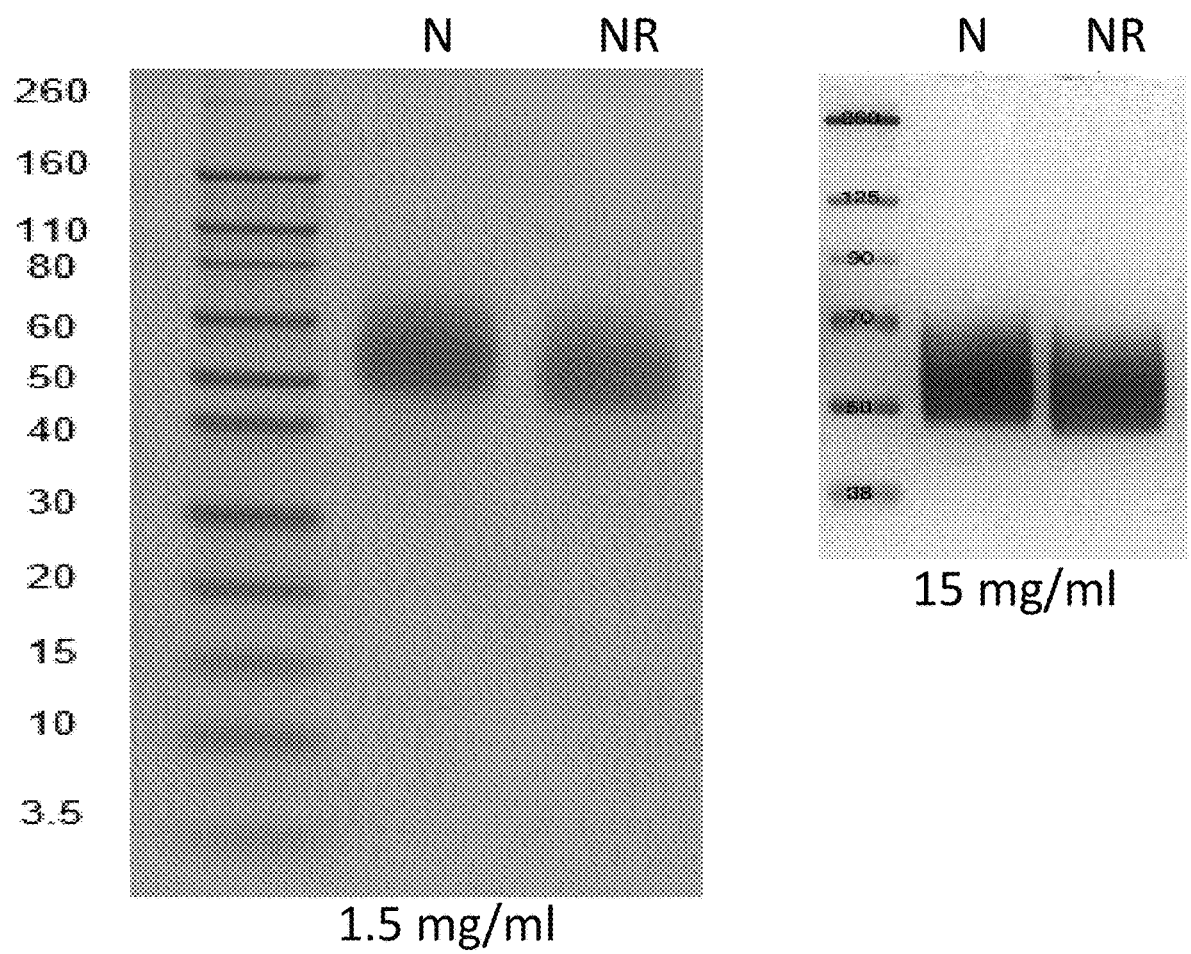

The sFGFR3_Del4-D3 and sFGFR3_Del4-C253S polypeptides were purified as described in Example 2. Modification of sFGFR3 Del4 to include either an extended Ig-like C2-type domain 3 (FGFR3_Del4-D3) or an amino acid substitution of a cysteine residue with a serine residue at position 253 (sFGFR3_Del4-C253S) improved production of the sFGFR3 polypeptides. In particular, there was less than about 2% aggregation of sFGFR3_Del4-D3 and sFGFR3_Del4-C253S (as observed upon loading using a concentration of 2.3 mg/ml or 23 mg/ml for FGFR3_Del4-D3 and 1.5 mg/ml and 15 mg/ml of sFGFR3_Del4-C253S) under both reducing and non-reducing conditions using sodium dodecyl sulfate polyacrylamide gel electrophoresis (SDS-PAGE; FIGS. 7A and 7B, respectively). Following production of sFGFR3_Del4-D3 and sFGFR3_Del4-C253S in fed-batch cultures, the top five clones were separated using capillary electrophoresis to yield 0.93 to 1.0 g/L and 0.98 to 1.1 g/L of sFGFR3_Del4-D3 and sFGFR3_Del4-C253S, respectively. Viral filtration using ion-exchange chromatography resulted in a yield of greater than 60% for both sFGFR3_Del4-D3 and sFGFR3_Del4-C253S.

Example 14: Pharmacokinetics and Tissue Distribution of sFGFR3_Del4-D3 In Vivo

In vivo studies were performed to investigate the pharmacokinetic parameters of sFGFR3_Del4-D3, the uptake of sFGFR3_Del4-D3 across the blood brain barrier, and the tissue distribution of sFGFR3_Del4-D3 in kidney, liver, spleen, lung, and heart. The studies described herein included four arms with five groups of C57BL/6J mice per arm and a total of four mice (n=4) per group (Table 3). Mice were male and weighed 25 to 30 grams.

TABLE 3

Overview of mice used in studies of sFGFR3_Del4-D3.

| Arm | sFGFR3_Del4-D3 (mg/kg) | Route | PK | BBB | Tissue distribution |
|---|---|---|---|---|---|
| 1 | 0.25 | SC | yes | no | no |
| 2 | 2.5 | SC | yes | no | yes |
| 3 | 2.5 | IV | yes | Yes | yes |
| 4 | 10 | SC | yes | no | no |

Group 1 was sampled at 1 minute, 15 minutes, and 30 minutes; group 2 was sampled at 4 hours; group 3 was sampled at 24 hours; group 4 was sampled at 36 hours; and group 5 was sampled at 48 hours. For Group 1, an indwelling intra-arterial catheter (PE-10) was inserted into one common carotid artery under isoflurane anesthesia and used for repeated blood sampling at the 30 minute final sampling time point. For intravenous injection, $^{125}$I-sFGFR3_Del4-D3 was injected intravenously into the jugular vein, which was exposed by skin incision under isoflurane anesthesia. Group 1 mice remained anesthetized throughout the experiments. Repeated blood samples (2×-50 µL) were drawn from the arterial catheter at 1 minute and 15 minutes after intravenous injection. For groups 2 to 5, after injection of $^{125}$I-sFGFR3_Del4-D3, the skin was closed with a surgical clip, and the mice were allowed to wake up and returned to the cage. At 5 minutes before termination time for group 3, mice were re-anesthetized and received an intravenous bolus of $^3$H-albumin into the jugular vein. The $^3$H tracer dose was targeted to yield a ratio of $^{125}$I to $^3$H in blood, which is suitable for double isotope labeling with a lower dose at later sampling times. At the terminal sampling time (2 hours, 3 hours, 24 hours, 36 hours, and 48 hours), a blood sample was collected, and the animal was euthanized. The brain was sampled for homogenization and determination of tissue concentration of tracers. Endpoints of the studies included pharmacokinetic parameters for sFGFR3_Del4-D3 (terminal half life), uptake of sFGFR3_Del4-D3 across the blood brain barrier, and the tissue distribution of sFGFR3_Del4-D3 in kidney, liver, spleen, lung, and heart.

Figure 8A:
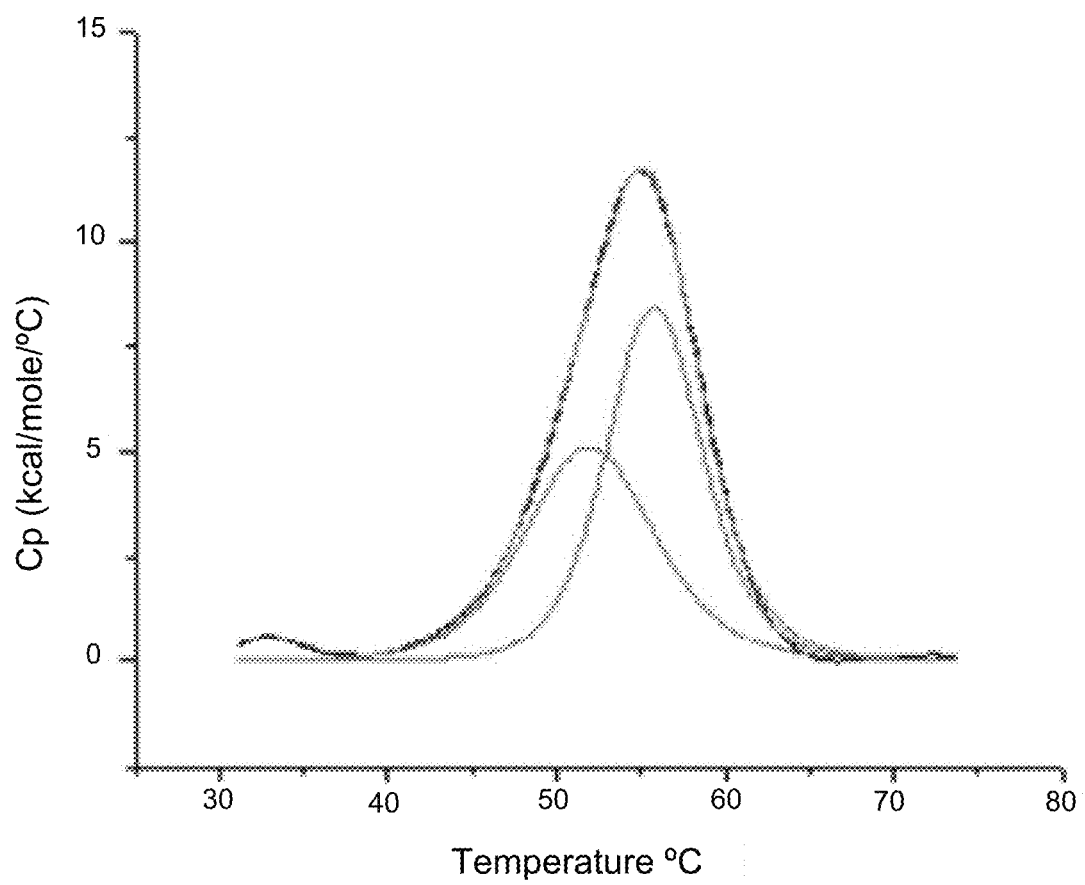
FIGS. 8A-8B are graphs showing the melting temperature ($T_m$) of sFGFR3_Del4-C253S in 20 mM phosphate, 40 mM NaCl, pH 7.5 buffer and 40 mM citrate, 40 mM NaCl, pH 6.5 buffer (FIG. 8A) and the $T_m$ of sFGFR3_Del4-D3 in 20 mM phosphate, 40 mM NaCl, pH 7.5 buffer and 20 mM citrate, 40 mM NaCl, pH 6.5 buffer (FIG. 8B).
Figure 8B:
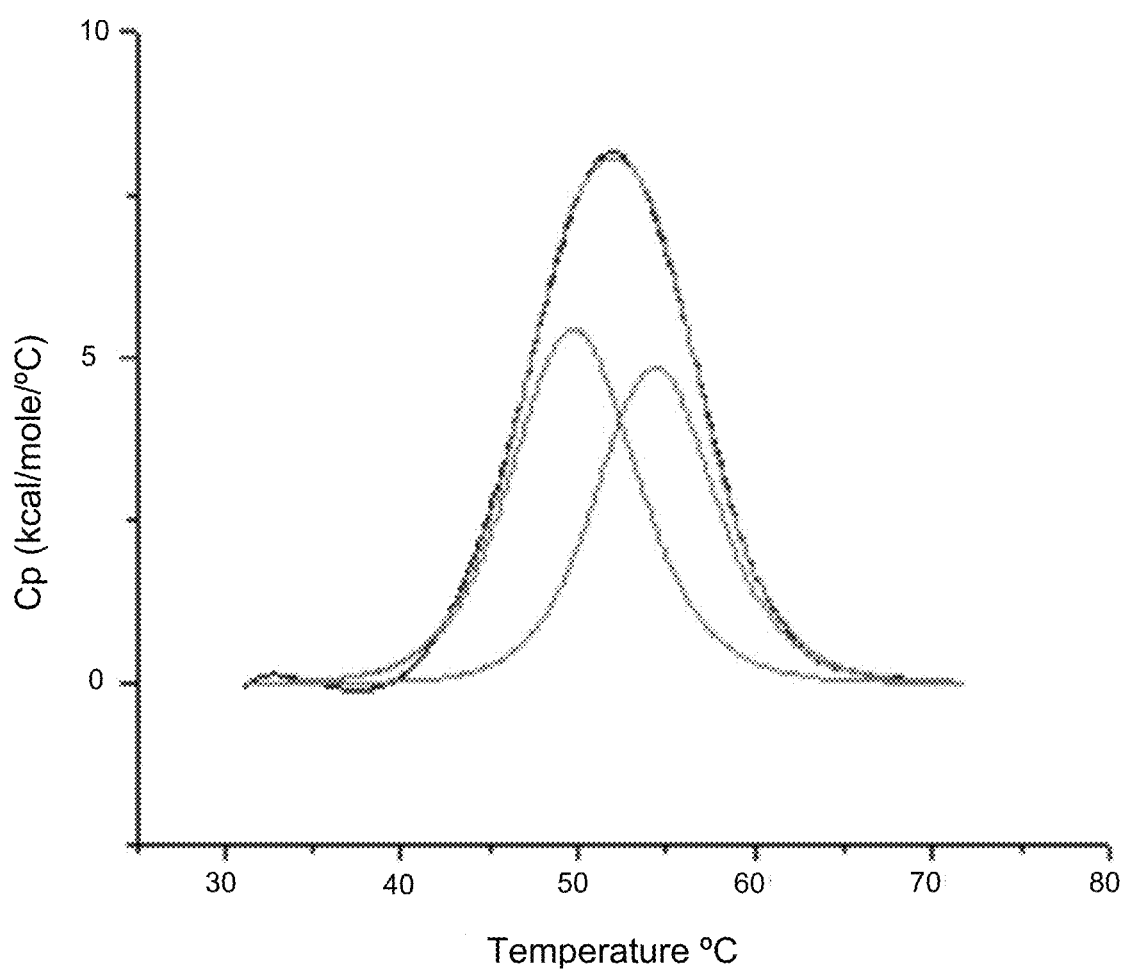

Example 15: Thermal and Plasma Stability of sFGFR3_Del4-D3 and sFGFR3_Del4-C253S The thermal stability of sFGFR3_Del4-D3 and sFGFR3_Del4-C253S in mouse plasma was investigated using differential scanning colorimetry. For sFGFR3_Del4-D3, two buffers (20 mM phosphate, 40 mM NaCl, pH 7.5, and 20 mM citrate, 40 mM NaCl, pH 6.5) were added to polypeptide samples. For sFGFR3_Del4-C253S, two buffers (20 mM phosphate, 40 mM NaCl, pH 7.5, and 40 mM citrate, 40 mM NaCl, pH 6.5) were added to polypeptide samples. The melting temperature ($T_m$) for sFGFR3_Del4-C253S in the 20 mM phosphate, 40 mM NaCl, pH 7.5 buffer was 52° C. and 56° C., and the $T_m$ for sFGFR3_Del4-C253S in the 40 mM citrate, 40 mM NaCl, pH 6.5 buffer was 55° C. and 60° C. (FIG. 8A). For sFGFR3_Del4-D3, two buffers (20 mM phosphate, 40 mM NaCl, pH 7.5, and 20 mM citrate, 40 mM NaCl, pH 6.5) were added to polypeptide samples. The $T_m$ for sFGFR3_Del4-D3 in the 20 mM phosphate, 40 mM NaCl, pH 7.5 buffer was 50° C. and 54° C., and the $T_m$ for sFGFR3_Del4-D3 in the 20 mM citrate, 40 mM NaCl, pH 6.5 buffer was 53° C. and 58° C. (FIG. 8B). These results indicate that both sFGFR3_Del4-D3 and sFGFR3_Del4-C253S show two domains of polypeptide stability and unfolding.

The ex vivo plasma stability of sFGFR3_Del4-D3 with a Histidine tag was determined by labeling purified sFGFR3_Del4-D3 with $^{125}$I-tracer using the Bolton-Hunter method, followed by purification on PD-10 (Sephadex® G-25) columns. The trichloroacetic acid (TCA) precipitability of peak fractions was also determined to confirm stability of the $^{125}$I-tracer. Mouse plasma (n=4) pre-warmed to 37° C. was spiked with the $^{125}$I-sFGFR3_Del4-D3 to a concentration of ~10 cpm/mL and then vortexed. The plasma samples were incubated with the $^{125}$I-sFGFR3_Del4-D3 in an Eppendorf ThermoMixer® under gentle rotation (300 rpm). Aliquots were then collected for TCA precipitation (10 µl sample and 100 µl 2% BSA) and for injection onto an Fast Performance Liquid Chromatography (FPLC) column (20 µl sample and 150 µl 10 mM PBS, pH 7.4) at intervals of 0, 30, 60, 120, 180, and 360 minutes. Aliquots were stored on ice until TCA precipitation or FPLC injection was performed.

Figure 9A:
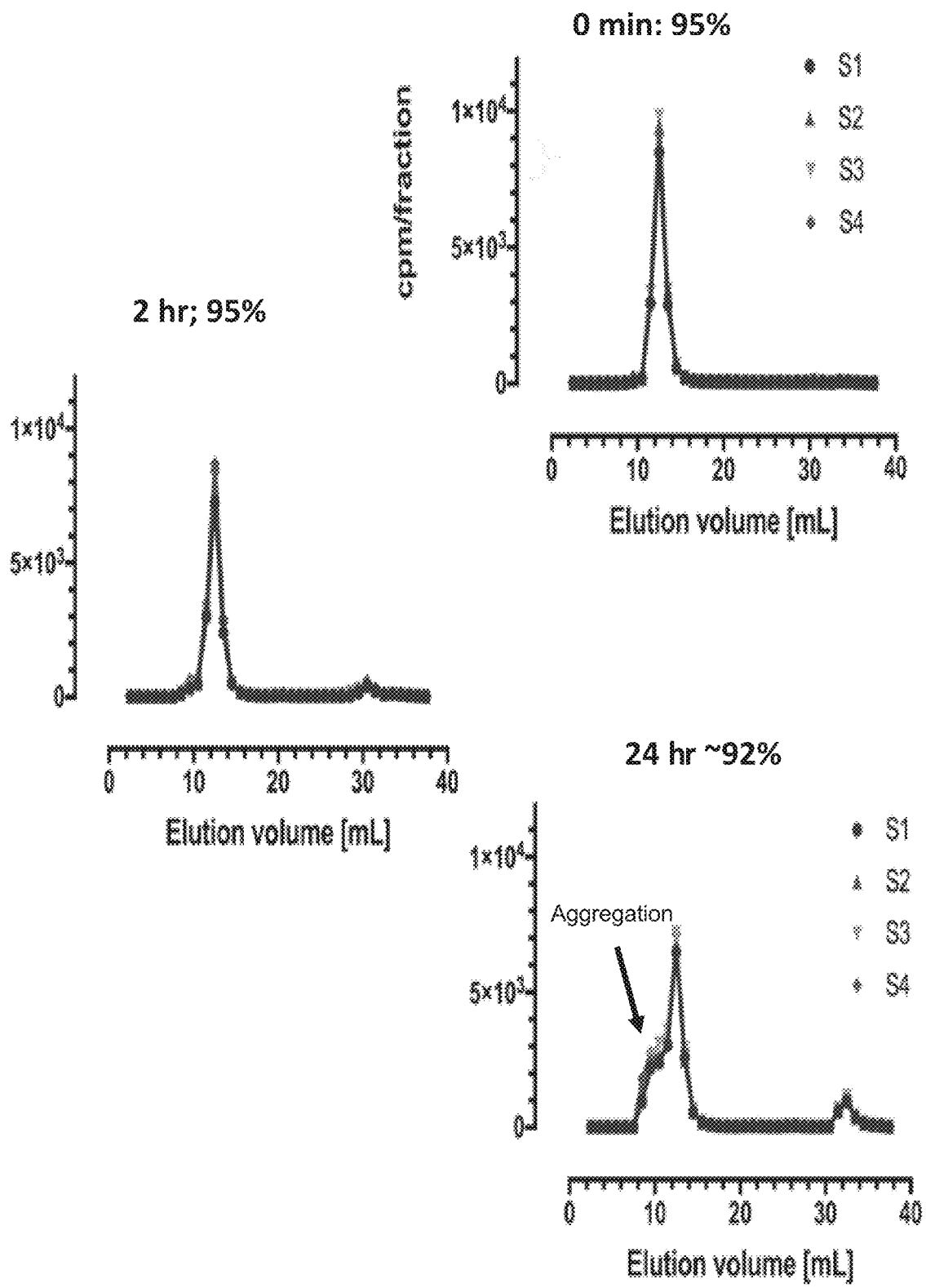
FIGS. 9A-9G are graphs showing the fast protein liquid chromatography (FPLC) elution profiles of sFGFR3_Del4-D3.

For TCA precipitation, 1 mL ice cold 10% TCA was added to plasma samples, incubated for 10 minutes on ice, centrifuged at 4,000 g for 5 minutes, and then the supernatant and pellet were separated and both were counted in a gamma counter. For evaluation of the ex vivo plasma stability, 100 µl of the sample was injected on an FPLC column (Superdex® 200 10/300 GL) and eluted at a rate of 0.75 ml/min for 1.5 column volumes. Fractions of 1 ml were collected from the column and then measured in a gamma counter. The plasma stability of sFGFR3_Del4-D3 at 37° C. was determined to be 95% at 0 minutes, 95% at 2 hours, and ~92% at 24 hours with only minor aggregation (FIG. 9A).

The in vivo stability of sFGFR3_Del4-D3 in plasma after administration by intravenous and subcutaneous injection was also determined. sFGFR3_Del4-D3 was labeled with $^{125}$I-tracer using the Bolton-Hunter method, followed by purification on PD-10 (Sephadex® G-25) columns. The $^{125}$I-labeled sFGFR3_Del4-D3 (10 µCi in ~50 µL PBS) was administered by intravenous or subcutaneous injection into anesthetized C57Bl/6 mice. The $^{125}$I-tracer protein dose (approximately 0.1 mg/kg) was complemented with unlabeled protein to a total dose of 2.5 mg/kg. Rat serum albumin used as a vascular marker was labeled with [$^3$H]-NSP (N-succininidyl[2,3-$^3$H]Propionate; Perkin Elmer) and purified on PD-10 (Sephadex® G25) columns.

Figure 9B:
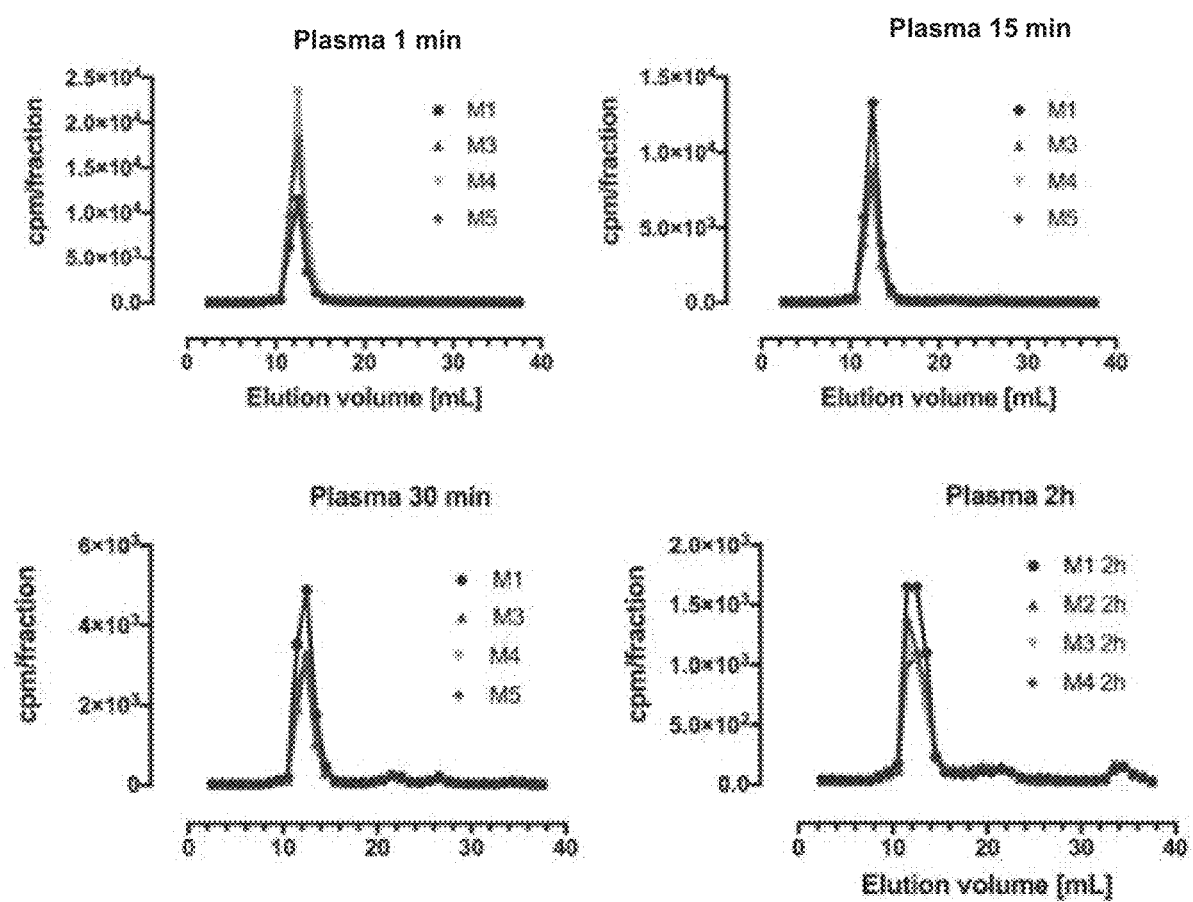
Figure 9C:
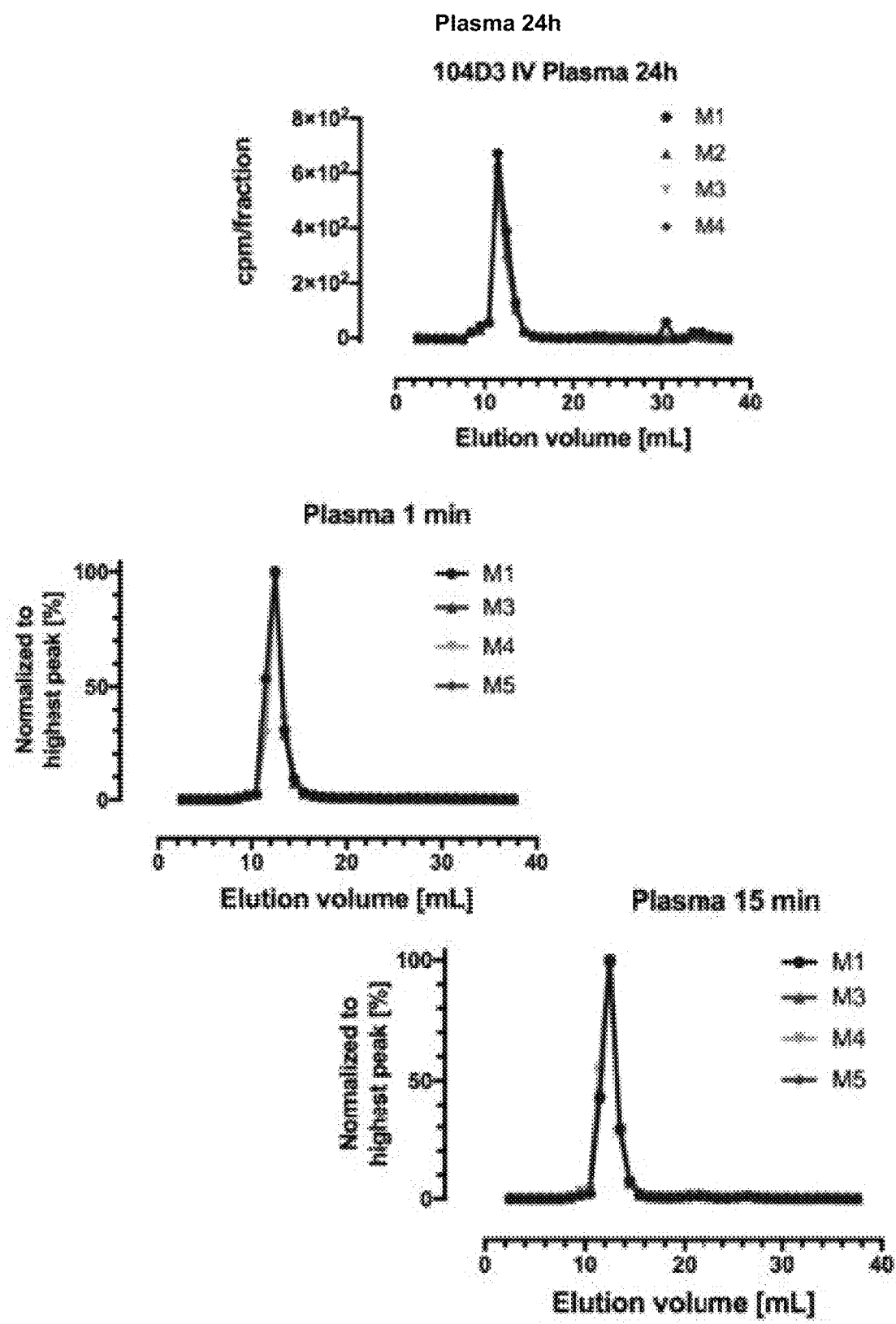
Figure 9D:
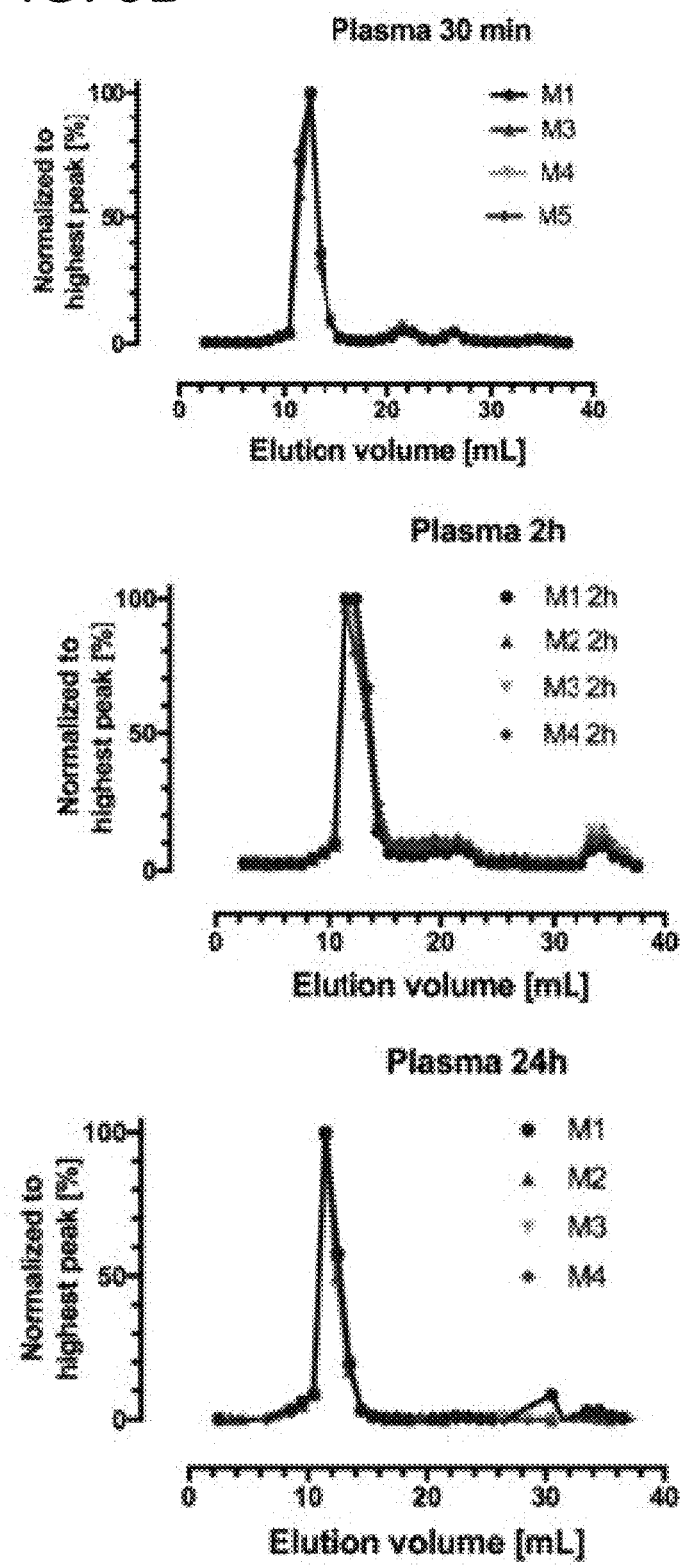
Figure 9E:
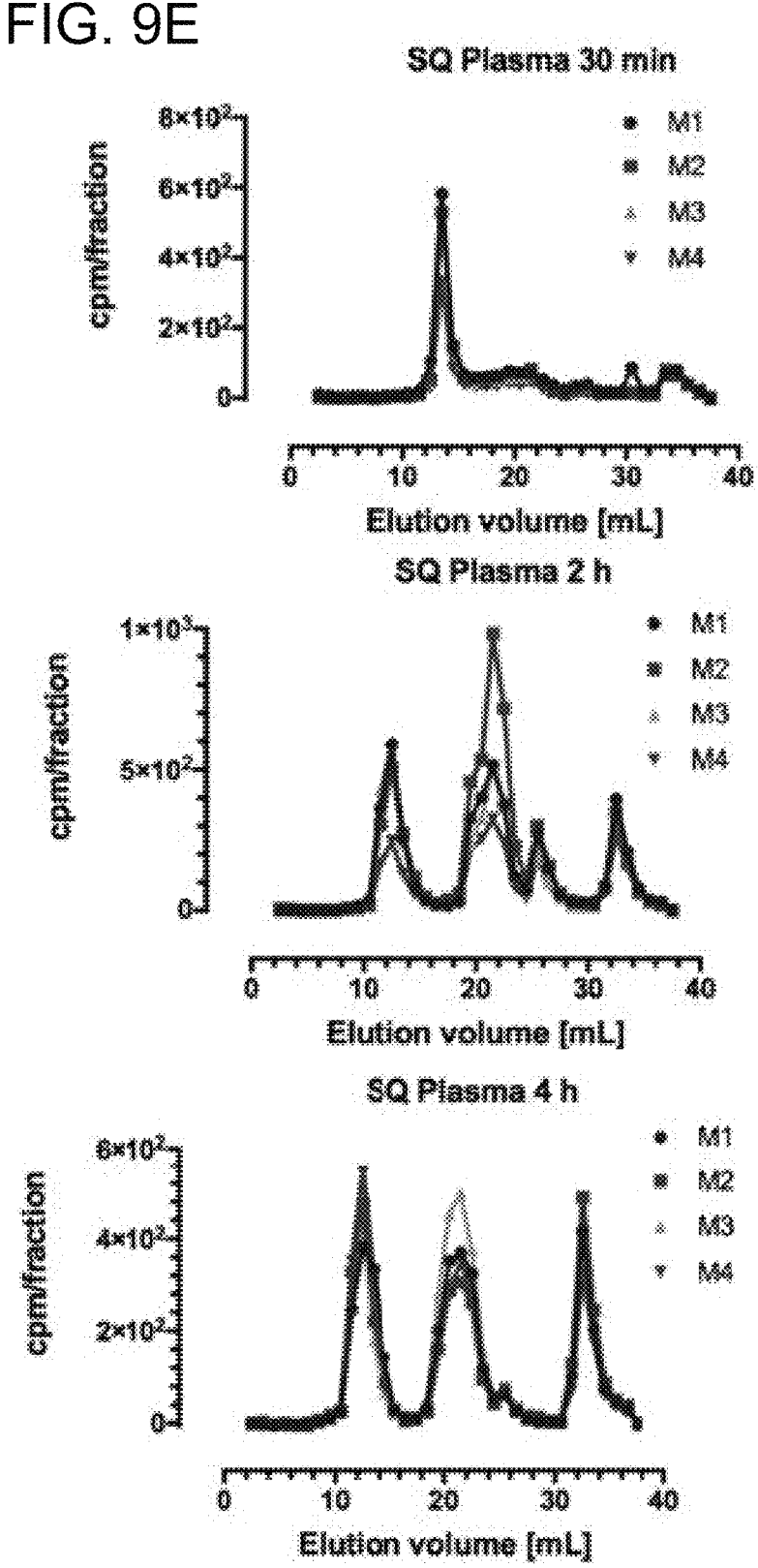
Figure 9F:
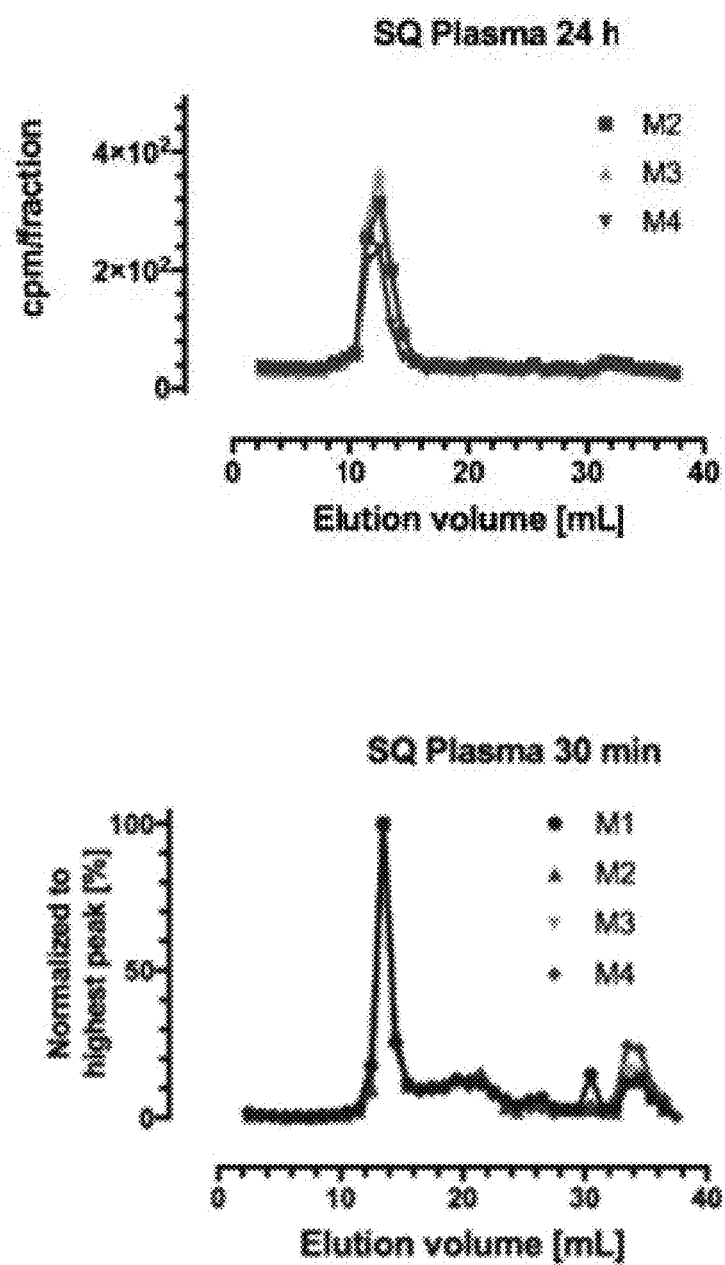
Figure 9G:
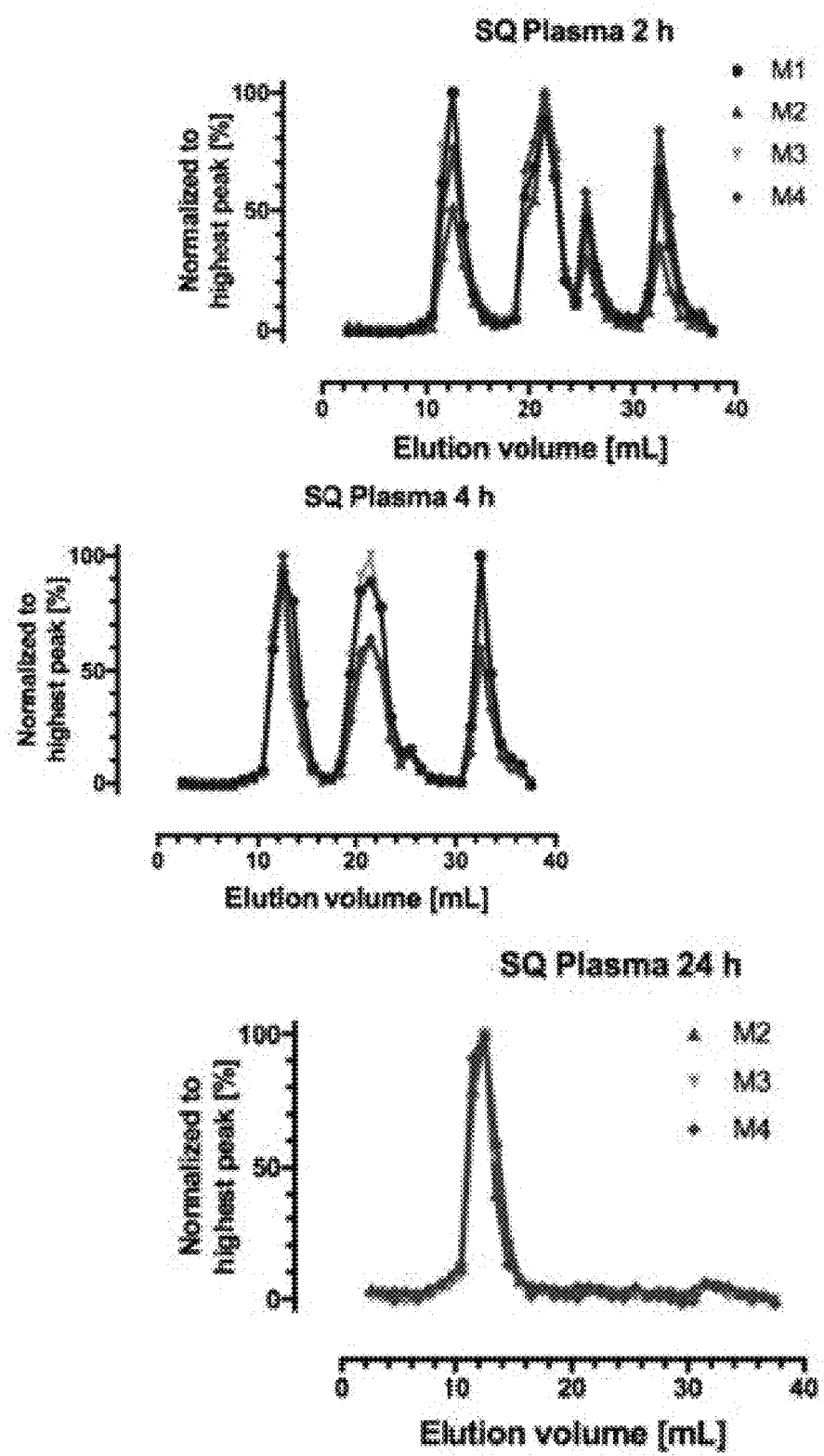

For the stability of sFGFR3_Del4-D3 in plasma after intravenous bolus injection, FPLC elution profiles showed no degradation products in plasma up to 15 minutes (FIGS. 9B-9D). At 30 minutes after administration of sFGFR3_Del4-D3, a small amount of low molecular weight degradation products appeared, which increased by 2 hours, but largely disappeared by 24 hours. For the stability of sFGFR3_Del4-D3 in plasma after subcutaneous injection, FPLC elution profiles showed some degradation products in plasma at 30 minutes, with increased degradation by 2 hours and 4 hours (FIGS. 9E-9G). The low amount of tracer left in plasma after 24 hours appears largely as the intact sFGFR3_Del4-D3 polypeptide. Chromatograms in FIGS. 9C-9D and 9F-9G are presented as normalized to the highest peak in each individual run for easier comparison of the elution patterns.

Example 16: Ligand Binding Activity of sFGFR3_Del4-D3 and sFGFR3_Del4-C253S

Experiments were performed to characterize the binding affinity of sFGFR3_Del4-D3 and sFGFR3_Del4-C253S for human FGF2. The dissociation constant (Kd) of sFGFR3_Del4-D3 and Kd of sFGFR3_Del4-C253S for FGF2 were determined as described in Example 3 with a regeneration buffer of 20 mM phosphate, 40 mM NaCl, pH 7.5. Concentrations of 13 nM, 6.5 nM, 3.25 nM, and 1.75 nM were tested for both sFGFR3_Del4-D3 and sFGFR3_Del4-C253S. The Kd of sFGFR3_Del4-D3 was determined to be ~3.6 nm, and the Kd of sFGFR3_Del4-C253S was determined to be ~6.9 nm. These results indicate that sFGFR3_Del4-D3 and sFGFR3_Del4-C253S have binding activity for FGF2 in the low nM range.

Figure 10A:
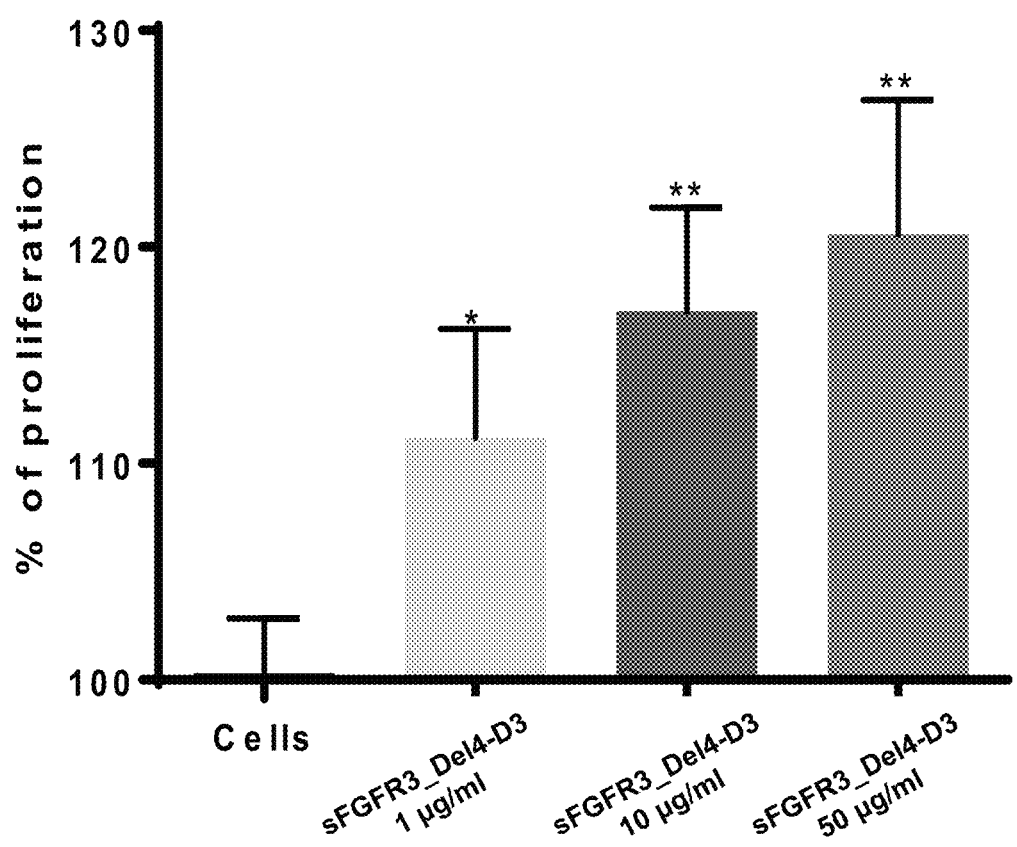
FIGS. 10A-10B are graphs showing the percentage (%) of proliferation of Fgfr3$^{ach/+}$ chondrocyte cells in the presence of the sFGFR3 polypeptides. Fgfr3$^{ach/+}$ chondrocyte proliferation is shown for 1 ug/ml, 10 ug/ml, and 50 ug/ml of sFGFR3_Del4-D3 (FIG. 10A) and for 1 ug/ml, 10 ug/ml, and 50 ug/ml of sFGFR3_Del4-C253S (FIG. 10B).
Figure 10B:
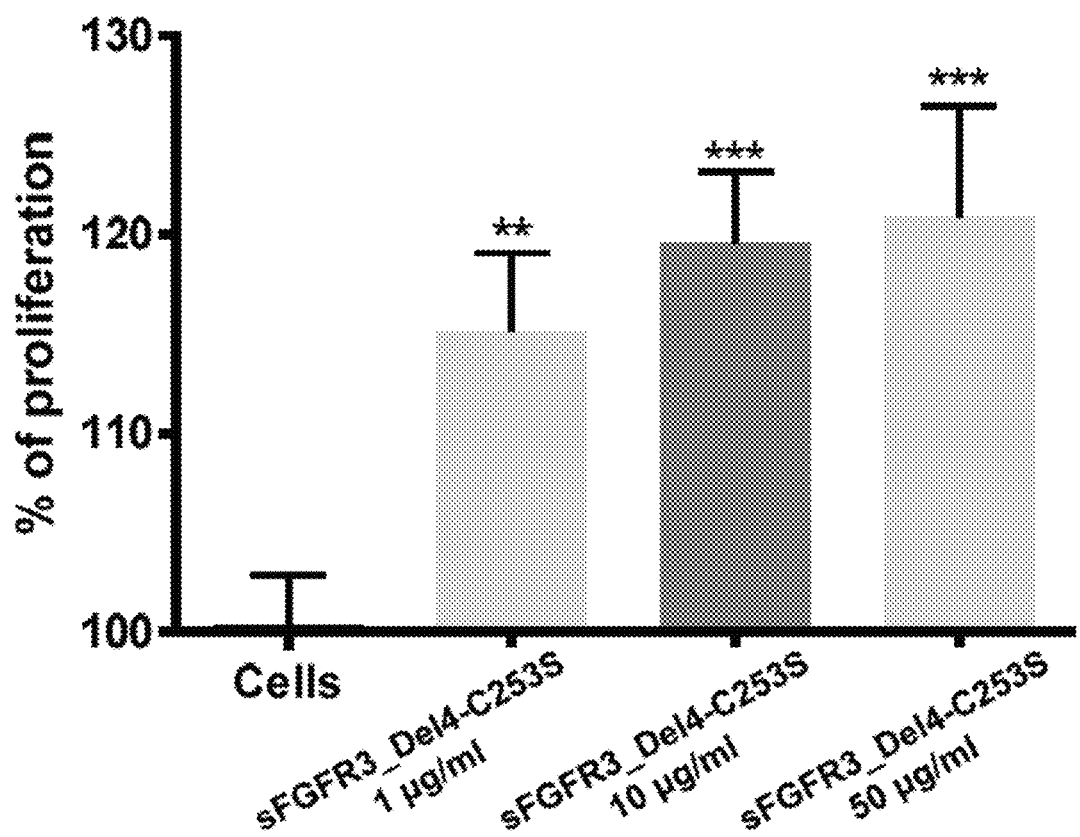

Example 17: sFGFR3_Del4-D3 and sFGFR3_Del4-C253S Exhibit Functional Activity In Vitro Functional activity of sFGFR3_Del4-D3 and sFGFR3_Del4-C253S was tested using a proliferation assay. Proliferation assays using ATDC5 cells genetically modified to overexpress the FGFR3$^{ach}$ mutation (ATDC5 FGFR3$^{G380R}$ cell lines) were performed as described in Example 4 with concentrations of 1 ug/ml, 10 ug/ml, and 50 ug/ml for sFGFR3_Del4-D3 and sFGFR3_Del4-C253S. At each of these concentrations, sFGFR3_Del4-C253S and sFGFR3_Del4-D3 restored proliferation of the FGFR3$^{G380R}$ cells (FIGS. 10A and 10B). The EC50 was determined to be about 10 nM for both sFGFR3_Del4-D3 and sFGFR3_Del4-C253S based on a concentration of 1 ug/ml. These results indicate that sFGFR3_Del4-D3 and sFGFR3_Del4-C253S are biologically active in the low nM range.

Example 18: Pharmacokinetic Profile of sFGFR3_Del4-D3 and sFGFR3_Del4-C253S

Figure 11:
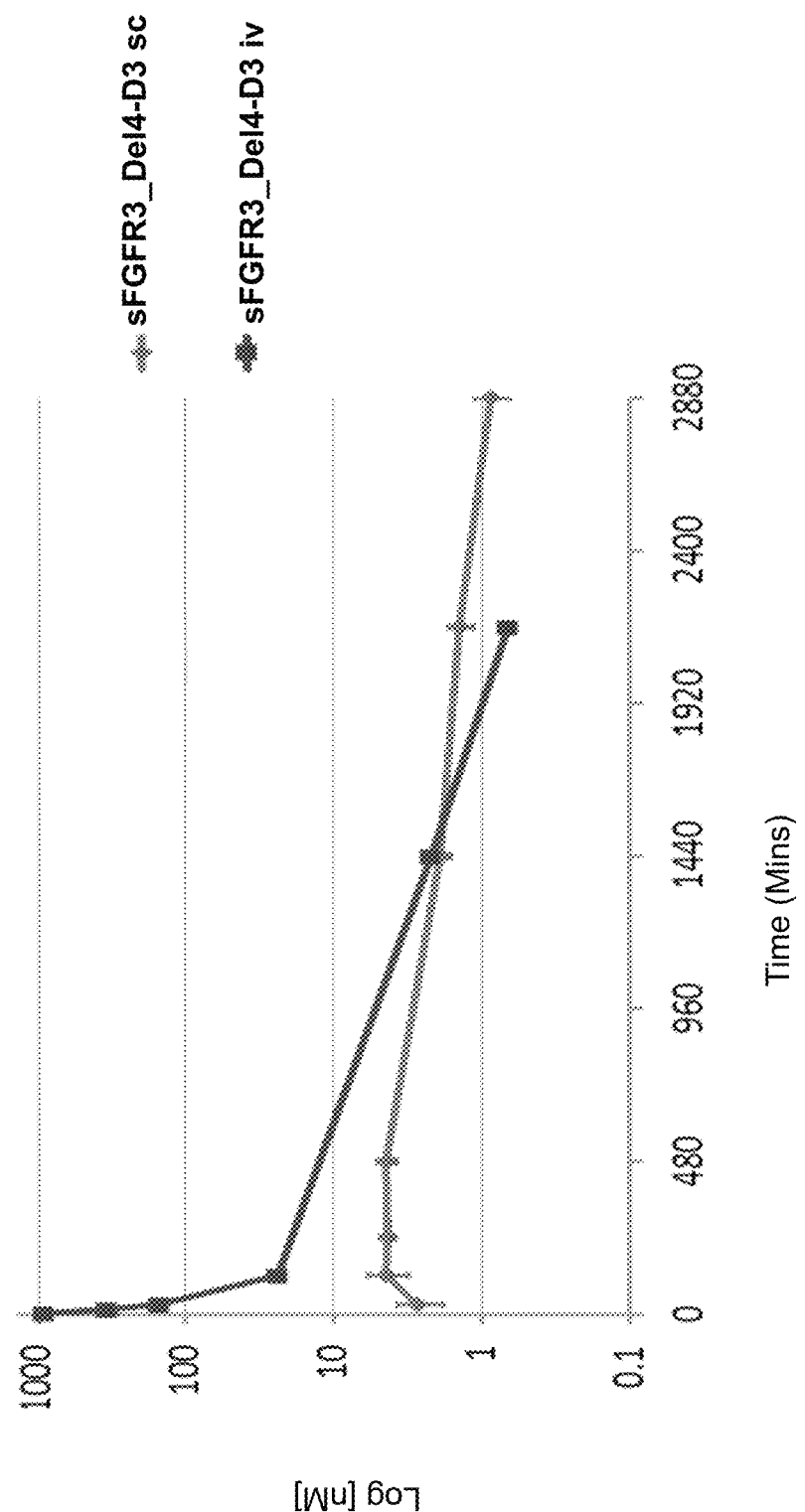
FIG. 11 is a graph showing the PK profiles of 2.5 mg/kg sFGFR3_Del4-D3 administered subcutaneously and 2.5 mg/kg sFGFR3_Del4-D3 administered intravenously.

The pharmacokinetic (PK) profile of sFGFR3_Del4-D3 administered subcutaneously or intravenously at a dose of 2.5 mg/kg was used to determine the terminal elimination half-life of sFGFR3_Del4-D3 (FIG. 11). Samples were collected at 30 minutes, 2 hours, 4 hours, 8 hours, 24 hours, 36 hours, and 48 hours for mice administered sFGFR3_Del4-D3 subcutaneously. Samples were collected at 1 minute, 15 minutes, 30 minutes, 2 hours, 24 hours, and 36 hours for mice administered sFGFR3_Del4-D3 intravenously. The subcutaneous terminal elimination half-life of 2.5 mg/kg sFGFR3_Del4-D3 was ~20 hours, while the intravenous terminal elimination half-life of 2.5 mg/kg sFGFR3_Del4-D3 was ~7 hours. From the PK profile, the $T_{max}$ was ~8 hours, the $C_{max}$ was ~4.5 nM, and the estimated bioavailability was ~30% for 2.5 mg/kg sFGFR3_Del4-D3 administered subcutaneously. There was rapid clearance of sFGFR3_Del4-D3 administered intravenously during the α phase followed by a slower β phase clearance, with a similar intravenous PK profile for sFGFR3_Del4-C253S.

Example 19: The Kidney and Liver are the Main Clearance Routes of sFGFR3_Del4-D3

Figure 12:
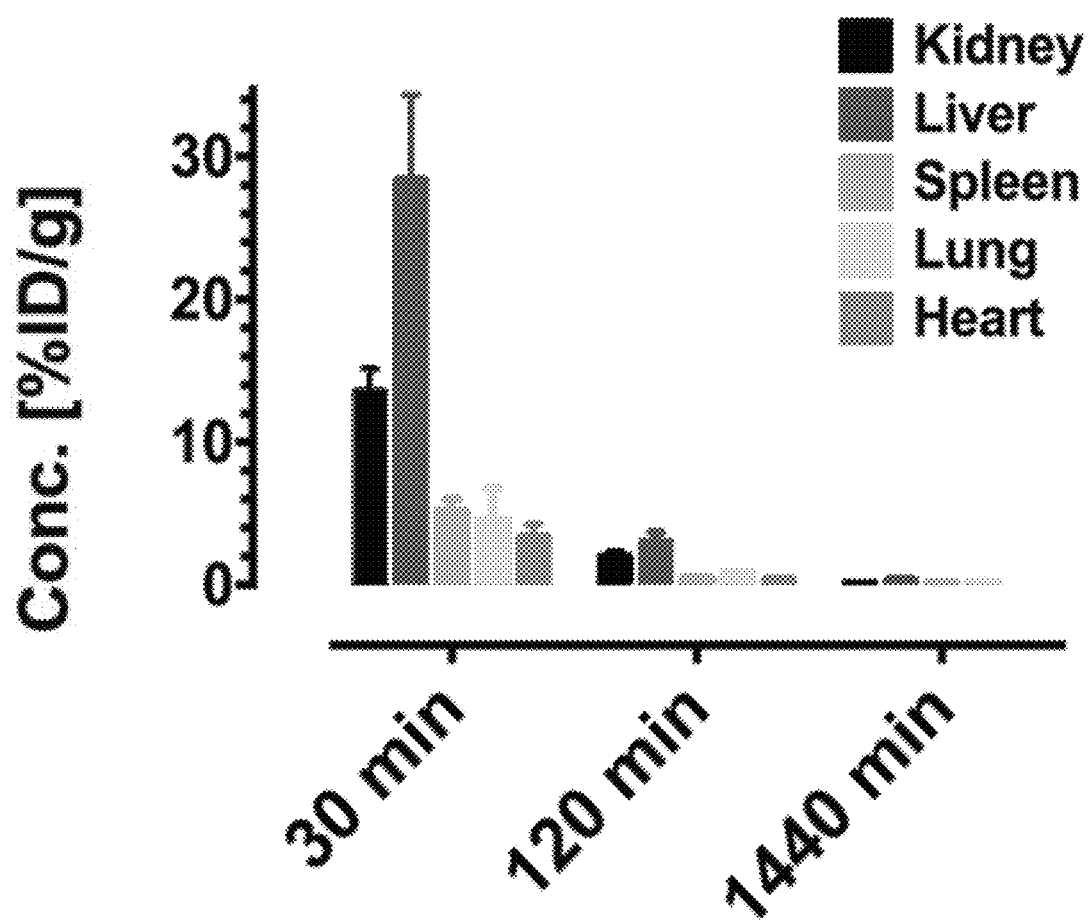
FIG. 12 is a graph showing the concentration of $^{125}$I-sFGFR3_Del4-D3 in kidney, liver, spleen, lung, and heart tissue at 30 minutes, 120 minutes, and 1440 minutes after intravenous administration. The concentration is expressed as the percent of injected dose per gram (% ID/g).
Figure 13:
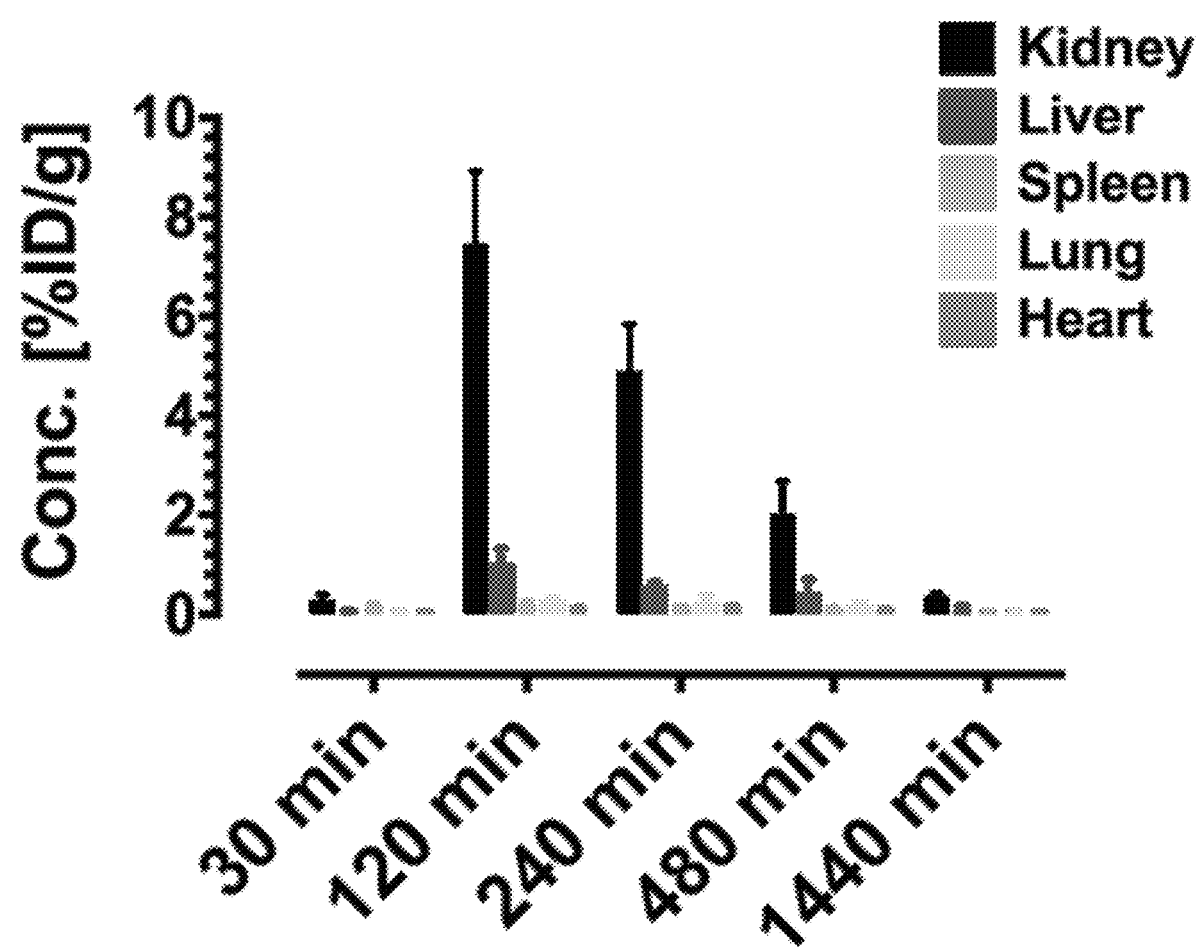
FIG. 13 is a graph showing the concentration of $^{125}$I-sFGFR3_Del4-D3 in kidney, liver, spleen, lung, and heart tissue at 30 minutes, 120 minutes, 240 minutes, 480 minutes, and 1440 minutes after subcutaneous administration. The concentration is expressed as % ID/g.

Clearance of sFGFR3_Del4-D3 was evaluated in kidney, liver, spleen, lung, and heart tissue after 30 minutes, 120 minutes, and 1440 minutes following intravenous administration of 2.5 mg/kg sFGFR3_Del4-D3 and after 30 minutes, 120 minutes, 240 minutes, 480 minutes, and 1440 minutes following subcutaneous administration of 2.5 mg/kg sFGFR3_Del4-D3. The liver and kidney were the major route of sFGFR3_Del4-D3 clearance for intravenous administration (FIG. 12). The kidney was the major route of sFGFR3_Del4-D3 clearance for subcutaneous administration (FIG. 13).

Example 20: sFGFR3_Del4-D3 does not Cross the Blood Brain Barrier

Pharmacokinetic studies were also performed to determine the uptake of sFGFR3_Del4-D3 across the blood brain barrier in wild-type mice. After intravenous bolus injection, brain tissue uptake of sFGFR3_Del4-D3 was measured at three time points (30 minutes, 2 hours, and 24 hours). sFGFR3_Del4-D3 was injected as radiolabeled tracer ($^{125}$I-sFGFR3_Del4-D3) with 2.5 mg/kg unlabeled sFGFR3_Del4-D3. The injected dose of $^{125}$I-sFGFR3_Del4-D3 was about 10 μCi per animal, which corresponds to less than 0.1 mg/kg. After euthanizing the mice at 30 minutes, 2 hours, and 24 hours, the concentration of $^{125}$I-sFGFR3_Del4-D3 in organs and plasma was measured by liquid scintillation counting.

The $^{125}$I-sFGFR3_Del4-D3 concentration was corrected for metabolism in plasma and in brain samples by measuring the fraction of trichloroacetic acid (TCA) precipitable material (e.g., intact tracer). The validity of the TCA correction was also confirmed by injecting samples on a size exclusion fast protein liquid chromatography (FPLC) column. The organ concentration of $^{125}$I-sFGFR3_Del4-D3 was corrected for intravascular content ($V_0$) by injecting radiolabeled albumin ($^3$H-RSA) shortly before sacrificing the animal. The apparent organ volume of distribution of RSA represents $V_0$. The dose of albumin was negligible (on the order of 1% of the physiological concentration). For all organs other than the brain, the concentrations were calculated by subtracting the vascular content and taking into account the TCA precipitable fraction in plasma. However, no correction was made for the uptake of degraded material into these organs other than the brain because no TCA precipitation was performed.

The brain concentrations were calculated by the following formula: $C_{brain(corr.)} = [V_d(sFGFR3\_Del4-D3) - V_0] \times C_{plasma\ (terminal)}$; in which $V_d$(sFGFR3_Del4-D3) is the volume of distribution of sFGFR3_Del4-D3 in brain (calculated as $C_{brain}/C_{plasma}$), $V_0$ is the volume of albumin distributed in the brain, and $C_{plasma(terminal)}$ is the plasma concentration of sFGFR3_Del4-D3 at the terminal sampling time. All concentrations were expressed as the percent of injected dose per gram or ml (% ID/g or % ID/mL), respectively, and the dose of the intravenous bolus equals 100%. These values can be converted to [mg/g] or [mg/mL] by multiplication with the injected dose: (body weight in g/1000 g)×2.5 mg. All body weights were in the range of 25 g-30 g.

Figure 14A:
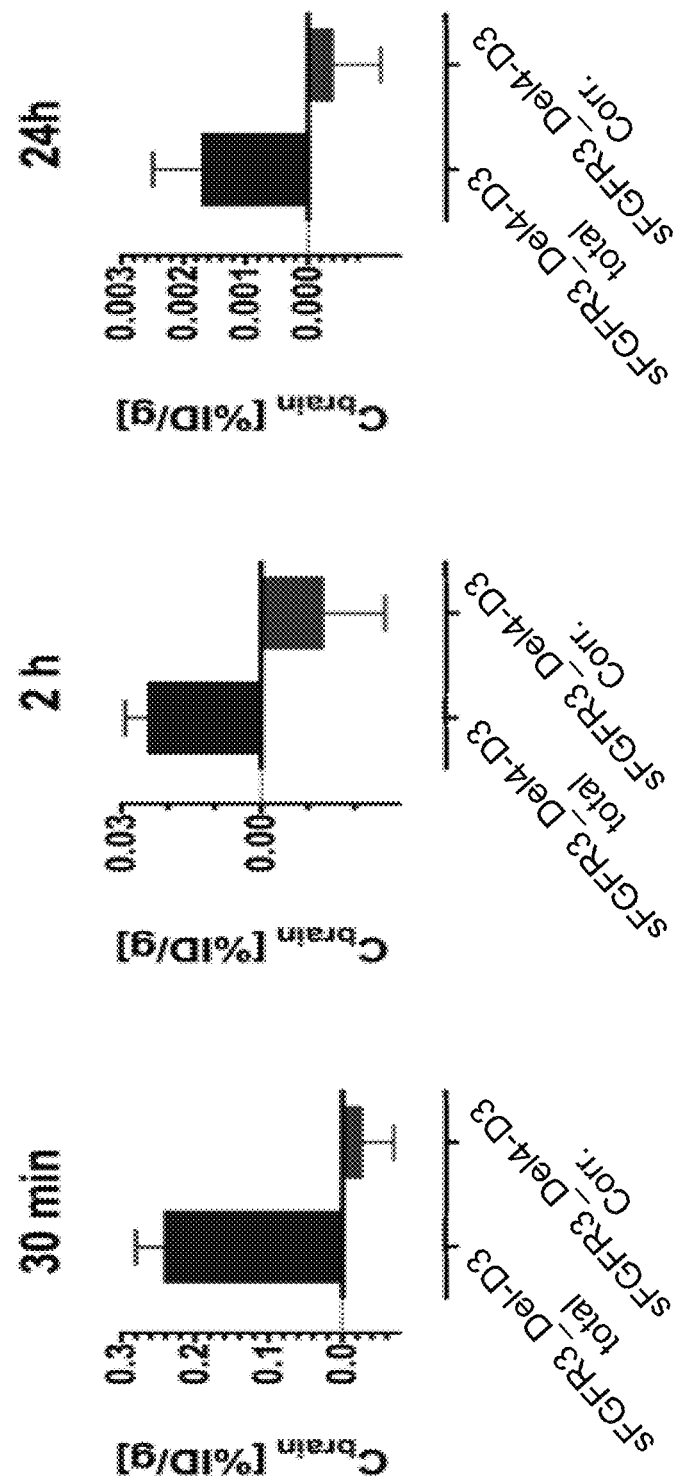
FIG. 14A-14B are graphs showing the concentration (c) and volume of distribution ($V_d$) of $^{125}$I-sFGFR3_Del4-D3 in brain tissue. Shown is the c of $^{125}$I-sFGFR3_Del4-D3 before and after correction for vascular content and degradation at 30 minutes, 2 hours, and 24 hours after intravenous bolus (FIG. 14A) and the $V_d$ of $^{125}$I-sFGFR3_Del4-D3 and RSA at 30 minutes, 2 hours, and 24 hours after intravenous bolus (FIG. 14B).
Figure 14B:
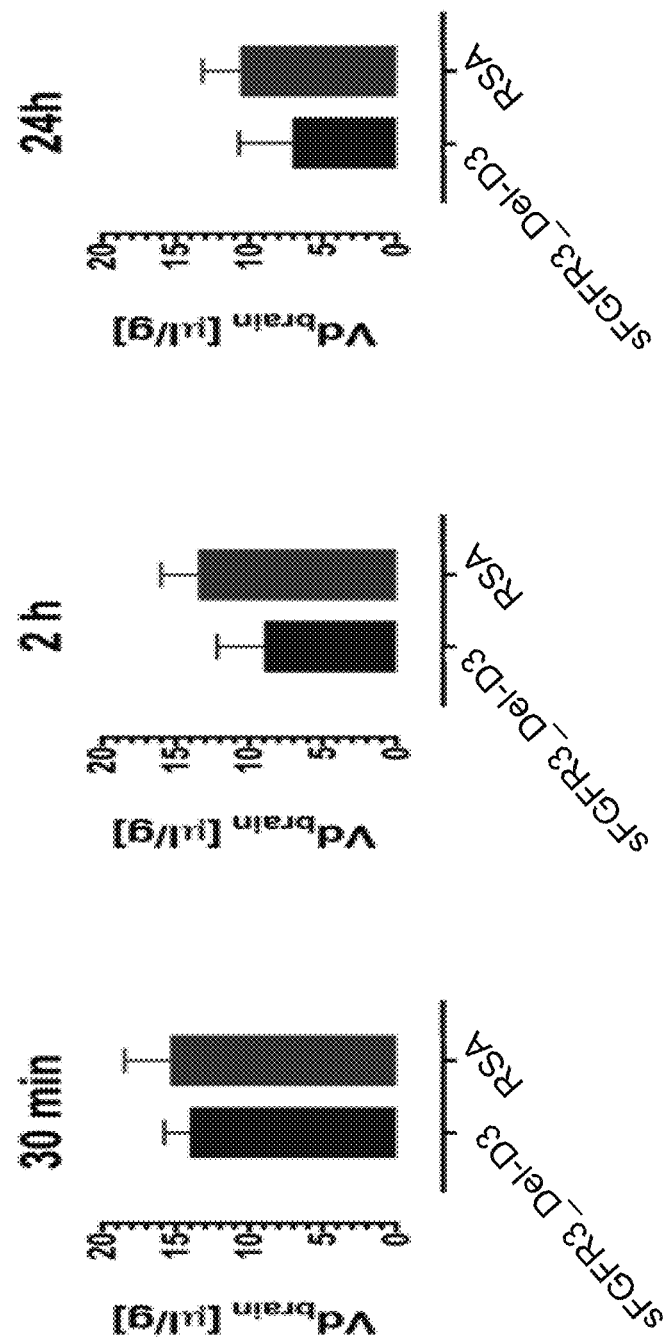

There was no detectable brain uptake of $^{125}$I-sFGFR3_Del4-D3, as indicated by corrected brain concentrations (after correction for vascular content and degradation (TCA precipitability)) at at any of the measured time points (FIG. 14A). Additionally, the $V_d$ of RSA (=V0) and $^{125}$I-sFGFR3_Del4-D3 was not significantly different at any of the measured time points (30 minutes, 2 hours, and 24 hours) as determined by a paired t-test (FIG. 14B). In conclusion, there is no measurable uptake of sFGFR3_Del4-D3 into brain tissue of mice at 30 minutes, 2 hours, and 24 hours at a dose of 2.5 mg/kg injected as an intravenous bolus.

Example 21: In Vivo Efficacy of sFGFR3_Del4-D3 for the Treatment of Achondroplasia sFGFR3_Del4-D3 and sFGFR3_Del4-C253S were each evaluated at a subcutaneous dose of 2.5 mg/kg once or twice weekly or 10 mg/kg twice weekly. Breeding was performed to generate 30 litters with half wild type and half heterozygous Fgfr3$^{ach/+}$ mice (Table 4).

TABLE 4

Subcutaneous administration of sFGFR3_Del4-D3 and sFGFR3_Del4-C253S to wild type (WT) and Fgfr3$^{ach/+}$ mice.

| | | PBS (pooled) | 2.5 mg 1 × week | 2.5 mg 2 × week | 10 mg 2 × week |
|---|---|---|---|---|---|
| sFGFR3_Del4-D3 | WT | 65 | 26 | 22 | 23 |
| | Fgfr3$^{ach/+}$ | 43 | 26 | 25 | 30 |
| | | | | | total N = 260 |

TABLE 4-continued

Subcutaneous administration of sFGFR3_Del4-D3 and
sFGFR3_Del4-C253S to wild type (WT) and Fgfr3$^{ach/+}$ mice.

|  |  | PBS (pooled) | 2.5 mg 1 × week | 2.5 mg 2 × week | 10 mg 2 × week |
|---|---|---|---|---|---|
| sFGFR3_Del4-C253S | WT | 65 | 26 | 22 | 23 |
|  | Fgfr3$^{ach/+}$ | 27 | 22 | 18 | 28 |
|  |  |  |  |  | total N = 231 |
|  | % survival | 62.8 | 84.6 | 72.0 | 93.3 |
|  | % mortality | 37.2 | 15.4 | 28.0 | 6.7 |

At day 3, all newborn mice from a single litter received the same dose. Control litters received 10 μl of PBS (vehicle). Thereafter, subcutaneous injections of sFGFR3_Del4-D3 and sFGFR3_Del4-C253S were administered at doses of 2.5 mg/kg once or twice weekly or 10 mg/kg twice a week for three weeks, alternatively on the left and right sides of the back. Mice were observed daily with particular attention to locomotion and urination alterations and weighed on days of injection. Mice with complications were observed twice a day for surveillance. Previous data indicated there was no statistical difference between males and females, and thus, males and females were considered one group for all analyses.

At day 22, all animals were sacrificed by lethal injection of pentobarbital, and gender was determined. All subsequent measurements and analyses were performed without knowledge of mice genotype to avoid investigator bias. Genotyping was performed at the end of the study to reveal the correspondence of data with a specific genotype. Since achondroplasia is a disease with phenotypic variability, all animals were included in the study. Animals dead before day 22 were used to investigate the impact of treatment on premature death. Surviving animals at day 22 were used for all analyses. All experiments and data measurements were performed by blinded experimenters at all time points.

Figure 15:
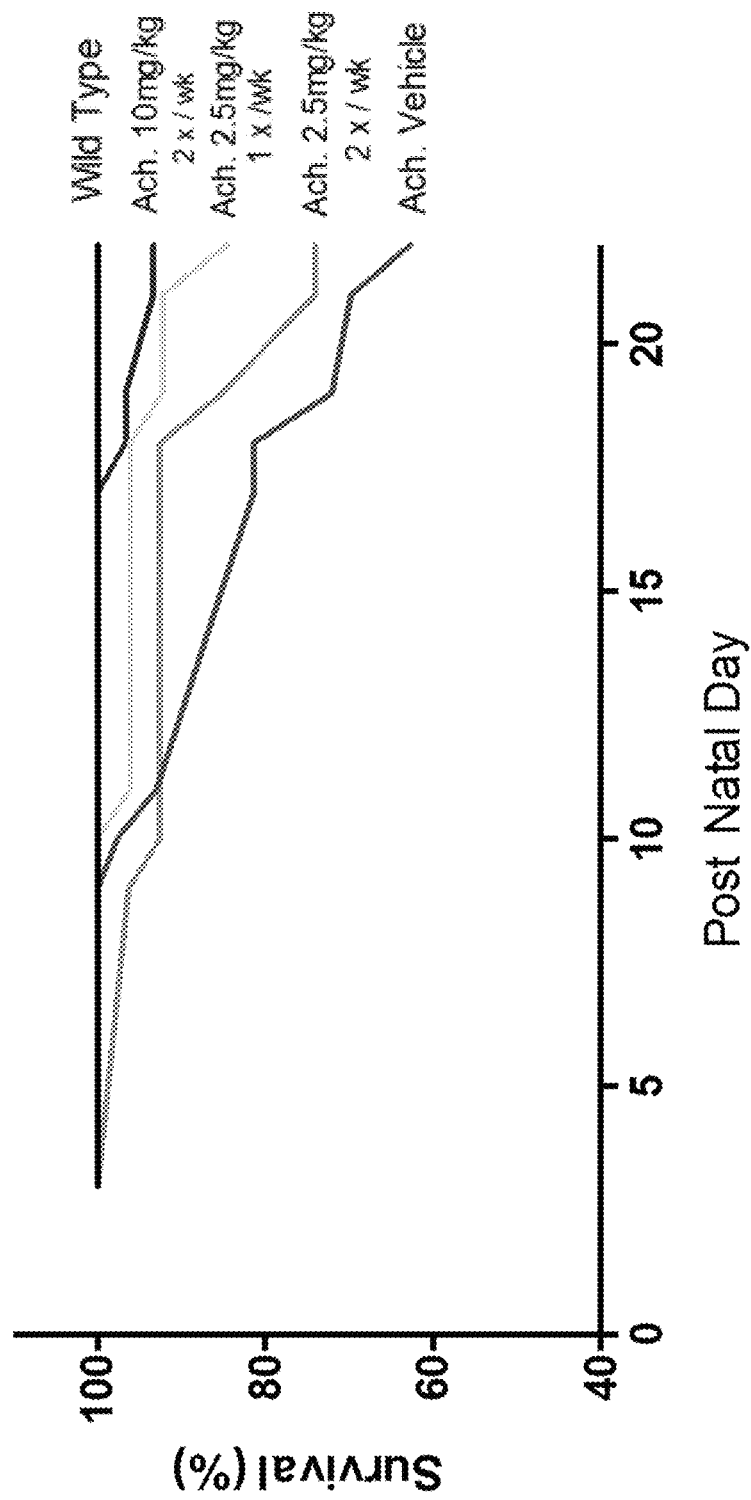
FIG. 15 is a graph showing the percentage of surviving Fgfr3$^{ach/+}$ mice administered sFGFR3_Del4-D3. Shown are the surviving wild type mice, Fgfr3$^{ach/+}$ mice administered PBS as vehicle, Fgfr3$^{ach/+}$ mice administered 2.5 mg/kg sFGFR3_Del4-D3 once weekly, Fgfr3$^{ach/+}$ mice administered 2.5 mg/kg sFGFR3_Del4-D3 twice weekly, and Fgfr3$^{ach/+}$ mice administered 10 mg/kg sFGFR3_Del4-D3 twice weekly over 22 days.

Subcutaneous administration of sFGFR3_Del4-D3 at 2.5 mg/kg once or twice weekly or 10 mg/kg twice weekly increased survival of Fgfr3$^{ach/+}$ mice relative to Fgfr3$^{ach/+}$ mice receiving PBS (FIG. 15 and Table 4). In particular, administration of 10 mg/kg sFGFR3_Del4-D3 twice weekly resulted in 93% survival of Fgfr3$^{ach/+}$ mice, administration of 2.5 mg/kg sFGFR3_Del4-D3 once weekly resulted in 84% survival in Fgfr3$^{ach/+}$ mice, and administration of 2.5 mg/kg sFGFR3_Del4-D3 twice weekly resulted in 72% survival in Fgfr3$^{ach/+}$ mice, while the survival of Fgfr3$^{ach/+}$ mice receiving PBS was 62.8%. The mortality of Fgfr3$^{ach/+}$ mice administered 10 mg/kg sFGFR3_Del4-D3 twice weekly was 6.7%, the mortality of Fgfr3$^{ach/+}$ mice administered 2.5 mg/kg sFGFR3_Del4-D3 once weekly was 15.4%, the mortality of Fgfr3$^{ach/+}$ mice administered 2.5 mg/kg sFGFR3_Del4-D3 twice weekly was 28.0%, and the mortality of Fgfr3$^{ach/+}$ mice administered PBS was 37.2%. Statistical analysis of Fgfr3$^{ach/+}$ mice survival following treatment with sFGFR3_Del4-D3 was performed using the Agostino and Pearson omnibus normality test following by a t-test. All investigated groups passed the normality tests. The P-values from these analyses are shown below, in which * represent a P-value of <0.05 and *** represents a P-value of <0.001 (Table 5).

TABLE 5

P-values for subcutaneous administration of sFGFR3_Del4-D3
to wild type (WT) and Fgfr3$^{ach/+}$ mice.

| Group Comparison | P Value |
|---|---|
| Wt vs ach | *** |
| Fgfr3$^{ach/+}$ PBS vs Fgfr3$^{ach/+}$ 2.5 mg/kg, 1× | *** |
| Fgfr3$^{ach/+}$ PBS vs Fgfr3$^{ach/+}$ 2.5 mg/kg, 2× | * |
| Fgfr3$^{ach/+}$ PBS vs Fgfr3$^{ach/+}$ 10 mg/kg, 2× | *** |
| Wt PBS vs Fgfr3$^{ach/+}$ 10 mg/kg, 2× | ns |

Figure 16:
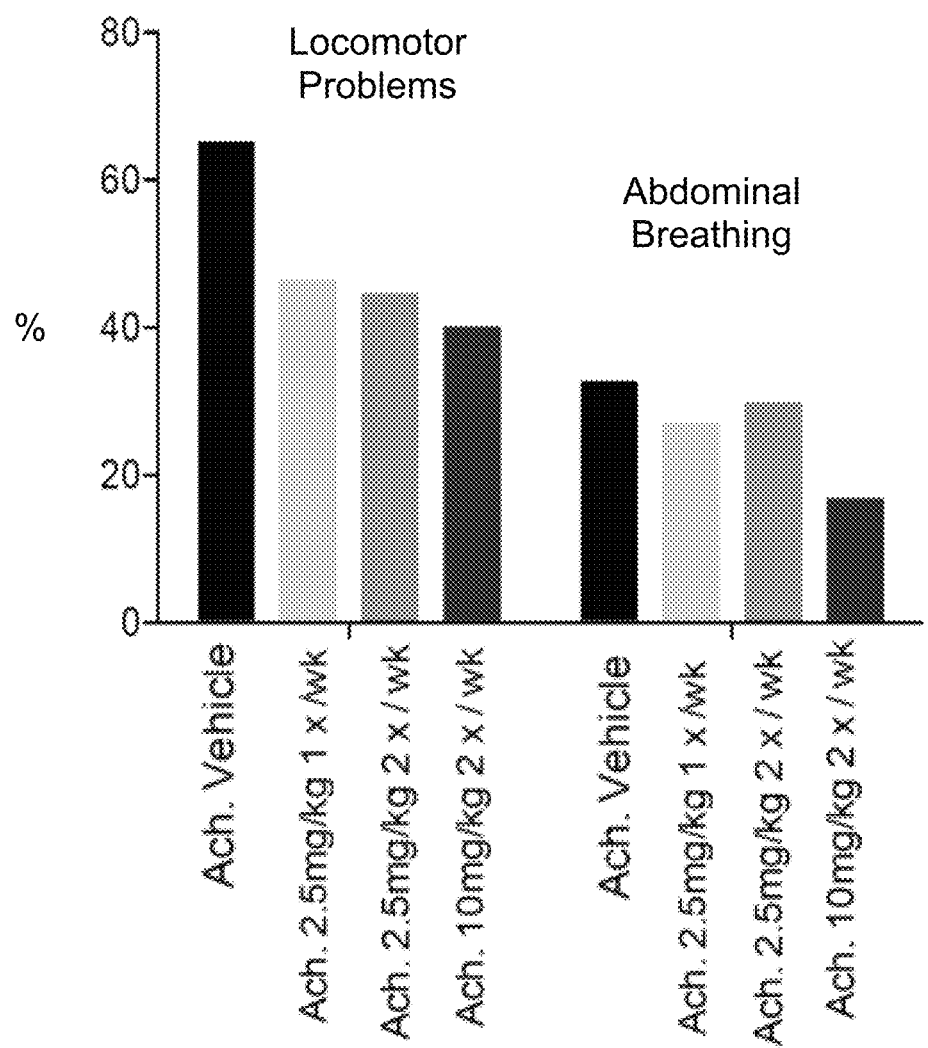
FIG. 16 is a graph showing the percentage (%) of loco-motor and abdominal breathing complications in Fgfr3$^{ach/+}$ mice administered PBS as vehicle, 2.5 mg/kg sFGFR3_Del4-D3 once weekly, 2.5 mg/kg sFGFR3_Del4-D3 twice weekly, and 10 mg/kg sFGFR3_Del4-D3 twice weekly.

Subcutaneous administration of sFGFR3_Del4-D3 at 2.5 mg/kg once or twice weekly or 10 mg/kg twice weekly also decreased the severity and frequency of locomotor problems and complications in abdominal breathing in Fgfr3$^{ach/+}$ mice relative to Fgfr3$^{ach/+}$ mice receiving PBS (FIG. 16). In particular, locomotor problems decreased the most in Fgfr3$^{ach/+}$ mice administered subcutaneously 10 mg/kg sFGFR3_Del4-D3 twice weekly followed by mice administered sFGFR3_Del4-D3 2.5 mg/kg twice weekly and mice administered sFGFR3_Del4-D3 2.5 mg/kg once weekly. Complications in abdominal breathing decreased the most in Fgfr3$^{ach/+}$ mice administered subcutaneously 10 mg/kg sFGFR3_Del4-D3 twice weekly followed by mice administered sFGFR3_Del4-D3 2.5 mg/kg once weekly and then mice administered sFGFR3_Del4-D3 2.5 mg/kg twice weekly. These results show that sFGFR3_Del4-D3 reduces symptoms of achondroplasia in Fgfr3$^{ach/+}$ mice.

Figure 17A:
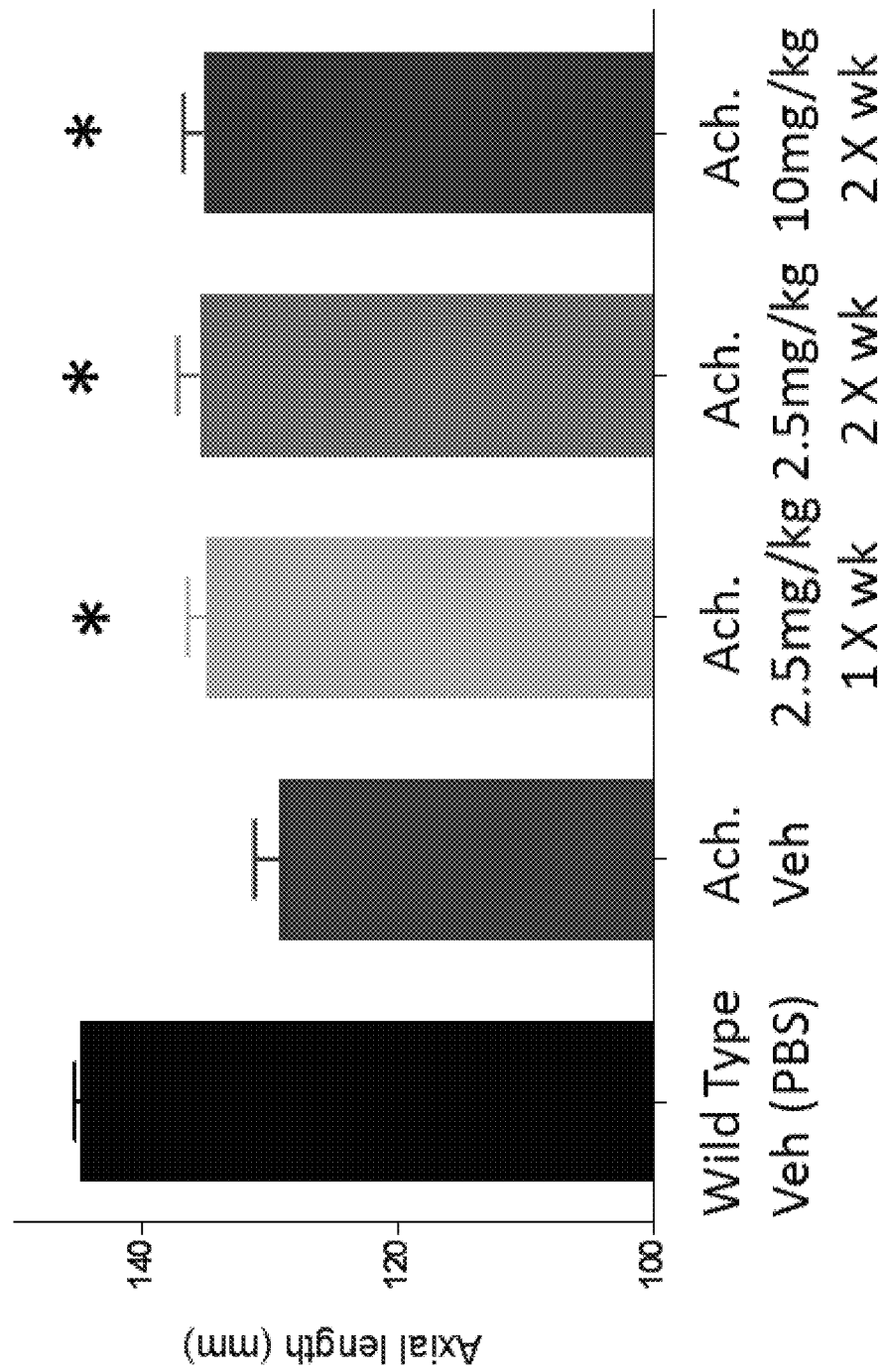
FIGS. 17A-17O are graphs and an x-ray radiograph showing the length of Fgfr3$^{ach/+}$ mice administered sFGFR3_Del4-D3. Shown are the axial length (FIG. 17A), tail length (FIG. 17B), and tibia length (FIG. 17C) of wild type mice administered PBS as vehicle, and Fgfr3$^{ach/+}$ mice administered PBS as vehicle, 2.5 mg/kg sFGFR3_Del4-D3 once weekly, 2.5 mg/kg sFGFR3_Del4-D3 twice weekly, and 10 mg/kg sFGFR3_Del4-D3 twice weekly. Also shown is the x-ray radiograph (FIG. 17D) of wild type mice administered PBS as vehicle and Fgfr3$^{ach/+}$ mice administered PBS as vehicle, 2.5 mg/kg sFGFR3_Del4-D3 twice weekly, and 10 mg/kg sFGFR3_Del4-D3 twice weekly. All measurements are in millimeters (mm).
Figure 17D:
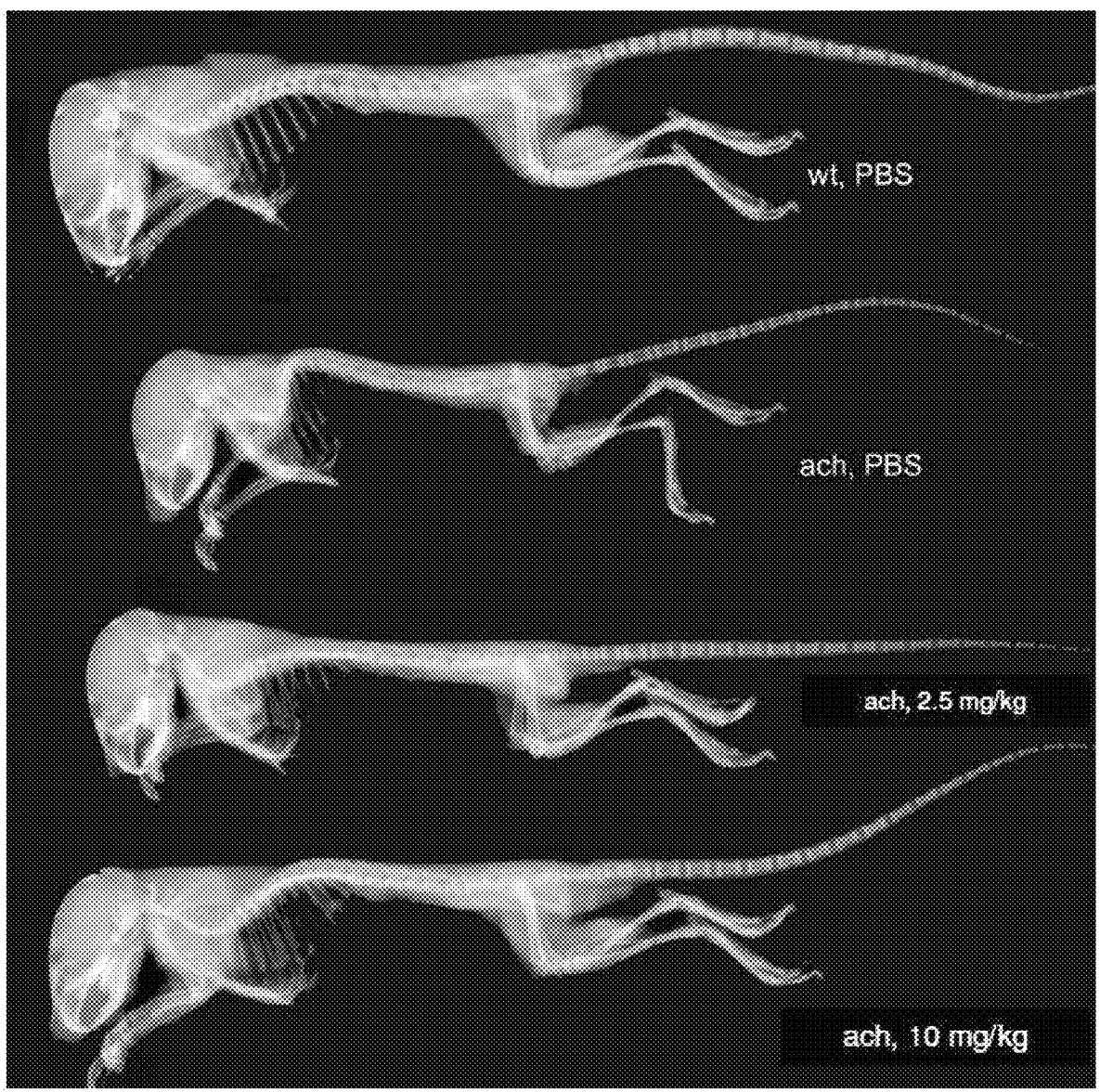

Subcutaneous administration of sFGFR3_Del4-D3 also significantly increased total body length, including axial length and tail length, and long bones (p=0.07) in Fgfr3$^{ach/+}$ mice receiving 2.5 mg/kg sFGFR3_Del4-D3 once or twice weekly or 10 mg/kg sFGFR3_Del4-D3 twice weekly relative to Fgfr3$^{ach/+}$ mice receiving PBS (FIGS. 17A-17C). Tail and body length (axial length) were measured using the same digital caliper on whole skeletons. Tibia length was measured on digital X-rays. Administration of 10 mg/kg sFGFR3_Del4-D3 twice weekly resulted in 51% axial correction (body and tail length) of Fgfr3$^{ach/+}$ mice, followed by 43% axial correction in Fgfr3$^{ach/+}$ receiving 2.5 mg/kg sFGFR3_Del4-D3 twice weekly, and 39% axial correction in Fgfr3$^{ach/+}$ mice receiving 2.5 mg/kg sFGFR3_Del4-D3 once weekly. Increases in bone and body length were also evident from x-ray radiographs of Fgfr3$^{ach/+}$ mice administered 2.5 mg/kg or 10 mg/kg sFGFR3_Del4-D3 twice weekly relative to Fgfr3$^{ach/+}$ mice receiving PBS (FIG. 17D). Administration of 10 mg/kg sFGFR3_Del4-D3 twice weekly resulted in 86% appendicular correction (tibia and femur length) of Fgfr3$^{ach/+}$ mice, followed by 68% appendicular correction in Fgfr3$^{ach/+}$ receiving 2.5 mg/kg sFGFR3_Del4-D3 twice weekly and 54% appendicular correction in Fgfr3$^{ach/+}$ mice receiving 2.5 mg/kg sFGFR3_Del4-D3 once weekly.

Figure 18B:
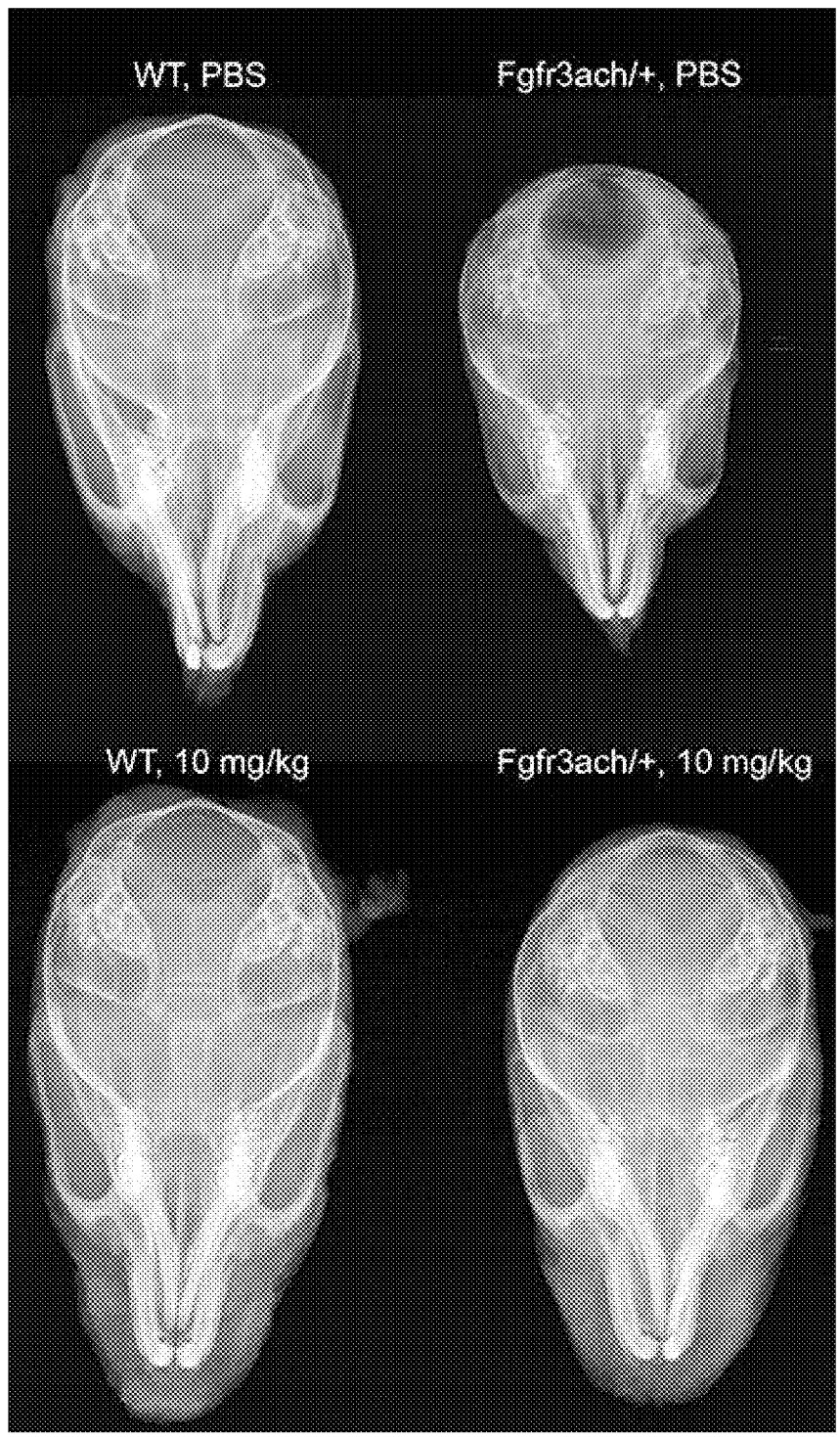

Subcutaneous administration of sFGFR3_Del4-D3 also resulted in a dose-dependent improvement in cranial ratio (length/width (L/VV)) in Fgfr3$^{ach/+}$ mice relative to Fgfr3$^{ach/+}$ mice receiving PBS (FIG. 18A). Fgfr3$^{ach/+}$ mice subcutaneously administered 10 mg/kg sFGFR3_Del4-D3 twice weekly exhibited the greatest improvement in the cranium ratio (LAN), followed by Fgfr3$^{ach/+}$ mice administered 2 mg/kg sFGFR3_Del4-D3 twice weekly and Fgfr3$^{ach/+}$ mice administered 2 mg/kg sFGFR3_Del4-D3 once weekly. In particular, administration of 10 mg/kg sFGFR3_Del4-D3 twice weekly resulted in 37% skull shape correction (L/VV ratio) of Fgfr3$^{ach/+}$ mice, followed by 29% skull shape correction in Fgfr3$^{ach/+}$ receiving 2.5 mg/kg sFGFR3_Del4-D3 twice weekly and 19% skull shape correction in Fgfr3$^{ach/+}$ mice receiving 2.5 mg/kg sFGFR3_Del4-D3 once weekly. Improvements in the cranial ratio were also evident from x-ray radiographs of Fgfr3$^{ach/+}$ mice administered 10 mg/kg sFGFR3_Del4-D3 relative to Fgfr3$^{ach/+}$ mice receiving PBS (FIG. 18B). Bone measurements (presented in mm and mean±SEM) for body length, tail, femur, tibia, and cranial ratio are shown below (Table 6). These results indicate the dose-dependent in vivo efficacy of sFGFR3_Del4-D3 as demonstrated by increased survival, reduced number of complications, increased bone growth, and improvements in skeletal proportions of Fgfr3$^{ach/+}$ mice.

Example 22: No Organ Toxicity Associated with Administration of sFGFR3_Del4-D3

Histopathological studies were performed to characterize organ toxicity associated with sFGFR3_Del4-D3 administration. Wild type mice (6 males and 6 females per dose) were administered PBS, 2.5 mg/kg sFGFR3_Del4-D3 once weekly, 2.5 mg/kg sFGFR3_Del4-D3 twice weekly, or 10 mg/kg sFGFR3_Del4-D3 twice weekly. Organs investigated included the kidney, skin, salivary glands, mandibular lymph nodes, gall bladder, spleen, pancreas, lungs, heart, aorta, jejunum, colon, and liver. There were no histopathological results indicating organ toxicity in wild-type mice administered any of the doses of sFGFR3_Del4-D3. These results indicate that there was no toxicity associated with administration of sFGFR3_Del4-D3 up 10 mg/kg twice weekly.

Figure 19B:
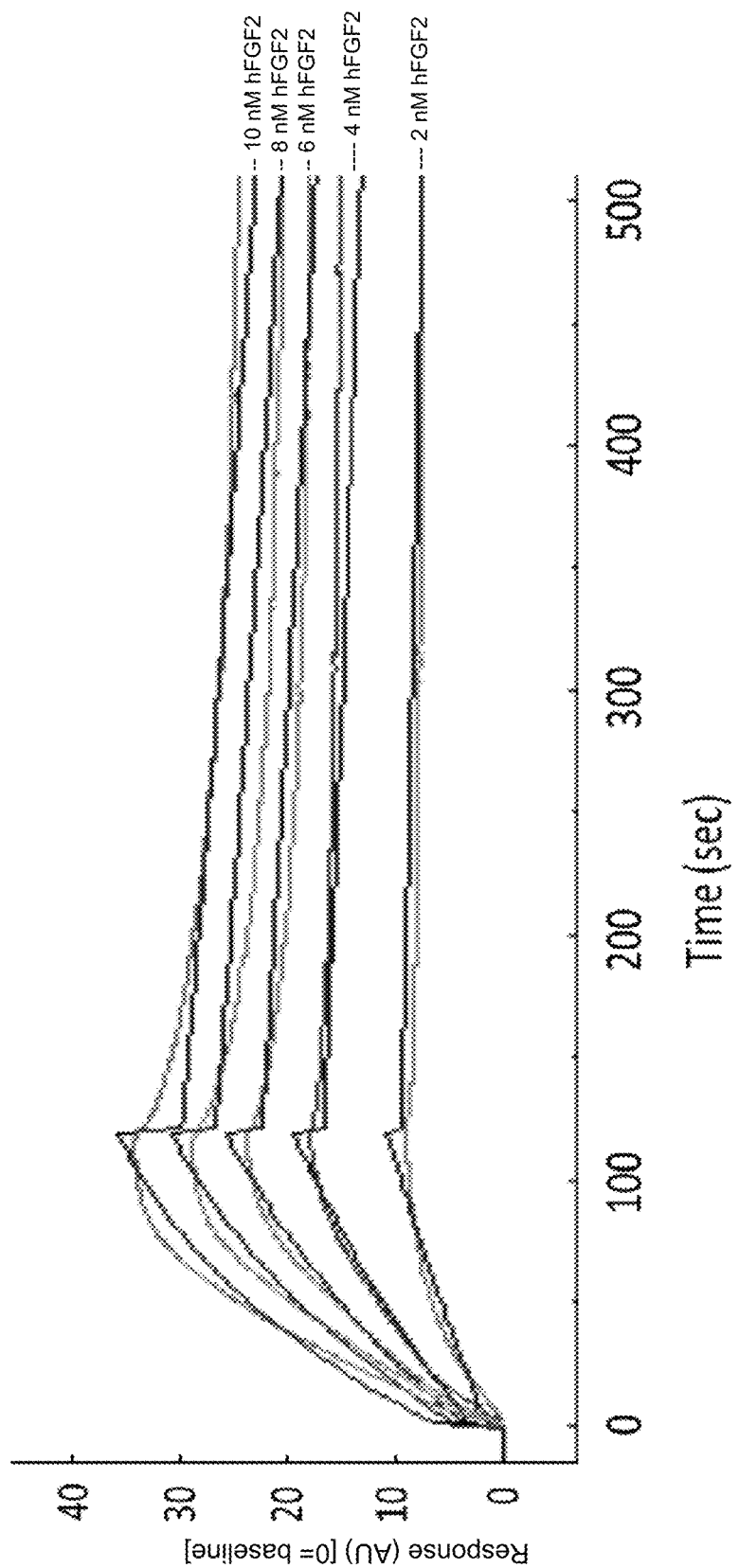
Figure 19C:
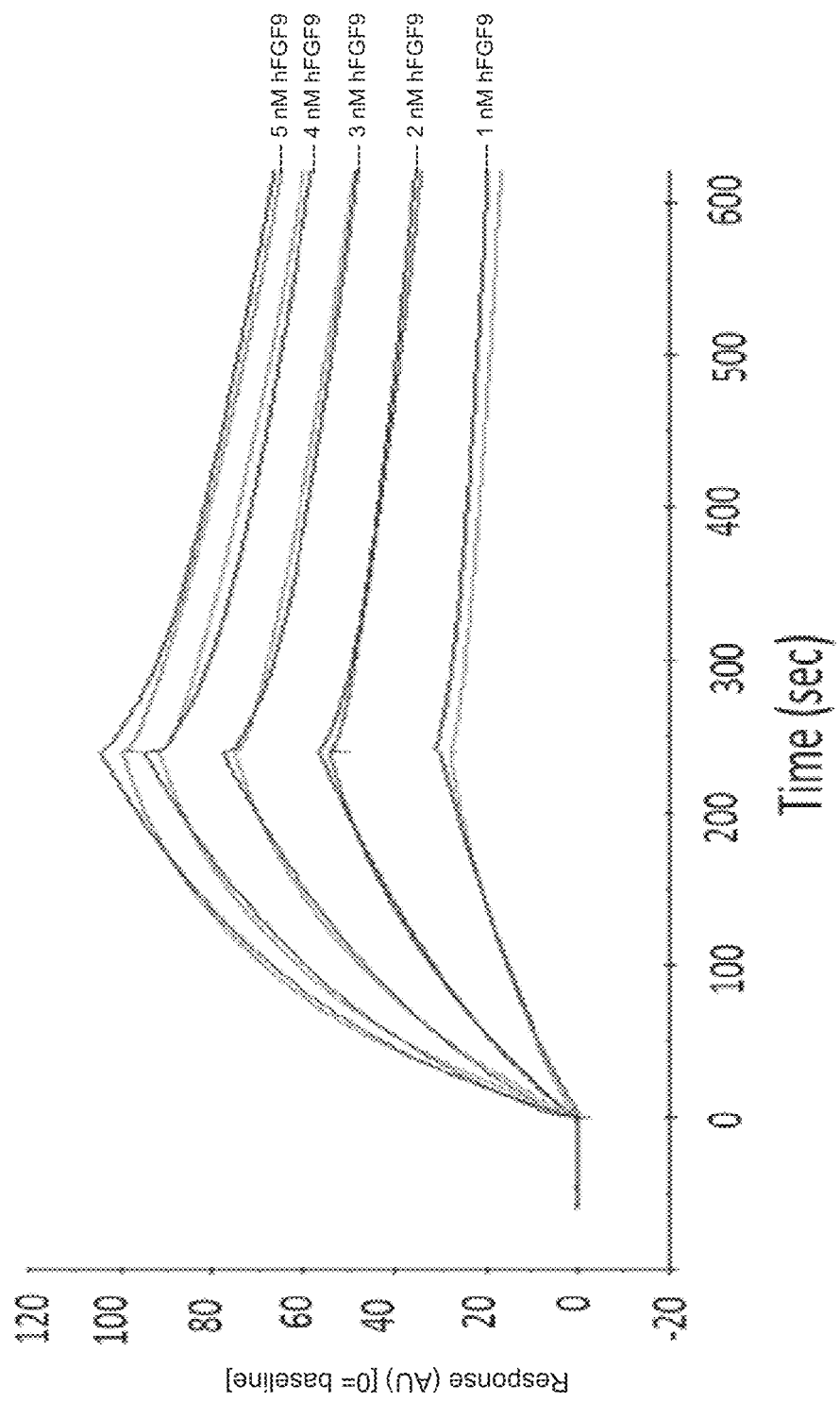
Figure 19D:
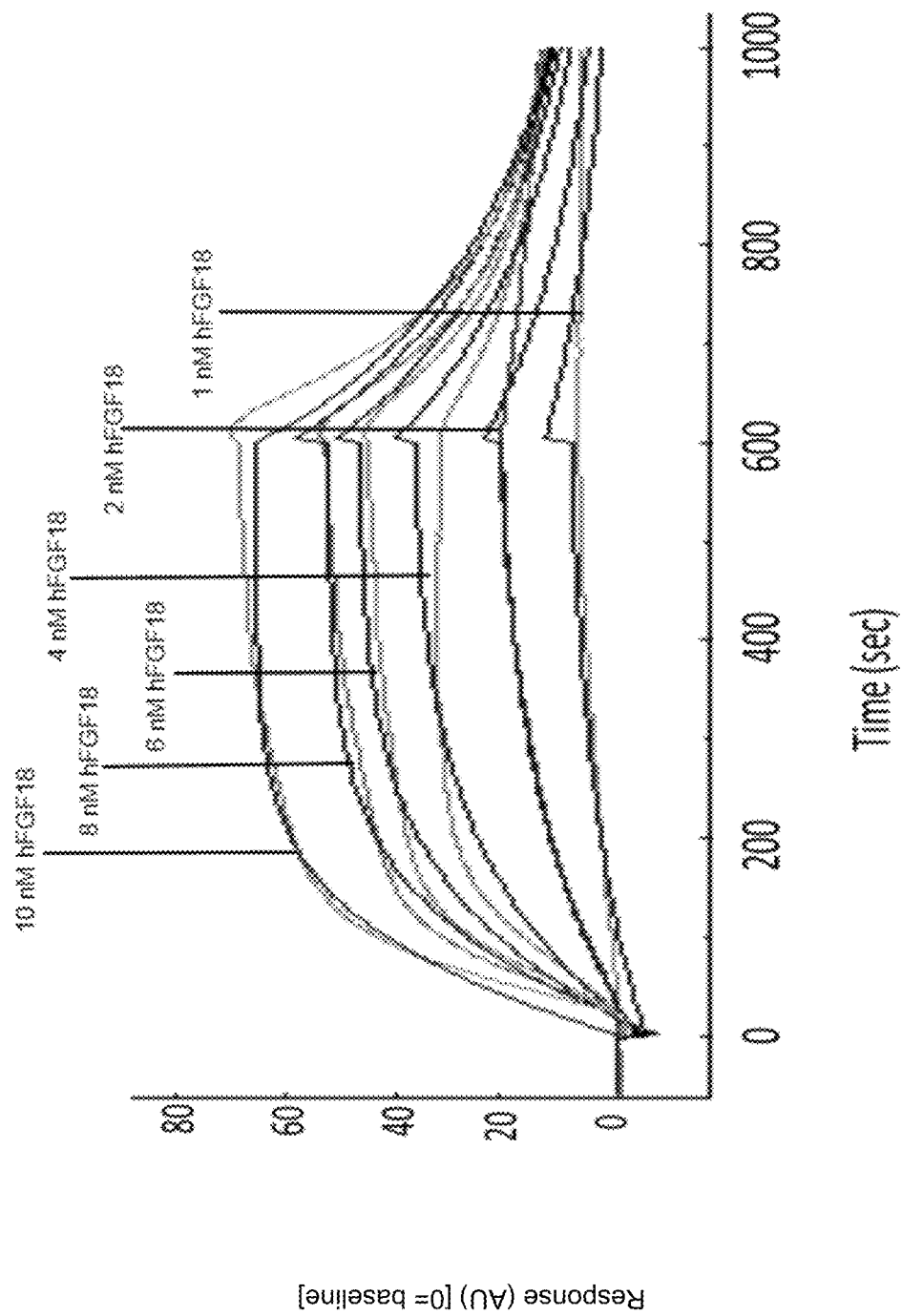
Figure 19E:
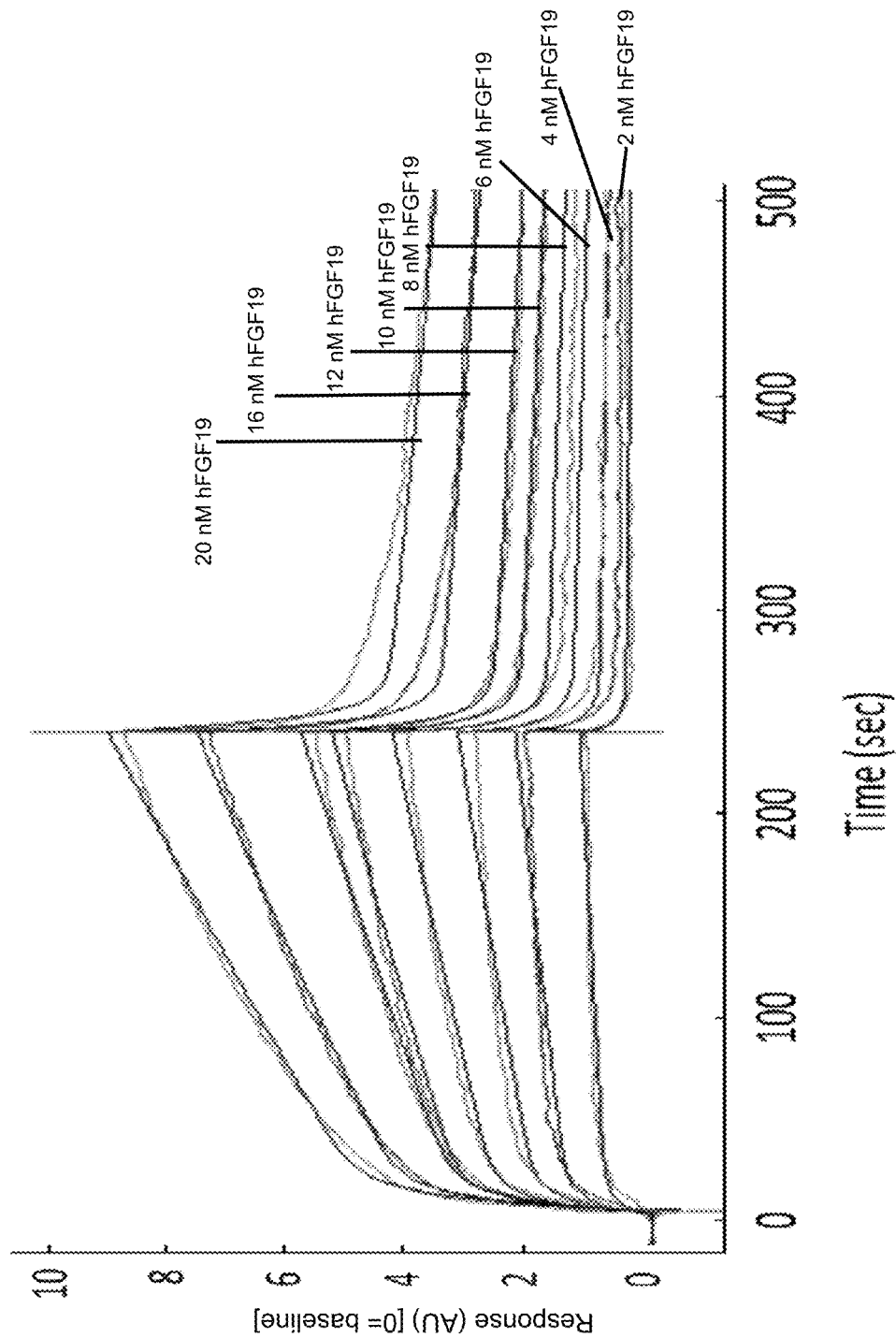
Figure 19F:
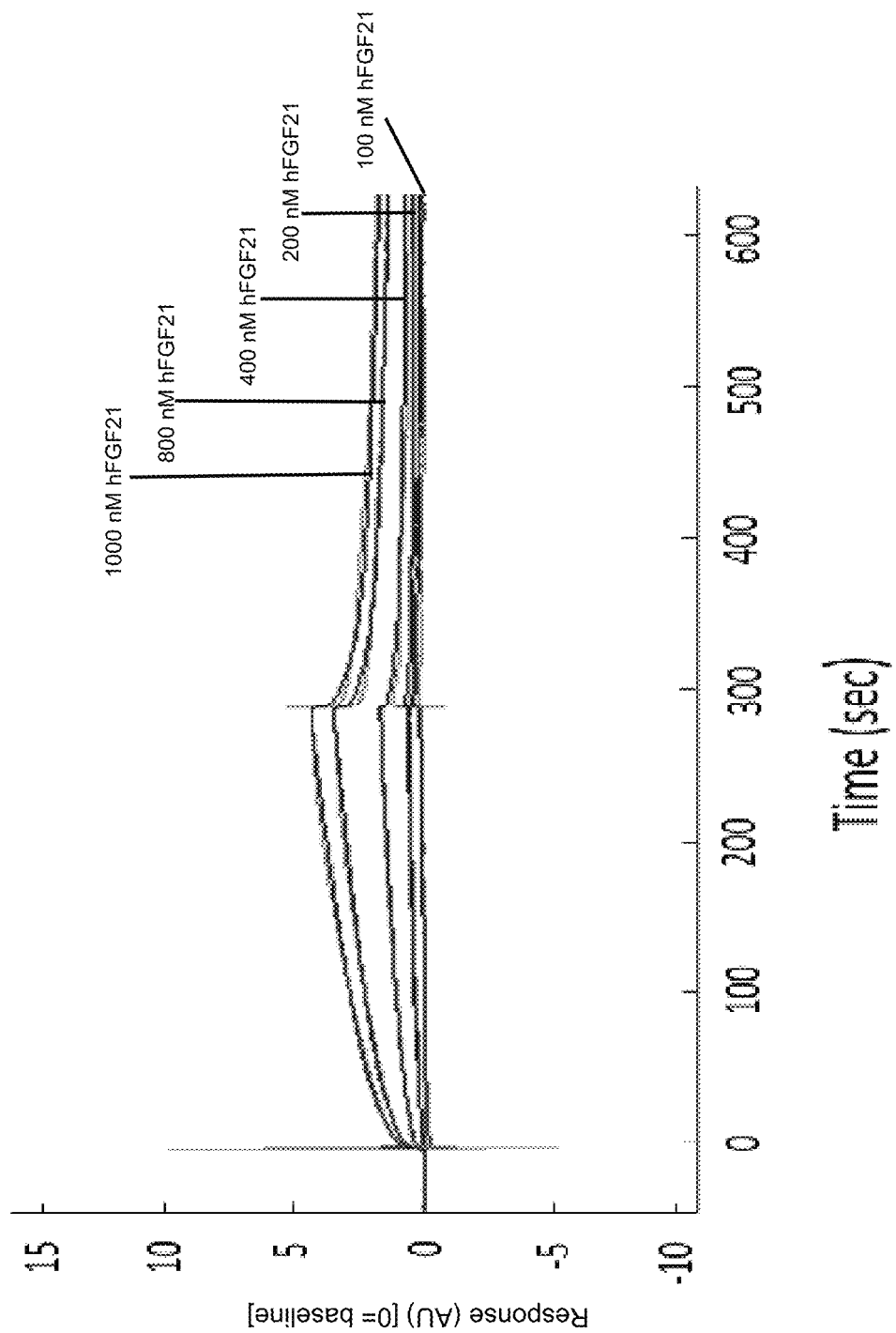

Example 23: Determination of Binding Affinity of sFGFR3_Del4-D3 to Fibroblast Growth Factors We determined that sFGFR3_Del4-D3 binds to Fibroblast Growth Factors (FGF) ligands and acts as a decoy to prevent the binding of FGFs to the membrane bound FGFR3. Surface Plasmon Resonance was performed using a BIACORE™ T200 (GE Healthcare) to determine the $K_d$ values for different human FGFs (hFGFs) binding to immobilized sFGFR3_Del4-D3. In particular, $K_d$ values for the paracrine hFGFs of hFGF1 (FIG. 19A), hFGF2 (FIG. 19B), hFGF9 (FIG. 19C), and hFGF18 (FIG. 19D) and the endocrine hFGFs of hFGF19 (FIG. 19E) and hFGF21 (FIG. 19F) were determined. All four paracrine FGF ligands bound sFGFR3_Del4-D3 with nanomolar (nM) affinity (Table 8).

TABLE 6

Bone measurements (presented in mm and mean ± SEM) for body length, tail, femur, tibia, and cranial ratio of WT and Fgfr3$^{ach/+}$ mice administered subcutaneously sFGFR3_Del4-D3.

| | | Efficacy of sFGFR3_Del4-D3 | | | |
|---|---|---|---|---|---|
| | WT | PBS in Fgfr3$^{ach/+}$ mice | 2.5 mg/kg once weekly | 2.5 mg/kg twice weekly | 10 mg/kg twice weekly |
| Body length | 144.8 ± 0.53 | 129.2 ± 1.98 | 135 ± 1.48 | 135.5 ± 1.75 | 135.2 ± 1.58 |
| Tail | 77.65 ± 0.39 | 70.25 ± 1.1 | 73.37 ± 1.66 | 73.69 ± 1.5 | 74.95 ± 0.91 |
| Femur | 10.94 ± 0.05 | 10.14 ± 0.13 | 10.47 ± 0.08 | 10.58 ± 0.09 | 10.63 ± 0.10 |
| Tibia | 14.19 ± 0.05 | 13.67 ± 0.14 | 14.02 ± 0.10 | 14.09 ± 0.12 | 14.25 ± 0.12 |
| Cranial ratio | 1.99 ± 0.01 | 1.79 ± 0.01 | 1.83 ± 0.02 | 1.85 ± 0.01 | 1.86 ± 0.02 |

Additionally, comparison of the bone measurements for Fgfr3$^{ach/+}$ mice administered sFGFR3 Del1 at a dosage of 2.5 mg/kg twice weekly show that administration sFGFR3_Del4-D3 at a dosage of 2.5 mg/kg twice weekly was comparable to or more effective in increasing the bone, tail, femur, and tibia length and improving the cranial ratio of Fgfr3$^{ach/+}$ mice (Table 7). In particular, the body length of Fgfr3$^{ach/+}$ mice administered sFGFR3_Del4-D3 improved to 135.5±1.75 mm relative to 134.4±1.17 mm for Fgfr3$^{ach/+}$ mice administered sFGFR3_Del1; the tail length of Fgfr3$^{ach/+}$ mice administered sFGFR3_Del4-D3 improved to 73.69±1.5 mm relative to 71.58±0.86 mm for Fgfr3$^{ach/+}$ mice administered sFGFR3_Del1; the femur length of Fgfr3$^{ach/+}$ mice administered sFGFR3_Del4-D3 improved to 10.58±0.09 mm relative to 10.01±0.06 mm for Fgfr3$^{ach/+}$ mice administered sFGFR3_Del1; the tibia length of Fgfr3$^{ach/+}$ mice administered sFGFR3_Del4-D3 improved to 14.09±0.12 mm relative to 13.27±0.31 mm for Fgfr3$^{ach/+}$ mice administered sFGFR3_Del1; and the cranial ratio of Fgfr3$^{ach/+}$ mice administered sFGFR3_Del4-D3 improved to 1.85±0.01 mm relative to 1.81±0.02 mm for Fgfr3$^{ach/+}$ mice administered sFGFR3 Del1.

TABLE 7

Bone measurements (presented in mm and mean ± SEM) for body length, tail, femur, tibia, and cranial ratio of WT and Fgfr3$^{ach/+}$ mice administered subcutaneously sFGFR3_Del1 (data described in Garcia et al. *Sci. Transl. Med.* 5:203ra124, 2013).

| | | Efficacy of sFGFR3_Del1 | | |
|---|---|---|---|---|
| | WT | PBS in Fgfr3$^{ach/+}$ mice | 0.25 mg/kg twice weekly | 2.5 mg/kg twice weekly |
| body length | 133.9 ± 0.8 | 118.5 ± 1.76 | 132.4 ± 1.26 | 134.4 ± 1.17 |
| tail | 71.9 ± 0.49 | 64.48 ± 1.1 | 71.05 ± 0.99 | 71.58 ± 0.86 |
| femur | 10.05 ± 0.17 | 9.67 ± 0.16 | 9.85 ± 0.10 | 10.01 ± 0.06 |
| tibia | 13.43 ± 0.19 | 12.62 ± 0.18 | 12.87 ± 0.14 | 13.27 ± 0.31 |
| cranial ratio | 1.94 ± 0.01 | 1.75 ± 0.01 | 1.77 ± 0.02 | 1.81 ± 0.02 |

TABLE 8

Summary of $K_d$ determination and values for human, paracrine FGFs (hFGF1, hFGF2, hFGF9, and hFGF18) and human, endocrine FGFs (hFGF19 and hFGF21).

| Paracrine FGFs | Binding | $k_{a1}$ (1/Ms) | $k_{a2}$ (1/Ms) | $k_{d1}$ (1/s) | $k_{d2}$ (1/s) | $K_D$ (M) Kinetic | Chi$^2$ (RU$^2$) average | $K_D$ (M) Steady state | Chi$^2$ (RU$^2$) average |
|---|---|---|---|---|---|---|---|---|---|
| FGF1 | 2:1 binding & steady state | 2.0* 10$^{+11}$ | 1.2* 10$^{-3}$ | 1610 | 6.4 * 10$^{-4}$ | 2.6* 10$^{-9}$ (+/− 1.9*10$^{-9}$, n = 3) | 0.138 | 5.7* 10$^{-9}$ (+/− 2.1 *10$^{-9}$, n = 3) | 0.247 |
| FGF2 | 1:1 binding | 9.0* 10$^{+5}$ | | 4.75* 10$^{-4}$ | | 6.1* 10$^{-10}$ (+/− 1.7*10$^{-10}$, n = 3) | 13.6 | | |
| FGF9 | 2:1 binding & steady state | 2.3* 10$^{+6}$ | 3.0* 10$^{-2}$ | 2.6* 10$^{-2}$ | 3.6* 10$^{-3}$ | 1.8* 10$^{-9}$ (+/− 0.25*10$^{-9}$, n = 3) | 0.14 | 3.6* 10$^{-9}$ (n = 1) | 0.25 |
| FGF18 | 1:1 binding & steady state | 2.0* 10$^{+5}$ | | 9.1* 10$^{-3}$ | | 4.5* 10$^{-9}$ (+/− 2.5*10$^{-9}$, n = 3) | 9.7 | 6.4*10$^{-9}$ (+/− 0.89*10$^{-9}$, n = 4) | 11.8 |
| Endocrine FGFs | | | | | | | | | |
| FGF19 | 2:1 binding | 5.4* 10$^{+4}$ | 7.3* 10$^{-3}$ | 1.5* 10$^{-1}$ | 3.6* 10$^{-3}$ | 4.8* 10$^{-7}$ (+/− 3.2*10$^{-7}$, n = 3) | 0.05 | | |
| FGF21 | 2:1 binding | 258 | 1.8* 10$^{-2}$ | 5.5* 10$^{-3}$ | 1.4* 10$^{-3}$ | 2.8* 10$^{-5}$ (n = 2) | 0.56 | | |

For FGF2 and FGF18, a good fit was achieved with a 1:1 binding model, which is the most direct model of binding affinity. This model describes a 1:1 binding interaction at the surface of the chip with immobilized SFGFR3_DEL4-D3 binding different FGFs: A+B=AB with single on- and off rate. The 2:1 model also describes a 1:1 interaction of FGF binding to SFGFR3_DEL4-D3, but also assumes a conformational change that stabilizes the complex: A+B=AB=AB* and represents two on- and off-rates. This model assumes that the conformationally changed complex (SFGFR3_DEL4-D3 bound to FGF) can only dissociate by reversing the conformational change. The experimental data for hFGF1, hFGF9, hFGF19, and hFGF21 were determined to fit the 2:1 model very well, and thus, $K_d$ for hFGF1, hFGF9, hFGF19, and hFGF21 were derived from the 2:1 model.

Despite hFGF1, hFGF9, hFGF19, and hFGF21 all having a $K_d$ in the low nM range, the kinetic profiles of these hFGFs differed significantly. For example, FGF1 binds sFGFR3_Del4-D3 with a very fast on-rate and off-rate, while FGF2 does not bind sFGFR3_Del4-D3 with as fast of an on-rate or off-rate as FGF1, resulting in an overall smaller $K_d$ for FGF2 compared to FGF1 (Table 8). A significantly lower affinity was measured between sFGFR3_Del4-D3 and hFGF19 or hFGF21, which are members of the endocrine FGF15/FGF19 subfamily, relative to the paracrine hFGFs (Table 8 and FIGS. 19D and 19E). The FGF15/FGF19 subfamily uses Klotho instead of proteoglycans as a cofactor and has evolved into endocrine-acting growth factors, which are important for the systemic regulation of metabolic parameters, such as phosphate, bile acid, carbohydrate, and lipid metabolism.

These results demonstrate that there was a high affinity interaction of sFGFR3_Del4-D3 with hFGF1, hFGF2, hFGF9, and hFGF18, while there was a low affinity interaction of sFGFR3_Del4-D3 with FGF19 and FGF21. The low affinity of sFGFR3_Del4-D3 for FGF19 and FGF21 is advantageous as sFGFR3_Del4-D3 will have a low probability of interfering with the function of these FGFs in vivo.

Example 24: In Vitro Proliferation Assay of sFGFR3_Del4-D3

Following binding of FGFs, FGFR3 dimerizes to initiate signaling cascades. Several downstream signaling pathways are associated with FGF signaling. In chondrocytes, dimerized FGFR3 results in an anti-proliferative signal/early differentiation signal into the chondrocyte, which eventually leads to inhibition of bone growth. For example, the RAS/MAPK pathway propagates signals to negatively affect proliferation, terminal differentiation, and post-mitotic matrix synthesis, and the STAT1 pathway mediates the inhibition of chondrocyte proliferation in concert with the cell cycle regulators p107 and 130 and cell cycle inhibitor p21Waf/Cip1. Gene expression studies suggest a number of other pathways are also involved in down-regulation of growth-promoting molecules or induction of anti-proliferative functions.

Figure 20:
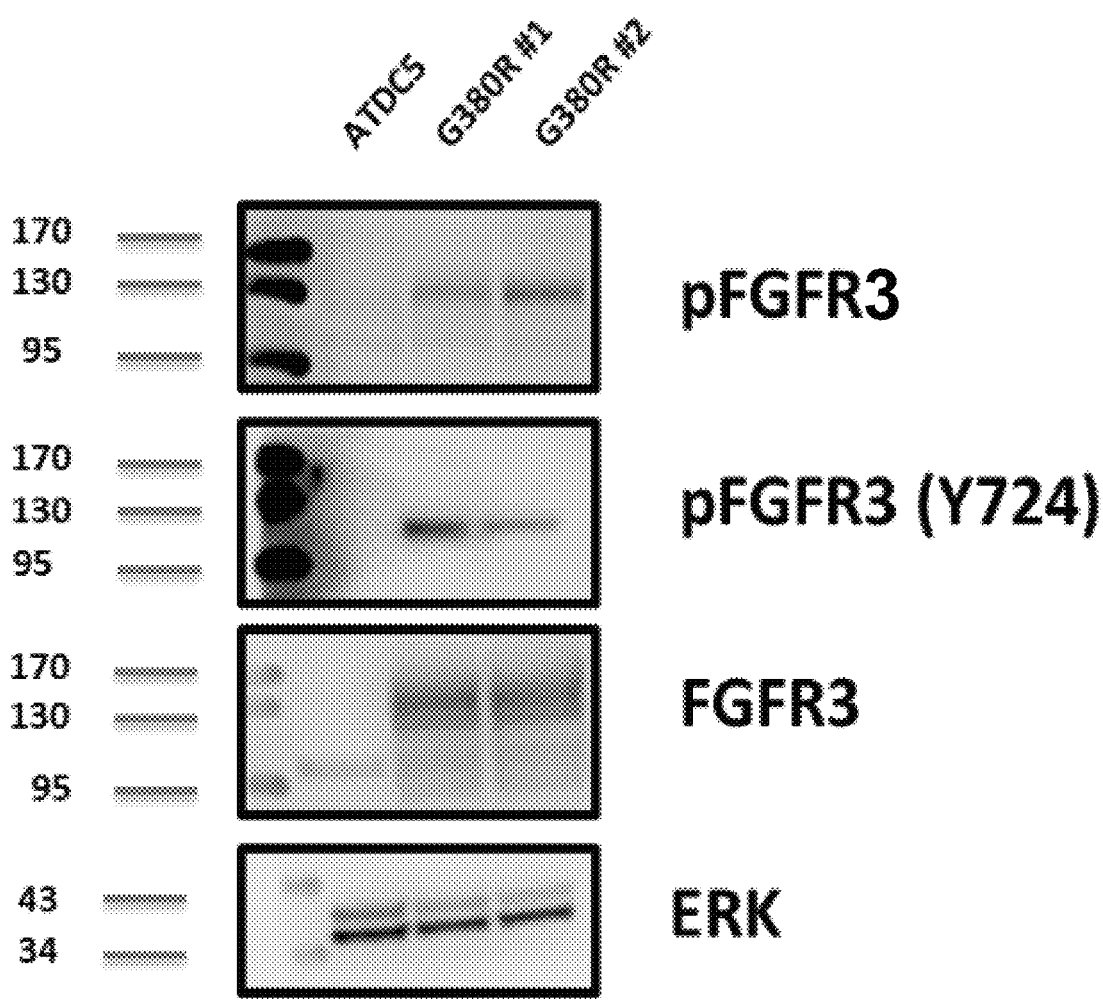
FIG. 20 is an image of a Western blot of non-induced wild type ATDC5 and retrovirally infected ATDC5 cells expressing FGFR3$^{G380R}$.

To study FGFR3-decoy induced inhibition of FGFR3$^{G380R}$ in a chondrocytic cell model, studies were performed to determine the effect of sFGFR3_Del4-D3 on the proliferation of ATDC5 cells genetically modified to overexpress the FGFR3$^{ach}$ mutation (ATDC5 FGFR3$^{G380R}$ cells). The chondrocytic cell line ATDC5 cell, which was first isolated from the differentiating teratocarcinoma stem cell line AT805, is commonly used as a model for in vitro chondrocyte research. ATDC5 cells were first infected with a retroviral expression vector and a stable cell line expressing FGFR3$^{G380R}$ was generated. The expression of FGFR3$^{G380R}$ in the ATDC5 cell line was determined via Western blot (FIG. 20). Extracts of ATDC5 cells expressing FGFR3$^{G380R}$ at passage one (G380R #1) and two (G380R

Figure 21:
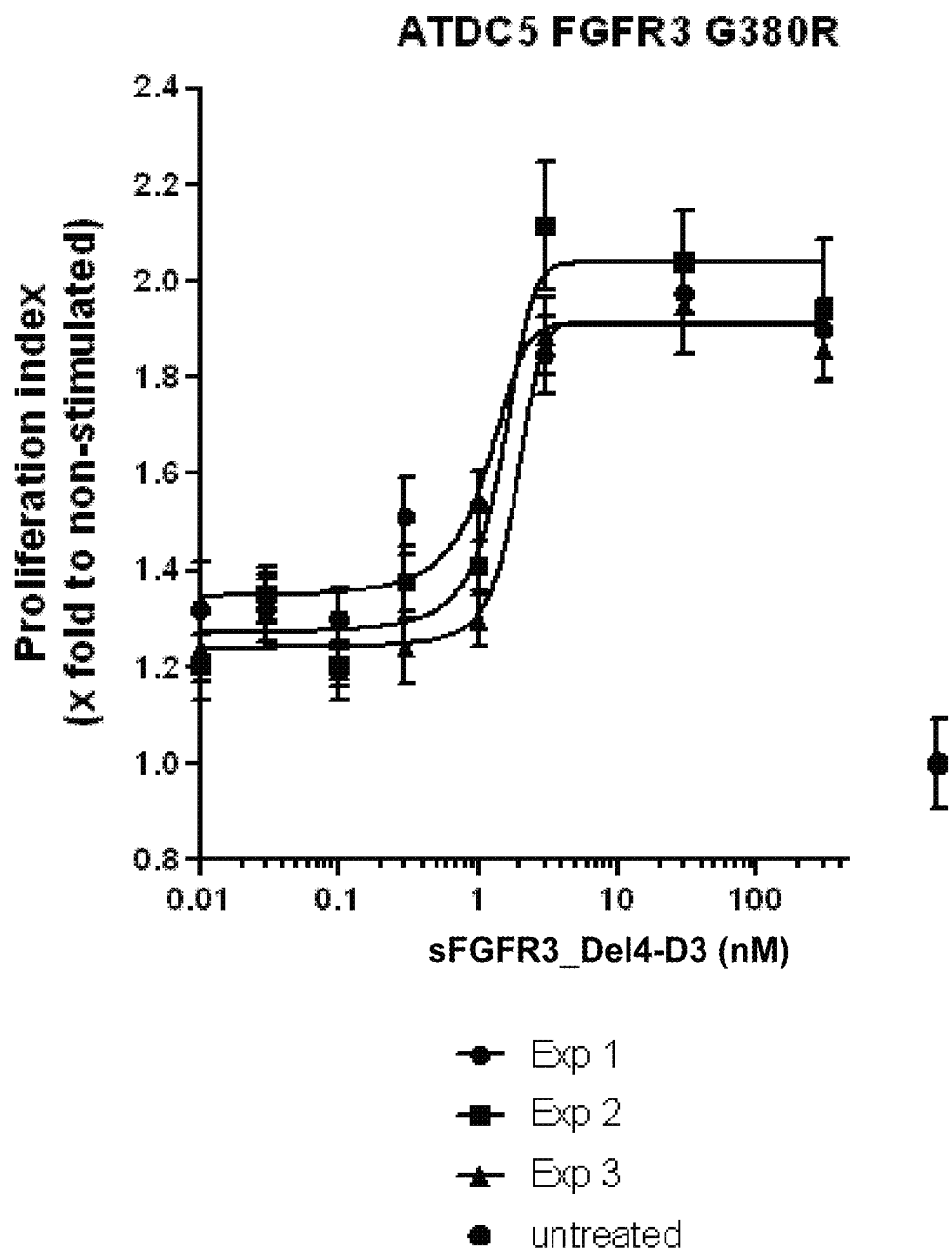
FIG. 21 is a graph showing the induction of proliferation of ATDC5 FGFR3$^{G380R}$ cells in the presence of SFGFR3_DEL4-D3 for three experiments. Untreated ATDC5 FGFR3$^{G380R}$ cells were used as a control.

2) after resistant cell selection and extracts of control ATDC5 cells were blotted and detected with antibodies for total phosphorylation of FGFR3 (pFGFR3), the specific phosphotyrosine 724 in FGFR3 (pFGFR3 Y724), and total FGFR3 expression (FGFR3). Total extracellular signal-related kinase expression was used as loading control (ERK). Addition of SFGFR3_DEL4-D3 to the ATDC5 FGFR3$^{G380R}$ cells dose-dependently increased the proliferation index of the ATDC5 FGFR3$^{G380R}$ cells by two-fold with an EC$_{50}$ of 1.25+/−0.27 nM (FIG. 21). These results demonstrate that addition of SFGFR3_DEL4-D3 to ATDC5 FGFR3$^{G380R}$ cells overcomes the negative growth signal mediated by FGFR3$^{G380R}$ in a cellular model of achondroplasia and are in line with the anti-proliferative signal mediated by FGFR3 in chondrocytes, which is more pronounced when the chondrocytes express a FGFR3 including the G380R mutation.

OTHER EMBODIMENTS

All publications, patents, and patent applications mentioned in the above specification are hereby incorporated by reference to the same extent as if each individual publication, patent or patent application was specifically and individually indicated to be incorporated by reference in its entirety. Various modifications and variations of the described methods, pharmaceutical compositions, and kits of the invention will be apparent to those skilled in the art without departing from the scope and spirit of the invention. Although the invention has been described in connection with specific embodiments, it will be understood that it is capable of further modifications and that the invention as claimed should not be unduly limited to such specific embodiments. Indeed, various modifications of the described modes for carrying out the invention that are obvious to those skilled in the art are intended to be within the scope of the invention. This application is intended to cover any variations, uses, or adaptations of the invention following, in general, the principles of the invention and including such departures from the present disclosure come within known customary practice within the art to which the invention pertains and may be applied to the essential features herein before set forth.

The invention claimed is:

1. A polynucleotide encoding a soluble fibroblast growth factor receptor 3 (sFGFR3) polypeptide comprising the amino acid sequence of SEQ ID NO: 33.

2. The polynucleotide of claim 1, wherein the polynucleotide comprises a nucleic acid sequence at least 80% identical to nucleotides 58-1104 of SEQ ID NO: 37.

3. The polynucleotide of claim 1, wherein the polynucleotide comprises the nucleic acid sequence of nucleotides 58-1104 of SEQ ID NO: 37.

4. The polynucleotide of claim 1, wherein the polynucleotide comprises a nucleic acid sequence at least 80% identical to nucleotides 52-1098 of SEQ ID NO: 21.

5. The polynucleotide of claim 1, wherein the polynucleotide comprises the nucleic acid sequence of nucleotides 52-1098 of SEQ ID NO: 21.

6. The polynucleotide of claim 1, wherein the sFGFR3 polypeptide binds to fibroblast growth factor 1 (FGF1), fibroblast growth factor 2 (FGF2), fibroblast growth factor 9 (FGF9), fibroblast growth factor 18 (FGF18), fibroblast growth factor 19 (FGF19), or fibroblast growth factor 21 (FGF21).

7. The polynucleotide of claim 6, wherein the binding is characterized by a $K_d$ of about 1 nM to about 10 nM.

8. A vector comprising the polynucleotide of claim 1.

9. The vector of claim 8, wherein the vector comprises the nucleic acid sequence of nucleotides 58-1104 of SEQ ID NO: 37.

10. The vector of claim 8, wherein the vector comprises the nucleic acid sequence of SEQ ID NO: 37.

11. The vector of claim 8, wherein the vector comprises the nucleic acid sequence of nucleotides 52-1098 of SEQ ID NO: 21.

12. The vector of claim 8, wherein the vector is a plasmid, an artificial chromosome, a viral vector or a phage vector.

13. A method of producing a soluble fibroblast growth factor receptor 3 (sFGFR3) polypeptide, the method comprising:
  (i) culturing a host cell comprising the polynucleotide of claim 1 in a culture medium under conditions suitable for expression of the sFGFR3 polypeptide; and
  (ii) recovering the sFGFR3 polypeptide from the culture medium.

14. The method of claim 13, wherein the polynucleotide comprises the nucleic acid sequence of nucleotides 58-1104 of SEQ ID NO: 37, or the nucleic acid sequence of nucleotides 52-1098 of SEQ ID NO: 21.

15. The method of claim 13, wherein the host cell is a HEK293 cell or CHO cell.

16. A method of producing a soluble fibroblast growth factor receptor 3 (sFGFR3) polypeptide, the method comprising:
  (i) culturing a host cell comprising the vector of claim 8 in a culture medium under conditions suitable for expression of the sFGFR3 polypeptide; and
  (ii) recovering the sFGFR3 polypeptide from the culture medium.

17. The method of claim 16, wherein the vector comprises the nucleic acid sequence of nucleotides 58-1104 of SEQ NO: 37, or the nucleic acid sequence of nucleotides 52-1098 of SEQ ID NO: 21.

18. The method of claim 16, wherein the vector comprises the nucleic acid sequence of SEQ ID NO: 37.

19. The method of claim 16, wherein the host cell is a HEK293 cell or CHO cell.

* * * * *

```
                      SEQUENCE LISTING

<160> NUMBER OF SEQ ID NOS: 39

<210> SEQ ID NO 1
<211> LENGTH: 301
<212> TYPE: PRT
<213> ORGANISM: Artificial Sequence
<220> FEATURE:
<223> OTHER INFORMATION: Synthetic construct

<400> SEQUENCE: 1

Glu Ser Leu Gly Thr Glu Gln Arg Val Val Gly Arg Ala Ala Glu Val
1               5                   10                  15

Pro Gly Pro Glu Pro Gly Gln Gln Glu Gln Leu Val Phe Gly Ser Gly
            20                  25                  30

Asp Ala Val Glu Leu Ser Cys Pro Pro Gly Gly Gly Pro Met Gly
        35                  40                  45

Pro Thr Val Trp Val Lys Asp Gly Thr Gly Leu Val Pro Ser Glu Arg
    50                  55                  60

Val Leu Val Gly Pro Gln Arg Leu Gln Val Leu Asn Ala Ser His Glu
65                  70                  75                  80

Asp Ser Gly Ala Tyr Ser Cys Arg Gln Arg Leu Thr Gln Arg Val Leu
                85                  90                  95

Cys His Phe Ser Val Arg Val Thr Asp Ala Pro Ser Ser Gly Asp Asp
                100                 105                 110

Glu Asp Gly Glu Asp Glu Ala Glu Asp Thr Gly Val Asp Thr Gly Ala
            115                 120                 125

Pro Tyr Trp Thr Arg Pro Glu Arg Met Asp Lys Lys Leu Leu Ala Val
    130                 135                 140

Pro Ala Ala Asn Thr Val Arg Phe Arg Cys Pro Ala Ala Gly Asn Pro
145                 150                 155                 160

Thr Pro Ser Ile Ser Trp Leu Lys Asn Gly Arg Glu Phe Arg Gly Glu
                165                 170                 175

His Arg Ile Gly Gly Ile Lys Leu Arg His Gln Gln Trp Ser Leu Val
            180                 185                 190

Met Glu Ser Val Val Pro Ser Asp Arg Gly Asn Tyr Thr Cys Val Val
        195                 200                 205

Glu Asn Lys Phe Gly Ser Ile Arg Gln Thr Tyr Thr Leu Asp Val Leu
```

```
                210                 215                 220
Glu Arg Ser Pro His Arg Pro Ile Leu Gln Ala Gly Leu Pro Ala Asn
225                 230                 235                 240

Gln Thr Ala Val Leu Gly Ser Asp Val Glu Phe His Cys Lys Val Tyr
                245                 250                 255

Ser Asp Ala Gln Pro His Ile Gln Trp Leu Lys His Val Glu Val Asn
                260                 265                 270

Gly Ser Lys Val Gly Pro Asp Gly Thr Pro Tyr Val Thr Val Leu Lys
                275                 280                 285

Val Ser Leu Glu Ser Asn Ala Ser Met Ser Ser Asn Thr
290                 295                 300

<210> SEQ ID NO 2
<211> LENGTH: 301
<212> TYPE: PRT
<213> ORGANISM: Artificial Sequence
<220> FEATURE:
<223> OTHER INFORMATION: Synthetic construct

<400> SEQUENCE: 2

Glu Ser Leu Gly Thr Glu Gln Arg Val Val Gly Arg Ala Ala Glu Val
1               5                   10                  15

Pro Gly Pro Glu Pro Gly Gln Gln Glu Gln Leu Val Phe Gly Ser Gly
                20                  25                  30

Asp Ala Val Glu Leu Ser Cys Pro Pro Pro Gly Gly Gly Pro Met Gly
                35                  40                  45

Pro Thr Val Trp Val Lys Asp Gly Thr Gly Leu Val Pro Ser Glu Arg
50                  55                  60

Val Leu Val Gly Pro Gln Arg Leu Gln Val Leu Asn Ala Ser His Glu
65                  70                  75                  80

Asp Ser Gly Ala Tyr Ser Cys Arg Gln Arg Leu Thr Gln Arg Val Leu
                85                  90                  95

Cys His Phe Ser Val Arg Val Thr Asp Ala Pro Ser Ser Gly Asp Asp
                100                 105                 110

Glu Asp Gly Glu Asp Glu Ala Glu Asp Thr Gly Val Asp Thr Gly Ala
                115                 120                 125

Pro Tyr Trp Thr Arg Pro Glu Arg Met Asp Lys Lys Leu Leu Ala Val
                130                 135                 140

Pro Ala Ala Asn Thr Val Arg Phe Arg Cys Pro Ala Ala Gly Asn Pro
145                 150                 155                 160

Thr Pro Ser Ile Ser Trp Leu Lys Asn Gly Arg Glu Phe Arg Gly Glu
                165                 170                 175

His Arg Ile Gly Gly Ile Lys Leu Arg His Gln Gln Trp Ser Leu Val
                180                 185                 190

Met Glu Ser Val Val Pro Ser Asp Arg Gly Asn Tyr Thr Cys Val Val
                195                 200                 205

Glu Asn Lys Phe Gly Ser Ile Arg Gln Thr Tyr Thr Leu Asp Val Leu
                210                 215                 220

Glu Arg Ser Pro His Arg Pro Ile Leu Gln Ala Gly Leu Pro Ala Asn
225                 230                 235                 240

Gln Thr Ala Val Leu Gly Ser Asp Val Glu Phe His Ser Lys Val Tyr
                245                 250                 255

Ser Asp Ala Gln Pro His Ile Gln Trp Leu Lys His Val Glu Val Asn
                260                 265                 270

Gly Ser Lys Val Gly Pro Asp Gly Thr Pro Tyr Val Thr Val Leu Lys
```

```
            275                 280                 285
Val Ser Leu Glu Ser Asn Ala Ser Met Ser Ser Asn Thr
    290                 295                 300

<210> SEQ ID NO 3
<211> LENGTH: 47
<212> TYPE: PRT
<213> ORGANISM: Artificial Sequence
<220> FEATURE:
<223> OTHER INFORMATION: Synthetic construct

<400> SEQUENCE: 3

Thr Ala Gly Ala Asn Thr Thr Asp Lys Glu Leu Glu Val Leu Ser Leu
1               5                   10                  15

Asn Val Thr Phe Glu Asp Ala Gly Glu Tyr Thr Cys Leu Ala Gly Asn
            20                  25                  30

Ser Ile Gly Phe Ser His His Ser Ala Trp Leu Val Val Leu Pro
        35                  40                  45

<210> SEQ ID NO 4
<211> LENGTH: 348
<212> TYPE: PRT
<213> ORGANISM: Artificial Sequence
<220> FEATURE:
<223> OTHER INFORMATION: Synthetic construct

<400> SEQUENCE: 4

Glu Ser Leu Gly Thr Glu Gln Arg Val Val Gly Arg Ala Ala Glu Val
1               5                   10                  15

Pro Gly Pro Glu Pro Gly Gln Gln Glu Gln Leu Val Phe Gly Ser Gly
            20                  25                  30

Asp Ala Val Glu Leu Ser Cys Pro Pro Pro Gly Gly Gly Pro Met Gly
        35                  40                  45

Pro Thr Val Trp Val Lys Asp Gly Thr Gly Leu Val Pro Ser Glu Arg
50                  55                  60

Val Leu Val Gly Pro Gln Arg Leu Gln Val Leu Asn Ala Ser His Glu
65                  70                  75                  80

Asp Ser Gly Ala Tyr Ser Cys Arg Gln Arg Leu Thr Gln Arg Val Leu
                85                  90                  95

Cys His Phe Ser Val Arg Val Thr Asp Ala Pro Ser Ser Gly Asp Asp
            100                 105                 110

Glu Asp Gly Glu Asp Glu Ala Glu Asp Thr Gly Val Asp Thr Gly Ala
        115                 120                 125

Pro Tyr Trp Thr Arg Pro Glu Arg Met Asp Lys Lys Leu Leu Ala Val
    130                 135                 140

Pro Ala Ala Asn Thr Val Arg Phe Arg Cys Pro Ala Ala Gly Asn Pro
145                 150                 155                 160

Thr Pro Ser Ile Ser Trp Leu Lys Asn Gly Arg Glu Phe Arg Gly Glu
                165                 170                 175

His Arg Ile Gly Gly Ile Lys Leu Arg His Gln Gln Trp Ser Leu Val
            180                 185                 190

Met Glu Ser Val Val Pro Ser Asp Arg Gly Asn Tyr Thr Cys Val Val
        195                 200                 205

Glu Asn Lys Phe Gly Ser Ile Arg Gln Thr Tyr Thr Leu Asp Val Leu
    210                 215                 220

Glu Arg Ser Pro His Arg Pro Ile Leu Gln Ala Gly Leu Pro Ala Asn
225                 230                 235                 240
```

```
Gln Thr Ala Val Leu Gly Ser Asp Val Glu Phe His Cys Lys Val Tyr
                245                 250                 255

Ser Asp Ala Gln Pro His Ile Gln Trp Leu Lys His Val Glu Val Asn
            260                 265                 270

Gly Ser Lys Val Gly Pro Asp Gly Thr Pro Tyr Val Thr Val Leu Lys
        275                 280                 285

Thr Ala Gly Ala Asn Thr Thr Asp Lys Glu Leu Glu Val Leu Ser Leu
    290                 295                 300

Asn Val Thr Phe Glu Asp Ala Gly Glu Tyr Thr Cys Leu Ala Gly Asn
305                 310                 315                 320

Ser Ile Gly Phe Ser His His Ser Ala Trp Leu Val Val Leu Pro Val
                325                 330                 335

Ser Leu Glu Ser Asn Ala Ser Met Ser Ser Asn Thr
            340                 345

<210> SEQ ID NO 5
<211> LENGTH: 784
<212> TYPE: PRT
<213> ORGANISM: Homo sapiens

<400> SEQUENCE: 5

Glu Ser Leu Gly Thr Glu Gln Arg Val Val Gly Arg Ala Ala Glu Val
1               5                   10                  15

Pro Gly Pro Glu Pro Gly Gln Gln Glu Gln Leu Val Phe Gly Ser Gly
            20                  25                  30

Asp Ala Val Glu Leu Ser Cys Pro Pro Pro Gly Gly Gly Pro Met Gly
        35                  40                  45

Pro Thr Val Trp Val Lys Asp Gly Thr Gly Leu Val Pro Ser Glu Arg
    50                  55                  60

Val Leu Val Gly Pro Gln Arg Leu Gln Val Leu Asn Ala Ser His Glu
65                  70                  75                  80

Asp Ser Gly Ala Tyr Ser Cys Arg Gln Arg Leu Thr Gln Arg Val Leu
                85                  90                  95

Cys His Phe Ser Val Arg Val Thr Asp Ala Pro Ser Ser Gly Asp Asp
            100                 105                 110

Glu Asp Gly Glu Asp Glu Ala Glu Asp Thr Gly Val Asp Thr Gly Ala
        115                 120                 125

Pro Tyr Trp Thr Arg Pro Glu Arg Met Asp Lys Lys Leu Leu Ala Val
    130                 135                 140

Pro Ala Ala Asn Thr Val Arg Phe Arg Cys Pro Ala Ala Gly Asn Pro
145                 150                 155                 160

Thr Pro Ser Ile Ser Trp Leu Lys Asn Gly Arg Glu Phe Arg Gly Glu
                165                 170                 175

His Arg Ile Gly Gly Ile Lys Leu Arg His Gln Gln Trp Ser Leu Val
            180                 185                 190

Met Glu Ser Val Val Pro Ser Asp Arg Gly Asn Tyr Thr Cys Val Val
        195                 200                 205

Glu Asn Lys Phe Gly Ser Ile Arg Gln Thr Tyr Thr Leu Asp Val Leu
    210                 215                 220

Glu Arg Ser Pro His Arg Pro Ile Leu Gln Ala Gly Leu Pro Ala Asn
225                 230                 235                 240

Gln Thr Ala Val Leu Gly Ser Asp Val Glu Phe His Cys Lys Val Tyr
                245                 250                 255

Ser Asp Ala Gln Pro His Ile Gln Trp Leu Lys His Val Glu Val Asn
            260                 265                 270
```

```
Gly Ser Lys Val Gly Pro Asp Gly Thr Pro Tyr Val Thr Val Leu Lys
        275                 280                 285

Thr Ala Gly Ala Asn Thr Thr Asp Lys Glu Leu Glu Val Leu Ser Leu
290                 295                 300

His Asn Val Thr Phe Glu Asp Ala Gly Glu Tyr Thr Cys Leu Ala Gly
305                 310                 315                 320

Asn Ser Ile Gly Phe Ser His His Ser Ala Trp Leu Val Val Leu Pro
                325                 330                 335

Ala Glu Glu Glu Leu Val Glu Ala Asp Glu Ala Gly Ser Val Tyr Ala
            340                 345                 350

Gly Ile Leu Ser Tyr Gly Val Gly Phe Phe Leu Phe Ile Leu Val Val
                355                 360                 365

Ala Ala Val Thr Leu Cys Arg Leu Arg Ser Pro Pro Lys Lys Gly Leu
            370                 375                 380

Gly Ser Pro Thr Val His Lys Ile Ser Arg Phe Pro Leu Lys Arg Gln
385                 390                 395                 400

Val Ser Leu Glu Ser Asn Ala Ser Met Ser Ser Asn Thr Pro Leu Val
                405                 410                 415

Arg Ile Ala Arg Leu Ser Ser Gly Glu Gly Pro Thr Leu Ala Asn Val
            420                 425                 430

Ser Glu Leu Glu Leu Pro Ala Asp Pro Lys Trp Glu Leu Ser Arg Ala
                435                 440                 445

Arg Leu Thr Leu Gly Lys Pro Leu Gly Glu Gly Cys Phe Gly Gln Val
            450                 455                 460

Val Met Ala Glu Ala Ile Gly Ile Asp Lys Asp Arg Ala Ala Lys Pro
465                 470                 475                 480

Val Thr Val Ala Val Lys Met Leu Lys Asp Asp Ala Thr Asp Lys Asp
                485                 490                 495

Leu Ser Asp Leu Val Ser Glu Met Glu Met Met Lys Met Ile Gly Lys
            500                 505                 510

His Lys Asn Ile Ile Asn Leu Leu Gly Ala Cys Thr Gln Gly Gly Pro
        515                 520                 525

Leu Tyr Val Leu Val Glu Tyr Ala Ala Lys Gly Asn Leu Arg Glu Phe
        530                 535                 540

Leu Arg Ala Arg Arg Pro Pro Gly Leu Asp Tyr Ser Phe Asp Thr Cys
545                 550                 555                 560

Lys Pro Pro Glu Glu Gln Leu Thr Phe Lys Asp Leu Val Ser Cys Ala
                565                 570                 575

Tyr Gln Val Ala Arg Gly Met Glu Tyr Leu Ala Ser Gln Lys Cys Ile
            580                 585                 590

His Arg Asp Leu Ala Ala Arg Asn Val Leu Val Thr Glu Asp Asn Val
        595                 600                 605

Met Lys Ile Ala Asp Phe Gly Leu Ala Arg Asp Val His Asn Leu Asp
        610                 615                 620

Tyr Tyr Lys Lys Thr Thr Asn Gly Arg Leu Pro Val Lys Trp Met Ala
625                 630                 635                 640

Pro Glu Ala Leu Phe Asp Arg Val Tyr Thr His Gln Ser Asp Val Trp
                645                 650                 655

Ser Phe Gly Val Leu Leu Trp Glu Ile Phe Thr Leu Gly Gly Ser Pro
            660                 665                 670

Tyr Pro Gly Ile Pro Val Glu Glu Leu Phe Lys Leu Leu Lys Glu Gly
        675                 680                 685
```

```
His Arg Met Asp Lys Pro Ala Asn Cys Thr His Asp Leu Tyr Met Ile
    690                 695                 700
Met Arg Glu Cys Trp His Ala Ala Pro Ser Gln Arg Pro Thr Phe Lys
705                 710                 715                 720
Gln Leu Val Glu Asp Leu Asp Arg Val Leu Thr Val Thr Ser Thr Asp
                725                 730                 735
Glu Tyr Leu Asp Leu Ser Ala Pro Phe Glu Gln Tyr Ser Pro Gly Gly
            740                 745                 750
Gln Asp Thr Pro Ser Ser Ser Ser Gly Asp Asp Ser Val Phe Ala
                755                 760                 765
His Asp Leu Leu Pro Pro Ala Pro Pro Ser Ser Gly Gly Ser Arg Thr
    770                 775                 780
```

<210> SEQ ID NO 6
<211> LENGTH: 22
<212> TYPE: PRT
<213> ORGANISM: Artificial Sequence
<220> FEATURE:
<223> OTHER INFORMATION: Synthetic construct

<400> SEQUENCE: 6

```
Met Gly Ala Pro Ala Cys Ala Leu Ala Leu Cys Val Ala Val Ala Ile
1               5                   10                  15
Val Ala Gly Ala Ser Ser
            20
```

<210> SEQ ID NO 7
<211> LENGTH: 672
<212> TYPE: PRT
<213> ORGANISM: Homo sapiens

<400> SEQUENCE: 7

```
Glu Ser Leu Gly Thr Glu Gln Arg Val Val Gly Arg Ala Ala Glu Val
1               5                   10                  15
Pro Gly Pro Glu Pro Gly Gln Gln Glu Gln Leu Val Phe Gly Ser Gly
                20                  25                  30
Asp Ala Val Glu Leu Ser Cys Pro Pro Pro Gly Gly Gly Pro Met Gly
            35                  40                  45
Pro Thr Val Trp Val Lys Asp Gly Thr Gly Leu Val Pro Ser Glu Arg
    50                  55                  60
Val Leu Val Gly Pro Gln Arg Leu Gln Val Leu Asn Ala Ser His Glu
65                  70                  75                  80
Asp Ser Gly Ala Tyr Ser Cys Arg Gln Arg Leu Thr Gln Arg Val Leu
                85                  90                  95
Cys His Phe Ser Val Arg Val Thr Asp Ala Pro Ser Ser Gly Asp Asp
                100                 105                 110
Glu Asp Gly Glu Asp Glu Ala Glu Asp Thr Gly Val Asp Thr Gly Ala
            115                 120                 125
Pro Tyr Trp Thr Arg Pro Glu Arg Met Asp Lys Lys Leu Leu Ala Val
    130                 135                 140
Pro Ala Ala Asn Thr Val Arg Phe Arg Cys Pro Ala Ala Gly Asn Pro
145                 150                 155                 160
Thr Pro Ser Ile Ser Trp Leu Lys Asn Gly Arg Glu Phe Arg Gly Glu
                165                 170                 175
His Arg Ile Gly Gly Ile Lys Leu Arg His Gln Gln Trp Ser Leu Val
                180                 185                 190
Met Glu Ser Val Val Pro Ser Asp Arg Gly Asn Tyr Thr Cys Val Val
```

```
              195                 200                 205
Glu Asn Lys Phe Gly Ser Ile Arg Gln Thr Tyr Thr Leu Asp Val Leu
210                 215                 220

Glu Arg Ser Pro His Arg Pro Ile Leu Gln Ala Gly Leu Pro Ala Asn
225                 230                 235                 240

Gln Thr Ala Val Leu Gly Ser Asp Val Glu Phe His Cys Lys Val Tyr
                245                 250                 255

Ser Asp Ala Gln Pro His Ile Gln Trp Leu Lys His Val Glu Val Asn
                260                 265                 270

Gly Ser Lys Val Gly Pro Asp Gly Thr Pro Tyr Val Thr Val Leu Lys
            275                 280                 285

Val Ser Leu Glu Ser Asn Ala Ser Met Ser Ser Asn Thr Pro Leu Val
290                 295                 300

Arg Ile Ala Arg Leu Ser Ser Gly Glu Gly Pro Thr Leu Ala Asn Val
305                 310                 315                 320

Ser Glu Leu Glu Leu Pro Ala Asp Pro Lys Trp Glu Leu Ser Arg Ala
                325                 330                 335

Arg Leu Thr Leu Gly Lys Pro Leu Gly Glu Gly Cys Phe Gly Gln Val
            340                 345                 350

Val Met Ala Glu Ala Ile Gly Ile Asp Lys Asp Arg Ala Ala Lys Pro
        355                 360                 365

Val Thr Val Ala Val Lys Met Leu Lys Asp Asp Ala Thr Asp Lys Asp
370                 375                 380

Leu Ser Asp Leu Val Ser Glu Met Glu Met Met Lys Met Ile Gly Lys
385                 390                 395                 400

His Lys Asn Ile Ile Asn Leu Leu Gly Ala Cys Thr Gln Gly Gly Pro
                405                 410                 415

Leu Tyr Val Leu Val Glu Tyr Ala Ala Lys Gly Asn Leu Arg Glu Phe
            420                 425                 430

Leu Arg Ala Arg Arg Pro Pro Gly Leu Asp Tyr Ser Phe Asp Thr Cys
        435                 440                 445

Lys Pro Pro Glu Glu Gln Leu Thr Phe Lys Asp Leu Val Ser Cys Ala
    450                 455                 460

Tyr Gln Val Ala Arg Gly Met Glu Tyr Leu Ala Ser Gln Lys Cys Ile
465                 470                 475                 480

His Arg Asp Leu Ala Ala Arg Asn Val Leu Val Thr Glu Asp Asn Val
                485                 490                 495

Met Lys Ile Ala Asp Phe Gly Leu Ala Arg Asp Val His Asn Leu Asp
            500                 505                 510

Tyr Tyr Lys Lys Thr Thr Asn Gly Arg Leu Pro Val Lys Trp Met Ala
        515                 520                 525

Pro Glu Ala Leu Phe Asp Arg Val Tyr Thr His Gln Ser Asp Val Trp
    530                 535                 540

Ser Phe Gly Val Leu Leu Trp Glu Ile Phe Thr Leu Gly Gly Ser Pro
545                 550                 555                 560

Tyr Pro Gly Ile Pro Val Glu Glu Leu Phe Lys Leu Leu Lys Glu Gly
                565                 570                 575

His Arg Met Asp Lys Pro Ala Asn Cys Thr His Asp Leu Tyr Met Ile
            580                 585                 590

Met Arg Glu Cys Trp His Ala Ala Pro Ser Gln Arg Pro Thr Phe Lys
        595                 600                 605

Gln Leu Val Glu Asp Leu Asp Arg Val Leu Thr Val Thr Ser Thr Asp
    610                 615                 620
```

Glu Tyr Leu Asp Leu Ser Ala Pro Phe Glu Gln Tyr Ser Pro Gly Gly
625                 630                 635                 640

Gln Asp Thr Pro Ser Ser Ser Ser Gly Asp Ser Val Phe Ala
        645                 650                 655

His Asp Leu Leu Pro Pro Ala Pro Pro Ser Ser Gly Gly Ser Arg Thr
            660                 665                 670

<210> SEQ ID NO 8
<211> LENGTH: 672
<212> TYPE: PRT
<213> ORGANISM: Artificial Sequence
<220> FEATURE:
<223> OTHER INFORMATION: Synthetic construct

<400> SEQUENCE: 8

Glu Ser Leu Gly Thr Glu Gln Arg Val Val Gly Arg Ala Ala Glu Val
1               5                   10                  15

Pro Gly Pro Glu Pro Gly Gln Gln Glu Gln Leu Val Phe Gly Ser Gly
            20                  25                  30

Asp Ala Val Glu Leu Ser Cys Pro Pro Gly Gly Gly Pro Met Gly
        35                  40                  45

Pro Thr Val Trp Val Lys Asp Gly Thr Gly Leu Val Pro Ser Glu Arg
50                  55                  60

Val Leu Val Gly Pro Gln Arg Leu Gln Val Leu Asn Ala Ser His Glu
65                  70                  75                  80

Asp Ser Gly Ala Tyr Ser Cys Arg Gln Arg Leu Thr Gln Arg Val Leu
                85                  90                  95

Cys His Phe Ser Val Arg Val Thr Asp Ala Pro Ser Ser Gly Asp Asp
            100                 105                 110

Glu Asp Gly Glu Asp Glu Ala Glu Asp Thr Gly Val Asp Thr Gly Ala
        115                 120                 125

Pro Tyr Trp Thr Arg Pro Glu Arg Met Asp Lys Lys Leu Leu Ala Val
    130                 135                 140

Pro Ala Ala Asn Thr Val Arg Phe Arg Cys Pro Ala Ala Gly Asn Pro
145                 150                 155                 160

Thr Pro Ser Ile Ser Trp Leu Lys Asn Gly Arg Glu Phe Arg Gly Glu
                165                 170                 175

His Arg Ile Gly Gly Ile Lys Leu Arg His Gln Gln Trp Ser Leu Val
            180                 185                 190

Met Glu Ser Val Val Pro Ser Asp Arg Gly Asn Tyr Thr Cys Val Val
        195                 200                 205

Glu Asn Lys Phe Gly Ser Ile Arg Gln Thr Tyr Thr Leu Asp Val Leu
    210                 215                 220

Glu Arg Ser Pro His Arg Pro Ile Leu Gln Ala Gly Leu Pro Ala Asn
225                 230                 235                 240

Gln Thr Ala Val Leu Gly Ser Asp Val Glu Phe His Ser Lys Val Tyr
                245                 250                 255

Ser Asp Ala Gln Pro His Ile Gln Trp Leu Lys His Val Glu Val Asn
            260                 265                 270

Gly Ser Lys Val Gly Pro Asp Gly Thr Pro Tyr Val Thr Val Leu Lys
        275                 280                 285

Val Ser Leu Glu Ser Asn Ala Ser Met Ser Ser Asn Thr Pro Leu Val
    290                 295                 300

Arg Ile Ala Arg Leu Ser Ser Gly Glu Gly Pro Thr Leu Ala Asn Val
305                 310                 315                 320

```
Ser Glu Leu Glu Leu Pro Ala Asp Pro Lys Trp Glu Leu Ser Arg Ala
            325                 330                 335

Arg Leu Thr Leu Gly Lys Pro Leu Gly Glu Gly Cys Phe Gly Gln Val
            340                 345                 350

Val Met Ala Glu Ala Ile Gly Ile Asp Lys Asp Arg Ala Ala Lys Pro
            355                 360                 365

Val Thr Val Ala Val Lys Met Leu Lys Asp Asp Ala Thr Asp Lys Asp
            370                 375                 380

Leu Ser Asp Leu Val Ser Glu Met Glu Met Met Lys Met Ile Gly Lys
385                 390                 395                 400

His Lys Asn Ile Ile Asn Leu Leu Gly Ala Cys Thr Gln Gly Gly Pro
                405                 410                 415

Leu Tyr Val Leu Val Glu Tyr Ala Ala Lys Gly Asn Leu Arg Glu Phe
            420                 425                 430

Leu Arg Ala Arg Arg Pro Pro Gly Leu Asp Tyr Ser Phe Asp Thr Cys
            435                 440                 445

Lys Pro Pro Glu Glu Gln Leu Thr Phe Lys Asp Leu Val Ser Cys Ala
            450                 455                 460

Tyr Gln Val Ala Arg Gly Met Glu Tyr Leu Ala Ser Gln Lys Cys Ile
465                 470                 475                 480

His Arg Asp Leu Ala Ala Arg Asn Val Leu Val Thr Glu Asp Asn Val
                485                 490                 495

Met Lys Ile Ala Asp Phe Gly Leu Ala Arg Asp Val His Asn Leu Asp
            500                 505                 510

Tyr Tyr Lys Lys Thr Thr Asn Gly Arg Leu Pro Val Lys Trp Met Ala
            515                 520                 525

Pro Glu Ala Leu Phe Asp Arg Val Tyr Thr His Gln Ser Asp Val Trp
            530                 535                 540

Ser Phe Gly Val Leu Leu Trp Glu Ile Phe Thr Leu Gly Gly Ser Pro
545                 550                 555                 560

Tyr Pro Gly Ile Pro Val Glu Glu Leu Phe Lys Leu Leu Lys Glu Gly
                565                 570                 575

His Arg Met Asp Lys Pro Ala Asn Cys Thr His Asp Leu Tyr Met Ile
            580                 585                 590

Met Arg Glu Cys Trp His Ala Ala Pro Ser Gln Arg Pro Thr Phe Lys
            595                 600                 605

Gln Leu Val Glu Asp Leu Asp Arg Val Leu Thr Val Thr Ser Thr Asp
            610                 615                 620

Glu Tyr Leu Asp Leu Ser Ala Pro Phe Glu Gln Tyr Ser Pro Gly Gly
625                 630                 635                 640

Gln Asp Thr Pro Ser Ser Ser Ser Gly Asp Asp Ser Val Phe Ala
                645                 650                 655

His Asp Leu Leu Pro Pro Ala Pro Pro Ser Ser Gly Gly Ser Arg Thr
            660                 665                 670
```

<210> SEQ ID NO 9
<211> LENGTH: 720
<212> TYPE: PRT
<213> ORGANISM: Artificial Sequence
<220> FEATURE:
<223> OTHER INFORMATION: Synthetic construct

<400> SEQUENCE: 9

```
Glu Ser Leu Gly Thr Glu Gln Arg Val Val Gly Arg Ala Ala Glu Val
1               5                   10                  15
```

```
Pro Gly Pro Glu Pro Gly Gln Gln Glu Gln Leu Val Phe Gly Ser Gly
            20                  25                  30

Asp Ala Val Glu Leu Ser Cys Pro Pro Gly Gly Pro Met Gly
            35                  40                  45

Pro Thr Val Trp Val Lys Asp Gly Thr Gly Leu Val Pro Ser Glu Arg
 50                  55                  60

Val Leu Val Gly Pro Gln Arg Leu Gln Val Leu Asn Ala Ser His Glu
 65                  70                  75                  80

Asp Ser Gly Ala Tyr Ser Cys Arg Gln Arg Leu Thr Gln Arg Val Leu
                85                  90                  95

Cys His Phe Ser Val Arg Val Thr Asp Ala Pro Ser Ser Gly Asp Asp
            100                 105                 110

Glu Asp Gly Glu Asp Glu Ala Glu Asp Thr Gly Val Asp Thr Gly Ala
            115                 120                 125

Pro Tyr Trp Thr Arg Pro Glu Arg Met Asp Lys Lys Leu Leu Ala Val
130                 135                 140

Pro Ala Ala Asn Thr Val Arg Phe Arg Cys Pro Ala Ala Gly Asn Pro
145                 150                 155                 160

Thr Pro Ser Ile Ser Trp Leu Lys Asn Gly Arg Glu Phe Arg Gly Glu
            165                 170                 175

His Arg Ile Gly Gly Ile Lys Leu Arg His Gln Gln Trp Ser Leu Val
            180                 185                 190

Met Glu Ser Val Val Pro Ser Asp Arg Gly Asn Tyr Thr Cys Val Val
            195                 200                 205

Glu Asn Lys Phe Gly Ser Ile Arg Gln Thr Tyr Thr Leu Asp Val Leu
            210                 215                 220

Glu Arg Ser Pro His Arg Pro Ile Leu Gln Ala Gly Leu Pro Ala Asn
225                 230                 235                 240

Gln Thr Ala Val Leu Gly Ser Asp Val Glu Phe His Cys Lys Val Tyr
            245                 250                 255

Ser Asp Ala Gln Pro His Ile Gln Trp Leu Lys His Val Glu Val Asn
            260                 265                 270

Gly Ser Lys Val Gly Pro Asp Gly Thr Pro Tyr Val Thr Val Leu Lys
            275                 280                 285

Thr Ala Gly Ala Asn Thr Thr Asp Lys Glu Leu Glu Val Leu Ser Leu
            290                 295                 300

His Asn Val Thr Phe Glu Asp Ala Gly Glu Tyr Thr Cys Leu Ala Gly
305                 310                 315                 320

Asn Ser Ile Gly Phe Ser His His Ser Ala Trp Leu Val Val Leu Pro
            325                 330                 335

Val Ser Leu Glu Ser Asn Ala Ser Met Ser Ser Asn Thr Pro Leu Val
            340                 345                 350

Arg Ile Ala Arg Leu Ser Ser Gly Glu Gly Pro Thr Leu Ala Asn Val
            355                 360                 365

Ser Glu Leu Glu Leu Pro Ala Asp Pro Lys Trp Glu Leu Ser Arg Ala
            370                 375                 380

Arg Leu Thr Leu Gly Lys Pro Leu Gly Glu Gly Cys Phe Gly Gln Val
385                 390                 395                 400

Val Met Ala Glu Ala Ile Gly Ile Asp Lys Asp Arg Ala Ala Lys Pro
            405                 410                 415

Val Thr Val Ala Val Lys Met Leu Lys Asp Asp Ala Thr Asp Lys Asp
            420                 425                 430
```

```
Leu Ser Asp Leu Val Ser Glu Met Glu Met Lys Met Ile Gly Lys
            435                 440                 445

His Lys Asn Ile Ile Asn Leu Leu Gly Ala Cys Thr Gln Gly Gly Pro
    450                 455                 460

Leu Tyr Val Leu Val Glu Tyr Ala Ala Lys Gly Asn Leu Arg Glu Phe
465                 470                 475                 480

Leu Arg Ala Arg Arg Pro Pro Gly Leu Asp Tyr Ser Phe Asp Thr Cys
                485                 490                 495

Lys Pro Pro Glu Glu Gln Leu Thr Phe Lys Asp Leu Val Ser Cys Ala
                500                 505                 510

Tyr Gln Val Ala Arg Gly Met Glu Tyr Leu Ala Ser Gln Lys Cys Ile
            515                 520                 525

His Arg Asp Leu Ala Ala Arg Asn Val Leu Val Thr Glu Asp Asn Val
    530                 535                 540

Met Lys Ile Ala Asp Phe Gly Leu Ala Arg Asp Val His Asn Leu Asp
545                 550                 555                 560

Tyr Tyr Lys Lys Thr Thr Asn Gly Arg Leu Pro Val Lys Trp Met Ala
                565                 570                 575

Pro Glu Ala Leu Phe Asp Arg Val Tyr Thr His Gln Ser Asp Val Trp
                580                 585                 590

Ser Phe Gly Val Leu Leu Trp Glu Ile Phe Thr Leu Gly Gly Ser Pro
            595                 600                 605

Tyr Pro Gly Ile Pro Val Glu Glu Leu Phe Lys Leu Leu Lys Glu Gly
            610                 615                 620

His Arg Met Asp Lys Pro Ala Asn Cys Thr His Asp Leu Tyr Met Ile
625                 630                 635                 640

Met Arg Glu Cys Trp His Ala Ala Pro Ser Gln Arg Pro Thr Phe Lys
                645                 650                 655

Gln Leu Val Glu Asp Leu Asp Arg Val Leu Thr Val Thr Ser Thr Asp
                660                 665                 670

Glu Tyr Leu Asp Leu Ser Ala Pro Phe Glu Gln Tyr Ser Pro Gly Gly
            675                 680                 685

Gln Asp Thr Pro Ser Ser Ser Ser Gly Asp Asp Ser Val Phe Ala
            690                 695                 700

His Asp Leu Leu Pro Pro Ala Pro Pro Ser Ser Gly Gly Ser Arg Thr
705                 710                 715                 720

<210> SEQ ID NO 10
<211> LENGTH: 512
<212> TYPE: PRT
<213> ORGANISM: Artificial Sequence
<220> FEATURE:
<223> OTHER INFORMATION: Synthetic construct

<400> SEQUENCE: 10

Glu Ser Leu Gly Thr Glu Gln Arg Val Val Gly Arg Ala Ala Glu Val
1               5                   10                  15

Pro Gly Pro Glu Pro Gly Gln Gln Glu Gln Leu Val Phe Gly Ser Gly
                20                  25                  30

Asp Ala Val Glu Leu Ser Cys Pro Pro Pro Gly Gly Gly Pro Met Gly
            35                  40                  45

Pro Thr Val Trp Val Lys Asp Gly Thr Gly Leu Val Pro Ser Glu Arg
        50                  55                  60

Val Leu Val Gly Pro Gln Arg Leu Gln Val Leu Asn Ala Ser His Glu
65              70                  75                  80
```

```
Asp Ser Gly Ala Tyr Ser Cys Arg Gln Arg Leu Thr Gln Arg Val Leu
            85                  90                  95
Cys His Phe Ser Val Arg Val Thr Asp Ala Pro Ser Ser Gly Asp Asp
            100                 105                 110
Glu Asp Gly Glu Asp Ala Glu Asp Thr Gly Val Asp Thr Gly Ala
            115                 120                 125
Pro Tyr Trp Thr Arg Pro Glu Arg Met Asp Lys Lys Leu Leu Ala Val
            130                 135                 140
Pro Ala Ala Asn Thr Val Arg Phe Arg Cys Pro Ala Ala Gly Asn Pro
145                 150                 155                 160
Thr Pro Ser Ile Ser Trp Leu Lys Asn Gly Arg Glu Phe Arg Gly Glu
            165                 170                 175
His Arg Ile Gly Gly Ile Lys Leu Arg His Gln Gln Trp Ser Leu Val
            180                 185                 190
Met Glu Ser Val Val Pro Ser Asp Arg Gly Asn Tyr Thr Cys Val Val
            195                 200                 205
Glu Asn Lys Phe Gly Ser Ile Arg Gln Thr Tyr Thr Leu Asp Val Leu
            210                 215                 220
Glu Arg Ser Pro His Arg Pro Ile Leu Gln Ala Gly Leu Pro Ala Asn
225                 230                 235                 240
Gln Thr Ala Val Leu Gly Ser Asp Val Glu Phe His Cys Lys Val Tyr
            245                 250                 255
Ser Asp Ala Gln Pro His Ile Gln Trp Leu Lys His Val Glu Val Asn
            260                 265                 270
Gly Ser Lys Val Gly Pro Asp Gly Thr Pro Tyr Val Thr Val Leu Lys
            275                 280                 285
Val Ser Leu Glu Ser Asn Ala Ser Met Ser Ser Asn Thr Ser Gly Ser
            290                 295                 300
Gly Ser Gly Ser Gly Ser Gly Ser Gly Ser Val Val Phe Pro
305                 310                 315                 320
Tyr Phe Pro Arg Leu Gly Arg Tyr Asn Leu Asn Phe His Glu Ala Gln
            325                 330                 335
Gln Ala Cys Leu Asp Gln Asp Ala Val Ile Ala Ser Phe Asp Gln Leu
            340                 345                 350
Tyr Asp Ala Trp Arg Gly Gly Leu Asp Trp Cys Asn Ala Gly Trp Leu
            355                 360                 365
Ser Asp Gly Ser Val Gln Tyr Pro Ile Thr Lys Pro Arg Glu Pro Cys
            370                 375                 380
Gly Gly Gln Asn Thr Val Pro Gly Val Arg Asn Tyr Gly Phe Trp Asp
385                 390                 395                 400
Lys Asp Lys Ser Arg Tyr Asp Val Phe Cys Phe Thr Ser Asn Phe Asn
            405                 410                 415
Gly Arg Phe Tyr Tyr Leu Ile His Pro Thr Lys Leu Thr Tyr Asp Glu
            420                 425                 430
Ala Val Gln Ala Cys Leu Asn Asp Gly Ala Gln Ile Ala Lys Val Gly
            435                 440                 445
Gln Ile Phe Ala Ala Trp Lys Ile Leu Gly Tyr Asp Arg Cys Asp Ala
            450                 455                 460
Gly Trp Leu Ala Asp Gly Ser Val Arg Tyr Pro Ile Ser Arg Pro Arg
465                 470                 475                 480
Arg Arg Cys Ser Pro Thr Glu Ala Ala Val Arg Phe Val Gly Phe Pro
            485                 490                 495
Asp Lys Lys His Lys Leu Tyr Gly Val Tyr Cys Phe Arg Ala Tyr Asn
```

<210> SEQ ID NO 11
<211> LENGTH: 512
<212> TYPE: PRT
<213> ORGANISM: Artificial Sequence
<220> FEATURE:
<223> OTHER INFORMATION: Synthetic construct

<400> SEQUENCE: 11

```
Glu Ser Leu Gly Thr Glu Gln Arg Val Val Gly Arg Ala Ala Glu Val
1               5                   10                  15

Pro Gly Pro Glu Pro Gly Gln Gln Glu Gln Leu Val Phe Gly Ser Gly
            20                  25                  30

Asp Ala Val Glu Leu Ser Cys Pro Pro Gly Gly Gly Pro Met Gly
            35                  40                  45

Pro Thr Val Trp Val Lys Asp Gly Thr Gly Leu Val Pro Ser Glu Arg
50                  55                  60

Val Leu Val Gly Pro Gln Arg Leu Gln Val Leu Asn Ala Ser His Glu
65                  70                  75                  80

Asp Ser Gly Ala Tyr Ser Cys Arg Gln Arg Leu Thr Gln Arg Val Leu
                85                  90                  95

Cys His Phe Ser Val Arg Val Thr Asp Ala Pro Ser Ser Gly Asp Asp
            100                 105                 110

Glu Asp Gly Glu Asp Glu Ala Glu Asp Thr Gly Val Asp Thr Gly Ala
            115                 120                 125

Pro Tyr Trp Thr Arg Pro Glu Arg Met Asp Lys Lys Leu Leu Ala Val
130                 135                 140

Pro Ala Ala Asn Thr Val Arg Phe Arg Cys Pro Ala Ala Gly Asn Pro
145                 150                 155                 160

Thr Pro Ser Ile Ser Trp Leu Lys Asn Gly Arg Glu Phe Arg Gly Glu
                165                 170                 175

His Arg Ile Gly Gly Ile Lys Leu Arg His Gln Gln Trp Ser Leu Val
            180                 185                 190

Met Glu Ser Val Val Pro Ser Asp Arg Gly Asn Tyr Thr Cys Val Val
            195                 200                 205

Glu Asn Lys Phe Gly Ser Ile Arg Gln Thr Tyr Thr Leu Asp Val Leu
        210                 215                 220

Glu Arg Ser Pro His Arg Pro Ile Leu Gln Ala Gly Leu Pro Ala Asn
225                 230                 235                 240

Gln Thr Ala Val Leu Gly Ser Asp Val Glu Phe His Ser Lys Val Tyr
                245                 250                 255

Ser Asp Ala Gln Pro His Ile Gln Trp Leu Lys His Val Glu Val Asn
            260                 265                 270

Gly Ser Lys Val Gly Pro Asp Gly Thr Pro Tyr Val Thr Val Leu Lys
        275                 280                 285

Val Ser Leu Glu Ser Asn Ala Ser Met Ser Ser Asn Thr Ser Gly Ser
290                 295                 300

Gly Ser Gly Ser Gly Ser Gly Ser Gly Ser Val Val Phe Pro
305                 310                 315                 320

Tyr Phe Pro Arg Leu Gly Arg Tyr Asn Leu Asn Phe His Glu Ala Gln
                325                 330                 335

Gln Ala Cys Leu Asp Gln Asp Ala Val Ile Ala Ser Phe Asp Gln Leu
            340                 345                 350

Tyr Asp Ala Trp Arg Gly Gly Leu Asp Trp Cys Asn Ala Gly Trp Leu
```

```
            355                 360                 365
Ser Asp Gly Ser Val Gln Tyr Pro Ile Thr Lys Pro Arg Glu Pro Cys
        370                 375                 380

Gly Gly Gln Asn Thr Val Pro Gly Val Arg Asn Tyr Gly Phe Trp Asp
385                 390                 395                 400

Lys Asp Lys Ser Arg Tyr Asp Val Phe Cys Phe Thr Ser Asn Phe Asn
                405                 410                 415

Gly Arg Phe Tyr Tyr Leu Ile His Pro Thr Lys Leu Thr Tyr Asp Glu
            420                 425                 430

Ala Val Gln Ala Cys Leu Asn Asp Gly Ala Gln Ile Ala Lys Val Gly
        435                 440                 445

Gln Ile Phe Ala Ala Trp Lys Ile Leu Gly Tyr Asp Arg Cys Asp Ala
    450                 455                 460

Gly Trp Leu Ala Asp Gly Ser Val Arg Tyr Pro Ile Ser Arg Pro Arg
465                 470                 475                 480

Arg Arg Cys Ser Pro Thr Glu Ala Ala Val Arg Phe Val Gly Phe Pro
                485                 490                 495

Asp Lys Lys His Lys Leu Tyr Gly Val Tyr Cys Phe Arg Ala Tyr Asn
                500                 505                 510

<210> SEQ ID NO 12
<211> LENGTH: 560
<212> TYPE: PRT
<213> ORGANISM: Artificial Sequence
<220> FEATURE:
<223> OTHER INFORMATION: Synthetic construct

<400> SEQUENCE: 12

Glu Ser Leu Gly Thr Glu Gln Arg Val Val Gly Arg Ala Ala Glu Val
1               5                   10                  15

Pro Gly Pro Glu Pro Gly Gln Gln Glu Gln Leu Val Phe Gly Ser Gly
            20                  25                  30

Asp Ala Val Glu Leu Ser Cys Pro Pro Pro Gly Gly Gly Pro Met Gly
        35                  40                  45

Pro Thr Val Trp Val Lys Asp Gly Thr Gly Leu Val Pro Ser Glu Arg
    50                  55                  60

Val Leu Val Gly Pro Gln Arg Leu Gln Val Leu Asn Ala Ser His Glu
65                  70                  75                  80

Asp Ser Gly Ala Tyr Ser Cys Arg Gln Arg Leu Thr Gln Arg Val Leu
                85                  90                  95

Cys His Phe Ser Val Arg Val Thr Asp Ala Pro Ser Ser Gly Asp Asp
            100                 105                 110

Glu Asp Gly Glu Asp Glu Ala Glu Asp Thr Gly Val Asp Thr Gly Ala
        115                 120                 125

Pro Tyr Trp Thr Arg Pro Glu Arg Met Asp Lys Lys Leu Leu Ala Val
    130                 135                 140

Pro Ala Ala Asn Thr Val Arg Phe Arg Cys Pro Ala Ala Gly Asn Pro
145                 150                 155                 160

Thr Pro Ser Ile Ser Trp Leu Lys Asn Gly Arg Glu Phe Arg Gly Glu
                165                 170                 175

His Arg Ile Gly Gly Ile Lys Leu Arg His Gln Gln Trp Ser Leu Val
            180                 185                 190

Met Glu Ser Val Val Pro Ser Asp Arg Gly Asn Tyr Thr Cys Val Val
        195                 200                 205

Glu Asn Lys Phe Gly Ser Ile Arg Gln Thr Tyr Thr Leu Asp Val Leu
```

```
            210                 215                 220
Glu Arg Ser Pro His Arg Pro Ile Leu Gln Ala Gly Leu Pro Ala Asn
225                 230                 235                 240

Gln Thr Ala Val Leu Gly Ser Asp Val Glu Phe His Cys Lys Val Tyr
                245                 250                 255

Ser Asp Ala Gln Pro His Ile Gln Trp Leu Lys His Val Glu Val Asn
                260                 265                 270

Gly Ser Lys Val Gly Pro Asp Gly Thr Pro Tyr Val Thr Val Leu Lys
            275                 280                 285

Thr Ala Gly Ala Asn Thr Thr Asp Lys Glu Leu Glu Val Leu Ser Leu
290                 295                 300

His Asn Val Thr Phe Glu Asp Ala Gly Glu Tyr Thr Cys Leu Ala Gly
305                 310                 315                 320

Asn Ser Ile Gly Phe Ser His His Ser Ala Trp Leu Val Val Leu Pro
                325                 330                 335

Val Ser Leu Glu Ser Asn Ala Ser Met Ser Ser Asn Thr Ser Gly Ser
                340                 345                 350

Gly Ser Gly Ser Gly Ser Gly Ser Gly Ser Val Val Phe Pro
            355                 360                 365

Tyr Phe Pro Arg Leu Gly Arg Tyr Asn Leu Asn Phe His Glu Ala Gln
370                 375                 380

Gln Ala Cys Leu Asp Gln Asp Ala Val Ile Ala Ser Phe Asp Gln Leu
385                 390                 395                 400

Tyr Asp Ala Trp Arg Gly Gly Leu Asp Trp Cys Asn Ala Gly Trp Leu
                405                 410                 415

Ser Asp Gly Ser Val Gln Tyr Pro Ile Thr Lys Pro Arg Glu Pro Cys
                420                 425                 430

Gly Gly Gln Asn Thr Val Pro Gly Val Arg Asn Tyr Gly Phe Trp Asp
            435                 440                 445

Lys Asp Lys Ser Arg Tyr Asp Val Phe Cys Phe Thr Ser Asn Phe Asn
450                 455                 460

Gly Arg Phe Tyr Tyr Leu Ile His Pro Thr Lys Leu Thr Tyr Asp Glu
465                 470                 475                 480

Ala Val Gln Ala Cys Leu Asn Asp Gly Ala Gln Ile Ala Lys Val Gly
                485                 490                 495

Gln Ile Phe Ala Ala Trp Lys Ile Leu Gly Tyr Asp Arg Cys Asp Ala
                500                 505                 510

Gly Trp Leu Ala Asp Gly Ser Val Arg Tyr Pro Ile Ser Arg Pro Arg
            515                 520                 525

Arg Arg Cys Ser Pro Thr Glu Ala Ala Val Arg Phe Val Gly Phe Pro
530                 535                 540

Asp Lys Lys His Lys Leu Tyr Gly Val Tyr Cys Phe Arg Ala Tyr Asn
545                 550                 555                 560

<210> SEQ ID NO 13
<211> LENGTH: 155
<212> TYPE: PRT
<213> ORGANISM: Homo sapiens

<400> SEQUENCE: 13

Met Ala Glu Gly Glu Ile Thr Thr Phe Thr Ala Leu Thr Glu Lys Phe
1               5                   10                  15

Asn Leu Pro Pro Gly Asn Tyr Lys Lys Pro Lys Leu Leu Tyr Cys Ser
                20                  25                  30
```

```
Asn Gly Gly His Phe Leu Arg Ile Leu Pro Asp Gly Thr Val Asp Gly
             35                  40                  45

Thr Arg Asp Arg Ser Asp Gln His Ile Gln Leu Gln Leu Ser Ala Glu
 50                  55                  60

Ser Val Gly Glu Val Tyr Ile Lys Ser Thr Glu Thr Gly Gln Tyr Leu
 65                  70                  75                  80

Ala Met Asp Thr Asp Gly Leu Leu Tyr Gly Ser Gln Thr Pro Asn Glu
                 85                  90                  95

Glu Cys Leu Phe Leu Glu Arg Leu Glu Glu Asn His Tyr Asn Thr Tyr
                100                 105                 110

Ile Ser Lys Lys His Ala Glu Lys Asn Trp Phe Val Gly Leu Lys Lys
                115                 120                 125

Asn Gly Ser Cys Lys Arg Gly Pro Arg Thr His Tyr Gly Gln Lys Ala
            130                 135                 140

Ile Leu Phe Leu Pro Leu Pro Val Ser Ser Asp
145                 150                 155
```

```
<210> SEQ ID NO 14
<211> LENGTH: 288
<212> TYPE: PRT
<213> ORGANISM: Homo sapiens

<400> SEQUENCE: 14

Met Val Gly Val Gly Gly Gly Asp Val Glu Asp Val Thr Pro Arg Pro
 1               5                  10                  15

Gly Gly Cys Gln Ile Ser Gly Arg Gly Ala Arg Gly Cys Asn Gly Ile
                 20                  25                  30

Pro Gly Ala Ala Ala Trp Glu Ala Ala Leu Pro Arg Arg Arg Pro Arg
             35                  40                  45

Arg His Pro Ser Val Asn Pro Arg Ser Arg Ala Ala Gly Ser Pro Arg
 50                  55                  60

Thr Arg Gly Arg Arg Thr Glu Glu Arg Pro Ser Gly Ser Arg Leu Gly
 65                  70                  75                  80

Asp Arg Gly Arg Gly Arg Ala Leu Pro Gly Gly Arg Leu Gly Gly Arg
                 85                  90                  95

Gly Arg Gly Arg Ala Pro Glu Arg Val Gly Gly Arg Gly Arg Gly Arg
                100                 105                 110

Gly Thr Ala Ala Pro Arg Ala Ala Pro Ala Ala Arg Gly Ser Arg Pro
            115                 120                 125

Gly Pro Ala Gly Thr Met Ala Ala Gly Ser Ile Thr Thr Leu Pro Ala
            130                 135                 140

Leu Pro Glu Asp Gly Gly Ser Gly Ala Phe Pro Pro Gly His Phe Lys
145                 150                 155                 160

Asp Pro Lys Arg Leu Tyr Cys Lys Asn Gly Gly Phe Phe Leu Arg Ile
                165                 170                 175

His Pro Asp Gly Arg Val Asp Gly Val Arg Glu Lys Ser Asp Pro His
                180                 185                 190

Ile Lys Leu Gln Leu Gln Ala Glu Glu Arg Gly Val Val Ser Ile Lys
            195                 200                 205

Gly Val Cys Ala Asn Arg Tyr Leu Ala Met Lys Glu Asp Gly Arg Leu
        210                 215                 220

Leu Ala Ser Lys Cys Val Thr Asp Glu Cys Phe Phe Phe Glu Arg Leu
225                 230                 235                 240

Glu Ser Asn Asn Tyr Asn Thr Tyr Arg Ser Arg Lys Tyr Thr Ser Trp
                245                 250                 255
```

Tyr Val Ala Leu Lys Arg Thr Gly Gln Tyr Lys Leu Gly Ser Lys Thr
                260                 265                 270

Gly Pro Gly Gln Lys Ala Ile Leu Phe Leu Pro Met Ser Ala Lys Ser
            275                 280                 285

<210> SEQ ID NO 15
<211> LENGTH: 208
<212> TYPE: PRT
<213> ORGANISM: Homo sapiens

<400> SEQUENCE: 15

Met Ala Pro Leu Gly Glu Val Gly Asn Tyr Phe Gly Val Gln Asp Ala
1               5                   10                  15

Val Pro Phe Gly Asn Val Pro Val Leu Pro Val Asp Ser Pro Val Leu
            20                  25                  30

Leu Ser Asp His Leu Gly Gln Ser Glu Ala Gly Gly Leu Pro Arg Gly
        35                  40                  45

Pro Ala Val Thr Asp Leu Asp His Leu Lys Gly Ile Leu Arg Arg Arg
    50                  55                  60

Gln Leu Tyr Cys Arg Thr Gly Phe His Leu Glu Ile Phe Pro Asn Gly
65                  70                  75                  80

Thr Ile Gln Gly Thr Arg Lys Asp His Ser Arg Phe Gly Ile Leu Glu
                85                  90                  95

Phe Ile Ser Ile Ala Val Gly Leu Val Ser Ile Arg Gly Val Asp Ser
            100                 105                 110

Gly Leu Tyr Leu Gly Met Asn Glu Lys Gly Glu Leu Tyr Gly Ser Glu
        115                 120                 125

Lys Leu Thr Gln Glu Cys Val Phe Arg Glu Gln Phe Glu Glu Asn Trp
130                 135                 140

Tyr Asn Thr Tyr Ser Ser Asn Leu Tyr Lys His Val Asp Thr Gly Arg
145                 150                 155                 160

Arg Tyr Tyr Val Ala Leu Asn Lys Asp Gly Thr Pro Arg Glu Gly Thr
                165                 170                 175

Arg Thr Lys Arg His Gln Lys Phe Thr His Phe Leu Pro Arg Pro Val
            180                 185                 190

Asp Pro Asp Lys Val Pro Glu Leu Tyr Lys Asp Ile Leu Ser Gln Ser
        195                 200                 205

<210> SEQ ID NO 16
<211> LENGTH: 207
<212> TYPE: PRT
<213> ORGANISM: Homo sapiens

<400> SEQUENCE: 16

Met Tyr Ser Ala Pro Ser Ala Cys Thr Cys Leu Cys Leu His Phe Leu
1               5                   10                  15

Leu Leu Cys Phe Gln Val Gln Val Leu Val Ala Glu Glu Asn Val Asp
            20                  25                  30

Phe Arg Ile His Val Glu Asn Gln Thr Arg Ala Arg Asp Asp Val Ser
        35                  40                  45

Arg Lys Gln Leu Arg Leu Tyr Gln Leu Tyr Ser Arg Thr Ser Gly Lys
    50                  55                  60

His Ile Gln Val Leu Gly Arg Arg Ile Ser Ala Arg Gly Glu Asp Gly
65                  70                  75                  80

Asp Lys Tyr Ala Gln Leu Leu Val Glu Thr Asp Thr Phe Gly Ser Gln
                85                  90                  95

```
Val Arg Ile Lys Gly Lys Glu Thr Glu Phe Tyr Leu Cys Met Asn Arg
                100                 105                 110

Lys Gly Lys Leu Val Gly Lys Pro Asp Gly Thr Ser Lys Glu Cys Val
            115                 120                 125

Phe Ile Glu Lys Val Leu Glu Asn Asn Tyr Thr Ala Leu Met Ser Ala
        130                 135                 140

Lys Tyr Ser Gly Trp Tyr Val Gly Phe Thr Lys Lys Gly Arg Pro Arg
145                 150                 155                 160

Lys Gly Pro Lys Thr Arg Glu Asn Gln Gln Asp Val His Phe Met Lys
                165                 170                 175

Arg Tyr Pro Lys Gly Gln Pro Glu Leu Gln Lys Pro Phe Lys Tyr Thr
            180                 185                 190

Thr Val Thr Lys Arg Ser Arg Arg Ile Arg Pro Thr His Pro Ala
        195                 200                 205

<210> SEQ ID NO 17
<211> LENGTH: 323
<212> TYPE: PRT
<213> ORGANISM: Artificial Sequence
<220> FEATURE:
<223> OTHER INFORMATION: Synthetic construct

<400> SEQUENCE: 17

Met Gly Ala Pro Ala Cys Ala Leu Ala Leu Cys Val Ala Val Ala Ile
1               5                   10                  15

Val Ala Gly Ala Ser Ser Glu Ser Leu Gly Thr Glu Gln Arg Val Val
            20                  25                  30

Gly Arg Ala Ala Glu Val Pro Gly Pro Glu Pro Gly Gln Gln Glu Gln
        35                  40                  45

Leu Val Phe Gly Ser Gly Asp Ala Val Glu Leu Ser Cys Pro Pro Pro
    50                  55                  60

Gly Gly Gly Pro Met Gly Pro Thr Val Trp Val Lys Asp Gly Thr Gly
65                  70                  75                  80

Leu Val Pro Ser Glu Arg Val Leu Val Gly Pro Gln Arg Leu Gln Val
                85                  90                  95

Leu Asn Ala Ser His Glu Asp Ser Gly Ala Tyr Ser Cys Arg Gln Arg
            100                 105                 110

Leu Thr Gln Arg Val Leu Cys His Phe Ser Val Arg Val Thr Asp Ala
        115                 120                 125

Pro Ser Ser Gly Asp Asp Glu Asp Gly Glu Asp Glu Ala Glu Asp Thr
    130                 135                 140

Gly Val Asp Thr Gly Ala Pro Tyr Trp Thr Arg Pro Glu Arg Met Asp
145                 150                 155                 160

Lys Lys Leu Leu Ala Val Pro Ala Ala Asn Thr Val Arg Phe Arg Cys
                165                 170                 175

Pro Ala Ala Gly Asn Pro Thr Pro Ser Ile Ser Trp Leu Lys Asn Gly
            180                 185                 190

Arg Glu Phe Arg Gly Glu His Arg Ile Gly Gly Ile Lys Leu Arg His
        195                 200                 205

Gln Gln Trp Ser Leu Val Met Glu Ser Val Val Pro Ser Asp Arg Gly
    210                 215                 220

Asn Tyr Thr Cys Val Val Glu Asn Lys Phe Gly Ser Ile Arg Gln Thr
225                 230                 235                 240

Tyr Thr Leu Asp Val Leu Glu Arg Ser Pro His Arg Pro Ile Leu Gln
                245                 250                 255
```

-continued

Ala Gly Leu Pro Ala Asn Gln Thr Ala Val Leu Gly Ser Asp Val Glu
              260                 265                 270

Phe His Cys Lys Val Tyr Ser Asp Ala Gln Pro His Ile Gln Trp Leu
              275                 280                 285

Lys His Val Glu Val Asn Gly Ser Lys Val Gly Pro Asp Gly Thr Pro
              290                 295                 300

Tyr Val Thr Val Leu Lys Val Ser Leu Glu Ser Asn Ala Ser Met Ser
305                 310                 315                 320

Ser Asn Thr

<210> SEQ ID NO 18
<211> LENGTH: 323
<212> TYPE: PRT
<213> ORGANISM: Artificial Sequence
<220> FEATURE:
<223> OTHER INFORMATION: Synthetic construct

<400> SEQUENCE: 18

Met Gly Ala Pro Ala Cys Ala Leu Ala Leu Cys Val Ala Val Ala Ile
1               5                   10                  15

Val Ala Gly Ala Ser Ser Glu Ser Leu Gly Thr Glu Gln Arg Val Val
              20                  25                  30

Gly Arg Ala Ala Glu Val Pro Gly Pro Glu Pro Gly Gln Gln Glu Gln
              35                  40                  45

Leu Val Phe Gly Ser Gly Asp Ala Val Glu Leu Ser Cys Pro Pro Pro
              50                  55                  60

Gly Gly Gly Pro Met Gly Pro Thr Val Trp Val Lys Asp Gly Thr Gly
65                  70                  75                  80

Leu Val Pro Ser Glu Arg Val Leu Val Gly Pro Gln Arg Leu Gln Val
              85                  90                  95

Leu Asn Ala Ser His Glu Asp Ser Gly Ala Tyr Ser Cys Arg Gln Arg
              100                 105                 110

Leu Thr Gln Arg Val Leu Cys His Phe Ser Val Arg Val Thr Asp Ala
              115                 120                 125

Pro Ser Ser Gly Asp Asp Glu Asp Gly Glu Asp Glu Ala Glu Asp Thr
              130                 135                 140

Gly Val Asp Thr Gly Ala Pro Tyr Trp Thr Arg Pro Glu Arg Met Asp
145                 150                 155                 160

Lys Lys Leu Leu Ala Val Pro Ala Ala Asn Thr Val Arg Phe Arg Cys
              165                 170                 175

Pro Ala Ala Gly Asn Pro Thr Pro Ser Ile Ser Trp Leu Lys Asn Gly
              180                 185                 190

Arg Glu Phe Arg Gly Glu His Arg Ile Gly Gly Ile Lys Leu Arg His
              195                 200                 205

Gln Gln Trp Ser Leu Val Met Glu Ser Val Val Pro Ser Asp Arg Gly
              210                 215                 220

Asn Tyr Thr Cys Val Val Glu Asn Lys Phe Gly Ser Ile Arg Gln Thr
225                 230                 235                 240

Tyr Thr Leu Asp Val Leu Glu Arg Ser Pro His Arg Pro Ile Leu Gln
              245                 250                 255

Ala Gly Leu Pro Ala Asn Gln Thr Ala Val Leu Gly Ser Asp Val Glu
              260                 265                 270

Phe His Cys Lys Val Tyr Ser Asp Ala Gln Pro His Ile Gln Trp Leu
              275                 280                 285

```
Lys His Val Glu Val Asn Gly Ser Lys Val Gly Pro Asp Gly Thr Pro
    290                 295                 300

Tyr Val Thr Val Leu Lys Val Ser Leu Glu Ser Asn Ala Ser Met Ser
305                 310                 315                 320

Ser Asn Thr

<210> SEQ ID NO 19
<211> LENGTH: 323
<212> TYPE: PRT
<213> ORGANISM: Artificial Sequence
<220> FEATURE:
<223> OTHER INFORMATION: Synthetic construct

<400> SEQUENCE: 19

Met Gly Ala Pro Ala Cys Ala Leu Ala Leu Cys Val Ala Val Ala Ile
1               5                   10                  15

Val Ala Gly Ala Ser Ser Glu Ser Leu Gly Thr Glu Gln Arg Val Val
                20                  25                  30

Gly Arg Ala Ala Glu Val Pro Gly Pro Glu Pro Gly Gln Gln Glu Gln
            35                  40                  45

Leu Val Phe Gly Ser Gly Asp Ala Val Glu Leu Ser Cys Pro Pro Pro
    50                  55                  60

Gly Gly Gly Pro Met Gly Pro Thr Val Trp Val Lys Asp Gly Thr Gly
65                  70                  75                  80

Leu Val Pro Ser Glu Arg Val Leu Val Gly Pro Gln Arg Leu Gln Val
                85                  90                  95

Leu Asn Ala Ser His Glu Asp Ser Gly Ala Tyr Ser Cys Arg Gln Arg
            100                 105                 110

Leu Thr Gln Arg Val Leu Cys His Phe Ser Val Arg Val Thr Asp Ala
    115                 120                 125

Pro Ser Ser Gly Asp Asp Glu Asp Gly Glu Asp Ala Glu Asp Thr
    130                 135                 140

Gly Val Asp Thr Gly Ala Pro Tyr Trp Thr Arg Pro Glu Arg Met Asp
145                 150                 155                 160

Lys Lys Leu Leu Ala Val Pro Ala Ala Asn Thr Val Arg Phe Arg Cys
                165                 170                 175

Pro Ala Ala Gly Asn Pro Thr Pro Ser Ile Ser Trp Leu Lys Asn Gly
            180                 185                 190

Arg Glu Phe Arg Gly Glu His Arg Ile Gly Gly Ile Lys Leu Arg His
    195                 200                 205

Gln Gln Trp Ser Leu Val Met Glu Ser Val Val Pro Ser Asp Arg Gly
210                 215                 220

Asn Tyr Thr Cys Val Val Glu Asn Lys Phe Gly Ser Ile Arg Gln Thr
225                 230                 235                 240

Tyr Thr Leu Asp Val Leu Glu Arg Ser Pro His Arg Pro Ile Leu Gln
                245                 250                 255

Ala Gly Leu Pro Ala Asn Gln Thr Ala Val Leu Gly Ser Asp Val Glu
            260                 265                 270

Phe His Ser Lys Val Tyr Ser Asp Ala Gln Pro His Ile Gln Trp Leu
    275                 280                 285

Lys His Val Glu Val Asn Gly Ser Lys Val Gly Pro Asp Gly Thr Pro
    290                 295                 300

Tyr Val Thr Val Leu Lys Val Ser Leu Glu Ser Asn Ala Ser Met Ser
305                 310                 315                 320

Ser Asn Thr
```

<210> SEQ ID NO 20
<211> LENGTH: 987
<212> TYPE: DNA
<213> ORGANISM: Artificial Sequence
<220> FEATURE:
<223> OTHER INFORMATION: Synthetic construct

<400> SEQUENCE: 20

```
atgggagtga aggtgctgtt cgccctgatc tgtatcgccg tggccgaggc cgagtctctg      60
ggcacagaac agagagtcgt gggcagagcc gccgaagtgc ctggacctga acctggccag     120
caggaacagc tggtgtttgg cagcggcgac gccgtgaaac tgagctgtcc tccacctggc     180
ggaggcccta tggacctac cgtgtgggtc aaggatggca ccggactggt gcctagcgag     240
agggtgctcg tggacctca gagactgcag gtgctgaacg ccagccacga ggatagcggc     300
gcctacagct gcagacagag actgacacag cgggtgctgt gccacttctc cgtcagagtg     360
accgacgccc ctagctccgg cgacgatgag gatggcgaag atgaggccga ggacaccggc     420
gtggacacag gcgctccata ctggaccaga cccgagcgga tggacaagaa actgctggcc     480
gtgcctgccg ccaacaccgt gcggtttaga tgtcctgccg ccggaaaccc cacccccagc     540
atcagctggc tgaagaacgg cagagagttc ggggcgagc acagaatcgg cggcatcaag     600
ctgagacacc agcagtggtc cctcgtgatg gaaagcgtgg tgcccagcga ccggggcaac     660
tacacctgtg tggtggaaaa caagttcggc agcatccggc agacctacac cctggacgtg     720
ctggaaagaa gccccacag acccatcctg caggccggac tgcctgccaa tcagacagcc     780
gtgctgggca gcgacgtgga atttcacagc aaggtgtaca gcgacgccca gccccacatc     840
cagtggctga acacgtgga agtgaacggc agcaaagtgg cccccgacgg caccccttat     900
gtgaccgtgc tgaaggtgtc cctggaaagc aacgccagca tgagcagcaa caccgactac     960
aaggacgacg acgacaagtg aaagctt                                         987
```

<210> SEQ ID NO 21
<211> LENGTH: 1131
<212> TYPE: DNA
<213> ORGANISM: Artificial Sequence
<220> FEATURE:
<223> OTHER INFORMATION: Synthetic construct

<400> SEQUENCE: 21

```
atgggagtga aggtgctgtt cgccctgatc tgtatcgccg tggccgaggc cgagtctctg      60
ggcacagaac agagagtcgt gggcagagcc gccgaagtgc ctggacctga acctggccag     120
caggaacagc tggtgtttgg cagcggcgac gccgtggaac tgagctgtcc tccacctggc     180
ggaggcccta tggacctac cgtgtgggtc aaggatggca ccggactggt gcctagcgag     240
agggtgctcg tggacctca gagactgcag gtgctgaacg ccagccacga ggatagcggc     300
gcctacagct gcagacagag actgacacag cgggtgctgt gccacttctc cgtcagagtg     360
accgacgccc ctagctccgg cgacgatgag gatggcgaag atgaggccga ggacaccggc     420
gtggacacag gcgctccata ctggaccaga cccgagcgga tggacaagaa actgctggcc     480
gtgcctgccg ccaacaccgt gcggtttaga tgtcctgccg ccggaaaccc cacccccagc     540
atcagctggc tgaagaacgg cagagagttc ggggcgagc acagaatcgg cggcatcaag     600
ctgagacacc agcagtggtc cctcgtgatg gaaagcgtgg tgcccagcga ccggggcaac     660
tacacctgtg tggtggaaaa caagttcggc agcatccggc agacctacac cctggacgtg     720
```

| | |
|---|---|
| ctggaaagaa gcccccacag acccatcctg caggccggac tgcctgccaa tcagacagcc | 780 |
| gtgctgggca gcgacgtgga atttcactgc aaggtgtaca gcgacgccca gccccacatc | 840 |
| cagtggctga acacgtgga agtgaacggc agcaaagtgg gccccgacgg cacccctttat | 900 |
| gtgaccgtgc tgaaaaccgc tggcgccaat accaccgaca agaactgga agtgctgagc | 960 |
| ctgcacaacg tgaccttcga ggatgccggc gagtacacct gtctggccgg caacagcatc | 1020 |
| ggcttcagcc accattctgc ctggctggtg gtgctgcccg tgtccctgga aagcaacgcc | 1080 |
| agcatgagca gcaacaccga ctacaaggac gacgacgaca agtgaaagct t | 1131 |

<210> SEQ ID NO 22
<211> LENGTH: 2019
<212> TYPE: DNA
<213> ORGANISM: Artificial Sequence
<220> FEATURE:
<223> OTHER INFORMATION: Synthetic construct

<400> SEQUENCE: 22

| | |
|---|---|
| atggagtctc tgggcacaga gcagagagtc gtgggcagag ccgctgaagt gcctggacct | 60 |
| gagcctggcc agcaggaaca gctggtcttt ggctctggcg acgccgtgga actgagctgt | 120 |
| cctccacctg gcggaggccc tatgggacct accgtgtggg tcaaggatgg caccggactg | 180 |
| gtgcctagcg agagggtgct cgtgggacct cagagactgc aggtcctgaa cgccagccac | 240 |
| gaggatagcg gcgcctacag ctgcagacag agactgaccc agcgggtgct gtgccacttc | 300 |
| agcgtcagag tgaccgatgc ccccagcagc ggagatgacg aggatggcga ggatgaggcc | 360 |
| gaggatacag gcgtggacac aggcgcccct tactggacca gacccgagcg gatggacaag | 420 |
| aaactgctgg ccgtgcctgc cgccaacacc gtgcggttta gatgccctgc cgccggaaac | 480 |
| cccacccccca gcatctcttg gctgaagaac ggcagagagt ccggggcga gcaccggatc | 540 |
| ggcggcatta agctgagaca ccagcagtgg tccctggtca tggaaagcgt ggtgcccagc | 600 |
| gaccggggca actacacctg tgtggtggaa acaagttcg gcagcatccg gcagacctac | 660 |
| accctggacg tgctggaaag aagcccccac agacctatcc tgcaggccgg actgcctgcc | 720 |
| aatcagacag ccgtgctggg cagcgacgtg gaatttcaca gcaaggtgta cagcgacgcc | 780 |
| cagcccccaca tccagtggct gaagcacgtg gaagtgaacg gcagcaaagt gggccccgac | 840 |
| ggcacccctt acgtgaccgt gctgaaagtg tccctggaaa gcaacgccag catgagcagc | 900 |
| aacacccccc tcgtgcggat cgccagactg tctagcggag agggccctac cctggccaac | 960 |
| gtgtccgaac tggaactgcc cgccgacccc aagtgggagc tgagcagagc tagactgacc | 1020 |
| ctgggcaagc tctgggcga gggctgtttt ggacaggtgg tcatggccga ggccatcggc | 1080 |
| atcgacaagg acagagccgc caagcctgtg accgtggccg tgaagatgct gaaggacgac | 1140 |
| gccaccgaca aggacctgag cgacctggtg tccgagatgg aaatgatgaa gatgatcggc | 1200 |
| aagcacaaga acatcatcaa cctgctgggc gcctgcaccc agggcggacc tctgtacgtg | 1260 |
| ctggtggaat acgccgccaa gggcaacctg agagagttcc tgagagccag aaggccccct | 1320 |
| ggcctggact acagcttcga tacctgcaag ccccccgaag aacagctgac cttcaaggat | 1380 |
| ctggtgtcct cgccctatca ggtgccaga ggcatggaat acctggccag ccagaagtgc | 1440 |
| atccaccggg atctggccgc cagaaacgtg ctggtcaccg aggacaacgt gatgaagatc | 1500 |
| gccgacttcg gcctggcccg ggacgtgcac aacctggact actacaagaa aaccaccaac | 1560 |
| ggccggctgc ccgtgaagtg gatggcccct gaggccctgt cgacagagt gtacacccac | 1620 |
| cagagcgacg tgtggtcctt cggcgtgctg ctgtgggaga tctttaccct gggcggcagc | 1680 |

```
ccttaccccg gcatccctgt ggaagaactg ttcaagctgc tgaaagaggg ccacagaatg    1740
gacaagcccg ccaactgcac ccacgacctg tacatgatca tgagagagtg ctggcacgcc    1800
gctcccagcc agaggcctac ctttaagcag ctggtggaag atctggaccg ggtgctgacc    1860
gtgaccagca ccgacgagta cctggatctg agcgccccct tcgagcagta ctctcctggc    1920
ggccaggata cccctagcag cagctctagc ggcgacgaca gcgtgttcgc ccacgatctg    1980
ctgcctccag cccctcctag ctctggcggc tctagaacc                           2019
```

<210> SEQ ID NO 23
<211> LENGTH: 1491
<212> TYPE: DNA
<213> ORGANISM: Artificial Sequence
<220> FEATURE:
<223> OTHER INFORMATION: Synthetic construct

<400> SEQUENCE: 23

```
atggagagcc tgggcacaga acagagagtc gtgggcagag ccgccgaagt gcctggacct      60
gaacctggcc agcaggaaca gctggtcttt ggctctggcg acgccgtgga actgagctgt     120
cctccacctg gcggaggccc tatgggacct accgtgtggg tcaaggatgg caccggactg     180
gtgcctagcg agagggtgct cgtgggacct cagagactgc aggtcctgaa cgccagccac     240
gaggatagcg gcgcctacag ctgcagacag agactgaccc agcgggtgct gtgccacttc     300
agcgtcagag tgaccgatgc ccccagcagc ggagatgacg aggatggcga ggatgaggcc     360
gaggatacag gcgtggacac aggcgcccct tactggacca gcccgagcg atggacaag       420 aaactgctgg ccgtgcctgc cgccaacacc gtgcggttta tgccctgc cgccggaaac      480 cccaccccca gcatctcttg gctgaagaac ggcagagagt tccggggcga gcaccggatc     540
ggcggcatta agctgagaca ccagcagtgg tccctggtca tggaaagcgt ggtgcccagc     600
gaccggggca actacacctg tgtggtggaa aacaagttcg gcagcatccg gcagacctac     660
accctggacg tgctggaaag aagcccccac agacctatcc tgcaggccgg actgcctgcc     720
aatcagacag ccgtgctggg cagcgacgtg gaatttcact gcaaggtgta cagcgacgcc     780 cagcccccaca tccagtggct gaagcacgtg gaagtgaacg gcagcaaagt gggcccccgac    840 ggcacccctt acgtgaccgt gctgaaagtg tccctggaaa gcaacgccag catgagcagc     900
aacaccagcg gcagcggctc tggcagcgga tctggttctg gctccggcag cgtggtgttc     960
ccctacttcc cccggctggg ccggtacaac ctgaactttc atgaggccca gcaggcctgc    1020
ctggaccagg atgccgtgat cgccagcttc gaccagctgt acgatgcttg agaggcggc    1080 ctggactggt gcaatgccgg ctggctgtct gacggcagcg tgcagtaccc catcaccaag    1140
cccagagagc cctgcggcgg acagaatacc gtgcccggcg tgcggaacta cggcttctgg    1200
gacaaggaca gagcagata cgacgtgttc tgcttcacca gcaacttcaa cggccggttc     1260
tactacctga tccacccccac caagctgacc tacgacgagg ccgtgcaggc ctgtctgaac    1320
gatggcgccc agatcgccaa gtgggacag atcttcgccg cctggaagat cctgggctac    1380
gacagatgtg acgccggatg gctggccgac ggctccgtgc ggtatcccat cagccggcct    1440
agaagaagat gcagccctac cgaggccgcc gtcagattcg tgggcttccc c            1491
```

<210> SEQ ID NO 24
<211> LENGTH: 1710
<212> TYPE: DNA
<213> ORGANISM: Artificial Sequence
<220> FEATURE:

<223> OTHER INFORMATION: Synthetic construct

<400> SEQUENCE: 24

```
atgggagcac cagcttgtgc cctggctctg tgtgtggccg tggctattgt ggctggcgcc      60
tctagcgaga gcctgggcac agaacagaga gtcgtgggca gagccgccga agtgcctgga     120
cctgaacctg gccagcagga acagctggtc tttggctctg gcgacgccgt ggaactgagc     180
tgtcctccac ctggcggagg ccctatggga cctaccgtgt gggtcaagga tgcaccggga     240
ctggtgccta gcgagagggt gctcgtggga cctcagagac tgcaggtcct gaacgccagc     300
cacgaggata gcggcgccta cagctgcaga cagagactga cccagcgggt gctgtgccac     360
ttcagcgtca gagtgaccga tgcccccagc agcggagatg acgaggatgg cgaggatgag     420
gccgaggata caggcgtgga cacaggcgcc ccttactgga ccagacccga gcggatggac     480
aagaaactgc tggccgtgcc tgccgccaac accgtgcggt tagatgccc tgccgccgga     540
aaccccaccc ccagcatctc ttggctgaag aacggcagag agttccgggg cgagcaccgg     600
atcggcggca ttaagctgag acaccagcag tggtccctgg tcatggaaag cgtggtgccc     660
agcgaccggg gcaactacac ctgtgtggtg aaaacaagt tcggcagcat ccggcagacc     720
tacaccctga cgtgctgga aagaagcccc acagaccta cctgcaggc cggactgcct     780
gccaatcaga cagccgtgct gggcagcgac gtggaatttc actgcaaggt gtacagcgac     840
gcccagcccc acatccagtg gctgaagcac gtggaagtga acggcagcaa agtgggcccc     900
gacggcaccc cttacgtgac cgtgctgaaa accgctggcg ccaacaccac cgacaaagaa     960
ctggaagtgc tgagcctgca aacgtgacc ttcgaggacg ccggcgagta cacctgtctg    1020
gccggcaata gcatcggctt cagccaccac tctgcctggc tggtggtgct gccaggcgga    1080
ggctctgtgt ccctggaaag caacgccagc atgagcagca caccagcgg cagcggctct    1140
ggcagcggat ctggttctgg ctccggcagc gtggtgttcc cctacttccc ccggctgggc    1200
cggtacaacc tgaactttca tgaggcccag caggcctgcc tggaccagga tgccgtgatc    1260
gccagcttcg accagctgta cgatgcttgg agaggcggcc tggactggtg caatgccggc    1320
tggctgtctg acggcagcgt gcagtacccc atcaccaagc ccagagagcc tgcggcgga    1380
cagaataccg tgcccggcgt gcggaactac ggcttctggg acaaggacaa gagcagatac    1440
gacgtgttct gcttcaccag caacttcaac ggccggttct actacctgat ccaccccacc    1500
aagctgacct acgacgaggc cgtgcaggcc tgtctgaacg atggcgccca gatcgccaaa    1560
gtgggacaga tcttcgccgc ctggaagatc ctgggctacg acagatgtga cgccggatgg    1620
ctggccgacg gctccgtgcg gtatcccatc agccggccta aagaagatg cagccctacc    1680
gaggccgccg tcagattcgt gggcttcccc                                     1710
```

<210> SEQ ID NO 25
<211> LENGTH: 236
<212> TYPE: PRT
<213> ORGANISM: Homo sapiens

<400> SEQUENCE: 25

Gly Gly Gly Gly Ala Gly Gly Gly Asp Lys Thr His Thr Cys Pro
1               5                   10                  15

Pro Cys Pro Ala Pro Glu Leu Leu Gly Gly Pro Ser Val Phe Leu Phe
                20                  25                  30

Pro Pro Lys Pro Lys Asp Thr Leu Met Ile Ser Arg Thr Pro Glu Val
            35                  40                  45

```
Thr Cys Val Val Asp Val Ser His Glu Asp Pro Glu Val Lys Phe
 50                  55                  60

Asn Trp Tyr Val Asp Gly Val Glu Val His Asn Ala Lys Thr Lys Pro
 65                  70                  75                  80

Arg Glu Glu Gln Tyr Asn Ser Thr Tyr Arg Val Val Ser Val Leu Thr
                 85                  90                  95

Val Leu His Gln Asp Trp Leu Asn Gly Lys Glu Tyr Lys Cys Lys Val
                100                 105                 110

Ser Asn Lys Ala Leu Pro Ala Pro Ile Glu Lys Thr Ile Ser Lys Ala
                115                 120                 125

Lys Gly Gln Pro Arg Glu Pro Gln Val Tyr Thr Leu Pro Pro Ser Arg
130                 135                 140

Asp Glu Leu Thr Lys Asn Gln Val Ser Leu Thr Cys Leu Val Lys Gly
145                 150                 155                 160

Phe Tyr Pro Ser Asp Ile Ala Val Glu Trp Glu Ser Asn Gly Gln Pro
                165                 170                 175

Glu Asn Asn Tyr Lys Thr Thr Pro Pro Val Leu Asp Ser Asp Gly Ser
                180                 185                 190

Phe Phe Leu Tyr Ser Lys Leu Thr Val Asp Lys Ser Arg Trp Gln Gln
                195                 200                 205

Gly Asn Val Phe Ser Cys Ser Val Met His Glu Ala Leu His Asn His
                210                 215                 220

Tyr Thr Gln Lys Ser Leu Ser Leu Ser Pro Gly Lys
225                 230                 235

<210> SEQ ID NO 26
<211> LENGTH: 236
<212> TYPE: PRT
<213> ORGANISM: Artificial Sequence
<220> FEATURE:
<223> OTHER INFORMATION: Synthetic construct

<400> SEQUENCE: 26

Gly Gly Gly Gly Ala Gly Gly Gly Asp Lys Thr His Thr Cys Pro
 1               5                  10                  15

Pro Cys Pro Ala Pro Glu Leu Leu Gly Gly Pro Ser Val Phe Leu Phe
                 20                  25                  30

Pro Pro Lys Pro Lys Asp Thr Leu Met Ile Ser Arg Thr Pro Glu Val
                 35                  40                  45

Thr Cys Val Val Asp Val Ser His Glu Asp Pro Glu Val Lys Phe
 50                  55                  60

Asn Trp Tyr Val Asp Gly Val Glu Val His Asn Ala Lys Thr Lys Pro
 65                  70                  75                  80

Arg Glu Glu Gln Tyr Ala Ser Thr Tyr Arg Val Val Ser Val Leu Thr
                 85                  90                  95

Val Leu His Gln Asp Trp Leu Asn Gly Lys Glu Tyr Lys Cys Lys Val
                100                 105                 110

Ser Asn Lys Ala Leu Pro Ala Pro Ile Glu Lys Thr Ile Ser Lys Ala
                115                 120                 125

Lys Gly Gln Pro Arg Glu Pro Gln Val Tyr Thr Leu Pro Pro Ser Arg
130                 135                 140

Glu Glu Met Thr Lys Asn Gln Val Ser Leu Thr Cys Leu Val Lys Gly
145                 150                 155                 160

Phe Tyr Pro Ser Asp Ile Ala Val Glu Trp Glu Ser Asn Gly Gln Pro
                165                 170                 175
```

```
Glu Asn Asn Tyr Lys Thr Thr Pro Val Leu Asp Ser Asp Gly Ser
            180                 185                 190

Phe Phe Leu Tyr Ser Lys Leu Thr Val Asp Lys Ser Arg Trp Gln Gln
        195                 200                 205

Gly Asn Val Phe Ser Cys Ser Val Met His Glu Ala Leu His Asn His
    210                 215                 220

Tyr Thr Gln Lys Ser Leu Ser Leu Ser Pro Gly Lys
225                 230                 235

<210> SEQ ID NO 27
<211> LENGTH: 585
<212> TYPE: PRT
<213> ORGANISM: Homo sapiens

<400> SEQUENCE: 27

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320
```

Glu Ala Lys Asp Val Phe Leu Gly Met Phe Leu Tyr Glu Tyr Ala Arg
                325                 330                 335

Arg His Pro Asp Tyr Ser Val Val Leu Leu Arg Leu Ala Lys Thr
            340                 345                 350

Tyr Glu Thr Thr Leu Glu Lys Cys Cys Ala Ala Ala Asp Pro His Glu
            355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
            435                 440                 445

Ala Glu Asp Tyr Leu Ser Val Val Leu Asn Gln Leu Cys Val Leu His
            450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
            515                 520                 525

Leu Val Glu Leu Val Lys His Lys Pro Lys Ala Thr Lys Glu Gln Leu
            530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585

<210> SEQ ID NO 28
<211> LENGTH: 9
<212> TYPE: PRT
<213> ORGANISM: Artificial Sequence
<220> FEATURE:
<223> OTHER INFORMATION: Synthetic construct

<400> SEQUENCE: 28

Gly Gly Gly Gly Ala Gly Gly Gly Gly
1               5

<210> SEQ ID NO 29
<211> LENGTH: 15
<212> TYPE: PRT
<213> ORGANISM: Artificial Sequence
<220> FEATURE:
<223> OTHER INFORMATION: Synthetic construct

<400> SEQUENCE: 29

Gly Gly Gly Gly Ser Gly Gly Gly Gly Ser Gly Gly Gly Gly Ser
1               5                   10                  15

<210> SEQ ID NO 30
<211> LENGTH: 24
<212> TYPE: PRT
<213> ORGANISM: Artificial Sequence
<220> FEATURE:
<223> OTHER INFORMATION: Synthetic construct

<400> SEQUENCE: 30

```
Ala Gly Gly Thr Gly Gly Cys Cys Thr Thr Thr Gly Ala Cys Ala Cys
1               5                   10                  15

Cys Thr Ala Cys Cys Ala Gly Gly
            20
```

<210> SEQ ID NO 31
<211> LENGTH: 24
<212> TYPE: PRT
<213> ORGANISM: Artificial Sequence
<220> FEATURE:
<223> OTHER INFORMATION: Synthetic construct

<400> SEQUENCE: 31

```
Thr Cys Thr Gly Thr Thr Gly Thr Gly Thr Thr Thr Cys Cys Thr Cys
1               5                   10                  15

Cys Cys Thr Gly Thr Thr Gly Gly
            20
```

<210> SEQ ID NO 32
<211> LENGTH: 806
<212> TYPE: PRT
<213> ORGANISM: Artificial Sequence
<220> FEATURE:
<223> OTHER INFORMATION: Synthetic construct

<400> SEQUENCE: 32

```
Met Gly Ala Pro Ala Cys Ala Leu Ala Leu Cys Val Ala Val Ala Ile
1               5                   10                  15

Val Ala Gly Ala Ser Ser Glu Ser Leu Gly Thr Glu Gln Arg Val Val
            20                  25                  30

Gly Arg Ala Ala Glu Val Pro Gly Pro Glu Pro Gly Gln Gln Glu Gln
        35                  40                  45

Leu Val Phe Gly Ser Gly Asp Ala Val Glu Leu Ser Cys Pro Pro Pro
    50                  55                  60

Gly Gly Gly Pro Met Gly Pro Thr Val Trp Val Lys Asp Gly Thr Gly
65                  70                  75                  80

Leu Val Pro Ser Glu Arg Val Leu Val Gly Pro Gln Arg Leu Gln Val
                85                  90                  95

Leu Asn Ala Ser His Glu Asp Ser Gly Ala Tyr Ser Cys Arg Gln Arg
            100                 105                 110

Leu Thr Gln Arg Val Leu Cys His Phe Ser Val Arg Val Thr Asp Ala
        115                 120                 125

Pro Ser Ser Gly Asp Asp Glu Asp Gly Glu Asp Glu Ala Glu Asp Thr
    130                 135                 140

Gly Val Asp Thr Gly Ala Pro Tyr Trp Thr Arg Pro Glu Arg Met Asp
145                 150                 155                 160

Lys Lys Leu Leu Ala Val Pro Ala Ala Asn Thr Val Arg Phe Arg Cys
                165                 170                 175

Pro Ala Ala Gly Asn Pro Thr Pro Ser Ile Ser Trp Leu Lys Asn Gly
            180                 185                 190

Arg Glu Phe Arg Gly Glu His Arg Ile Gly Gly Ile Lys Leu Arg His
        195                 200                 205
```

```
Gln Gln Trp Ser Leu Val Met Glu Ser Val Val Pro Ser Asp Arg Gly
        210                 215                 220
Asn Tyr Thr Cys Val Val Glu Asn Lys Phe Gly Ser Ile Arg Gln Thr
225                 230                 235                 240
Tyr Thr Leu Asp Val Leu Glu Arg Ser Pro His Arg Pro Ile Leu Gln
            245                 250                 255
Ala Gly Leu Pro Ala Asn Gln Thr Ala Val Leu Gly Ser Asp Val Glu
        260                 265                 270
Phe His Cys Lys Val Tyr Ser Asp Ala Gln Pro His Ile Gln Trp Leu
        275                 280                 285
Lys His Val Glu Val Asn Gly Ser Lys Val Gly Pro Asp Gly Thr Pro
290                 295                 300
Tyr Val Thr Val Leu Lys Thr Ala Gly Ala Asn Thr Thr Asp Lys Glu
305                 310                 315                 320
Leu Glu Val Leu Ser Leu His Asn Val Thr Phe Glu Asp Ala Gly Glu
            325                 330                 335
Tyr Thr Cys Leu Ala Gly Asn Ser Ile Gly Phe Ser His His Ser Ala
            340                 345                 350
Trp Leu Val Val Leu Pro Ala Glu Glu Leu Val Glu Ala Asp Glu
        355                 360                 365
Ala Gly Ser Val Tyr Ala Gly Ile Leu Ser Tyr Gly Val Gly Phe Phe
        370                 375                 380
Leu Phe Ile Leu Val Val Ala Ala Val Thr Leu Cys Arg Leu Arg Ser
385                 390                 395                 400
Pro Pro Lys Lys Gly Leu Gly Ser Pro Thr Val His Lys Ile Ser Arg
            405                 410                 415
Phe Pro Leu Lys Arg Gln Val Ser Leu Glu Ser Asn Ala Ser Met Ser
            420                 425                 430
Ser Asn Thr Pro Leu Val Arg Ile Ala Arg Leu Ser Ser Gly Glu Gly
        435                 440                 445
Pro Thr Leu Ala Asn Val Ser Glu Leu Glu Leu Pro Ala Asp Pro Lys
    450                 455                 460
Trp Glu Leu Ser Arg Ala Arg Leu Thr Leu Gly Lys Pro Leu Gly Glu
465                 470                 475                 480
Gly Cys Phe Gly Gln Val Val Met Ala Glu Ala Ile Gly Ile Asp Lys
            485                 490                 495
Asp Arg Ala Ala Lys Pro Val Thr Val Ala Val Lys Met Leu Lys Asp
        500                 505                 510
Asp Ala Thr Asp Lys Asp Leu Ser Asp Leu Val Ser Glu Met Glu Met
        515                 520                 525
Met Lys Met Ile Gly Lys His Lys Asn Ile Ile Asn Leu Leu Gly Ala
530                 535                 540
Cys Thr Gln Gly Gly Pro Leu Tyr Val Leu Val Glu Tyr Ala Ala Lys
545                 550                 555                 560
Gly Asn Leu Arg Glu Phe Leu Arg Ala Arg Arg Pro Pro Gly Leu Asp
            565                 570                 575
Tyr Ser Phe Asp Thr Cys Lys Pro Pro Glu Glu Gln Leu Thr Phe Lys
            580                 585                 590
Asp Leu Val Ser Cys Ala Tyr Gln Val Ala Arg Gly Met Glu Tyr Leu
        595                 600                 605
Ala Ser Gln Lys Cys Ile His Arg Asp Leu Ala Ala Arg Asn Val Leu
610                 615                 620
```

```
Val Thr Glu Asp Asn Val Met Lys Ile Ala Asp Phe Gly Leu Ala Arg
625                 630                 635                 640

Asp Val His Asn Leu Asp Tyr Tyr Lys Lys Thr Thr Asn Gly Arg Leu
                645                 650                 655

Pro Val Lys Trp Met Ala Pro Glu Ala Leu Phe Asp Arg Val Tyr Thr
            660                 665                 670

His Gln Ser Asp Val Trp Ser Phe Gly Val Leu Leu Trp Glu Ile Phe
        675                 680                 685

Thr Leu Gly Gly Ser Pro Tyr Pro Gly Ile Pro Val Glu Glu Leu Phe
    690                 695                 700

Lys Leu Lys Glu Gly His Arg Met Asp Lys Pro Ala Asn Cys Thr
705                 710                 715                 720

His Asp Leu Tyr Met Ile Met Arg Glu Cys Trp His Ala Ala Pro Ser
                725                 730                 735

Gln Arg Pro Thr Phe Lys Gln Leu Val Glu Asp Leu Asp Arg Val Leu
            740                 745                 750

Thr Val Thr Ser Thr Asp Glu Tyr Leu Asp Leu Ser Ala Pro Phe Glu
        755                 760                 765

Gln Tyr Ser Pro Gly Gln Asp Thr Pro Ser Ser Ser Ser Gly
770                 775                 780

Asp Asp Ser Val Phe Ala His Asp Leu Leu Pro Pro Ala Pro Pro Ser
785                 790                 795                 800

Ser Gly Gly Ser Arg Thr
                805

<210> SEQ ID NO 33
<211> LENGTH: 349
<212> TYPE: PRT
<213> ORGANISM: Artificial Sequence
<220> FEATURE:
<223> OTHER INFORMATION: Synthetic construct

<400> SEQUENCE: 33

Glu Ser Leu Gly Thr Glu Gln Arg Val Val Gly Arg Ala Ala Glu Val
1               5                   10                  15

Pro Gly Pro Glu Pro Gly Gln Gln Glu Gln Leu Val Phe Gly Ser Gly
            20                  25                  30

Asp Ala Val Glu Leu Ser Cys Pro Pro Pro Gly Gly Gly Pro Met Gly
        35                  40                  45

Pro Thr Val Trp Val Lys Asp Gly Thr Gly Leu Val Pro Ser Glu Arg
    50                  55                  60

Val Leu Val Gly Pro Gln Arg Leu Gln Val Leu Asn Ala Ser His Glu
65                  70                  75                  80

Asp Ser Gly Ala Tyr Ser Cys Arg Gln Arg Leu Thr Gln Arg Val Leu
                85                  90                  95

Cys His Phe Ser Val Arg Val Thr Asp Ala Pro Ser Ser Gly Asp Asp
                100                 105                 110

Glu Asp Gly Glu Asp Glu Ala Glu Asp Thr Gly Val Asp Thr Gly Ala
            115                 120                 125

Pro Tyr Trp Thr Arg Pro Glu Arg Met Asp Lys Lys Leu Leu Ala Val
    130                 135                 140

Pro Ala Ala Asn Thr Val Arg Phe Arg Cys Pro Ala Ala Gly Asn Pro
145                 150                 155                 160

Thr Pro Ser Ile Ser Trp Leu Lys Asn Gly Arg Glu Phe Arg Gly Glu
                165                 170                 175
```

His Arg Ile Gly Gly Ile Lys Leu Arg His Gln Gln Trp Ser Leu Val
                180                 185                 190

Met Glu Ser Val Val Pro Ser Asp Arg Gly Asn Tyr Thr Cys Val Val
            195                 200                 205

Glu Asn Lys Phe Gly Ser Ile Arg Gln Thr Tyr Thr Leu Asp Val Leu
        210                 215                 220

Glu Arg Ser Pro His Arg Pro Ile Leu Gln Ala Gly Leu Pro Ala Asn
225                 230                 235                 240

Gln Thr Ala Val Leu Gly Ser Asp Val Glu Phe His Cys Lys Val Tyr
                245                 250                 255

Ser Asp Ala Gln Pro His Ile Gln Trp Leu Lys His Val Glu Val Asn
            260                 265                 270

Gly Ser Lys Val Gly Pro Asp Gly Thr Pro Tyr Val Thr Val Leu Lys
        275                 280                 285

Thr Ala Gly Ala Asn Thr Thr Asp Lys Glu Leu Glu Val Leu Ser Leu
        290                 295                 300

His Asn Val Thr Phe Glu Asp Ala Gly Glu Tyr Thr Cys Leu Ala Gly
305                 310                 315                 320

Asn Ser Ile Gly Phe Ser His His Ser Ala Trp Leu Val Val Leu Pro
                325                 330                 335

Val Ser Leu Glu Ser Asn Ala Ser Met Ser Ser Asn Thr
            340                 345

<210> SEQ ID NO 34
<211> LENGTH: 368
<212> TYPE: PRT
<213> ORGANISM: Artificial Sequence
<220> FEATURE:
<223> OTHER INFORMATION: Synthetic construct

<400> SEQUENCE: 34

Met Met Ser Phe Val Ser Leu Leu Leu Val Gly Ile Leu Phe His Ala
1               5                   10                  15

Thr Gln Ala Glu Ser Leu Gly Thr Glu Gln Arg Val Val Gly Arg Ala
            20                  25                  30

Ala Glu Val Pro Gly Pro Glu Pro Gly Gln Gln Glu Gln Leu Val Phe
        35                  40                  45

Gly Ser Gly Asp Ala Val Glu Leu Ser Cys Pro Pro Pro Gly Gly Gly
    50                  55                  60

Pro Met Gly Pro Thr Val Trp Val Lys Asp Gly Thr Gly Leu Val Pro
65                  70                  75                  80

Ser Glu Arg Val Leu Val Gly Pro Gln Arg Leu Gln Val Leu Asn Ala
                85                  90                  95

Ser His Glu Asp Ser Gly Ala Tyr Ser Cys Arg Gln Arg Leu Thr Gln
            100                 105                 110

Arg Val Leu Cys His Phe Ser Val Arg Val Thr Asp Ala Pro Ser Ser
        115                 120                 125

Gly Asp Asp Glu Asp Gly Glu Asp Glu Ala Glu Thr Gly Val Asp
        130                 135                 140

Thr Gly Ala Pro Tyr Trp Thr Arg Pro Glu Arg Met Asp Lys Lys Leu
145                 150                 155                 160

Leu Ala Val Pro Ala Ala Asn Thr Val Arg Phe Arg Cys Pro Ala Ala
                165                 170                 175

Gly Asn Pro Thr Pro Ser Ile Ser Trp Leu Lys Asn Gly Arg Glu Phe
            180                 185                 190

```
Arg Gly Glu His Arg Ile Gly Ile Lys Leu Arg His Gln Gln Trp
            195                 200                 205

Ser Leu Val Met Glu Ser Val Val Pro Ser Asp Arg Gly Asn Tyr Thr
    210                 215                 220

Cys Val Val Glu Asn Lys Phe Gly Ser Ile Arg Gln Thr Tyr Thr Leu
225                 230                 235                 240

Asp Val Leu Glu Arg Ser Pro His Arg Pro Ile Leu Gln Ala Gly Leu
                245                 250                 255

Pro Ala Asn Gln Thr Ala Val Leu Gly Ser Asp Val Glu Phe His Cys
            260                 265                 270

Lys Val Tyr Ser Asp Ala Gln Pro His Ile Gln Trp Leu Lys His Val
        275                 280                 285

Glu Val Asn Gly Ser Lys Val Gly Pro Asp Gly Thr Pro Tyr Val Thr
    290                 295                 300

Val Leu Lys Thr Ala Gly Ala Asn Thr Thr Asp Lys Glu Leu Glu Val
305                 310                 315                 320

Leu Ser Leu His Asn Val Thr Phe Glu Asp Ala Gly Glu Tyr Thr Cys
                325                 330                 335

Leu Ala Gly Asn Ser Ile Gly Phe Ser His His Ser Ala Trp Leu Val
            340                 345                 350

Val Leu Pro Val Ser Leu Glu Ser Asn Ala Ser Met Ser Ser Asn Thr
        355                 360                 365
```

<210> SEQ ID NO 35
<211> LENGTH: 19
<212> TYPE: PRT
<213> ORGANISM: Artificial Sequence
<220> FEATURE:
<223> OTHER INFORMATION: Synthetic construct

<400> SEQUENCE: 35

```
Met Met Ser Phe Val Ser Leu Leu Leu Val Gly Ile Leu Phe His Ala
1               5                   10                  15

Thr Gln Ala
```

<210> SEQ ID NO 36
<211> LENGTH: 963
<212> TYPE: DNA
<213> ORGANISM: Artificial Sequence
<220> FEATURE:
<223> OTHER INFORMATION: Synthetic construct

<400> SEQUENCE: 36

```
atgatgtcct tgtctctct gctcctggtt ggcatcctat tccatgccac ccaggccgag     60
tccttgggga cggagcagcg cgtcgtgggg cgagcggcag aagtcccggg cccagagccc    120
ggccagcagg agcagttggt cttcggcagc ggggatgctg tggagctgag ctgtccccg     180 cccgggggtg gtcccatggg gcccactgtc tgggtcaagg atggcacagg gctggtgccc    240
tcggagcgtg tcctggtggg gccccagcgg ctgcaggtgc tgaatgcctc ccacgaggac    300
tccggggcct acagctgccg gcagcggctc acgcagcgcg tactgtgcca cttcagtgtg    360
cgggtgacag acgctccatc ctcgggagat gacgaagacg gggaggacga ggctgaggac    420
acaggtgtgg acacagggc cccttactgg acacggcccg agcggatgga caagaagctg    480
ctggccgtgc cggccgccaa caccgtccgc ttcgctgcc agccgctgg caaccccact     540 ccctccatct cctggctgaa gaacggcagg gagttccgcg cgagcaccg cattggaggc    600 atcaagctgc ggcatcagca gtggagcctg gtcatggaaa gcgtggtgcc ctcggaccgc    660
```

```
ggcaactaca cctgcgtcgt ggagaacaag tttggcagca tccggcagac gtacacgctg    720
gacgtgctgg agcgctcccc gcaccggccc atcctgcagg cggggctgcc ggccaaccag    780
acggcggtgc tgggcagcga cgtggagttc cactccaagg tgtacagtga cgcacagccc    840
cacatccagt ggctcaagca cgtggaggtg aatggcagca aggtgggccc ggacggcaca    900
ccctacgtta ccgtgctcaa ggtgtccctg gagtccaacg cgtccatgag ctccaacaca    960
tga                                                                  963
```

<210> SEQ ID NO 37
<211> LENGTH: 1107
<212> TYPE: DNA
<213> ORGANISM: Artificial Sequence
<220> FEATURE:
<223> OTHER INFORMATION: Synthetic construct

<400> SEQUENCE: 37

```
atgatgtcct ttgtctctct gctcctggtt ggcatcctat tccatgccac ccaggccgag     60
tccttgggga cggagcagcg cgtcgtgggg cgagcggcag aagtcccggg cccagagccc    120
ggccagcagg agcagttggt cttcggcagc ggggatgctg tggagctgag ctgtcccccg    180 cccggggtg gtcccatggg gcccactgtc tgggtcaagg atggcacagg ctggtgccc     240 tcggagcgtg tcctggtggg gcccagcgg ctgcaggtgc tgaatgcctc ccacgaggac    300
tccggggcct acagctgccg gcagcggctc acgcagcgcg tactgtgcca cttcagtgtg    360
cgggtgacag acgctccatc ctcgggagat gacgaagacg gggaggacga ggctgaggac    420
acaggtgtgg acacaggggc cccttactgg acacggcccg agcggatgga caagaagctg    480
ctggccgtgc cggccgccaa caccgtccgc ttccgctgcc cagccgctgg caaccccact    540
ccctccatct cctggctgaa aaacggcagg gagttccgcg gcgagcaccg cattggaggc    600
atcaagctgc ggcatcagca gtggagcctg gtcatggaaa gcgtggtgcc ctcggaccgc    660
ggcaactaca cctgcgtcgt ggagaacaag tttggcagca tccggcagac gtacacgctg    720
gacgtgctgg agcgctcccc gcaccggccc atcctgcagg ctgggctgcc tgctaaccag    780
acagcggtgc tgggcagcga cgtggagttc cactgcaagg tgtacagtga cgcacagccc    840
cacatccagt ggctcaagca cgtggaggtg aatggcagca aggtgggccc ggacggcaca    900
ccctacgtta ccgtgctcaa gacggcgggc gctaacacca ccgacaagga gctagaggtt    960
ctctccttgc acaacgtcac ctttgaggac gccggggagt cacctgcct ggcgggcaat   1020 tctattgggt ttctcatca ctctgcgtgg ctggtggtgc tgccagtgtc cctggagtcc   1080
aacgcgtcca tgagctccaa cacatga                                       1107
```

<210> SEQ ID NO 38
<211> LENGTH: 216
<212> TYPE: PRT
<213> ORGANISM: Homo sapiens

<400> SEQUENCE: 38

```
Met Arg Ser Gly Cys Val Val His Val Trp Ile Leu Ala Gly Leu
1               5                   10                  15

Trp Leu Ala Val Ala Gly Arg Pro Leu Ala Phe Ser Asp Ala Gly Pro
                20                  25                  30

His Val His Tyr Gly Trp Gly Asp Pro Ile Arg Leu Arg His Leu Tyr
            35                  40                  45

Thr Ser Gly Pro His Gly Leu Ser Ser Cys Phe Leu Arg Ile Arg Ala
```

```
            50                  55                  60
Asp Gly Val Val Asp Cys Ala Arg Gly Gln Ser Ala His Ser Leu Leu
 65                  70                  75                  80

Glu Ile Lys Ala Val Ala Leu Arg Thr Val Ala Ile Lys Gly Val His
                 85                  90                  95

Ser Val Arg Tyr Leu Cys Met Gly Ala Asp Gly Lys Met Gln Gly Leu
                100                 105                 110

Leu Gln Tyr Ser Glu Glu Asp Cys Ala Phe Glu Glu Ile Arg Pro
            115                 120                 125

Asp Gly Tyr Asn Val Tyr Arg Ser Glu Lys His Arg Leu Pro Val Ser
            130                 135                 140

Leu Ser Ser Ala Lys Gln Arg Gln Leu Tyr Lys Asn Arg Gly Phe Leu
145                 150                 155                 160

Pro Leu Ser His Phe Leu Pro Met Leu Pro Met Val Pro Glu Glu Pro
                165                 170                 175

Glu Asp Leu Arg Gly His Leu Glu Ser Asp Met Phe Ser Ser Pro Leu
                180                 185                 190

Glu Thr Asp Ser Met Asp Pro Phe Gly Leu Val Thr Gly Leu Glu Ala
                195                 200                 205

Val Arg Ser Pro Ser Phe Glu Lys
                210                 215

<210> SEQ ID NO 39
<211> LENGTH: 209
<212> TYPE: PRT
<213> ORGANISM: Homo sapiens

<400> SEQUENCE: 39

Met Asp Ser Asp Glu Thr Gly Phe Glu His Ser Gly Leu Trp Val Ser
 1               5                  10                  15

Val Leu Ala Gly Leu Leu Gly Ala Cys Gln Ala His Pro Ile Pro
                 20                  25                  30

Asp Ser Ser Pro Leu Leu Gln Phe Gly Gly Gln Val Arg Gln Arg Tyr
             35                  40                  45

Leu Tyr Thr Asp Asp Ala Gln Gln Thr Glu Ala His Leu Glu Ile Arg
 50                  55                  60

Glu Asp Gly Thr Val Gly Gly Ala Ala Asp Gln Ser Pro Glu Ser Leu
 65                  70                  75                  80

Leu Gln Leu Lys Ala Leu Lys Pro Gly Val Ile Gln Ile Leu Gly Val
                 85                  90                  95

Lys Thr Ser Arg Phe Leu Cys Gln Arg Pro Asp Gly Ala Leu Tyr Gly
                100                 105                 110

Ser Leu His Phe Asp Pro Glu Ala Cys Ser Phe Arg Glu Leu Leu Leu
            115                 120                 125

Glu Asp Gly Tyr Asn Val Tyr Gln Ser Glu Ala His Gly Leu Pro Leu
            130                 135                 140

His Leu Pro Gly Asn Lys Ser Pro His Arg Asp Pro Ala Pro Arg Gly
145                 150                 155                 160

Pro Ala Arg Phe Leu Pro Leu Pro Gly Leu Pro Pro Ala Leu Pro Glu
                165                 170                 175

Pro Pro Gly Ile Leu Ala Pro Gln Pro Pro Asp Val Gly Ser Ser Asp
                180                 185                 190
```

```
Pro Leu Ser Met Val Gly Pro Ser Gln Gly Arg Ser Pro Ser Tyr Ala
        195                 200                 205
Ser
```